United States Patent
Schneider et al.

(10) Patent No.: US 8,741,297 B2
(45) Date of Patent: *Jun. 3, 2014

(54) PREPARATION OF ISOLATED AGONIST ANTI-EDAR MONOCLONAL ANTIBODIES

(71) Applicants: Edimer Pharmaceuticals, Inc., Cambridge, MA (US); Universite de Lausanne, Lausanne (CH)

(72) Inventors: Pascal Schneider, Epalinges (CH); Nathalie Dunkel, Carouge (CH); Stéphane Demotz, Epalinges (CH)

(73) Assignees: Edimer Pharmaceuticals, Inc., Cambridge, MA (US); Universite de Lausanne, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/791,055

(22) Filed: Mar. 8, 2013

(65) Prior Publication Data
US 2013/0273046 A1 Oct. 17, 2013

Related U.S. Application Data

(63) Continuation-in-part of application No. 13/260,937, filed as application No. PCT/IB2010/051385 on Mar. 30, 2010, now Pat. No. 8,496,937.

(30) Foreign Application Priority Data

Mar. 30, 2009 (WO) .................. PCT/IB2009/005118

(51) Int. Cl.
*A61K 39/395* (2006.01)
*C07K 16/28* (2006.01)
(52) U.S. Cl.
CPC ....... *C07K 16/2863* (2013.01); *C07K 2317/565* (2013.01); *C07K 2317/75* (2013.01); *C07K 2317/92* (2013.01); *A61K 39/39541* (2013.01)
USPC .................. 424/143.1; 424/133.1; 424/141.1; 424/152.1; 424/172.1; 514/16.5; 514/20.7
(58) Field of Classification Search
None
See application file for complete search history.

(56) References Cited

U.S. PATENT DOCUMENTS

2003/0023991 A1* 1/2003 Zonana et al. .................... 800/8

OTHER PUBLICATIONS

Botchkarev et al., J Investig Dermatol Symp Proc. Dec. 2005;10(3):247-51.*
Amit et al., Science, 233(4765):747-753 (1986). "Three-Dimensional Structure of an Antigen-Antibody Complex at 2.8 A Resolufion.".
Foote et al., J. Mol. Biol., 224:487-499 (1992). "Antibody Framework Residues Affecting the Conformation of the Hypervariable Loops."
Declerck et al., J. Biol. Chem. Apr. 14, 1995; 270(15):8397-400.
Headon, D. et al., "Involvement of a novel Tnf receptor homologue in hair follicle induction," Nature Genetics, vol. 22, 370-374, 1999.
Janeway et al., Immunobiology, 3rd edition, 1997, Garland Press, pp. 3:1-3:11.
Portolano et al., J. Immunol. Feb. 1, 1993; 150(3):880-7.
Rudikoff et al., Proc Natl Acad Sci U S A Mar. 1982; 79(6):1979-83.
William E. Paul, M.D., editor, Fundamental Immunology, 3d ed. Raven Press, 1993, p. 242.
Zlot et al. J Lipid Res. Jan. 1999; 40(1):76-84.
Article 34 Amendment and PCT Demand for PCT/IB2010/051385.

* cited by examiner

*Primary Examiner* — Michael Szperka
(74) *Attorney, Agent, or Firm* — DT Ward, PC; Donna T. Ward; Lingyun Jia

(57) ABSTRACT

The present invention concerns the preparation of substantially purified agonist anti-EDAR monoclonal antibodies or isolated monoclonal antibody fragments or antigen binding portions or fragments thereof. The invention further relates to isolated agonist anti-EDAR monoclonal antibodies or isolated monoclonal antibody fragments or antigen binding portions or fragments thereof as well as their use in the treatment of X-linked hypohidrotic ectodermal dysplasia and tooth agenesis. The invention also relates to a pharmaceutical composition comprising said isolated agonist anti-EDAR monoclonal antibodies or isolated monoclonal antibody fragments or antigen binding portions or fragments thereof and to a method of treating X-linked hypohidrotic ectodermal dysplasia and tooth agenesis. Finally, the present invention concerns a pharmaceutical kit comprising said isolated agonist anti-EDAR monoclonal antibodies or isolated monoclonal antibody fragments or antigen binding portions or fragments thereof.

24 Claims, 58 Drawing Sheets mAbEDAR1 Heavy chain (Amino acid: SEQ ID NO: 197. Nucleotide: SEQ ID NO: 243)
GAG GTN NAG CTG GAG GAG TCT GGG GGA GGC TTA GTG CAG CCT GGA GGG TCC CGT AAA CTC TCC TGT GCA GCC TCT GGA TTC
 E   V   X   L   E   E   S   G   G   G   L   V   Q   P   G   G   S   R   K   L   S   C   A   A   S   G   F
ACT TTC AGT GAC CAT GGA ATG CAC TGG GTC CAG CAG GCT CCA GAG AAG GGC CTG GAG TGG ATT GCA TAC ATT AGT AGT GGC
 T   F   S   D   H   G   M   H   W   V   R   Q   A   P   E   K   G   L   E   W   I   A   Y   I   S   S   G
AGT AAT GTC TAC TAT GCA GAC ACA GTG AAG GGC CGA TTC ACC ATC TCC AGA GAC AAT GCC AAG AAC ACC CTG TTC CTG
 S   N   V   Y   Y   A   D   T   V   K   G   R   F   T   I   S   R   D   N   A   K   N   T   L   F   L
CAA ATG ACC AGT CTA AGG TCT GAG GAC ACA GCC ATG TAT TAC TGT GCA AGG AGG GAA TTG CTA CGA TTT TAC TTC GAT GTC
 Q   M   T   S   L   R   S   E   D   T   A   M   Y   Y   C   A   R   R   E   L   L   R   F   Y   F   D   V
TGG GGC GCA GGG ACC ACG GTC ACC GTC TCC TCA GCC AAA ACG ACA CCC CCA TCT GTC
 W   G   A   G   T   T   V   T   V   S   S   A   K   T   T   P   P   S   V mAbEDAR2 Heavy chain (Amino acid: SEQ ID NO: 170. Nucleotide: SEQ ID NO: 198)
CAG GTC CAG CTG CAG CAG CCT GGG GCT GAA CTG GTG AAG CCT GGG GCT TCA GTG AAG CTG TCC TGC AAG GCT TCT GGC TAC
 Q   V   Q   L   Q   Q   P   G   A   E   L   V   K   P   G   A   S   V   K   L   S   C   K   A   S   G   Y
ACC TTC ACT AGC TAC TGG ATG CAG TGG GTA AAA CAG AGG CCT GGA CAA GGC CTT GAG TGG ATT GGA GAA ATT GAT CCT TCT
 T   F   T   S   Y   W   M   Q   W   V   K   Q   R   P   G   Q   G   L   E   W   I   G   E   I   D   P   S
GAT AGT TAT ACT TAC TAT AAT CAA AAG TTC AAG GGC AAG GCC ACA TTG ACT GTA GAC AAA TCC TCC AGC ACA GCC TAC ATG
 D   S   Y   T   Y   Y   N   Q   K   F   K   G   K   A   T   L   T   V   D   K   S   S   S   T   A   Y   M
CAA CTC AGC AGC CTG ACA TCT GAG GAC TCT GCG GTC TAT TAT TGT GCG AGA AGG AAG AAT TAC TAT AGG GGT ATG GAC TAC TGG
 Q   L   S   S   L   T   S   E   D   S   A   V   Y   Y   C   A   R   R   K   N   Y   Y   R   G   M   D   Y   W
GGT CAA GGA ACC TCA GTC ACC GTC TCC TCA GCC AAA ACG ACA CCC CCA TCT GTC
 G   Q   G   T   S   V   T   V   S   S   A   K   T   T   P   P   S   V mAbEDAR3 Heavy chain (Amino acid: SEQ ID NO: 199. Nucleotide: SEQ ID NO: 244)
GAG GTN NAG CTG GAG GAG TCT GGG GGA GGC TTA GTG CAG CCT GGA GGG TCC CGA AAA CTC TCC TGT GCA GCC TCT GGA TTC
 E   V   X   L   E   E   S   G   G   G   L   V   Q   P   G   G   S   R   K   L   S   C   A   A   S   G   F
ACT TTC AGT GCC ATC TAC TAT GCA GAC ACA GTG AAG GGC CGA TTC ACC ATC TCC AGA GAC AAT GCC AAG AGC ACC CTG TTC CTG
 T   F   S   A   I   Y   Y   A   D   T   V   K   G   R   F   T   I   S   R   D   N   A   K   S   T   L   F   L
AGT AGT AAT GTC TAC TAT GCA GAC ACA GTG AAG GGC CGA TTC ACC ATC TCC AGA GAC AAT GCC AAG AGC ACC CTG TTC CTG
 S   S   N   V   Y   Y   A   D   T   V   K   G   R   F   T   I   S   R   D   N   A   K   S   T   L   F   L
CAA ATG ACC AGT CTA AGG TCT GAG GAC ACA GCC ATG TAT TAC TGT GCA AGG AGG CGG GAG ATA CTG CGC TAC TAC TTC GAT GTC
 Q   M   T   S   L   R   S   E   D   T   A   M   Y   Y   C   A   R   R   R   E   I   L   R   Y   Y   F   D   V
TGG GGC GCA GGG ACC ACG GTC TCC TCA GCC GTC TCC TCA GCC AAA ACC CCA TCT GTC
 W   G   A   G   T   T   V   S   S   A   V   S   S   A   K   T   P   S   V

FIG. 3A mAbEDAR5 Heavy chain (Amino acid: SEQ ID NO: 172, Nucleotide: SEQ ID NO: 200)

```
CAG GTG CAG CTG AAG CAG TCA GGA CCT CTA GTG CAG CCC TCA CAG AGC CTG TCC ATC ACC TGC ACA GTC TCT GGT TTC
 Q   V   Q   L   K   Q   S   G   P   L   V   Q   P   S   Q   S   L   S   I   T   C   T   V   S   G   F
TCA TTA TCT AAC TAT GGT GTA CAC TGG ATT CGC CAG TCT CCA GGA AAG GGT CTG GAA TGG CTG GGA GTG ATA TGG GGT GGT
 S   L   S   N   Y   G   V   H   W   I   R   Q   S   P   G   K   G   L   E   W   L   G   V   I   W   G   G
GGA AGC ACA GAC TAT AAT GCA GCT TTC ATA TCC AGA CTG AGC ATC AGC AAG GAC AAT AGC AAG AGC CAA GTT TTC TTT AAA
 G   S   T   D   Y   N   A   A   F   I   S   R   L   S   I   S   K   D   N   S   K   S   Q   V   F   F   K
ATG AAC AGT CTG CAA GCT GAT GAC ACA GCC ATA TAT TAC TGT GCC AGC TAT GGT TAC TAC GAC TGG TTT GCT TAC TGG
 M   N   S   L   Q   A   D   D   T   A   I   Y   Y   C   A   S   Y   G   Y   Y   D   W   F   A   Y   W
GGC CAA GGG ACT CTG GTC ACT GTC TCC GCA GCC AAA ACA ACA CCC CCA TCA GTC
 G   Q   G   T   L   V   T   V   S   A   A   K   T   T   P   P   S   V
``` mAbEDAR6 Heavy chain (Amino acid: SEQ ID NO: 173, Nucleotide: SEQ ID NO: 201)

```
GAG GTC CAG CTG CAG CAG TCT GGA CCT GAA CTG GTG AAG CCT GGG GCT TCA GTG AAG ATG TCC TGC AAG GCT TCT GGT TAC
 E   V   Q   L   Q   Q   S   G   P   E   L   V   K   P   G   A   S   V   K   M   S   C   K   A   S   G   Y
TCA TTC ACT GGC TAC AAC ATG CAC TGG GTA AAG CAG AGC CAT GGA AAG AGC CTT GAG TGG ATT GGT TAT ATT GAT CCT TAC
 S   F   T   G   Y   N   M   H   W   V   K   Q   S   H   G   K   S   L   E   W   I   G   Y   I   D   P   Y
AAT GGT GCT ACT AGC TAC AAT CAG AAA TTC AAG GGC AAG GCC ACA TTG ACT GTA GAC AAA TCT TCC AGC ACA GCC TAC ATA
 N   G   A   T   S   Y   N   Q   K   F   K   G   K   A   T   L   T   V   D   K   S   S   T   T   A   Y   I
CAA CTC AAC AGC CTG ACA TCT GAG GAC TCT GCA GTC TAT TAC TGT GCA AGA TAC TAC GGT GAC TAT TAC CAC TGG TAC TTC
 Q   L   N   S   L   T   S   E   D   S   A   V   Y   Y   C   A   R   Y   Y   G   D   Y   Y   H   W   Y   F
GAT GTC TGG GGC GCA GGG ACC ACG GTC ACC GTC TCC TCA GCC AAA ACA ACA CCC CCA TCG GTC
 D   V   W   G   A   G   T   T   V   T   V   S   S   A   K   T   T   P   P   S   V
``` mAbEDAR7 Heavy chain (Amino acid: SEQ ID NO: 245, Nucleotide: SEQ ID NO: 202)

```
GAG GTN NAG CTG GAG GAG TCT GGA GGA GGC TTG GTA CAG CCT GGG GGT TCT CTG AGT CTC TCC TGT GCA ACT TCT GGA TTC
 E   V   X   L   E   E   S   G   G   G   L   V   Q   P   G   G   S   L   S   L   S   C   A   T   S   G   F
CCC TTC AGT GAT TAC TAC ATG TAC TGG GTT CGC CAG ACT CCA GAG AAG CTT GCA CTT TGG CTT GCT TTG ATT AGA AAC AAA
 P   F   S   D   Y   Y   M   Y   W   V   R   Q   T   P   E   K   L   A   L   W   L   A   L   I   R   N   K
GCT AAT GGT TAC ACA ACA GAG TAT AGT GCC TCT GTG AAA GGT CGG TTC ACC ATC TCC AGA GAT GAT TCC CAA AGC ATC CTC
 A   N   G   Y   T   T   E   Y   S   A   S   V   K   G   R   F   T   I   S   R   D   D   S   Q   R   I   L
TAT CTT CAA ATG AAT GCC CTG AGA GAC GAT TCT GCA ACA TAC TAC TGT GCA ACA GTG GGA GGT TAC TGG TAC AGG TTT CCT
 Y   L   Q   M   N   A   L   R   D   D   S   A   T   Y   Y   C   A   T   V   G   G   Y   W   Y   R   F   P
TCC TGG GGC CAA GGG ACT CTG GTC ACT GTC TCT GCA GCC AAA ACG ACA CCC CCA TCT GTC
 S   W   G   Q   G   T   L   V   T   V   S   A   A   K   T   T   P   P   S   V
```

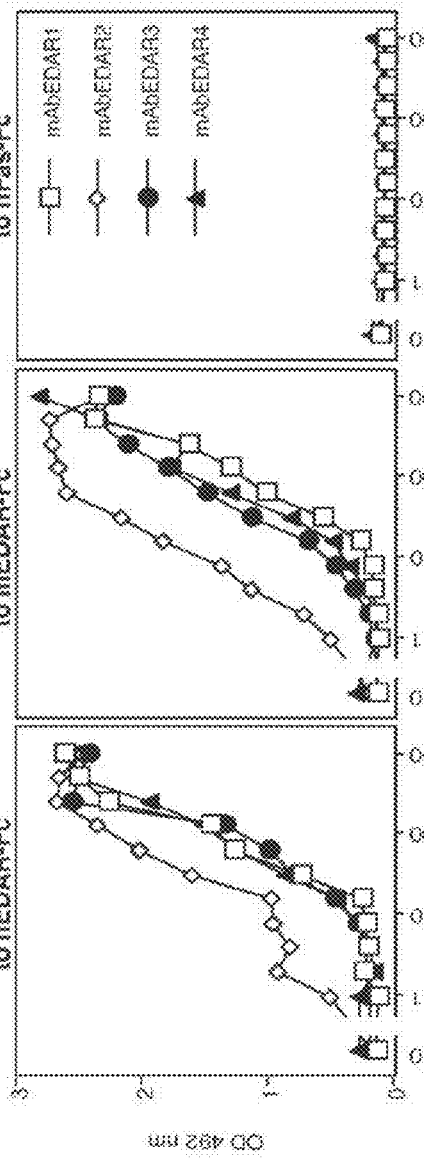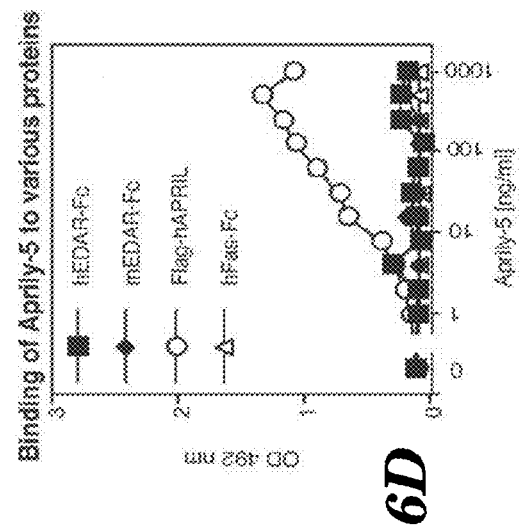

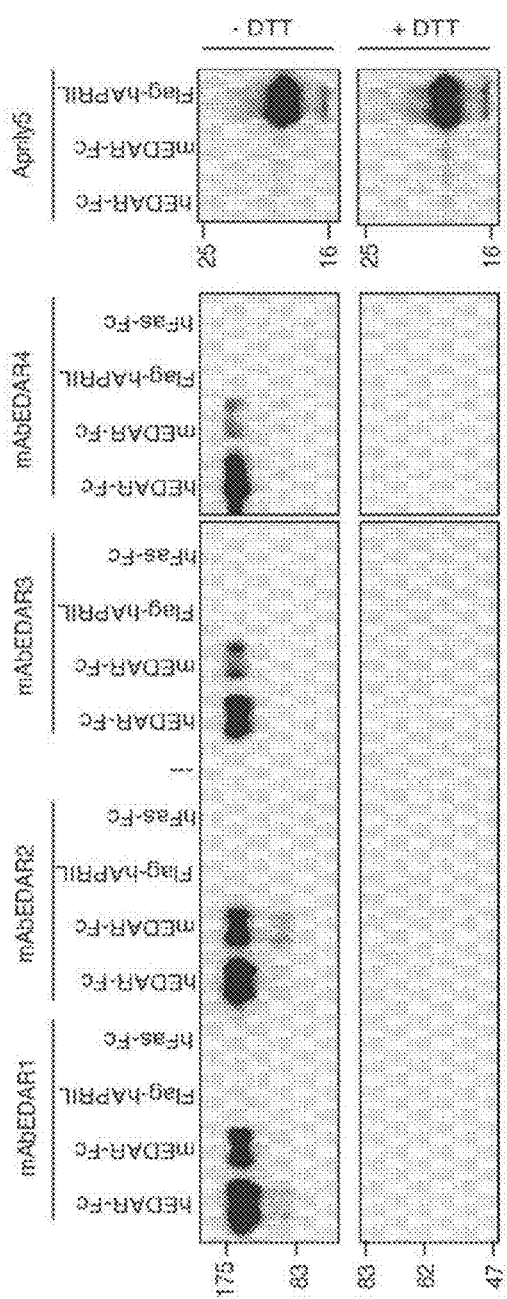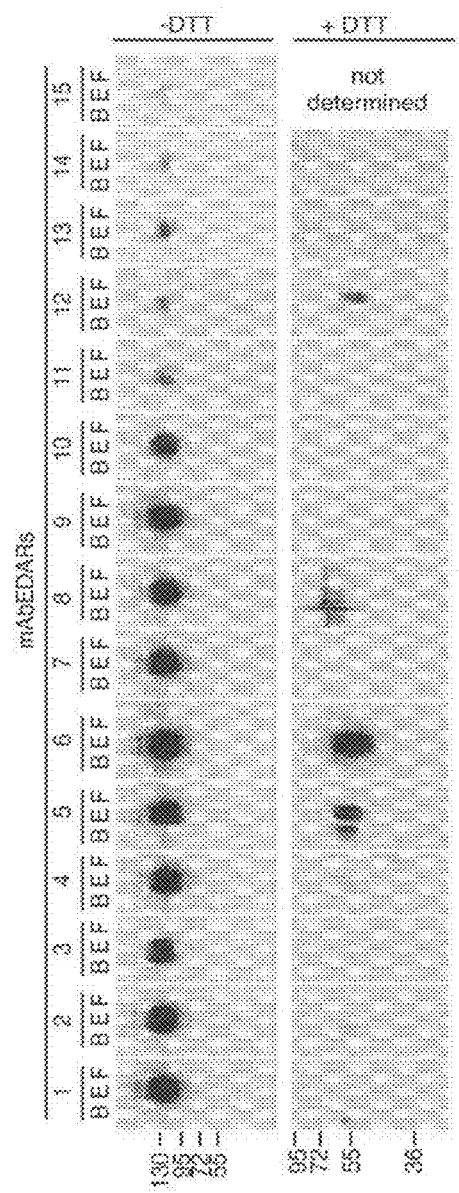

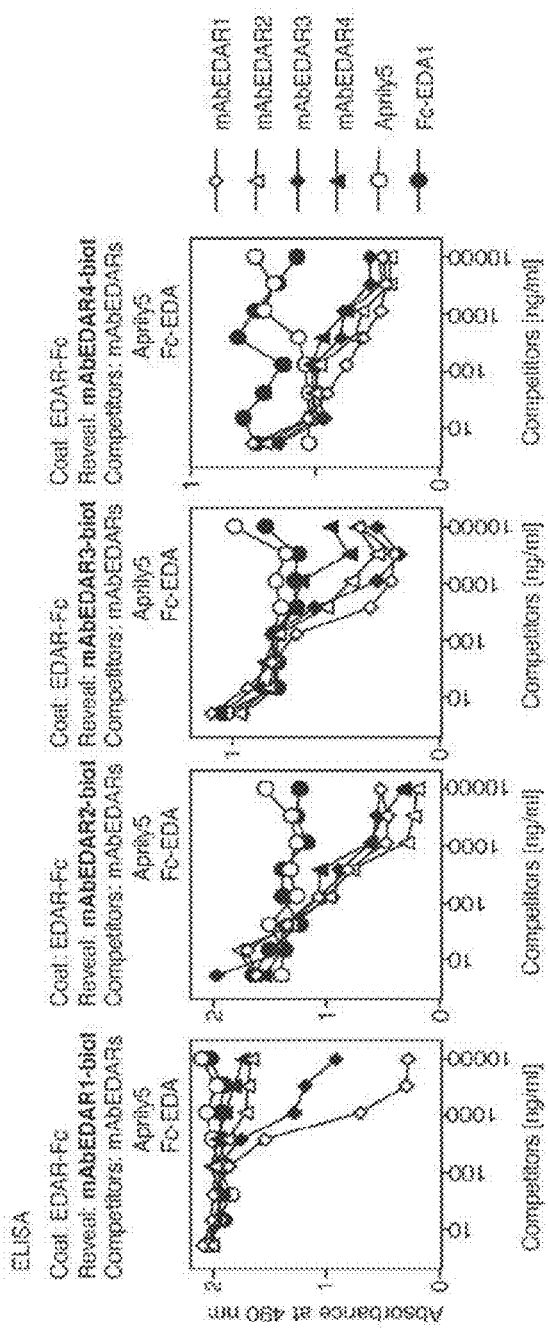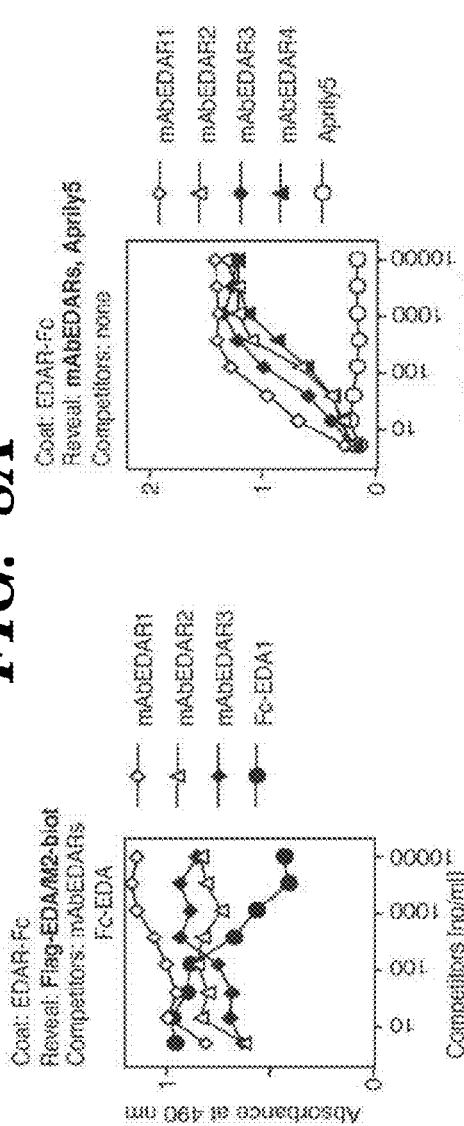
FIG. 8A
FIG. 8B
FIG. 8C

Administration of mAbEDAR3 in newborn, wild-type mice
Growth curve

Administration of mAbEDAR1 in newborn, EDA-deficient mice
External appearance and hair morphology at Day 21

Depilation and administration of mAbEDAR1 in 3 weeks-old wild-type mice; external appearance at indicated times FIG. 32 Superdex 200 gel filtration elution profiles

| mAbEDAR | IGHV gene | D gene | J gene | heavy chain V-D-J junction | IGLV gene | J gene | light chain V-J junction | Antigen | Isotype | Epitope | cross-reaction |
|---|---|---|---|---|---|---|---|---|---|---|---|
| 9 | 1-63 | 2-13 | 4 | CHFYDGSDQYAMDYW | 1-117 | 4 | CFQGSHVPPTF | mEDAR | IgG1 | full | h, rt |
| 15 | 1-63 | 2-11 | 1 | CARRSGYFDVW | 1-2-44 | 2 | CQHYGTPYTF | mEDAR | IgG1 | full | h, rt |
| 2 | 1-69 | 1-1 | 2 | CSRHNYYRGMDYW | 1-117 | 2 | CFQVSHVPYTF | mEDAR | IgG1 | I-II | h, rt |
| 12 | 1-18 | 2-3 | 3 | CASRAAYVVGNAMDSW | 17-3.23 | 5 | CLQSGNVPLTF | mEDAR | IgG1 | full | h, rt |
| 10 | 1-82 | 3-2 | 1 | CTRSSGFPYW | 10-94 | 5 | CQQYSKLPYTF | mEDAR | IgG1 | full | h, rt |
| 14 | 1-39 | 3-3 | 3 | CARGGVREL PGWFTYW | 4-55 | 1 | CQQWSSYPLTF | mEDAR | IgG1 | full | h, rt |
| 11 | 1-39 | 3-3 | 3 | CARGGVREL PGWFTYW | 10-94 | 9 | CQQYSKLPPTF | mEDAR | IgG2a | I-II | h, rt |
| 8 | 1515 | - | 1 | CARYYYGDYHWYFDVW | 1-110 | 1 | CSQDNTHVPPTF | mEDAR | IgG1 | full | h, rt |
| 1 | 1S135 | 1-1 | 1 | CVRYYYGDYHWYFDVW | 10-96 | 9 | CQQGNTLPATF | mEDAR | IgG1 | I-II | h, rt |
| 7 | 5-17 | 1-1 | 1 | CARRELLRYYFDVW | 10-96 | 2 | CHQGKTLPYTF | mEDAR | IgG1 | I-II | h, rt |
| 3 | 5-17 | 1-3 | 2 | CARRELLRYYFEYW | 10-96 | 2 | CQQGKTLPYTF | mEDAR | IgG1 | I-II | h, rt |
| 5 | 7-3 | 1-3 | 3 | CATMGK YTRPDSW | 4-57 | 2 | CKSDYPLTF | mEDAR | IgG2b | I-II | h, rt |
| 4 | 2-2 | 2-3 | 2 | CASYYYGYCWPAYW | 8-61 | 4 | CQQGSSIPRTF | mEDAR | IgG1 | - | h, rt |
| 13 | ND | ND | ND | ND | 1-117 | 4 | CFQGSHVPYTF | mEDAR | IgG1 | I-II | h, rt |

FROM FIG. 40A

FIG. 45

SEQUENCE LISTING

<160> NUMBER OF SEQ ID NOS: 288

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

```
Gly Phe Thr Phe Ser Asp His Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Ser Ser Gly Ser Ser Asn Val
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Arg Glu Leu Leu Arg Phe Tyr Phe Asp Val
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Asp Ile Gly Asn His
1               5

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Thr Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Gly Asn Thr Leu Pro Trp Thr
1               5

<210> SEQ ID NO 7
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 7

Gly Tyr Thr Phe Thr Ser Tyr Trp
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Asp Pro Ser Asp Ser Tyr Thr
1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Arg Lys Asn Tyr Tyr Arg Gly Met Asp Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Asn Ile Val Gln Ser Asn Gly Asn Thr Tyr
1               5                   10

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Val Ser
1

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Gln Val Ser His Val Pro Tyr Thr
1               5

<210> SEQ ID NO 13
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Phe Thr Phe Ser Asp Tyr Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Ser Ser Gly Ser Ser Ala Ile
1               5

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Arg Arg Glu Ile Leu Arg Tyr Tyr Phe Asp Val
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Asp Ile Ser Asn Asn
1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Thr Ser
1

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His Gln Gly Lys Thr Leu Pro Tyr Thr
```

```
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Ser Leu Ser Asn Tyr Gly
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Trp Gly Gly Gly Ser Thr
1               5

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ser Tyr Tyr Gly Tyr Tyr Asp Trp Phe Ala Tyr
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Ile Ile Ser Ser Asn Tyr
1               5

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Thr Ser
1

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 24

Gln Gln Gly Ser Ser Ile Pro Arg Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Tyr Ser Phe Thr Gly Tyr Asn
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Asp Pro Tyr Asn Gly Ala Thr
1               5

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Arg Tyr Tyr Tyr Gly Asp Tyr His Trp Tyr Phe Asp Val
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Leu Val His Ser Asn Gly Asn Thr Tyr
1               5                   10

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Val Ser
1

<210> SEQ ID NO 30
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 30

Ser Gln His Thr His Val Pro Pro Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Phe Pro Phe Ser Asp Tyr Tyr
1               5

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Arg Asn Lys Ala Asn Gly Tyr Thr Thr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Thr Val Gly Gly Tyr Tyr Arg Phe Pro Ser
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Ser Val Ser Ser Ser Tyr
1               5

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Thr Ser
1
```

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Tyr Ser Asp Tyr Pro Leu Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Phe Thr Phe Ser Asp Tyr Gly
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Ser Ser Gly Ser Ser Thr Ile
1               5

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Arg Arg Glu Leu Leu Arg Tyr Tyr Phe Glu Tyr
1               5                   10

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Asp Ile Ser Asn His
1               5

<210> SEQ ID NO 41
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Tyr Thr Ser
1

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Gln Gly Asn Thr Leu Pro Tyr Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Tyr Thr Phe Thr Asn Tyr Trp
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Tyr Pro Gly Gly Leu Tyr Thr
1               5

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

His Phe Tyr Asp Gly Asp Gln Tyr Ala Met Asp Tyr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ser Ile Val His Ser Asn Gly Asn Thr Phe
1               5                   10

<210> SEQ ID NO 47
<211> LENGTH: 3
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 47

Arg Val Ser
1

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Gln Gly Ser His Val Pro Phe Thr
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Tyr Ser Phe Thr Gly Tyr Asn
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Asn Pro Tyr Tyr Gly Ser Thr
1               5

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Arg Gly Gly Val Arg Glu Leu Pro Gly
1               5                   10

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Ser Val Ser Tyr
1               5

<210> SEQ ID NO 53

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Thr Ser
1

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Gln Trp Ser Ser Tyr Pro Leu Thr
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Tyr Ser Phe Thr Gly Tyr Asn
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Asn Pro Tyr Tyr Gly Ser Thr
1               5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Arg Gly Gly Val Arg Glu Leu Pro Gly
1               5                   10

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Gly Ile Ser Asn Tyr
```

<210> SEQ ID NO 59
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Thr Ser
1

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Gln Tyr Ser Lys Leu Pro Pro
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Pro Ala Phe Thr Thr Tyr Val
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Asn Pro Tyr Asn Asp Tyr Thr
1               5

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Ser Lys Ala Ala Tyr Tyr Val Gly Asn Ala Met Asp Ser
1               5                   10

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 64

Thr Asn Ile Asp Asp Asp
1               5

<210> SEQ ID NO 65
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Gly Asn
1

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Gln Ser Asp Asn Val Pro Leu Thr
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Tyr Ser Phe Thr Gly Tyr Asn
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Asp Pro Tyr Asn Gly Ala Thr
1               5

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Arg Tyr Tyr Tyr Gly Asp Tyr His Trp Tyr Phe Asp Val
1               5                   10

<210> SEQ ID NO 70
<211> LENGTH: 11
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 70

Gln Ser Leu Val His Ser Asn Gly Asn Thr Tyr
1               5                   10

<210> SEQ ID NO 71
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Val Ser
1

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Gln Asn Thr His Val Pro Pro Thr
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Tyr Ser Phe Thr Asp Tyr Trp
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Asn Pro Ser Thr Gly Gly Ile
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Arg Ser Gly Gly Phe Pro Tyr
1               5

```
<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Gly Ile Ser Asn Tyr
1               5

<210> SEQ ID NO 77
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Tyr Thr Ser
1

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Gln Tyr Ser Lys Leu Pro Tyr Thr
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Tyr Thr Phe Thr Asn Tyr Trp
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ile Tyr Pro Gly Gly Gly Tyr Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81
```

```
Ala Arg Arg Arg Gly Tyr Phe Asp Val
1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Asn Ile Tyr Ser Tyr
1               5

<210> SEQ ID NO 83
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asn Ala Lys
1

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln His His Tyr Gly Thr Pro Tyr Thr
1               5

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ggattcactt tcagtgacca tgga                                          24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
attagtagtg gcagtagtaa tgtc                                          24

<210> SEQ ID NO 87
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 87
gcaaggaggg aattgctacg attttacttc gatgtc                                36

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
caggacattg gcaatcat                                                    18

<210> SEQ ID NO 89
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89 tacacatca                                                               9

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
caacagggta atacgcttcc gtggacg                                          27

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ggatacacct tcactagcta ctgg                                             24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
attgatcctt ctgatagtta tact                                             24

<210> SEQ ID NO 93
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
```
tcgagaaaga attactatag gggtatggac tac                                    33

<210> SEQ ID NO 94
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
cagaacattg tacaaagtaa tggaaacacc tat                                    33

<210> SEQ ID NO 95
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95 aaagtttcc                                                                9

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tttcaagttt cacatgttcc gtacacg                                           27

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ggattcactt tcagtgacta tgga                                              24

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
attagtagtg gcagtagtgc catc                                              24

<210> SEQ ID NO 99
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gcaaggcggg agatactgcg ctactacttc gatgtc                                 36

```
<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
caggacatta gcaataac                                                 18

<210> SEQ ID NO 101
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101 tacacatca                                                            9

<210> SEQ ID NO 102
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
catcagggta aaacgcttcc gtacacg                                       27

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ggtttctcat tatctaacta tggt                                          24

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
atatggggtg gtggaagcac a                                             21

<210> SEQ ID NO 105
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gccagctatt atggttacta cgactggttt gcttac                             36
```

```
<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tcaattataa gttctaatta c                                              21

<210> SEQ ID NO 107
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107 aggacatcc                                                             9

<210> SEQ ID NO 108
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cagcagggta gtagtatacc acgcacg                                        27

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ggttactcat tcactggcta caac                                           24

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
attgatcctt acaatggtgc tact                                           24

<210> SEQ ID NO 111
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gcaagatact actatggtga ctaccactgg tacttcgatg tc                       42

<210> SEQ ID NO 112
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
cagagccttg tacacagtaa tggaaacacc tat                                    33

<210> SEQ ID NO 113
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113 aaagtttcc                                                                9

<210> SEQ ID NO 114
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tctcaacata cacatgttcc tcctacg                                           27

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ggattcccct tcagtgatta ctac                                              24

<210> SEQ ID NO 116
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
attagaaaca aagctaatgg ttacacaaca                                        30

<210> SEQ ID NO 117
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gcaacagtgg gaggttacta caggtttcct tcc                                    33

<210> SEQ ID NO 118
<211> LENGTH: 21
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 118
tcaagtgtaa gttccagtta c                                              21

<210> SEQ ID NO 119
<211> LENGTH: 9
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 119 agcacatcc                                                             9

<210> SEQ ID NO 120
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
cagcagtaca gtgattaccc actcacg                                        27

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 121
ggattcactt tcagtgacta tgga                                           24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
attagtagtg gcagtagtac catc                                           24

<210> SEQ ID NO 123
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 123
gcaaggaggg agttactacg atattatttt gagtac                              36

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 124
caggacatta gcaatcat                                                                 18

<210> SEQ ID NO 125
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125 tacacatca                                                                            9

<210> SEQ ID NO 126
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
caacagggta atacgcttcc gtacacg                                                       27

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ggatacacct tcactaacta ctgg                                                          24

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
atttaccctg gaggtcttta tact                                                          24

<210> SEQ ID NO 129
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
catttctacg atggtgacca gtatgctatg gactac                                             36

<210> SEQ ID NO 130
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 130
cagagcattg tacatagtaa tggaaacacc ttt                                33

<210> SEQ ID NO 131
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131 agagtttcc                                                           9

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tttcaaggtt cacatgttcc attcacg                                      27

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ggttattcat tcactggcta caac                                         24

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
attaatcctt actatggtag tact                                         24

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gcaagagggg gcgttaggga actaccaggc                                   30

<210> SEQ ID NO 136
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
```
tcaagtgtaa gttac                                              15

<210> SEQ ID NO 137
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137 gacacatcc                                                      9

<210> SEQ ID NO 138
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
cagcagtgga gtagttaccc gctcacg                                 27

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ggttattcat tcactggcta caac                                    24

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
attaatcctt actatggtag tact                                    24

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gcaagagggg gcgttaggga actaccaggc                              30

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
cagggcatta gcaattat                                           18

```
<210> SEQ ID NO 143
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143 tccacatca                                                                  9

<210> SEQ ID NO 144
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
cagcagtata gtaagcttcc tccg                                                24

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ggacccgact tcactaccta tgtt                                                24

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
attaatcctt acaatgatta tact                                                24

<210> SEQ ID NO 147
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gcaagcaaag ctgcctacta cgtggggaat gctatggact ca                            42

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
actaatattg atgatgat                                                       18

<210> SEQ ID NO 149
```

```
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149 gaaggcaat                                                                  9

<210> SEQ ID NO 150
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ttgcaaagtg ataacgtgcc gctcacg                                             27

<210> SEQ ID NO 151
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ggttactcat tcactggcta caac                                                24

<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
attgatcctt acaatggtgc tacc                                                24

<210> SEQ ID NO 153
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gtaagatact actatggtga ctaccactgg tacttcgatg tc                            42

<210> SEQ ID NO 154
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
cagagccttg tacacagtaa tggaaacacc tat                                      33

<210> SEQ ID NO 155
<211> LENGTH: 9
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 155 aaagtttcc                                                                 9

<210> SEQ ID NO 156
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tctcaaaata cacatgttcc tcctacg                                            27

<210> SEQ ID NO 157
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ggttactcat tcaccgacta ctgg                                               24

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
attaatccta gcactggtgg tatc                                               24

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
acaagatcgg gaggctttcc ttac                                               24

<210> SEQ ID NO 160
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cagggcatta gcaattat                                                      18

<210> SEQ ID NO 161
<211> LENGTH: 9
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 161 tacacatca                                                              9

<210> SEQ ID NO 162
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
cagcagtaca gtaagcttcc gtacacg                                         27

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ggatacacct tcactaacta ctgg                                            24

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
atttaccctg gaggtggtta tact                                            24

<210> SEQ ID NO 165
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gcaagaagga gggggtactt cgatgtc                                         27

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
gaaaatattt acagttat                                                   18

<210> SEQ ID NO 167
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167 aatgcaaaa                                                                                          9

<210> SEQ ID NO 168
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
caacatcatt atggtactcc gtacacg                                                                     27

<210> SEQ ID NO 169
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Glu Val Pro Leu Glu Glu Ser Gly Gly Gly Leu Val Lys Pro Gly Gly
1               5                   10                  15

Ser Arg Lys Leu Ser Cys Ala Ala Ser Gly Phe Thr Phe Ser Asp His
            20                  25                  30

Gly Met His Trp Val Arg Gln Ala Pro Glu Lys Gly Leu Glu Trp Ile
        35                  40                  45

Ala Tyr Ile Ser Ser Gly Ser Ser Asn Val Tyr Tyr Ser Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Glu Leu Leu Arg Phe Tyr Phe Asp Val Trp Gly Ala Gly
            100                 105                 110

Thr Thr Val Thr Val Ser Ser Ala Lys Thr Thr Pro Pro Ser Val
        115                 120                 125

<210> SEQ ID NO 170
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Ile Glu Trp Ile
        35                  40                  45

Gly Glu Ile Asp Pro Ser Asp Ser Tyr Thr Tyr Tyr Asn Gln Lys Phe
    50                  55                  60

Lys Gly Lys Ala Thr Leu Thr Ile Asp Lys Ser Ser Ser Thr Ala Tyr
65                  70                  75                  80

Met Gln Leu Ser Ser Leu Thr Ser Glu Asp Ser Ala Val Tyr Tyr Cys

```
                85                  90                  95
Ser Arg Lys Asn Tyr Tyr Arg Gly Met Asp Tyr Trp Gly Gln Gly Thr
            100                 105                 110
Ser Val Thr Val Ser Ser Ala Lys Thr Thr Pro Pro Ser Val
            115                 120                 125

<210> SEQ ID NO 171
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Glu Val Pro Leu Glu Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ala Ile Tyr Tyr Ala Asp Thr Val
    50                  55                  60

Lys Gly Arg Phe Thr Ile Ser Arg Asp Asn Ala Lys Ser Thr Leu Phe
65                  70                  75                  80

Leu Gln Met Thr Ser Leu Arg Ser Glu Asp Thr Ala Met Tyr Tyr Cys
                85                  90                  95

Ala Arg Arg Glu Ile Leu Arg Tyr Tyr Phe Asp Val Trp Gly Ala Gly
            100                 105                 110

Thr Thr Val Thr Val Ser Ser Ala Lys Thr Thr Pro Pro Ser Val
            115                 120                 125

<210> SEQ ID NO 172
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ser Asn Tyr
            20                  25                  30

Gly Val His Trp Ile Arg Gln Ser Pro Gly Lys Gly Leu Glu Trp Leu
        35                  40                  45

Gly Val Ile Trp Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Ser Tyr Tyr Gly Tyr Tyr Asp Trp Phe Ala Tyr Trp Gly Gln Gly Thr
            100                 105                 110

Leu Val Thr Val Ser Ala Ala Lys Thr Thr Pro Pro Ser Val
            115                 120                 125

<210> SEQ ID NO 173
```

```
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173
```

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ser Phe Thr Gly Tyr
            20                  25                  30

Asn Met His Trp Val Lys Gln Ser His Gly Lys Ser Leu Glu Trp Ile
        35                  40                  45

Gly Tyr Ile Asp Pro Tyr Asn Gly Ala Thr Ser Lys Asn Gln Lys Phe
    50                  55                  60

Lys Gly Lys Ala Thr Leu Thr Val Asp Lys Ser Ser Thr Thr Ala Tyr
65                  70                  75                  80

Ile Gln Leu Asn Ser Leu Thr Ser Glu Asp Ser Ala Val Tyr Tyr Cys
                85                  90                  95

Ala Arg Tyr Tyr Tyr Gly Asp Tyr His Trp Tyr Phe Asp Val Trp Gly
            100                 105                 110

Ala Gly Thr Thr Val Thr Val Ser Ser Ala Lys Thr Thr Ala Pro Ser
        115                 120                 125

Val

```
<210> SEQ ID NO 174
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid

<400> SEQUENCE: 174
```

Glu Val Xaa Leu Glu Glu Ser Gly Gly Gly Leu Val Gln Pro Gly Gly
1               5                   10                  15

Ser Leu Ser Leu Ser Cys Ala Thr Ser Gly Phe Pro Phe Ser Asp Tyr
            20                  25                  30

Tyr Met Thr Trp Ile Arg Gln Pro Pro Gly Lys Ala Leu Glu Trp Leu
        35                  40                  45

Ala Leu Ile Arg Asn Lys Ala Asn Gly Tyr Thr Thr Glu Asp Ser Pro
    50                  55                  60

Ser Val Lys Gly Arg Phe Ile Ile Ser Arg Asp Asp Ser Gln Arg Ile
65                  70                  75                  80

Leu Tyr Leu Gln Met Asn Ala Leu Arg Asp Glu Asp Ser Ala Thr Tyr
                85                  90                  95

Tyr Cys Ala Thr Val Gly Gly Tyr Tyr Arg Phe Pro Ser Trp Gly Gln
            100                 105                 110

Gly Thr Thr Val Thr Val Ser Ala Ala Lys Thr Thr Pro Pro Ser Val
        115                 120                 125

```
<210> SEQ ID NO 175
<211> LENGTH: 127
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Lys, Glu or Gln

<400> SEQUENCE: 175

Glu Val Xaa Leu Glu Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Glu Leu Leu Arg Tyr Tyr Phe Glu Tyr Trp Gly Gln Gly
            100                 105                 110

Thr Thr Leu Thr Val Ser Ser Ala Lys Thr Thr Pro Pro Ser Val
        115                 120                 125

<210> SEQ ID NO 176
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Glu or Gln
<220> FEATURE:
<221> NAME/KEY: MOD_RES
<222> LOCATION: (6)..(6)
<223> OTHER INFORMATION: Lys, Glu or Gln

<400> SEQUENCE: 176

Glu Val Gln Leu Xaa Xaa Ser Gly Ala Glu Leu Val Arg Pro Gly Thr
1               5                   10                  15

Ser Val Lys Met Ser Cys Arg Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile Tyr Pro Gly Gly Leu Tyr Thr Asn Tyr Asn Glu Lys Phe
    50                  55                  60

Lys Asp Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

His Phe Tyr Asp Gly Asp Gln Tyr Ala Met Asp Tyr Trp Gly Gln Gly
            100                 105                 110

Thr Ser Val Thr Val Ser Ser Ala Lys Thr Thr Pro Pro Ser Val
        115                 120                 125

<210> SEQ ID NO 177
<211> LENGTH: 129
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys, Asn, Glu, Asp, Gln, His or Tyr
<220> FEATURE:
<221> NAME/KEY: MOD_RES
<222> LOCATION: (6)..(6)
<223> OTHER INFORMATION: Lys, Glu or Gln

<400> SEQUENCE: 177

```
Glu Val Gln Leu Xaa Xaa Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Met Lys Gln Ser His Gly Lys Ser Leu Glu Trp Ile
        35                  40                  45

Gly Asn Ile Asn Pro Tyr Tyr Gly Ser Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Gly Val Arg Glu Leu Pro Gly Trp Phe Thr Tyr Trp Gly
            100                 105                 110

Gln Gly Thr Leu Val Thr Val Ser Ala Ala Lys Thr Pro Pro Ser
        115                 120                 125

Val
```

<210> SEQ ID NO 178
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Glu or Gln
<220> FEATURE:
<221> NAME/KEY: MOD_RES
<222> LOCATION: (6)..(6)
<223> OTHER INFORMATION: Lys, Glu or Gln

<400> SEQUENCE: 178

```
Glu Val Gln Leu Xaa Xaa Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Met Lys Gln Ser His Gly Lys Ser Leu Glu Trp Ile
        35                  40                  45

Gly Asn Ile Asn Pro Tyr Tyr Gly Ser Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Gly Val Arg Glu Leu Pro Gly Trp Phe Thr Tyr Trp Gly
            100                 105                 110
```

```
Gln Gly Thr Leu Val Thr Val Ser Ala Ala Lys Thr Thr Pro Pro Ser
            115                 120                 125

Val
```

<210> SEQ ID NO 179
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys, Asn, Glu, Asp, Gln, His or Tyr
<220> FEATURE:
<221> NAME/KEY: MOD_RES
<222> LOCATION: (6)..(6)
<223> OTHER INFORMATION: Lys, Glu or Gln

<400> SEQUENCE: 179

```
Glu Val Gln Leu Xaa Xaa Ser Gly Pro Glu Leu Val Lys Pro Gly Ala
1               5                   10                  15

Ser Val Lys Met Ser Cys Lys Ala Ser Gly Pro Ala Phe Thr Thr Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Tyr Thr Lys Tyr Asp Glu Lys Phe
    50                  55                  60

Arg Gly Lys Ala Thr Leu Thr Ser Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ser Lys Ala Ala Tyr Tyr Val Gly Asn Ala Met Asp Ser Trp Gly
            100                 105                 110

Gln Gly Thr Ser Ile Thr Val Ser Ser Ala Lys Thr Thr Pro Pro Ser
            115                 120                 125

Val
```

<210> SEQ ID NO 180
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(6)
<223> OTHER INFORMATION: Lys, Glu or Gln

<400> SEQUENCE: 180

```
Glu Val Gln Leu Xaa Xaa Ser Gly Pro Glu Leu Val Lys Pro Gly Ala
1               5                   10                  15

Ser Val Lys Met Ser Cys Lys Ala Ser Gly Tyr Ser Phe Thr Gly Tyr
            20                  25                  30

Asn Met His Trp Val Lys Gln Ser His Gly Lys Ser Leu Glu Trp Ile
        35                  40                  45

Gly Tyr Ile Asp Pro Tyr Asn Gly Ala Thr Ser Asn Asn Gln Arg Phe
    50                  55                  60

Lys Gly Lys Ala Thr Leu Thr Ala Asp Lys Ser Ser Ser Thr Ala Tyr
65                  70                  75                  80
```

```
Ile Gln Leu Asn Ser Leu Thr Ser Glu Asp Ser Ala Phe Tyr Tyr Cys
                85                  90                  95

Val Arg Tyr Tyr Tyr Gly Asp Tyr His Trp Tyr Phe Asp Val Trp Gly
            100                 105                 110

Ala Gly Thr Thr Val Thr Val Ser Ser Ala Lys Thr Thr Pro Pro Ser
        115                 120                 125

Val

<210> SEQ ID NO 181
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Glu Val Gln Leu Glu Glu Ser Gly Pro Glu Leu Val Lys Pro Gly Ala
1               5                   10                  15

Ser Val Arg Ile Ser Cys Lys Ala Ser Gly Tyr Ser Phe Thr Asp Tyr
            20                  25                  30

Trp Met His Trp Val Lys Gln Gly Pro Glu Lys Ser Leu Glu Trp Ile
        35                  40                  45

Gly Glu Ile Asn Pro Ser Thr Gly Gly Ile Ile Tyr Asn Gln Lys Phe
    50                  55                  60

Glu Ala Lys Ala Thr Leu Thr Val Asp Ile Ser Ser Ser Thr Thr Tyr
65                  70                  75                  80

Met Gln Leu Lys Ser Leu Thr Ser Glu Asp Ser Ala Val Tyr Tyr Cys
                85                  90                  95

Thr Arg Ser Gly Gly Phe Pro Tyr Trp Gly Gln Gly Thr Leu Val Thr
            100                 105                 110

Val Ser Ala Ala Lys Thr Thr Pro Pro Ser Val
        115                 120

<210> SEQ ID NO 182
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, Glu or Gln
<220> FEATURE:
<221> NAME/KEY: MOD_RES
<222> LOCATION: (5)..(6)
<223> OTHER INFORMATION: Lys, Glu or Gln

<400> SEQUENCE: 182

Xaa Val Gln Leu Xaa Xaa Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asn Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80
```

```
Met Gln Leu Ser Ser Leu Thr Ser Glu Asp Ser Ala Ile Tyr Tyr Cys
                85                  90                  95

Ala Arg Arg Arg Gly Tyr Phe Asp Val Trp Gly Ala Gly Thr Thr Val
            100                 105                 110

Thr Val Ser Ser Ala Lys Thr Thr Pro Pro Ser Val
            115                 120
```

<210> SEQ ID NO 183
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Gly Asn His
            20                  25                  30

Leu Asn Trp Tyr Gln Gln Lys Pro Asp Gly Thr Val Lys Leu Leu Ile
        35                  40                  45

Tyr Tyr Thr Ser Arg Ile His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg Ala Asp Ala Ala
            100                 105                 110

Pro
```

<210> SEQ ID NO 184
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val Gln Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Tyr Cys Phe Gln Val
                85                  90                  95

Ser His Val Pro Tyr Thr Phe Gly Gly Gly Thr Lys Leu Glu Ile Lys
            100                 105                 110

Arg Ala Asp Ala Ala Pro
            115
```

<210> SEQ ID NO 185
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Asn
            20                  25                  30

Leu Asn Trp Tyr Gln Gln Arg Pro Asp Gly Thr Val Lys Leu Leu Ile
        35                  40                  45

Tyr Tyr Thr Ser Arg Ser Gln Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Val Ala Thr Tyr Phe Cys His Gln Gly Lys Thr Leu Pro Tyr
                85                  90                  95

Thr Phe Gly Gly Gly Thr Lys Leu Glu Ile Lys Arg Ala Asp Ala Ala
            100                 105                 110

Pro

<210> SEQ ID NO 186
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ile Ile Ser Ser Asn
            20                  25                  30

Tyr Leu His Trp Tyr Gln Gln Lys Pro Gly Phe Ser Pro Lys Pro Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Arg Thr Phe Gly Ser Gly Thr Lys Leu Glu Ile Lys Arg Ala Asp Ala
            100                 105                 110

Ala Pro

<210> SEQ ID NO 187
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Gln Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln His
                85                  90                  95

Thr His Val Pro Pro Thr Phe Gly Ala Gly Thr Lys Leu Glu Leu Lys
                100                 105                 110

Arg Ala Asp Ala Ala Pro
            115

<210> SEQ ID NO 188
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Met or Leu

<400> SEQUENCE: 188

Asp Ile Val Xaa Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
                20                  25                  30

Tyr Leu His Trp Tyr Gln Gln Lys Ser Gly Val Ser Pro Lys Leu Trp
            35                  40                  45

Ile Tyr Ser Thr Ser Asn Leu Ala Ser Gly Val Pro Val Arg Phe Ser
    50                  55                  60

Gly Ser Gly Ser Gly Thr Ser Tyr Ser Leu Thr Val Ser Ser Val Glu
65                  70                  75                  80

Ala Glu Asp Ala Ala Thr Tyr Tyr Cys Gln Gln Tyr Ser Asp Tyr Pro
                85                  90                  95

Leu Thr Phe Gly Gly Gly Thr Lys Leu Glu Ile Lys Arg Ala Asp Ala
                100                 105                 110

Ala Pro

<210> SEQ ID NO 189
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Met, Val or Leu

<400> SEQUENCE: 189

Asp Ile Val Xaa Thr Gln Ser Pro Ser Ser Leu Ser Ala Ser Leu Gly
1               5                   10                  15

Asp Arg Val Thr Ile Ser Cys Arg Ala Ser Gln Asp Ile Ser Asn His
                20                  25                  30

```
Leu Asn Trp Tyr Gln Gln Lys Pro Asp Gly Thr Val Lys Leu Leu Ile
             35                  40                  45

Tyr Tyr Thr Ser Arg Leu His Ser Gly Leu Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Lys Arg Ala Asp Ala Ala
            100                 105                 110

Pro

<210> SEQ ID NO 190
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (4)..(4)
<223> OTHER INFORMATION: Met, Val or Leu

<400> SEQUENCE: 190

Xaa Ile Val Xaa Thr Gln Ser Pro Leu Ser Leu Pro Val Ser Leu Gly
 1               5                  10                  15

Asp Gln Ala Ser Ile Ser Cys Arg Ser Ser Gln Ser Ile Val His Ser
             20                  25                  30

Asn Gly Asn Thr Phe Leu Glu Trp Tyr Leu Gln Lys Pro Gly Gln Ser
             35                  40                  45

Pro Asn Leu Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Phe Thr Phe Gly Ser Gly Thr Lys Leu Glu Ile Lys
            100                 105                 110

Arg Ala Asp Ala Ala Pro
            115

<210> SEQ ID NO 191
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Met, Val or Leu
<220> FEATURE:
<221> NAME/KEY: MOD_RES
<222> LOCATION: (7)..(7)
<223> OTHER INFORMATION: Thr, Ala, Pro or Ser

<400> SEQUENCE: 191
```

-continued

```
Asp Ile Val Xaa Thr Gln Xaa Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Ala Ser Tyr Ser Leu Thr Ile Ser Arg Met Glu Ala Glu
65              70                  75                  80

Asp Ala Ala Thr Tyr Tyr Cys Gln Gln Trp Ser Ser Tyr Pro Leu Thr
                85                  90                  95

Phe Gly Ala Gly Thr Lys Leu Glu Leu Lys Arg Ala Asp Ala Ala Pro
            100                 105                 110
```

<210> SEQ ID NO 192
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Met, Val or Leu

<400> SEQUENCE: 192

```
Asp Ile Val Xaa Thr Gln Ser Pro Pro Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Ala Asp Gly Thr Val Glu Leu Leu Ile
        35                  40                  45

Tyr Ser Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65              70                  75                  80

Glu Asp Ile Ala Thr Tyr Tyr Cys Gln Gln Tyr Ser Lys Leu Pro Pro
                85                  90                  95

Thr Phe Gly Gly Gly Thr Lys Leu Glu Ile Lys Arg Ala Asp Ala Ala
            100                 105                 110

Pro
```

<210> SEQ ID NO 193
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Met, Val or Leu

<400> SEQUENCE: 193

```
Asp Ile Val Xaa Thr Gln Ser Pro Ala Ser Leu Ser Met Ala Leu Gly
1               5                   10                  15

Glu Lys Val Thr Ile Arg Cys Ile Thr Ser Thr Asn Ile Asp Asp Asp
            20                  25                  30
```

```
Met Asn Trp Tyr Gln Gln Lys Pro Gly Glu Pro Pro Lys Leu Leu Ile
        35                  40                  45

Ser Glu Gly Asn Ser Leu Arg Pro Gly Val Pro Ser Arg Phe Ser Ser
    50                  55                  60

Ser Gly Tyr Asp Thr Asp Phe Val Phe Thr Ile Glu Asn Ile Leu Ser
65                  70                  75                  80

Glu Asp Val Ala Asp Tyr Tyr Cys Leu Gln Ser Asp Asn Val Pro Leu
                85                  90                  95

Thr Phe Gly Thr Gly Thr Lys Leu Val Leu Lys Arg Ala Asp Ala Ala
            100                 105                 110

Pro

<210> SEQ ID NO 194
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Met, Val or Leu

<400> SEQUENCE: 194

Asp Ile Val Xaa Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Pro Thr Phe Gly Ala Gly Thr Lys Leu Glu Leu Lys
            100                 105                 110

Arg Ala Asp Ala Ala Pro
        115

<210> SEQ ID NO 195
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Met, Val or Leu

<400> SEQUENCE: 195

Asp Ile Val Xaa Thr Gln Ser Pro Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45
```

```
Phe Tyr Thr Ser Ser Leu His Ser Gly Val Pro Ser Arg Phe Ser Gly
    50                  55                  60

Ser Gly Ser Gly Thr Asp Tyr Tyr Leu Thr Ile Ser Asn Leu Glu Thr
65                  70                  75                  80

Glu Asp Val Ala Ile Tyr Tyr Cys Gln Gln Tyr Ser Lys Leu Pro Tyr
                85                  90                  95

Thr Phe Gly Gly Gly Thr Lys Leu Glu Ile Lys Arg Ala Asp Ala Ala
            100                 105                 110

Pro

<210> SEQ ID NO 196
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Met, Val or Leu

<400> SEQUENCE: 196

Asp Ile Val Xaa Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
                20                  25                  30

Leu Ala Trp Phe Gln Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Tyr
                85                  90                  95

Thr Phe Gly Gly Gly Thr Lys Leu Glu Ile Lys Arg Ala Asp Ala Ala
            100                 105                 110

Pro

<210> SEQ ID NO 197
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(381)
<220> FEATURE:
<221> NAME/KEY: modified_base
<222> LOCATION: (6)..(6)
<223> OTHER INFORMATION: a, c, t or g

<400> SEQUENCE: 197 gag gtn vag ctg gag gag tct ggg gga ggc tta gtg aag cct gga ggg      48
Glu Val Xaa Leu Glu Glu Ser Gly Gly Gly Leu Val Lys Pro Gly Gly
1               5                   10                  15 tcc cgt aaa ctc tcc tgt gca gcc tct gga ttc act ttc agt gac cat      96
Ser Arg Lys Leu Ser Cys Ala Ala Ser Gly Phe Thr Phe Ser Asp His
                20                  25                  30 gga atg cac tgg gtc cgt cag gct cca gag aag ggg ctg gag tgg att     144
Gly Met His Trp Val Arg Gln Ala Pro Glu Lys Gly Leu Glu Trp Ile
```

```
                35                  40                  45
gca tac att agt agt ggc agt agt aat gtc tac tat tca gac aca gtg      192
Ala Tyr Ile Ser Ser Gly Ser Ser Asn Val Tyr Tyr Ser Asp Thr Val
 50                  55                  60 aag ggc cga ttc acc atc tcc aga gac aat gcc aag aac acc ctg ttc      240
Lys Gly Arg Phe Thr Ile Ser Arg Asp Asn Ala Lys Asn Thr Leu Phe
65                  70                  75                  80 ctg caa atg acc agt cta agg tct gag gac aca gcc atg tat tac tgt      288
Leu Gln Met Thr Ser Leu Arg Ser Glu Asp Thr Ala Met Tyr Tyr Cys
                85                  90                  95 gca agg agg gaa ttg cta cga ttt tac ttc gat gtc tgg ggc gca ggg      336
Ala Arg Arg Glu Leu Leu Arg Phe Tyr Phe Asp Val Trp Gly Ala Gly
            100                 105                 110 acc acg gtc acc gtc tcc tca gcc aaa acg aca ccc cca tct gtc          381
Thr Thr Val Thr Val Ser Ser Ala Lys Thr Thr Pro Pro Ser Val
        115                 120                 125

<210> SEQ ID NO 198
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(378)

<400> SEQUENCE: 198 cag gtc cag ctg cag cag cct ggg gct gaa ctg gtg aag cct ggg gct       48
Gln Val Gln Leu Gln Gln Pro Gly Ala Glu Leu Val Lys Pro Gly Ala
1               5                   10                  15 tca gtg aag ctg tcc tgc aag gct tct gga tac acc ttc act agc tac       96
Ser Val Lys Leu Ser Cys Lys Ala Ser Gly Tyr Thr Phe Thr Ser Tyr
            20                  25                  30 tgg atg cag tgg gtg aaa cag agg cct gga caa ggc att gag tgg atc      144
Trp Met Gln Trp Val Lys Gln Arg Pro Gly Gln Gly Ile Glu Trp Ile
        35                  40                  45 gga gaa att gat cct tct gat agt tat act tac tac aat caa aag ttc      192
Gly Glu Ile Asp Pro Ser Asp Ser Tyr Thr Tyr Tyr Asn Gln Lys Phe
 50                  55                  60 aag ggc aag gcc aca ttg act ata gac aaa tcc tcc agc aca gcc tac      240
Lys Gly Lys Ala Thr Leu Thr Ile Asp Lys Ser Ser Ser Thr Ala Tyr
65                  70                  75                  80 atg caa ctc agc agc ctg aca tct gag gac tct gcg gtc tat tat tgt      288
Met Gln Leu Ser Ser Leu Thr Ser Glu Asp Ser Ala Val Tyr Tyr Cys
                85                  90                  95 tcg aga aag aat tac tat agg ggt atg gac tac tgg ggt caa gga acc      336
Ser Arg Lys Asn Tyr Tyr Arg Gly Met Asp Tyr Trp Gly Gln Gly Thr
            100                 105                 110 tca gtc acc gtc tcc tca gcc aaa acg aca ccc cca tct gtc              378
Ser Val Thr Val Ser Ser Ala Lys Thr Thr Pro Pro Ser Val
        115                 120                 125

<210> SEQ ID NO 199
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(381)
<220> FEATURE:
```

```
<221> NAME/KEY: modified_base
<222> LOCATION: (6)..(6)
<223> OTHER INFORMATION: a, c, t or g

<400> SEQUENCE: 199 gag gtn vag ctg gag gag tct ggg gga ggc tta gtg aag cct gga ggg        48
Glu Val Xaa Leu Glu Glu Ser Gly Gly Gly Leu Val Lys Pro Gly Gly
1               5                   10                  15 tcc cgg aaa ctc tcc tgt gca gcc tct gga ttc act ttc agt gac tat        96
Ser Arg Lys Leu Ser Cys Ala Ala Ser Gly Phe Thr Phe Ser Asp Tyr
            20                  25                  30 gga atg cac tgg gtc cgt cag gct cca gag aag ggg ctg gag tgg gtt       144
Gly Met His Trp Val Arg Gln Ala Pro Glu Lys Gly Leu Glu Trp Val
        35                  40                  45 gca tac att agt agt ggc agt agt gcc atc tac tat gca gac aca gtg       192
Ala Tyr Ile Ser Ser Gly Ser Ser Ala Ile Tyr Tyr Ala Asp Thr Val
50                  55                  60 aag ggc cga ttc acc atc tcc aga gac aat gcc aag agc acc ctg ttc       240
Lys Gly Arg Phe Thr Ile Ser Arg Asp Asn Ala Lys Ser Thr Leu Phe
65                  70                  75                  80 ctg caa atg acc agt cta agg tct gag gac aca gcc atg tat tac tgt       288
Leu Gln Met Thr Ser Leu Arg Ser Glu Asp Thr Ala Met Tyr Tyr Cys
                85                  90                  95 gca agg cgg gag ata ctg cgc tac tac ttc gat gtc tgg ggc gca ggg       336
Ala Arg Arg Glu Ile Leu Arg Tyr Tyr Phe Asp Val Trp Gly Ala Gly
            100                 105                 110 acc acg gtc acc gtc tcc tca gcc aaa acg aca ccc cca tct gtc           381
Thr Thr Val Thr Val Ser Ser Ala Lys Thr Thr Pro Pro Ser Val
        115                 120                 125

<210> SEQ ID NO 200
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(378)

<400> SEQUENCE: 200 cag gtg cag ctg aag cag tca gga cct ggc cta gtg cag ccc tca cag        48
Gln Val Gln Leu Lys Gln Ser Gly Pro Gly Leu Val Gln Pro Ser Gln
1               5                   10                  15 agc ctg tcc atc acc tgc aca gtc tct ggt ttc tca tta tct aac tat        96
Ser Leu Ser Ile Thr Cys Thr Val Ser Gly Phe Ser Leu Ser Asn Tyr
            20                  25                  30 ggt gta cac tgg att cgc cag tct cca gga aag ggt ctg gag tgg ctg       144
Gly Val His Trp Ile Arg Gln Ser Pro Gly Lys Gly Leu Glu Trp Leu
        35                  40                  45 gga gtg ata tgg ggt ggt gga agc aca gac tat aat gca gct ttc ata       192
Gly Val Ile Trp Gly Gly Gly Ser Thr Asp Tyr Asn Ala Ala Phe Ile
50                  55                  60 tcc aga ctg agc atc agc aag gac aat tcc aag agc caa gtt ttc ttt       240
Ser Arg Leu Ser Ile Ser Lys Asp Asn Ser Lys Ser Gln Val Phe Phe
65                  70                  75                  80 aaa atg aac agt ctg caa gct gat gac aca gcc ata tat tac tgt gcc       288
Lys Met Asn Ser Leu Gln Ala Asp Asp Thr Ala Ile Tyr Tyr Cys Ala
                85                  90                  95 agc tat tat ggt tac tac gac tgg ttt gct tac tgg ggc caa ggg act       336
Ser Tyr Tyr Gly Tyr Tyr Asp Trp Phe Ala Tyr Trp Gly Gln Gly Thr
            100                 105                 110
```

```
ctg gtc act gtc tcc gca gcc aaa aca aca ccc cca tca gtc        378
Leu Val Thr Val Ser Ala Ala Lys Thr Thr Pro Pro Ser Val
        115                 120                 125

<210> SEQ ID NO 201
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(387)

<400> SEQUENCE: 201 gag gtc cag ctg cag cag tct ggg cct gaa ctg gtg aag cct gga gct        48
Glu Val Gln Leu Gln Gln Ser Gly Pro Glu Leu Val Lys Pro Gly Ala
1               5                   10                  15 tca gtg aag atg tcc tgc aag gct tct ggt tac tca ttc act ggc tac        96
Ser Val Lys Met Ser Cys Lys Ala Ser Gly Tyr Ser Phe Thr Gly Tyr
            20                  25                  30 aac atg cac tgg gtg aag cag agc cat gga aag agc ctt gag tgg att       144
Asn Met His Trp Val Lys Gln Ser His Gly Lys Ser Leu Glu Trp Ile
        35                  40                  45 ggg tat att gat cct tac aat ggt gct act agc aaa aat cag aaa ttc       192
Gly Tyr Ile Asp Pro Tyr Asn Gly Ala Thr Ser Lys Asn Gln Lys Phe
    50                  55                  60 aag ggc aag gcc aca ttg act gta gac aaa tct tcc acc aca gcc tac       240
Lys Gly Lys Ala Thr Leu Thr Val Asp Lys Ser Ser Thr Thr Ala Tyr
65                  70                  75                  80 ata caa ctc aac agc ctg aca tct gag gac tct gca gtc tat tac tgt       288
Ile Gln Leu Asn Ser Leu Thr Ser Glu Asp Ser Ala Val Tyr Tyr Cys
                85                  90                  95 gca aga tac tac tat ggt gac tac cac tgg tac ttc gat gtc tgg ggc       336
Ala Arg Tyr Tyr Tyr Gly Asp Tyr His Trp Tyr Phe Asp Val Trp Gly
            100                 105                 110 gca ggg acc acg gtc acc gtc tcc tca gcc aaa aca aca gcc cca tcg       384
Ala Gly Thr Thr Val Thr Val Ser Ser Ala Lys Thr Thr Ala Pro Ser
        115                 120                 125 gtc                                                                    387
Val

<210> SEQ ID NO 202
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(384)
<220> FEATURE:
<221> NAME/KEY: modified_base
<222> LOCATION: (6)..(6)
<223> OTHER INFORMATION: a, c, t or g

<400> SEQUENCE: 202 gag gtn vag ctg gag gag tct gga gga ggc ttg gta cag cct ggg ggt        48
Glu Val Xaa Leu Glu Glu Ser Gly Gly Gly Leu Val Gln Pro Gly Gly
1               5                   10                  15 tct ctg agt ctc tcc tgt gca act tct gga ttc ccc ttc agt gat tac        96
Ser Leu Ser Leu Ser Cys Ala Thr Ser Gly Phe Pro Phe Ser Asp Tyr
            20                  25                  30 tac atg acc tgg atc cgc cag cct cca ggg aag gca ctt gag tgg ttg       144
```

```
Tyr Met Thr Trp Ile Arg Gln Pro Pro Gly Lys Ala Leu Glu Trp Leu
         35                  40                  45 gct ttg att aga aac aaa gct aat ggt tac aca aca gag gat agt cca      192
Ala Leu Ile Arg Asn Lys Ala Asn Gly Tyr Thr Thr Glu Asp Ser Pro
 50                  55                  60 tct gtg aag ggt cgc ttt att atc tcc aga gat gat tcc caa cgc atc      240
Ser Val Lys Gly Arg Phe Ile Ile Ser Arg Asp Asp Ser Gln Arg Ile
65                  70                  75                  80 ctc tat ctt caa atg aat gcc ctg aga gat gag gac agt gcc act tat      288
Leu Tyr Leu Gln Met Asn Ala Leu Arg Asp Glu Asp Ser Ala Thr Tyr
                 85                  90                  95 tac tgt gca aca gtg gga ggt tac tac agg ttt cct tcc tgg ggc caa      336
Tyr Cys Ala Thr Val Gly Gly Tyr Tyr Arg Phe Pro Ser Trp Gly Gln
            100                 105                 110 ggg act ctg gtc act gtc tct gca gcc aaa acg aca ccc cca tct gtc      384
Gly Thr Leu Val Thr Val Ser Ala Ala Lys Thr Thr Pro Pro Ser Val
        115                 120                 125

<210> SEQ ID NO 203
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(381)
<220> FEATURE:
<221> NAME/KEY: modified_base
<222> LOCATION: (6)..(6)
<223> OTHER INFORMATION: a, c, t or g

<400> SEQUENCE: 203 gag gtn vag ctg gag gag tct ggg gga ggc tta gtg aag cct gga ggg       48
Glu Val Xaa Leu Glu Glu Ser Gly Gly Gly Leu Val Lys Pro Gly Gly
1               5                   10                  15 tcc cgg aaa ctc tcc tgt gca gcc tct gga ttc act ttc agt gac tat       96
Ser Arg Lys Leu Ser Cys Ala Ala Ser Gly Phe Thr Phe Ser Asp Tyr
            20                  25                  30 gga atg cac tgg gtc cgt cag gcc cca gag aag ggg ctg gag tgg gtt      144
Gly Met His Trp Val Arg Gln Ala Pro Glu Lys Gly Leu Glu Trp Val
         35                  40                  45 gca tac att agt agt ggc agt agt acc atc tac tat gca gac aca gtg      192
Ala Tyr Ile Ser Ser Gly Ser Ser Thr Ile Tyr Tyr Ala Asp Thr Val
 50                  55                  60 aag ggc cga ttc acc atc tcc aga gac aat gcc aag aac acc ctg ttc      240
Lys Gly Arg Phe Thr Ile Ser Arg Asp Asn Ala Lys Asn Thr Leu Phe
65                  70                  75                  80 ctg caa atg acc agt cta agg tct gag gac aca gcc atg tat tac tgt      288
Leu Gln Met Thr Ser Leu Arg Ser Glu Asp Thr Ala Met Tyr Tyr Cys
                 85                  90                  95 gca agg agg gag tta cta cga tat tat ttt gag tac tgg ggc caa ggc      336
Ala Arg Arg Glu Leu Leu Arg Tyr Tyr Phe Glu Tyr Trp Gly Gln Gly
            100                 105                 110 acc act ctc aca gtc tcc tca gcc aaa acg aca ccc cca tct gtc          381
Thr Thr Leu Thr Val Ser Ser Ala Lys Thr Thr Pro Pro Ser Val
        115                 120                 125

<210> SEQ ID NO 204
<211> LENGTH: 381
<212> TYPE: DNA
<213> ORGANISM: Artificial Sequence
<220> FEATURE:
<223> OTHER INFORMATION: Description of Artificial Sequence: Synthetic
```

-continued

```
        polynucleotide
<220> FEATURE:
<221> NAME/KEY: CDS
<222> LOCATION: (1)..(381)
<220> FEATURE:
<221> NAME/KEY: modified_base
<222> LOCATION: (6)..(6)
<223> OTHER INFORMATION: a, c, t or g

<400> SEQUENCE: 204 gag gtn cag ctg sar vag tct gga gct gag ctg gta agg cct ggg acc      48
Glu Val Gln Leu Xaa Xaa Ser Gly Ala Glu Leu Val Arg Pro Gly Thr
1               5                   10                  15 tca gtg aag atg tcc tgc agg gct gct gga tac acc ttc act aac tac      96
Ser Val Lys Met Ser Cys Arg Ala Ala Gly Tyr Thr Phe Thr Asn Tyr
            20                  25                  30 tgg ata ggc tgg gta aag caa agg cct gga cat ggc ctt gag tgg att     144
Trp Ile Gly Trp Val Lys Gln Arg Pro Gly His Gly Leu Glu Trp Ile
        35                  40                  45 gga gat att tac cct ggt ggt ctt tat act aat tac aat gag aag ttc     192
Gly Asp Ile Tyr Pro Gly Gly Leu Tyr Thr Asn Tyr Asn Glu Lys Phe
    50                  55                  60 aag gac aag gcc aca ctg act gca gac aca tcc tcc agt aca gcc tat     240
Lys Asp Lys Ala Thr Leu Thr Ala Asp Thr Ser Ser Ser Thr Ala Tyr
65                  70                  75                  80 atg cag ctc agc agc ctg aca tct gag gac tct gcc atc tat tac tgt     288
Met Gln Leu Ser Ser Leu Thr Ser Glu Asp Ser Ala Ile Tyr Tyr Cys
                85                  90                  95 cat ttc tac gat ggt gac cag tat gct atg gac tac tgg ggt caa gga     336
His Phe Tyr Asp Gly Asp Gln Tyr Ala Met Asp Tyr Trp Gly Gln Gly
            100                 105                 110 acc tca gtc acc gtc tcc tca gcc aaa acg aca ccc cca tct gtc         381
Thr Ser Val Thr Val Ser Ser Ala Lys Thr Thr Pro Pro Ser Val
        115                 120                 125

<210> SEQ ID NO 205
<211> LENGTH: 387
<212> TYPE: DNA
<213> ORGANISM: Artificial Sequence
<220> FEATURE:
<223> OTHER INFORMATION: Description of Artificial Sequence: Synthetic
        polynucleotide
<220> FEATURE:
<221> NAME/KEY: CDS
<222> LOCATION: (1)..(387)
<220> FEATURE:
<221> NAME/KEY: modified_base
<222> LOCATION: (6)..(6)
<223> OTHER INFORMATION: a, c, t or g
<220> FEATURE:
<221> NAME/KEY: modified_base
<222> LOCATION: (13)..(13)
<223> OTHER INFORMATION: a, c, t or g
<220> FEATURE:
<221> NAME/KEY: modified_base
<222> LOCATION: (15)..(15)
<223> OTHER INFORMATION: a, c, t or g

<400> SEQUENCE: 205 gag gtn cag ctg nan vag tct gga gct gag ctg gtg aag cct ggg gct      48
Glu Val Gln Leu Xaa Xaa Ser Gly Ala Glu Leu Val Lys Pro Gly Ala
1               5                   10                  15 tca gtg aag ata tcc tgc aag gcc tct ggt tat tca ttc act ggc tac      96
Ser Val Lys Ile Ser Cys Lys Ala Ser Gly Tyr Ser Phe Thr Gly Tyr
            20                  25                  30 aac atg aac tgg atg aag cag agt cat gga aag agc ctt gag tgg att     144
Asn Met Asn Trp Met Lys Gln Ser His Gly Lys Ser Leu Glu Trp Ile
        35                  40                  45
```

```
gga aat att aat cct tac tat ggt agt act aac tat aat cag aag ttc       192
Gly Asn Ile Asn Pro Tyr Tyr Gly Ser Thr Asn Tyr Asn Gln Lys Phe
 50                  55                  60 aag ggc aag gcc aca ttg act gtg gac aaa tct tcc agc aca gcc tac       240
Lys Gly Lys Ala Thr Leu Thr Val Asp Lys Ser Ser Ser Thr Ala Tyr
 65                  70                  75                  80 atg cag ctc aac agc ctg aca tct gag gac tct gca gtc tat tac tgt       288
Met Gln Leu Asn Ser Leu Thr Ser Glu Asp Ser Ala Val Tyr Tyr Cys
                 85                  90                  95 gca aga ggg ggc gtt agg gaa cta cca ggc tgg ttt act tac tgg ggc       336
Ala Arg Gly Gly Val Arg Glu Leu Pro Gly Trp Phe Thr Tyr Trp Gly
             100                 105                 110 caa ggg act ctg gtc act gtc tct gca gcc aaa acg aca ccc cca tct       384
Gln Gly Thr Leu Val Thr Val Ser Ala Ala Lys Thr Thr Pro Pro Ser
         115                 120                 125 gtc                                                                   387
Val

<210> SEQ ID NO 206
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(387)
<220> FEATURE:
<221> NAME/KEY: modified_base
<222> LOCATION: (6)..(6)
<223> OTHER INFORMATION: a, c, t or g

<400> SEQUENCE: 206 gag gtn cag ctg sar vag tct gga gct gag ctg gtg aag cct ggg gct        48
Glu Val Gln Leu Xaa Xaa Ser Gly Ala Glu Leu Val Lys Pro Gly Ala
  1               5                  10                  15 tca gtg aag ata tcc tgc aag gcc tct ggt tat tca ttc act ggc tac        96
Ser Val Lys Ile Ser Cys Lys Ala Ser Gly Tyr Ser Phe Thr Gly Tyr
                 20                  25                  30 aac atg aac tgg atg aag cag agt cat gga aag agc ctt gag tgg att       144
Asn Met Asn Trp Met Lys Gln Ser His Gly Lys Ser Leu Glu Trp Ile
             35                  40                  45 gga aat att aat cct tac tat ggt agt act aac tat aat cag aag ttc       192
Gly Asn Ile Asn Pro Tyr Tyr Gly Ser Thr Asn Tyr Asn Gln Lys Phe
 50                  55                  60 aag ggc aag gcc aca ttg act gtg gac aaa tct tcc agc aca gcc tac       240
Lys Gly Lys Ala Thr Leu Thr Val Asp Lys Ser Ser Ser Thr Ala Tyr
 65                  70                  75                  80 atg cag ctc aac agc ctg aca tct gag gac tct gca gtc tat tac tgt       288
Met Gln Leu Asn Ser Leu Thr Ser Glu Asp Ser Ala Val Tyr Tyr Cys
                 85                  90                  95 gca aga ggg ggc gtt agg gaa cta cca ggc tgg ttt act tac tgg ggc       336
Ala Arg Gly Gly Val Arg Glu Leu Pro Gly Trp Phe Thr Tyr Trp Gly
             100                 105                 110 caa ggg act ctg gtc act gtc tct gca gcc aaa acg aca ccc cca tct       384
Gln Gly Thr Leu Val Thr Val Ser Ala Ala Lys Thr Thr Pro Pro Ser
         115                 120                 125 gtc                                                                   387
Val

<210> SEQ ID NO 207
<211> LENGTH: 387
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(387)
<220> FEATURE:
<221> NAME/KEY: modified_base
<222> LOCATION: (6)..(6)
<223> OTHER INFORMATION: a, c, t or g
<220> FEATURE:
<221> NAME/KEY: modified_base
<222> LOCATION: (13)..(13)
<223> OTHER INFORMATION: a, c, t or g
<220> FEATURE:
<221> NAME/KEY: modified_base
<222> LOCATION: (15)..(15)
<223> OTHER INFORMATION: a, c, t or g

<400> SEQUENCE: 207 gag gtn cag ctg nan vag tct gga cct gag ctg gta aag cct ggg gct        48
Glu Val Gln Leu Xaa Xaa Ser Gly Pro Glu Leu Val Lys Pro Gly Ala
1               5                   10                  15 tca gtg aag atg tcc tgc aag gct tct gga ccc gca ttc act acc tat        96
Ser Val Lys Met Ser Cys Lys Ala Ser Gly Pro Ala Phe Thr Thr Tyr
                20                  25                  30 gtt ata cac tgg gtg aag cag aag cct ggg cag ggc ctt gag tgg att       144
Val Ile His Trp Val Lys Gln Lys Pro Gly Gln Gly Leu Glu Trp Ile
            35                  40                  45 gga tat att aat cct tac aat gat tat act aag tac gat gag aag ttc       192
Gly Tyr Ile Asn Pro Tyr Asn Asp Tyr Thr Lys Tyr Asp Glu Lys Phe
        50                  55                  60 aga ggc aag gcc aca ctg act tca gac aaa tct tcc agc aca gcc tac       240
Arg Gly Lys Ala Thr Leu Thr Ser Asp Lys Ser Ser Ser Thr Ala Tyr
65                  70                  75                  80 atg gag ctc agg agc ctg acc tct gag gac tct gcg gtc tat tac tgt       288
Met Glu Leu Arg Ser Leu Thr Ser Glu Asp Ser Ala Val Tyr Tyr Cys
                85                  90                  95 gca agc aaa gct gcc tac tac gtg ggg aat gct atg gac tca tgg ggt       336
Ala Ser Lys Ala Ala Tyr Tyr Val Gly Asn Ala Met Asp Ser Trp Gly
                100                 105                 110 caa ggc acc tca atc acc gtc tcc tca gcc aaa acg aca ccc cca tct       384
Gln Gly Thr Ser Ile Thr Val Ser Ser Ala Lys Thr Thr Pro Pro Ser
            115                 120                 125 gtc                                                                   387
Val

<210> SEQ ID NO 208
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(387)
<220> FEATURE:
<221> NAME/KEY: modified_base
<222> LOCATION: (6)..(6)
<223> OTHER INFORMATION: a, c, t or g

<400> SEQUENCE: 208 gag gtn cag ctg vag vag tct ggg cct gag ctg gtg aag cct gga gct        48
Glu Val Gln Leu Xaa Xaa Ser Gly Pro Glu Leu Val Lys Pro Gly Ala
1               5                   10                  15
```

-continued

```
tca gtg aag atg tcc tgc aag gct tct ggt tac tca ttc act ggc tac        96
Ser Val Lys Met Ser Cys Lys Ala Ser Gly Tyr Ser Phe Thr Gly Tyr
         20                  25                  30 aac atg cac tgg gtg aag cag agc cat gga aag agc ctt gag tgg att       144
Asn Met His Trp Val Lys Gln Ser His Gly Lys Ser Leu Glu Trp Ile
     35                  40                  45 ggg tat att gat cct tac aat ggt gct acc agc aac aac cag aga ttc       192
Gly Tyr Ile Asp Pro Tyr Asn Gly Ala Thr Ser Asn Asn Gln Arg Phe
 50                  55                  60 aag ggc aag gcc aca ttg act gca gac aaa tct tcc agc aca gcc tac       240
Lys Gly Lys Ala Thr Leu Thr Ala Asp Lys Ser Ser Ser Thr Ala Tyr
65                  70                  75                  80 ata cag ctc aac agc ctg aca tct gag gac tct gca ttc tat tac tgt       288
Ile Gln Leu Asn Ser Leu Thr Ser Glu Asp Ser Ala Phe Tyr Tyr Cys
                 85                  90                  95 gta aga tac tac tat ggt gac tac cac tgg tac ttc gat gtc tgg ggc       336
Val Arg Tyr Tyr Tyr Gly Asp Tyr His Trp Tyr Phe Asp Val Trp Gly
            100                 105                 110 gca ggg acc acg gtc acc gtc tcc tca gcc aaa acg aca ccc cca tct       384
Ala Gly Thr Thr Val Thr Val Ser Ser Ala Lys Thr Thr Pro Pro Ser
        115                 120                 125 gtc                                                                   387
Val
```

<210> SEQ ID NO 209
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(369)
<220> FEATURE:
<221> NAME/KEY: modified_base
<222> LOCATION: (6)..(6)
<223> OTHER INFORMATION: a, c, t or g
<220> FEATURE:
<221> NAME/KEY: modified_base
<222> LOCATION: (357)..(357)
<223> OTHER INFORMATION: a, c, t or g

<400> SEQUENCE: 209

```
gag gtn cag ctg gag gag tct gga cct gag ctg gtg aag cct ggg gct        48
Glu Val Gln Leu Glu Glu Ser Gly Pro Glu Leu Val Lys Pro Gly Ala
1               5                   10                  15 tca gtg agg ata tcc tgc aag gct tct ggt tac tca ttc acc gac tac        96
Ser Val Arg Ile Ser Cys Lys Ala Ser Gly Tyr Ser Phe Thr Asp Tyr
             20                  25                  30 tgg atg cac tgg gtg aaa caa ggt cct gaa aag agc ctt gag tgg att       144
Trp Met His Trp Val Lys Gln Gly Pro Glu Lys Ser Leu Glu Trp Ile
         35                  40                  45 gga gag att aat cct agc act ggt ggt atc ata tac aac cag aag ttc       192
Gly Glu Ile Asn Pro Ser Thr Gly Gly Ile Ile Tyr Asn Gln Lys Phe
     50                  55                  60 gag gcc aag gcc aca ttg act gta gac ata tcc agc aca acc tac           240
Glu Ala Lys Ala Thr Leu Thr Val Asp Ile Ser Ser Thr Thr Tyr
65                  70                  75                  80 atg cag ctc aag agc ctg aca tct gag gac tct gca gtc tac tat tgt       288
Met Gln Leu Lys Ser Leu Thr Ser Glu Asp Ser Ala Val Tyr Tyr Cys
                 85                  90                  95 aca aga tcg gga ggc ttt cct tac tgg ggc cag ggg act ctg gtc act       336
Thr Arg Ser Gly Gly Phe Pro Tyr Trp Gly Gln Gly Thr Leu Val Thr
            100                 105                 110
```

```
gtc tct gca gcc aaa acg acn ccc cca tct gtc                           369
Val Ser Ala Ala Lys Thr Thr Pro Pro Ser Val
        115                 120

<210> SEQ ID NO 210
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(372)
<220> FEATURE:
<221> NAME/KEY: modified_base
<222> LOCATION: (6)..(6)
<223> OTHER INFORMATION: a, c, t or g

<400> SEQUENCE: 210 vag gtn cag ctg vag vag tct gga gct gag ctg gta agg cct ggg act        48
Xaa Val Gln Leu Xaa Xaa Ser Gly Ala Glu Leu Val Arg Pro Gly Thr
1               5                   10                  15 tca gtg aag atg tcc tgc aag gct gct gga tac acc ttc act aac tac        96
Ser Val Lys Met Ser Cys Lys Ala Ala Gly Tyr Thr Phe Thr Asn Tyr
                20                  25                  30 tgg ata ggt tgg gta aag cag agg cct gga cat ggc ctt gag tgg att       144
Trp Ile Gly Trp Val Lys Gln Arg Pro Gly His Gly Leu Glu Trp Ile
            35                  40                  45 gga aat att tac cct gga ggt ggt tat act aat tac aat gag aag ttc       192
Gly Asn Ile Tyr Pro Gly Gly Gly Tyr Thr Asn Tyr Asn Glu Lys Phe
        50                  55                  60 aag ggc aag gcc aca ctg act gca gac aca tcc tcc agc aca gcc tac       240
Lys Gly Lys Ala Thr Leu Thr Ala Asp Thr Ser Ser Ser Thr Ala Tyr
65                  70                  75                  80 atg cag ctc agc agc ctg aca tct gag gac tct gcc atc tat tac tgt       288
Met Gln Leu Ser Ser Leu Thr Ser Glu Asp Ser Ala Ile Tyr Tyr Cys
                85                  90                  95 gca aga agg agg ggg tac ttc gat gtc tgg ggc gca ggg acc acg gtc       336
Ala Arg Arg Arg Gly Tyr Phe Asp Val Trp Gly Ala Gly Thr Thr Val
            100                 105                 110 acc gtc tcc tca gcc aaa acg aca ccc cca tct gtc                       372
Thr Val Ser Ser Ala Lys Thr Thr Pro Pro Ser Val
        115                 120

<210> SEQ ID NO 211
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 211 gat atc cag atg aca cag act aca tcc tcc ctg tct gcc tct ctg gga        48
Asp Ile Gln Met Thr Gln Thr Thr Ser Ser Leu Ser Ala Ser Leu Gly
1               5                   10                  15 gac aga gtc acc atc agt tgc agg gca agt cag gac att ggc aat cat        96
Asp Arg Val Thr Ile Ser Cys Arg Ala Ser Gln Asp Ile Gly Asn His
                20                  25                  30 tta aac tgg tat cag cag aaa cca gat gga act gtt aaa ctc ctg atc       144
Leu Asn Trp Tyr Gln Gln Lys Pro Asp Gly Thr Val Lys Leu Leu Ile
            35                  40                  45
```

```
tac tac aca tca aga ata cac tct gga gtc cca tca agg ttc agt ggc      192
Tyr Tyr Thr Ser Arg Ile His Ser Gly Val Pro Ser Arg Phe Ser Gly
     50                  55                  60 agt ggg tct gga aca gat tat tct ctc acc att agt aac ctg gaa caa      240
Ser Gly Ser Gly Thr Asp Tyr Ser Leu Thr Ile Ser Asn Leu Glu Gln
 65                  70                  75                  80 gaa gat att gcc act tac ttt tgc caa cag ggt aat acg ctt ccg tgg      288
Glu Asp Ile Ala Thr Tyr Phe Cys Gln Gln Gly Asn Thr Leu Pro Trp
                 85                  90                  95 acg ttc ggt gga ggc acc aag ctg gag atc aaa cgg gct gat gct gca      336
Thr Phe Gly Gly Gly Thr Lys Leu Glu Ile Lys Arg Ala Asp Ala Ala
            100                 105                 110 cca                                                                   339
Pro

<210> SEQ ID NO 212
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(354)

<400> SEQUENCE: 212 gat gtt ttg atg acc caa act cca ctc tcc ctg cct gtc agt ctt gga       48
Asp Val Leu Met Thr Gln Thr Pro Leu Ser Leu Pro Val Ser Leu Gly
 1               5                  10                  15 gat caa gcc tcc atc tct tgt aga tct agt cag aac att gta caa agt       96
Asp Gln Ala Ser Ile Ser Cys Arg Ser Ser Gln Asn Ile Val Gln Ser
             20                  25                  30 aat gga aac acc tat tta gaa tgg tac ctg cag aaa cca ggc cag tct      144
Asn Gly Asn Thr Tyr Leu Glu Trp Tyr Leu Gln Lys Pro Gly Gln Ser
         35                  40                  45 cca aaa ctc ctg atc tac aaa gtt tcc aac cga ttt tct ggg gtc cca      192
Pro Lys Leu Leu Ile Tyr Lys Val Ser Asn Arg Phe Ser Gly Val Pro
     50                  55                  60 gac agg ttc agt ggc agt gga tca ggg aca gat ttc aca ctc aag atc      240
Asp Arg Phe Ser Gly Ser Gly Ser Gly Thr Asp Phe Thr Leu Lys Ile
 65                  70                  75                  80 agc aga gtg gag gct gac gat ctg gga gtt tat tac tgc ttt caa gtt      288
Ser Arg Val Glu Ala Asp Asp Leu Gly Val Tyr Tyr Cys Phe Gln Val
                 85                  90                  95 tca cat gtt ccg tac acg ttc gga ggg ggg acc aag ctg gaa ata aaa      336
Ser His Val Pro Tyr Thr Phe Gly Gly Gly Thr Lys Leu Glu Ile Lys
            100                 105                 110 cgg gct gat gct gca cca                                              354
Arg Ala Asp Ala Ala Pro
            115

<210> SEQ ID NO 213
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 213
```

-continued

| | | |
|---|---|---|
| gat atc cag atg aca cag agt aca tcc tcc ctg tct gcc tct ctg gga<br>Asp Ile Gln Met Thr Gln Ser Thr Ser Ser Leu Ser Ala Ser Leu Gly<br>1               5                   10                  15 | | 48 |
| gac aga gtc acc atc agt tgc agg gca agt cag gac att agc aat aac<br>Asp Arg Val Thr Ile Ser Cys Arg Ala Ser Gln Asp Ile Ser Asn Asn<br>            20                  25                  30 | | 96 |
| tta aac tgg tat caa cag aga cca gat gga act gtt aaa ctc ctg atc<br>Leu Asn Trp Tyr Gln Gln Arg Pro Asp Gly Thr Val Lys Leu Leu Ile<br>        35                  40                  45 | | 144 |
| tac tac aca tca aga tca cag tcc gga gtc cca tca agg ttc agt ggc<br>Tyr Tyr Thr Ser Arg Ser Gln Ser Gly Val Pro Ser Arg Phe Ser Gly<br>    50                  55                  60 | | 192 |
| agt ggg tct gga aca gat tat tct ctc acc att agc aac ctg gag caa<br>Ser Gly Ser Gly Thr Asp Tyr Ser Leu Thr Ile Ser Asn Leu Glu Gln<br>65                  70                  75                  80 | | 240 |
| gaa gat gtt gcc act tac ttt tgc cat cag ggt aaa acg ctt ccg tac<br>Glu Asp Val Ala Thr Tyr Phe Cys His Gln Gly Lys Thr Leu Pro Tyr<br>                85                  90                  95 | | 288 |
| acg ttc gga ggg ggg acc aag ctg gaa ata aag cgg gct gat gct gca<br>Thr Phe Gly Gly Gly Thr Lys Leu Glu Ile Lys Arg Ala Asp Ala Ala<br>            100                 105                 110 | | 336 |
| cca<br>Pro | | 339 |

<210> SEQ ID NO 214
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(342)

<400> SEQUENCE: 214

| | | |
|---|---|---|
| gaa att gtg ctc acc cag tct cca acc acc atg gct gca tct ccc ggg<br>Glu Ile Val Leu Thr Gln Ser Pro Thr Thr Met Ala Ala Ser Pro Gly<br>1               5                   10                  15 | | 48 |
| gag aag atc act atc acc tgc agt gcc agc tca att ata agt tct aat<br>Glu Lys Ile Thr Ile Thr Cys Ser Ala Ser Ser Ile Ile Ser Ser Asn<br>            20                  25                  30 | | 96 |
| tac ttg cat tgg tat cag cag aag cca gga ttc tcc cct aaa ccc ttg<br>Tyr Leu His Trp Tyr Gln Gln Lys Pro Gly Phe Ser Pro Lys Pro Leu<br>        35                  40                  45 | | 144 |
| att tat agg aca tcc aat ctg gct tct gga gtc cca gct cgc ttc agt<br>Ile Tyr Arg Thr Ser Asn Leu Ala Ser Gly Val Pro Ala Arg Phe Ser<br>    50                  55                  60 | | 192 |
| ggt agt ggg tct ggg acc tct tac tct ctc aca att ggc acc atg gag<br>Gly Ser Gly Ser Gly Thr Ser Tyr Ser Leu Thr Ile Gly Thr Met Glu<br>65                  70                  75                  80 | | 240 |
| gct gaa gat gtt gcc act tac tac tgc cag cag ggt agt agt ata cca<br>Ala Glu Asp Val Ala Thr Tyr Tyr Cys Gln Gln Gly Ser Ser Ile Pro<br>                85                  90                  95 | | 288 |
| cgc acg ttc ggc tcg ggg aca aag ttg gaa ata aaa cgg gct gat gct<br>Arg Thr Phe Gly Ser Gly Thr Lys Leu Glu Ile Lys Arg Ala Asp Ala<br>            100                 105                 110 | | 336 |
| gca cca<br>Ala Pro | | 342 |

<210> SEQ ID NO 215
<211> LENGTH: 354
<212> TYPE: DNA

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(354)

<400> SEQUENCE: 215 gat gtt gtg atg acc caa act cca ctc tcc ctg cct gtc agt ctt gga       48
Asp Val Val Met Thr Gln Thr Pro Leu Ser Leu Pro Val Ser Leu Gly
1               5                   10                  15 gat cag gcc tcc atc tct tgc aga tct agt cag agc ctt gta cac agt       96
Asp Gln Ala Ser Ile Ser Cys Arg Ser Ser Gln Ser Leu Val His Ser
            20                  25                  30 aat gga aac acc tat tta cat tgg tac ctg cag cag cca ggc cag tct      144
Asn Gly Asn Thr Tyr Leu His Trp Tyr Leu Gln Gln Pro Gly Gln Ser
        35                  40                  45 cca aag ctc ctg atc tac aaa gtt tcc aac cga ttt tct ggg gtc cca      192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc      240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa cat      288
Ser Arg Val Glu Ala Glu Asp Leu Gly Val Tyr Phe Cys Ser Gln His
                85                  90                  95 aca cat gtt cct cct acg ttc ggt gct ggg acc aag ctg gag ctg aaa      336
Thr His Val Pro Pro Thr Phe Gly Ala Gly Thr Lys Leu Glu Leu Lys
            100                 105                 110 cgg gct gat gct gca cca                                              354
Arg Ala Asp Ala Ala Pro
        115

<210> SEQ ID NO 216
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(342)

<400> SEQUENCE: 216 gat att gtg mtg acc cag tct cca gca atc atg tct gca tct cca ggg       48
Asp Ile Val Xaa Thr Gln Ser Pro Ala Ile Met Ser Ala Ser Pro Gly
1               5                   10                  15 gaa aag gtc acc atg acc tgc agg gcc agc tca agt gta agt tcc agt       96
Glu Lys Val Thr Met Thr Cys Arg Ala Ser Ser Ser Val Ser Ser Ser
            20                  25                  30 tac ttg cac tgg tac cag cag aag tca ggt gtc tcc ccc aaa ctc tgg      144
Tyr Leu His Trp Tyr Gln Gln Lys Ser Gly Val Ser Pro Lys Leu Trp
        35                  40                  45 att tat agc aca tcc aac ttg gct tct gga gtc cct gtt cgc ttc agt      192
Ile Tyr Ser Thr Ser Asn Leu Ala Ser Gly Val Pro Val Arg Phe Ser
    50                  55                  60 ggc agt ggg tct ggg acc tct tac tct ctc aca gtc agt agt gtg gag      240
Gly Ser Gly Ser Gly Thr Ser Tyr Ser Leu Thr Val Ser Ser Val Glu
65                  70                  75                  80 gct gaa gat gct gcc act tat tac tgc cag cag tac agt gat tac cca      288
Ala Glu Asp Ala Ala Thr Tyr Tyr Cys Gln Gln Tyr Ser Asp Tyr Pro
                85                  90                  95
```

```
ctc acg ttc gga ggg ggg acc aag ctg gaa ata aaa cgg gct gat gct      336
Leu Thr Phe Gly Gly Gly Thr Lys Leu Glu Ile Lys Arg Ala Asp Ala
                100                 105                 110 gca cca                                                              342
Ala Pro <210> SEQ ID NO 217
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 217 gat att gtg vtg acc cag tct cca tcc tcc ctg tct gcc tct ctg gga       48
Asp Ile Val Xaa Thr Gln Ser Pro Ser Ser Leu Ser Ala Ser Leu Gly
1               5                   10                  15 gac aga gtc acc atc agt tgc agg gca agt cag gac att agc aat cat       96
Asp Arg Val Thr Ile Ser Cys Arg Ala Ser Gln Asp Ile Ser Asn His
                20                  25                  30 tta aac tgg tat cag cag aaa cca gat gga act gtt aaa ctc ctg atc      144
Leu Asn Trp Tyr Gln Gln Lys Pro Asp Gly Thr Val Lys Leu Leu Ile
            35                  40                  45 tac tac aca tca aga tta cac tca gga ctc cca tca agg ttc agt ggc      192
Tyr Tyr Thr Ser Arg Leu His Ser Gly Leu Pro Ser Arg Phe Ser Gly
        50                  55                  60 agt ggg tct gga aca gat tat tct ctc acc att agc aac ctg gag caa      240
Ser Gly Ser Gly Thr Asp Tyr Ser Leu Thr Ile Ser Asn Leu Glu Gln
65                  70                  75                  80 gaa gat att gcc act tac ttt tgc caa cag ggt aat acg ctt ccg tac      288
Glu Asp Ile Ala Thr Tyr Phe Cys Gln Gln Gly Asn Thr Leu Pro Tyr
                85                  90                  95 acg ttc gga ggg ggg acc aag ctg gaa ata aaa cgg gct gat gct gca      336
Thr Phe Gly Gly Gly Thr Lys Leu Glu Ile Lys Arg Ala Asp Ala Ala
                100                 105                 110 cca                                                                  339
Pro

<210> SEQ ID NO 218
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(354)
<220> FEATURE:
<221> NAME/KEY: modified_base
<222> LOCATION: (3)..(3)
<223> OTHER INFORMATION: a, c, t or g

<400> SEQUENCE: 218 gan att gtg vtg acc cag tct cca ctc tcc ctg cct gtc agt ctt gga       48
Xaa Ile Val Xaa Thr Gln Ser Pro Leu Ser Leu Pro Val Ser Leu Gly
1               5                   10                  15 gat caa gcc tcc atc tct tgc aga tct agt cag agc att gta cat agt       96
Asp Gln Ala Ser Ile Ser Cys Arg Ser Ser Gln Ser Ile Val His Ser
                20                  25                  30 aat gga aac acc ttt tta gaa tgg tac ctg cag aaa cca ggc cag tct      144
Asn Gly Asn Thr Phe Leu Glu Trp Tyr Leu Gln Lys Pro Gly Gln Ser
```

```
cca aac ctc ctg atc tac aga gtt tcc aac cga ttt tct ggg gtc cca        192
Pro Asn Leu Leu Ile Tyr Arg Val Ser Asn Arg Phe Ser Gly Val Pro
        50                  55                  60 gac agg ttc agt ggc agt gga tca ggg aca gat ttc aca ctc aag atc        240
Asp Arg Phe Ser Gly Ser Gly Ser Gly Thr Asp Phe Thr Leu Lys Ile
65                  70                  75                  80 agc aga gtg gag gct gag gat ctg gga gtt tat tac tgc ttt caa ggt        288
Ser Arg Val Glu Ala Glu Asp Leu Gly Val Tyr Tyr Cys Phe Gln Gly
                85                  90                  95 tca cat gtt cca ttc acg ttc ggc tcg ggg aca aag ttg gaa ata aaa        336
Ser His Val Pro Phe Thr Phe Gly Ser Gly Thr Lys Leu Glu Ile Lys
            100                 105                 110 cgg gct gat gct gca cca                                                354
Arg Ala Asp Ala Ala Pro
            115

<210> SEQ ID NO 219
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)
<220> FEATURE:
<221> NAME/KEY: modified_base
<222> LOCATION: (19)..(19)
<223> OTHER INFORMATION: a, c, t or g

<400> SEQUENCE: 219 gat att gtg vtg acc cag nct cca gca atc atg tct gca tct cca ggg        48
Asp Ile Val Xaa Thr Gln Xaa Pro Ala Ile Met Ser Ala Ser Pro Gly
1               5                   10                  15 gag aag gtc acc atg acc tgc agt gcc agc tca agt gta agt tac atg        96
Glu Lys Val Thr Met Thr Cys Ser Ala Ser Ser Ser Val Ser Tyr Met
            20                  25                  30 tac tgg tac cag cag aag cca gga tcc tcc ccc aga ctc ctg att tat       144
Tyr Trp Tyr Gln Gln Lys Pro Gly Ser Ser Pro Arg Leu Leu Ile Tyr
        35                  40                  45 gac aca tcc aac ctg gct tct gga gtc cct gtt cgc ttc agt ggc agt       192
Asp Thr Ser Asn Leu Ala Ser Gly Val Pro Val Arg Phe Ser Gly Ser
    50                  55                  60 ggg tct ggg gcc tct tac tct ctc aca atc agc cga atg gag gct gaa       240
Gly Ser Gly Ala Ser Tyr Ser Leu Thr Ile Ser Arg Met Glu Ala Glu
65                  70                  75                  80 gat gct gcc act tat tac tgc cag cag tgg agt agt tac ccg ctc acg       288
Asp Ala Ala Thr Tyr Tyr Cys Gln Gln Trp Ser Ser Tyr Pro Leu Thr
                85                  90                  95 ttc ggt gct ggg acc aag ctg gag ctg aaa cgg gct gat gct gca cca       336
Phe Gly Ala Gly Thr Lys Leu Glu Leu Lys Arg Ala Asp Ala Ala Pro
            100                 105                 110

<210> SEQ ID NO 220
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)
```

-continued

<400> SEQUENCE: 220

```
gay att gtg vtg acc cag tct cca ccc tcc ctg tct gcc tct ctg gga        48
Asp Ile Val Xaa Thr Gln Ser Pro Pro Ser Leu Ser Ala Ser Leu Gly
1               5                   10                  15 gac aga gtc acc atc agt tgc agt gca agt cag ggc att agc aat tat        96
Asp Arg Val Thr Ile Ser Cys Ser Ala Ser Gln Gly Ile Ser Asn Tyr
            20                  25                  30 tta aac tgg tat cag cag aaa gca gat gga act gtt gaa ctc ctg atc       144
Leu Asn Trp Tyr Gln Gln Lys Ala Asp Gly Thr Val Glu Leu Leu Ile
        35                  40                  45 tat tcc aca tca agt tta cac tca gga gtc cca tca agg ttc agt ggc       192
Tyr Ser Thr Ser Ser Leu His Ser Gly Val Pro Ser Arg Phe Ser Gly
    50                  55                  60 agt ggg tct ggg aca gat tat tct ctc acc atc agc aac ctg gaa cct       240
Ser Gly Ser Gly Thr Asp Tyr Ser Leu Thr Ile Ser Asn Leu Glu Pro
65                  70                  75                  80 gaa gat att gcc act tac tat tgt cag cag tat agt aag ctt cct ccg       288
Glu Asp Ile Ala Thr Tyr Tyr Cys Gln Gln Tyr Ser Lys Leu Pro Pro
                85                  90                  95 acg ttc ggt gga ggc acc aag ctg gaa atc aaa cgg gct gat gct gca       336
Thr Phe Gly Gly Gly Thr Lys Leu Glu Ile Lys Arg Ala Asp Ala Ala
            100                 105                 110 cca                                                                    339
Pro
```

<210> SEQ ID NO 221
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 221

```
gat att gtg vtg acc cag tct cca gca tcc ctg tcc atg gct tta gga        48
Asp Ile Val Xaa Thr Gln Ser Pro Ala Ser Leu Ser Met Ala Leu Gly
1               5                   10                  15 gag aaa gtc acc atc aga tgc ata acc agc act aat att gat gat gat        96
Glu Lys Val Thr Ile Arg Cys Ile Thr Ser Thr Asn Ile Asp Asp Asp
            20                  25                  30 atg aac tgg tac cag cag aag cca ggg gaa cct cct aaa ctc ctt att       144
Met Asn Trp Tyr Gln Gln Lys Pro Gly Glu Pro Pro Lys Leu Leu Ile
        35                  40                  45 tca gaa ggc aat tct ctt cgt cct gga gtc ccg tcc cga ttc tcc agc       192
Ser Glu Gly Asn Ser Leu Arg Pro Gly Val Pro Ser Arg Phe Ser Ser
    50                  55                  60 agt ggc tat gac aca gat ttt gtt ttt aca att gag aac ata ctc tca       240
Ser Gly Tyr Asp Thr Asp Phe Val Phe Thr Ile Glu Asn Ile Leu Ser
65                  70                  75                  80 gag gat gtt gca gat tat tac tgt ttg caa agt gat aac gtg ccg ctc       288
Glu Asp Val Ala Asp Tyr Tyr Cys Leu Gln Ser Asp Asn Val Pro Leu
                85                  90                  95 acg ttc ggt act ggg acc aag ctg gta ctg aag cgg gct gat gct gca       336
Thr Phe Gly Thr Gly Thr Lys Leu Val Leu Lys Arg Ala Asp Ala Ala
            100                 105                 110 cca                                                                    339
Pro
```

<210> SEQ ID NO 222

```
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(354)

<400> SEQUENCE: 222 gat att gtg vtg acc cag tct cca ctc tcc ctg cct gtc agt ctt gga       48
Asp Ile Val Xaa Thr Gln Ser Pro Leu Ser Leu Pro Val Ser Leu Gly
1               5                   10                  15 gat caa gcc tcc atc tct tgc aga tct agt cag agc ctt gta cac agt       96
Asp Gln Ala Ser Ile Ser Cys Arg Ser Ser Gln Ser Leu Val His Ser
            20                  25                  30 aat gga aac acc tat tta cat tgg tac ctg cag aag cca ggc cag tct      144
Asn Gly Asn Thr Tyr Leu His Trp Tyr Leu Gln Lys Pro Gly Gln Ser
        35                  40                  45 cca aac ctc ctg atc tac aaa gtt tcc aac cga ttt tct ggg gtc cca      192
Pro Asn Leu Leu Ile Tyr Lys Val Ser Asn Arg Phe Ser Gly Val Pro
    50                  55                  60 gac agg ttc agt ggc agt gga tca ggg aca gat ttc aca ctc aag atc      240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa aat      288
Ser Arg Val Glu Ala Glu Asp Leu Gly Val Tyr Phe Cys Ser Gln Asn
                85                  90                  95 aca cat gtt cct cct acg ttc ggt gct ggg acc aag ctg gag ctg aaa      336
Thr His Val Pro Pro Thr Phe Gly Ala Gly Thr Lys Leu Glu Leu Lys
            100                 105                 110 cgg gct gat gct gca cca                                              354
Arg Ala Asp Ala Ala Pro
        115

<210> SEQ ID NO 223
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 223 gat att gtg vtg acc cag tct cca tcc tcc ctg tct gcc tct ctg gga       48
Asp Ile Val Xaa Thr Gln Ser Pro Ser Ser Leu Ser Ala Ser Leu Gly
1               5                   10                  15 gac aga gtc acc atc agt tgc agt gca agt cag ggc att agc aat tat       96
Asp Arg Val Thr Ile Ser Cys Ser Ala Ser Gln Gly Ile Ser Asn Tyr
            20                  25                  30 tta aac tgg ttt cag cag aaa cca gat ggt act att aaa ctc ctg atc      144
Leu Asn Trp Phe Gln Gln Lys Pro Asp Gly Thr Ile Lys Leu Leu Ile
        35                  40                  45 ttt tac aca tca agt tta cat tca gga gtc cca tca agg ttc agt ggc      192
Phe Tyr Thr Ser Ser Leu His Ser Gly Val Pro Ser Arg Phe Ser Gly
    50                  55                  60 agt ggg tct ggg aca gat tat tat ctc acc atc agc aac ctg gaa act      240
Ser Gly Ser Gly Thr Asp Tyr Tyr Leu Thr Ile Ser Asn Leu Glu Thr
65                  70                  75                  80 gaa gat gtc gcc att tac tat tgt cag cag tac agt aag ctt ccg tac      288
Glu Asp Val Ala Ile Tyr Tyr Cys Gln Gln Tyr Ser Lys Leu Pro Tyr
```

```
                    85                  90                  95
acg ttc gga ggg ggg acc aag ctg gaa ata aaa cgg gct gat gct gca      336
Thr Phe Gly Gly Gly Thr Lys Leu Glu Ile Lys Arg Ala Asp Ala Ala
                100                 105                 110 cca                                                                  339
Pro

<210> SEQ ID NO 224
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 224 gat att gtg vtg acc cag tct cca gcc tcc cta tct gca tct gtg gga       48
Asp Ile Val Xaa Thr Gln Ser Pro Ala Ser Leu Ser Ala Ser Val Gly
1               5                   10                  15 gaa act gtc acc atc aca tgt cga gca agt gaa aat att tac agt tat       96
Glu Thr Val Thr Ile Thr Cys Arg Ala Ser Glu Asn Ile Tyr Ser Tyr
                20                  25                  30 tta gca tgg ttt cag cag aaa cag gga aaa tct cct cag ctc ctg gtc      144
Leu Ala Trp Phe Gln Gln Lys Gln Gly Lys Ser Pro Gln Leu Leu Val
            35                  40                  45 tat aat gca aaa acc tta gca gaa ggt gtg cca tca agg ttc agt ggc      192
Tyr Asn Ala Lys Thr Leu Ala Glu Gly Val Pro Ser Arg Phe Ser Gly
        50                  55                  60 agt gga tca ggc aca cag ttt tct ctg aag atc aac agc ctg cag cct      240
Ser Gly Ser Gly Thr Gln Phe Ser Leu Lys Ile Asn Ser Leu Gln Pro
65                  70                  75                  80 gaa gat ttt ggg agt tat tac tgt caa cat cat tat ggt act ccg tac      288
Glu Asp Phe Gly Ser Tyr Tyr Cys Gln His His Tyr Gly Thr Pro Tyr
                85                  90                  95 acg ttc gga ggg ggg acc aag ctg gaa ata aaa cgg gct gat gct gca      336
Thr Phe Gly Gly Gly Thr Lys Leu Glu Ile Lys Arg Ala Asp Ala Ala
                100                 105                 110 cca                                                                  339
Pro

<210> SEQ ID NO 225
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (39)..(1271)

<400> SEQUENCE: 225
taatacgact cactataggg agacccaagc ttgccacc atg gcc cac gtc ggg gac     56
                                          Met Ala His Val Gly Asp
                                          1               5 tgc aaa tgg atg tcc tgg ctc cca gtg ctg gtg gtg tct ctg atg tgc     104
Cys Lys Trp Met Ser Trp Leu Pro Val Leu Val Val Ser Leu Met Cys
            10                  15                  20 tca gcc aag gcg gag gac tcc aac tgt ggt gag aac gaa tac cac aac     152
Ser Ala Lys Ala Glu Asp Ser Asn Cys Gly Glu Asn Glu Tyr His Asn
        25                  30                  35
```

-continued

| | |
|---|---|
| cag act acc ggg ctg tgc cag cag tgt cct cca tgc aga cca ggg gag<br>Gln Thr Thr Gly Leu Cys Gln Gln Cys Pro Pro Cys Arg Pro Gly Glu<br>     40                       45                    50 | 200 |
| gag ccc tac atg tcc tgt gga tac ggc act aaa gac gac gac tat ggc<br>Glu Pro Tyr Met Ser Cys Gly Tyr Gly Thr Lys Asp Asp Asp Tyr Gly<br>55                     60                       65                   70 | 248 |
| tgt gtg ccc tgc cct gca gag aag ttc tcc aaa gga ggt tat cag ata<br>Cys Val Pro Cys Pro Ala Glu Lys Phe Ser Lys Gly Gly Tyr Gln Ile<br>                75                       80                      85 | 296 |
| tgc agg cgc cac aaa gac tgt gag ggc ttc ttc cgg gcc act gtg ctg<br>Cys Arg Arg His Lys Asp Cys Glu Gly Phe Phe Arg Ala Thr Val Leu<br>          90                       95                     100 | 344 |
| aca cca gga gac atg gaa aac gac gct gag tgt ggc cca tgt ctc cct<br>Thr Pro Gly Asp Met Glu Asn Asp Ala Glu Cys Gly Pro Cys Leu Pro<br>        105                   110                     115 | 392 |
| ggc tac tac atg ctg gaa aac aga ccc agg aac atc tat ggc atg gtc<br>Gly Tyr Tyr Met Leu Glu Asn Arg Pro Arg Asn Ile Tyr Gly Met Val<br>120                   125                    130 | 440 |
| tgc tac tcc tgt ctc ttg gca cct ccc aac acc aag gaa tgt gtg gga<br>Cys Tyr Ser Cys Leu Leu Ala Pro Pro Asn Thr Lys Glu Cys Val Gly<br>135                   140                    145                150 | 488 |
| gcc act tct ggg gtt tca gca cac tca tcc agc act tcc ggt ggc agc<br>Ala Thr Ser Gly Val Ser Ala His Ser Ser Ser Thr Ser Gly Gly Ser<br>               155                    160                    165 | 536 |
| acc ttg tct ccc ttc cag cat gct cac aaa gag ctc tca ggc caa gga<br>Thr Leu Ser Pro Phe Gln His Ala His Lys Glu Leu Ser Gly Gln Gly<br>               170                    175                    180 | 584 |
| cac gtc gac aaa act cac aca tgc cca ccg tgc cca gca cct gaa ctc<br>His Val Asp Lys Thr His Thr Cys Pro Pro Cys Pro Ala Pro Glu Leu<br>             185                    190                    195 | 632 |
| ctg ggg gga ccg tca gtc ttc ctc ttc ccc cca aaa ccc aag gac acc<br>Leu Gly Gly Pro Ser Val Phe Leu Phe Pro Pro Lys Pro Lys Asp Thr<br>        200                   205                    210 | 680 |
| ctc atg atc tcc cgg acc cct gag gtc aca tgc gtg gtg gtg gac gtg<br>Leu Met Ile Ser Arg Thr Pro Glu Val Thr Cys Val Val Val Asp Val<br>215                 220                    225                230 | 728 |
| agc cac gaa gac cct gag gtc aag ttc aac tgg tac gtg gac ggc gtg<br>Ser His Glu Asp Pro Glu Val Lys Phe Asn Trp Tyr Val Asp Gly Val<br>               235                    240                    245 | 776 |
| gag gtg cat aat gcc aag aca aag ccg cgg gag gag cag tac aac agc<br>Glu Val His Asn Ala Lys Thr Lys Pro Arg Glu Glu Gln Tyr Asn Ser<br>        250                   255                    260 | 824 |
| acg tac cgt gtg gtc agc gtc ctc acc gtc ctg cac cag gac tgg ctg<br>Thr Tyr Arg Val Val Ser Val Leu Thr Val Leu His Gln Asp Trp Leu<br>        265                   270                    275 | 872 |
| aat ggc aag gag tac aag tgc aag gtc tcc aac aaa gcc ctc cca gcc<br>Asn Gly Lys Glu Tyr Lys Cys Lys Val Ser Asn Lys Ala Leu Pro Ala<br>280                 285                    290 | 920 |
| ccc atc gag aaa acc atc tcc aaa gcc aaa ggg cag ccc cga gaa cca<br>Pro Ile Glu Lys Thr Ile Ser Lys Ala Lys Gly Gln Pro Arg Glu Pro<br>295                 300                    305                310 | 968 |
| cag gtg tac acc ctg ccc cca tcc cgg gat gag ctg acc aag aac cag<br>Gln Val Tyr Thr Leu Pro Pro Ser Arg Asp Glu Leu Thr Lys Asn Gln<br>               315                    320                    325 | 1016 |
| gtc agc ctg acc tgc ctg gtc aaa ggc ttc tat ccc agc gac atc gcc<br>Val Ser Leu Thr Cys Leu Val Lys Gly Phe Tyr Pro Ser Asp Ile Ala<br>             330                    335                    340 | 1064 |
| gtg gag tgg gag agc aat ggg cag ccg gag aac aac tac aag acc acg<br>Val Glu Trp Glu Ser Asn Gly Gln Pro Glu Asn Asn Tyr Lys Thr Thr<br>        345                   350                    355 | 1112 |

```
cct ccc gtg ttg gac tcc gac ggc tcc ttc ttc ctc tac agc aag ctc    1160
Pro Pro Val Leu Asp Ser Asp Gly Ser Phe Phe Leu Tyr Ser Lys Leu
    360             365                 370 acc gtg gac aag agc agg tgg cag cag ggg aac gtc ttc tca tgc tcc    1208
Thr Val Asp Lys Ser Arg Trp Gln Gln Gly Asn Val Phe Ser Cys Ser
375             380                 385 gtg atg cat gag gct ctg cac aac cac tac acg cag aag agc ctc tcc    1256
Val Met His Glu Ala Leu His Asn His Tyr Thr Gln Lys Ser Leu Ser
            395                 400                 405 ctg tct ccg ggt aaa tgagtgcgcg cggccgctcg agtagatgac tagtctagag    1311
Leu Ser Pro Gly Lys
            410 ggccctattc tatagtgtca cctaaat                                      1338

<210> SEQ ID NO 226
<211> LENGTH: 411
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Met Ala His Val Gly Asp Cys Lys Trp Met Ser Trp Leu Pro Val Leu
1               5                   10                  15

Val Val Ser Leu Met Cys Ser Ala Lys Ala Glu Asp Ser Asn Cys Gly
            20                  25                  30

Glu Asn Glu Tyr His Asn Gln Thr Thr Gly Leu Cys Gln Gln Cys Pro
        35                  40                  45

Pro Cys Arg Pro Gly Glu Glu Pro Tyr Met Ser Cys Gly Tyr Gly Thr
    50                  55                  60

Lys Asp Asp Asp Tyr Gly Cys Val Pro Cys Pro Ala Glu Lys Phe Ser
65                  70                  75                  80

Lys Gly Gly Tyr Gln Ile Cys Arg Arg His Lys Asp Cys Glu Gly Phe
                85                  90                  95

Phe Arg Ala Thr Val Leu Thr Pro Gly Asp Met Glu Asn Asp Ala Glu
            100                 105                 110

Cys Gly Pro Cys Leu Pro Gly Tyr Tyr Met Leu Glu Asn Arg Pro Arg
        115                 120                 125

Asn Ile Tyr Gly Met Val Cys Tyr Ser Cys Leu Leu Ala Pro Pro Asn
    130                 135                 140

Thr Lys Glu Cys Val Gly Ala Thr Ser Gly Val Ser Ala His Ser Ser
145                 150                 155                 160

Ser Thr Ser Gly Gly Ser Thr Leu Ser Pro Phe Gln His Ala His Lys
                165                 170                 175

Glu Leu Ser Gly Gln Gly His Val Asp Lys Thr His Thr Cys Pro Pro
            180                 185                 190

Cys Pro Ala Pro Glu Leu Leu Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Asn Ser Thr Tyr Arg Val Val Ser Val Leu Thr Val
            260                 265                 270
```

```
Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
290                 295                 300

Gly Gln Pro Arg Glu Pro Gln Val Tyr Thr Leu Pro Pro Ser Arg Asp
305                 310                 315                 320

Glu Leu Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Lys Leu Thr Val Asp Lys Ser Arg Trp Gln Gln Gly
370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410

<210> SEQ ID NO 227
<211> LENGTH: 1337
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (39)..(1271)

<400> SEQUENCE: 227
taatacgact cactataggg agacccaagc ttgccacc atg gcc cat gtg ggg gac      56
                                          Met Ala His Val Gly Asp
                                            1               5 tgc acg cag acg ccc tgg ctc ccc gtc ctg gtg gtg tct ctg atg tgc      104
Cys Thr Gln Thr Pro Trp Leu Pro Val Leu Val Val Ser Leu Met Cys
            10                  15                  20 tca gcc cga gcg gaa tac tca aac tgc ggt gag aac gag tac tac aac      152
Ser Ala Arg Ala Glu Tyr Ser Asn Cys Gly Glu Asn Glu Tyr Tyr Asn
        25                  30                  35 cag act acg ggg ctg tgc cag gag tgc ccc ccg tgt ggg ccg gga gag      200
Gln Thr Thr Gly Leu Cys Gln Glu Cys Pro Pro Cys Gly Pro Gly Glu
    40                  45                  50 gag ccc tac ctg tcc tgt ggc tac ggc acc aaa gac gag gac tac ggc      248
Glu Pro Tyr Leu Ser Cys Gly Tyr Gly Thr Lys Asp Glu Asp Tyr Gly
55                  60                  65                  70 tgc gtc ccc tgc ccg gcg gag aag ttt tcc aaa gga ggc tac cag ata      296
Cys Val Pro Cys Pro Ala Glu Lys Phe Ser Lys Gly Gly Tyr Gln Ile
                75                  80                  85 tgc agg cgt cac aaa gac tgt gag ggc ttc ttc cgg gcc acc gtg ctg      344
Cys Arg Arg His Lys Asp Cys Glu Gly Phe Phe Arg Ala Thr Val Leu
            90                  95                  100 aca cca ggg gac atg gag aat gac gct gag tgt ggc cct tgc ctc cct      392
Thr Pro Gly Asp Met Glu Asn Asp Ala Glu Cys Gly Pro Cys Leu Pro
        105                 110                 115 ggc tac tac atg ctg gag aac aga ccg agg aac atc tat ggc atg gtc      440
Gly Tyr Tyr Met Leu Glu Asn Arg Pro Arg Asn Ile Tyr Gly Met Val
    120                 125                 130 tgc tac tcc tgc ctc ctg gca ccc ccc aac acc aag gaa tgt gtg gga      488
Cys Tyr Ser Cys Leu Leu Ala Pro Pro Asn Thr Lys Glu Cys Val Gly
135                 140                 145                 150
```

```
gcc act tca gga gct tct gcc aac ttc cct ggc acc tcg ggc agc agc      536
Ala Thr Ser Gly Ala Ser Ala Asn Phe Pro Gly Thr Ser Gly Ser Ser
            155                 160                 165 acc ctg tct ccc ttc cag cac gcc cac aaa gaa ctc tca ggc caa gga      584
Thr Leu Ser Pro Phe Gln His Ala His Lys Glu Leu Ser Gly Gln Gly
        170                 175                 180 cac gtc gac aaa act cac aca tgc cca ccg tgc cca gca cct gaa ctc      632
His Val Asp Lys Thr His Thr Cys Pro Pro Cys Pro Ala Pro Glu Leu
    185                 190                 195 ctg ggg gga ccg tca gtc ttc ctc ttc ccc cca aaa ccc aag gac acc      680
Leu Gly Gly Pro Ser Val Phe Leu Phe Pro Pro Lys Pro Lys Asp Thr
200                 205                 210 ctc atg atc tcc cgg acc cct gag gtc aca tgc gtg gtg gtg gac gtg      728
Leu Met Ile Ser Arg Thr Pro Glu Val Thr Cys Val Val Val Asp Val
215                 220                 225                 230 agc cac gaa gac cct gag gtc aag ttc aac tgg tac gtg gac ggc gtg      776
Ser His Glu Asp Pro Glu Val Lys Phe Asn Trp Tyr Val Asp Gly Val
                235                 240                 245 gag gtg cat aat gcc aag aca aag ccg cgg gag gag cag tac aac agc      824
Glu Val His Asn Ala Lys Thr Lys Pro Arg Glu Glu Gln Tyr Asn Ser
            250                 255                 260 acg tac cgt gtg gtc agc gtc ctc acc gtc ctg cac cag gac tgg ctg      872
Thr Tyr Arg Val Val Ser Val Leu Thr Val Leu His Gln Asp Trp Leu
        265                 270                 275 aat ggc aag gag tac aag tgc aag gtc tcc aac aaa gcc ctc cca gcc      920
Asn Gly Lys Glu Tyr Lys Cys Lys Val Ser Asn Lys Ala Leu Pro Ala
    280                 285                 290 ccc atc gag aaa acc atc tcc aaa gcc aaa ggg cag ccc cga gaa cca      968
Pro Ile Glu Lys Thr Ile Ser Lys Ala Lys Gly Gln Pro Arg Glu Pro
295                 300                 305                 310 cag gtg tac acc ctg ccc cca tcc cgg gat gag ctg acc aag aac cag     1016
Gln Val Tyr Thr Leu Pro Pro Ser Arg Asp Glu Leu Thr Lys Asn Gln
                315                 320                 325 gtc agc ctg acc tgc ctg gtc aaa ggc ttc tat ccc agc gac atc gcc     1064
Val Ser Leu Thr Cys Leu Val Lys Gly Phe Tyr Pro Ser Asp Ile Ala
            330                 335                 340 gtg gag tgg gag agc aat ggg cag ccg gag aac aac tac aag acc acg     1112
Val Glu Trp Glu Ser Asn Gly Gln Pro Glu Asn Asn Tyr Lys Thr Thr
        345                 350                 355 cct ccc gtg ttg gac tcc gac ggc tcc ttc ttc ctc tac agc aag ctc     1160
Pro Pro Val Leu Asp Ser Asp Gly Ser Phe Phe Leu Tyr Ser Lys Leu
    360                 365                 370 acc gtg gac aag agc agg tgg cag cag ggg aac gtc ttc tca tgc tcc     1208
Thr Val Asp Lys Ser Arg Trp Gln Gln Gly Asn Val Phe Ser Cys Ser
375                 380                 385                 390 gtg atg cat gag gct ctg cac aac cac tac acg cag aag agc ctc tcc     1256
Val Met His Glu Ala Leu His Asn His Tyr Thr Gln Lys Ser Leu Ser
                395                 400                 405 ctg tct ccg ggt aaa tgagtgccgc ggccgctcga gtagatgact agtctagagg     1311
Leu Ser Pro Gly Lys
            410 gccctattct atagtgtcac ctaaat                                         1337

<210> SEQ ID NO 228
<211> LENGTH: 411
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 228

```
Met Ala His Val Gly Asp Cys Thr Gln Thr Pro Trp Leu Pro Val Leu
1               5                   10                  15

Val Val Ser Leu Met Cys Ser Ala Arg Ala Glu Tyr Ser Asn Cys Gly
            20                  25                  30

Glu Asn Glu Tyr Tyr Asn Gln Thr Thr Gly Leu Cys Gln Glu Cys Pro
        35                  40                  45

Pro Cys Gly Pro Gly Glu Glu Pro Tyr Leu Ser Cys Gly Tyr Gly Thr
    50                  55                  60

Lys Asp Glu Asp Tyr Gly Cys Val Pro Cys Pro Ala Glu Lys Phe Ser
65                  70                  75                  80

Lys Gly Gly Tyr Gln Ile Cys Arg Arg His Lys Asp Cys Glu Gly Phe
                85                  90                  95

Phe Arg Ala Thr Val Leu Thr Pro Gly Asp Met Glu Asn Asp Ala Glu
            100                 105                 110

Cys Gly Pro Cys Leu Pro Gly Tyr Tyr Met Leu Glu Asn Arg Pro Arg
        115                 120                 125

Asn Ile Tyr Gly Met Val Cys Tyr Ser Cys Leu Leu Ala Pro Pro Asn
    130                 135                 140

Thr Lys Glu Cys Val Gly Ala Thr Ser Gly Ala Ser Ala Asn Phe Pro
145                 150                 155                 160

Gly Thr Ser Gly Ser Ser Thr Leu Ser Pro Phe Gln His Ala His Lys
                165                 170                 175

Glu Leu Ser Gly Gln Gly His Val Asp Lys Thr His Thr Cys Pro Pro
            180                 185                 190

Cys Pro Ala Pro Glu Leu Leu Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Asn Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
    290                 295                 300

Gly Gln Pro Arg Glu Pro Gln Val Tyr Thr Leu Pro Pro Ser Arg Asp
305                 310                 315                 320

Glu Leu Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Lys Leu Thr Val Asp Lys Ser Arg Trp Gln Gln Gly
    370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410
```

<210> SEQ ID NO 229
<211> LENGTH: 1467
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: CDS
<222> LOCATION: (39)..(1382)

<400> SEQUENCE: 229

```
ta ata cga ctc act ata ggg aga ccc aag ctt gcc acc atg gcc cat        47
                                            Met Ala His
                                            1 gtg ggg gac tgc acg cag acg ccc tgg ctc ccc gtc ctg gtg gtg tct        95
Val Gly Asp Cys Thr Gln Thr Pro Trp Leu Pro Val Leu Val Val Ser
      5              10                 15 ctg atg tgc tca gcc cga gcg gaa tac tca aac tgc ggt gag aac gag       143
Leu Met Cys Ser Ala Arg Ala Glu Tyr Ser Asn Cys Gly Glu Asn Glu
 20              25                 30                 35 tac tac aac cag act acg ggg ctg tgc cag gag tgc ccc ccg tgt ggg       191
Tyr Tyr Asn Gln Thr Thr Gly Leu Cys Gln Glu Cys Pro Pro Cys Gly
              40                 45                 50 ccg gga gag gag ccc tac ctg tcc tgt ggc tac ggc acc aaa gac gag       239
Pro Gly Glu Glu Pro Tyr Leu Ser Cys Gly Tyr Gly Thr Lys Asp Glu
         55                 60                 65 gac tac ggc tgc gtc ccc tgc ccg gcg gag aag ttt tcc aaa gga ggc       287
Asp Tyr Gly Cys Val Pro Cys Pro Ala Glu Lys Phe Ser Lys Gly Gly
     70                 75                 80 tac cag ata tgc agg cgt cac aaa gac tgt gag ggc ttc ttc cgg gcc       335
Tyr Gln Ile Cys Arg Arg His Lys Asp Cys Glu Gly Phe Phe Arg Ala
 85                 90                 95 acc gtg ctg aca cca ggg gac atg gag aat gac gct gag tgt ggc cct       383
Thr Val Leu Thr Pro Gly Asp Met Glu Asn Asp Ala Glu Cys Gly Pro
100                105                110                115 tgc ctc cct ggc tac tac atg ctg gag aac aga ccg agg aac atc tat       431
Cys Leu Pro Gly Tyr Tyr Met Leu Glu Asn Arg Pro Arg Asn Ile Tyr
             120                125                130 ggc atg gtc tgc tac tcc tgc ctc ctg gca ccc ccc aac acc aag gaa       479
Gly Met Val Cys Tyr Ser Cys Leu Leu Ala Pro Pro Asn Thr Lys Glu
         135                140                145 tgt gtg gga gcc act tca gga gct tct gcc aac ttc cct ggc acc tcg       527
Cys Val Gly Ala Thr Ser Gly Ala Ser Ala Asn Phe Pro Gly Thr Ser
     150                155                160 ggc agc agc acc ctg tct ccc ttc cag cac gcc cac aaa gaa ctc tca       575
Gly Ser Ser Thr Leu Ser Pro Phe Gln His Ala His Lys Glu Leu Ser
165                170                175 ggc caa gga cac ctg gcc act gcc ctg atc att gca atg tcc acc atc       623
Gly Gln Gly His Leu Ala Thr Ala Leu Ile Ile Ala Met Ser Thr Ile
             185                190                195
180 ttc atc atg gcc atc gcc atc gtc ctc atc atc atg ttc tac atc ctg       671
Phe Ile Met Ala Ile Ala Ile Val Leu Ile Ile Met Phe Tyr Ile Leu
             200                205                210 aag aca aag ccc tct gcc cca gcc tgt tgc acc agc cac ccg ggg aag       719
Lys Thr Lys Pro Ser Ala Pro Ala Cys Cys Thr Ser His Pro Gly Lys
             215                220                225 agc gtg gag gcc caa gtg agc aag gac gag gag aag aaa gag gcc cca       767
Ser Val Glu Ala Gln Val Ser Lys Asp Glu Glu Lys Lys Glu Ala Pro
         230                235                240 gac aac gtg gtg atg ttc tcc gag aag gat gaa ttt gag aag ctg aca       815
Asp Asn Val Val Met Phe Ser Glu Lys Asp Glu Phe Glu Lys Leu Thr
```

```
                    245                 250                 255
gca act cca gca aag ccc acc aag agc gag aac gat gcc tca tcc gag        863
Ala Thr Pro Ala Lys Pro Thr Lys Ser Glu Asn Asp Ala Ser Ser Glu
260                 265                 270                 275 aat gag cag ctg ctg agc cgg agc gtc gac agt gat gag gag ccc gcc        911
Asn Glu Gln Leu Leu Ser Arg Ser Val Asp Ser Asp Glu Glu Pro Ala
                    280                 285                 290 cct gac aag cag ggc tcc ccg gag ctg tgc ctg ctg tcg ctg gtt cac        959
Pro Asp Lys Gln Gly Ser Pro Glu Leu Cys Leu Leu Ser Leu Val His
                295                 300                 305 ctg gcc agg gag aag tct gcc acc agc aac aag tca gcc ggg att caa       1007
Leu Ala Arg Glu Lys Ser Ala Thr Ser Asn Lys Ser Ala Gly Ile Gln
            310                 315                 320 agc cgg agg aaa aag atc ctc gat gtg tat gcc aac gtg tgt gga gtc       1055
Ser Arg Arg Lys Lys Ile Leu Asp Val Tyr Ala Asn Val Cys Gly Val
        325                 330                 335 gtg gaa ggt ctt agc ccc acg gag ctg cca ttt gat tgc ctc gag aag       1103
Val Glu Gly Leu Ser Pro Thr Glu Leu Pro Phe Asp Cys Leu Glu Lys
340                 345                 350                 355 act agc cga atg ctc agc tcc acg tac aac tct gag aag gct gtt gtg       1151
Thr Ser Arg Met Leu Ser Ser Thr Tyr Asn Ser Glu Lys Ala Val Val
                    360                 365                 370 aaa acg tgg cgc cac ctc gcc gag agc ttc ggc ctg aag agg gat gag       1199
Lys Thr Trp Arg His Leu Ala Glu Ser Phe Gly Leu Lys Arg Asp Glu
                375                 380                 385 att ggg ggc atg aca gac ggc atg caa ctc ttt gac cgc atc agc acg       1247
Ile Gly Gly Met Thr Asp Gly Met Gln Leu Phe Asp Arg Ile Ser Thr
            390                 395                 400 gca ggc tac agc atc cct gag cta ctc aca aaa ctg gtg cag att gag       1295
Ala Gly Tyr Ser Ile Pro Glu Leu Leu Thr Lys Leu Val Gln Ile Glu
        405                 410                 415 cgg ctg gat gct gtg gag tcc ttg tgt gca gac ata ctg gag tgg gcg       1343
Arg Leu Asp Ala Val Glu Ser Leu Cys Ala Asp Ile Leu Glu Trp Ala
420                 425                 430                 435 ggg gtt gtg cca cct gcc tcc cag cca cat gct gca tcc tgacctgaat        1392
Gly Val Val Pro Pro Ala Ser Gln Pro His Ala Ala Ser
                    440                 445 tctgcagata tccatcacac tggcggccgc tcgagcatgc atctagaggg ccctattcta     1452
tagtgtcacc taaat                                                      1467

<210> SEQ ID NO 230
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Met Ala His Val Gly Asp Cys Thr Gln Thr Pro Trp Leu Pro Val Leu
1               5                   10                  15

Val Val Ser Leu Met Cys Ser Ala Arg Ala Glu Tyr Ser Asn Cys Gly
                20                  25                  30

Glu Asn Glu Tyr Tyr Asn Gln Thr Thr Gly Leu Cys Gln Glu Cys Pro
            35                  40                  45

Pro Cys Gly Pro Gly Glu Glu Pro Tyr Leu Ser Cys Gly Tyr Gly Thr
        50                  55                  60

Lys Asp Glu Asp Tyr Gly Cys Val Pro Cys Pro Ala Glu Lys Phe Ser
65                  70                  75                  80
```

```
Lys Gly Gly Tyr Gln Ile Cys Arg Arg His Lys Asp Cys Glu Gly Phe
                    85                  90                  95

Phe Arg Ala Thr Val Leu Thr Pro Gly Asp Met Glu Asn Asp Ala Glu
            100                 105                 110

Cys Gly Pro Cys Leu Pro Gly Tyr Tyr Met Leu Glu Asn Arg Pro Arg
        115                 120                 125

Asn Ile Tyr Gly Met Val Cys Tyr Ser Cys Leu Leu Ala Pro Pro Asn
    130                 135                 140

Thr Lys Glu Cys Val Gly Ala Thr Ser Gly Ala Ser Ala Asn Phe Pro
145                 150                 155                 160

Gly Thr Ser Gly Ser Thr Leu Ser Pro Phe Gln His Ala His Lys
                165                 170                 175

Glu Leu Ser Gly Gln Gly His Leu Ala Thr Ala Leu Ile Ile Ala Met
            180                 185                 190

Ser Thr Ile Phe Ile Met Ala Ile Ala Ile Val Leu Ile Ile Met Phe
        195                 200                 205

Tyr Ile Leu Lys Thr Lys Pro Ser Ala Pro Ala Cys Cys Thr Ser His
    210                 215                 220

Pro Gly Lys Ser Val Glu Ala Gln Val Ser Lys Asp Glu Glu Lys Lys
225                 230                 235                 240

Glu Ala Pro Asp Asn Val Val Met Phe Ser Glu Lys Asp Glu Phe Glu
                245                 250                 255

Lys Leu Thr Ala Thr Pro Ala Lys Pro Thr Lys Ser Glu Asn Asp Ala
            260                 265                 270

Ser Ser Glu Asn Glu Gln Leu Leu Ser Arg Ser Val Asp Ser Asp Glu
        275                 280                 285

Glu Pro Ala Pro Asp Lys Gln Gly Ser Pro Glu Leu Cys Leu Leu Ser
290                 295                 300

Leu Val His Leu Ala Arg Glu Lys Ser Ala Thr Ser Asn Lys Ser Ala
305                 310                 315                 320

Gly Ile Gln Ser Arg Arg Lys Lys Ile Leu Asp Val Tyr Ala Asn Val
                325                 330                 335

Cys Gly Val Val Glu Gly Leu Ser Pro Thr Glu Leu Pro Phe Asp Cys
            340                 345                 350

Leu Glu Lys Thr Ser Arg Met Leu Ser Ser Thr Tyr Asn Ser Glu Lys
        355                 360                 365

Ala Val Val Lys Thr Trp Arg His Leu Ala Glu Ser Phe Gly Leu Lys
370                 375                 380

Arg Asp Glu Ile Gly Gly Met Thr Asp Gly Met Gln Leu Phe Asp Arg
385                 390                 395                 400

Ile Ser Thr Ala Gly Tyr Ser Ile Pro Glu Leu Leu Thr Lys Leu Val
                405                 410                 415

Gln Ile Glu Arg Leu Asp Ala Val Glu Ser Leu Cys Ala Asp Ile Leu
            420                 425                 430

Glu Trp Ala Gly Val Val Pro Pro Ala Ser Gln Pro His Ala Ala Ser
        435                 440                 445

<210> SEQ ID NO 231
<211> LENGTH: 989
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (39)..(938)
```

<400> SEQUENCE: 231

```
taatacgact cactataggg agacccaagc ttgccacc atg gcc cat gtg ggg gac         56
                                          Met Ala His Val Gly Asp
                                          1               5 tgc acg cag acg ccc tgg ctc ccc gtc ctg gtg gtg tct ctg atg tgc         104
Cys Thr Gln Thr Pro Trp Leu Pro Val Leu Val Val Ser Leu Met Cys
             10                  15                  20 tca gcc cga gcg gaa tac tca aac tgc ggt gag aac gag tac tac aac         152
Ser Ala Arg Ala Glu Tyr Ser Asn Cys Gly Glu Asn Glu Tyr Tyr Asn
         25                  30                  35 cag act acg ggg ctg tgc cag gag tgc ccc ccg tgt ggg ccg gga gag         200
Gln Thr Thr Gly Leu Cys Gln Glu Cys Pro Pro Cys Gly Pro Gly Glu
     40                  45                  50 gag ccc tac ctg tcc tgt ggc tac ggc acc aaa gac gag gac tac ggc         248
Glu Pro Tyr Leu Ser Cys Gly Tyr Gly Thr Lys Asp Glu Asp Tyr Gly
 55                  60                  65                  70 tgc gtc gtc gac aaa act cac aca tgc cca ccg tgc cca gca cct gaa         296
Cys Val Val Asp Lys Thr His Thr Cys Pro Pro Cys Pro Ala Pro Glu
                 75                  80                  85 ctc ctg ggg gga ccg tca gtc ttc ctc ttc ccc cca aaa ccc aag gac         344
Leu Leu Gly Gly Pro Ser Val Phe Leu Phe Pro Pro Lys Pro Lys Asp
             90                  95                 100 acc ctc atg atc tcc cgg acc cct gag gtc aca tgc gtg gtg gtg gac         392
Thr Leu Met Ile Ser Arg Thr Pro Glu Val Thr Cys Val Val Val Asp
         105                 110                 115 gtg agc cac gaa gac cct gag gtc aag ttc aac tgg tac gtg gac ggc         440
Val Ser His Glu Asp Pro Glu Val Lys Phe Asn Trp Tyr Val Asp Gly
    120                 125                 130 gtg gag gtg cat aat gcc aag aca aag ccg cgg gag gag cag tac aac         488
Val Glu Val His Asn Ala Lys Thr Lys Pro Arg Glu Glu Gln Tyr Asn
135                 140                 145                 150 agc acg tac cgt gtg gtc agc gtc ctc acc gtc ctg cac cag gac tgg         536
Ser Thr Tyr Arg Val Val Ser Val Leu Thr Val Leu His Gln Asp Trp
                155                 160                 165 ctg aat ggc aag gag tac aag tgc aag gtc tcc aac aaa gcc ctc cca         584
Leu Asn Gly Lys Glu Tyr Lys Cys Lys Val Ser Asn Lys Ala Leu Pro
            170                 175                 180 gcc ccc atc gag aaa acc atc tcc aaa gcc aaa ggg cag ccc cga gaa         632
Ala Pro Ile Glu Lys Thr Ile Ser Lys Ala Lys Gly Gln Pro Arg Glu
        185                 190                 195 cca cag gtg tac acc ctg ccc cca tcc cgg gat gag ctg acc aag aac         680
Pro Gln Val Tyr Thr Leu Pro Pro Ser Arg Asp Glu Leu Thr Lys Asn
    200                 205                 210 cag gtc agc ctg acc tgc ctg gtc aaa ggc ttc tat ccc agc gac atc         728
Gln Val Ser Leu Thr Cys Leu Val Lys Gly Phe Tyr Pro Ser Asp Ile
215                 220                 225                 230 gcc gtg gag tgg gag agc aat ggg cag ccg gag aac aac tac aag acc         776
Ala Val Glu Trp Glu Ser Asn Gly Gln Pro Glu Asn Asn Tyr Lys Thr
                235                 240                 245 acg cct ccc gtg ttg gac tcc gac ggc tcc ttc ttc ctc tac agc aag         824
Thr Pro Pro Val Leu Asp Ser Asp Gly Ser Phe Phe Leu Tyr Ser Lys
            250                 255                 260 ctc acc gtg gac aag agc agg tgg cag cag ggg aac gtc ttc tca tgc         872
Leu Thr Val Asp Lys Ser Arg Trp Gln Gln Gly Asn Val Phe Ser Cys
        265                 270                 275 tcc gtg atg cat gag gct ctg cac aac cac tac acg cag aag agc ctc         920
Ser Val Met His Glu Ala Leu His Asn His Tyr Thr Gln Lys Ser Leu
    280                 285                 290 tcc ctg tct ccg ggt aaa tgagtgcgcg cggccgctct agagggccct attctatagt     978
Ser Leu Ser Pro Gly Lys
```

```
Ser Leu Ser Pro Gly Lys
295             300 gtcacctaaa t                                                        989

<210> SEQ ID NO 232
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Met Ala His Val Gly Asp Cys Thr Gln Thr Pro Trp Leu Pro Val Leu
1               5                   10                  15

Val Val Ser Leu Met Cys Ser Ala Arg Ala Glu Tyr Ser Asn Cys Gly
            20                  25                  30

Glu Asn Glu Tyr Tyr Asn Gln Thr Thr Gly Leu Cys Gln Glu Cys Pro
        35                  40                  45

Pro Cys Gly Pro Gly Glu Pro Tyr Leu Ser Cys Gly Tyr Gly Thr
    50                  55                  60

Lys Asp Glu Asp Tyr Gly Cys Val Val Asp Lys Thr His Thr Cys Pro
65                  70                  75                  80

Pro Cys Pro Ala Pro Glu Leu Leu Gly Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
        115                 120                 125

Asn Trp Tyr Val Asp Gly Val Glu Val His Asn Ala Lys Thr Lys Pro
    130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
                165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
        195                 200                 205

Asp Glu Leu Thr Lys Asn Gln Val Ser Leu Thr Cys Leu Val Lys Gly
    210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Val Leu Asp Ser Asp Gly Ser
                245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
        275                 280                 285

Tyr Thr Gln Lys Ser Leu Ser Leu Ser Pro Gly Lys
    290                 295                 300

<210> SEQ ID NO 233
<211> LENGTH: 1115
<212> TYPE: DNA
<213> ORGANISM: Artificial Sequence
<220> FEATURE:
<223> OTHER INFORMATION: Description of Artificial Sequence: Synthetic
```

```
        polynucleotide
<220> FEATURE:
<221> NAME/KEY: CDS
<222> LOCATION: (39)..(1064)

<400> SEQUENCE: 233
taatacgact cactataggg agacccaagc ttgccacc atg gcc cat gtg ggg gac      56
                                          Met Ala His Val Gly Asp
                                          1               5 tgc acg cag acg ccc tgg ctc ccc gtc ctg gtg gtg tct ctg atg tgc     104
Cys Thr Gln Thr Pro Trp Leu Pro Val Leu Val Val Ser Leu Met Cys
                10                  15                  20 tca gcc cga gcg gaa tac tca aac tgc ggt gag aac gag tac tac aac     152
Ser Ala Arg Ala Glu Tyr Ser Asn Cys Gly Glu Asn Glu Tyr Tyr Asn
        25                  30                  35 cag act acg ggg ctg tgc cag gag tgc ccc ccg tgt ggg ccg gga gag     200
Gln Thr Thr Gly Leu Cys Gln Glu Cys Pro Pro Cys Gly Pro Gly Glu
40                  45                  50 gag ccc tac ctg tcc tgt ggc tac ggc acc aaa gac gag gac tac ggc     248
Glu Pro Tyr Leu Ser Cys Gly Tyr Gly Thr Lys Asp Glu Asp Tyr Gly
55                  60                  65                  70 tgc gtc ccc tgc ccg gcg gag aag ttt tcc aaa gga ggc tac cag ata     296
Cys Val Pro Cys Pro Ala Glu Lys Phe Ser Lys Gly Gly Tyr Gln Ile
                75                  80                  85 tgc agg cgt cac aaa gac tgt gag ggc ttc ttc cgg gcc acc gtg ctg     344
Cys Arg Arg His Lys Asp Cys Glu Gly Phe Phe Arg Ala Thr Val Leu
                90                  95                 100 aca cca ggg gac atg gag aat gac gct gag tgt ggc gtc gac aaa act     392
Thr Pro Gly Asp Met Glu Asn Asp Ala Glu Cys Gly Val Asp Lys Thr
            105                 110                 115 cac aca tgc cca ccg tgc cca gca cct gaa ctc ctg ggg gga ccg tca     440
His Thr Cys Pro Pro Cys Pro Ala Pro Glu Leu Leu Gly Gly Pro Ser
        120                 125                 130 gtc ttc ctc ttc ccc cca aaa ccc aag gac acc ctc atg atc tcc cgg     488
Val Phe Leu Phe Pro Pro Lys Pro Lys Asp Thr Leu Met Ile Ser Arg
135                 140                 145                 150 acc cct gag gtc aca tgc gtg gtg gtg gac gtg agc cac gaa gac cct     536
Thr Pro Glu Val Thr Cys Val Val Val Asp Val Ser His Glu Asp Pro
                155                 160                 165 gag gtc aag ttc aac tgg tac gtg gac ggc gtg gag gtg cat aat gcc     584
Glu Val Lys Phe Asn Trp Tyr Val Asp Gly Val Glu Val His Asn Ala
            170                 175                 180 aag aca aag ccg cgg gag gag cag tac aac agc acg tac cgt gtg gtc     632
Lys Thr Lys Pro Arg Glu Glu Gln Tyr Asn Ser Thr Tyr Arg Val Val
        185                 190                 195 agc gtc ctc acc gtc ctg cac cag gac tgg ctg aat ggc aag gag tac     680
Ser Val Leu Thr Val Leu His Gln Asp Trp Leu Asn Gly Lys Glu Tyr
200                 205                 210 aag tgc aag gtc tcc aac aaa gcc ctc cca gcc ccc atc gag aaa acc     728
Lys Cys Lys Val Ser Asn Lys Ala Leu Pro Ala Pro Ile Glu Lys Thr
215                 220                 225                 230 atc tcc aaa gcc aaa ggg cag ccc cga gaa cca cag gtg tac acc ctg     776
Ile Ser Lys Ala Lys Gly Gln Pro Arg Glu Pro Gln Val Tyr Thr Leu
                235                 240                 245 ccc cca tcc cgg gat gag ctg acc aag aac cag gtc agc ctg acc tgc     824
Pro Pro Ser Arg Asp Glu Leu Thr Lys Asn Gln Val Ser Leu Thr Cys
            250                 255                 260 ctg gtc aaa ggc ttc tat ccc agc gac atc gcc gtg gag tgg gag agc     872
Leu Val Lys Gly Phe Tyr Pro Ser Asp Ile Ala Val Glu Trp Glu Ser
        265                 270                 275 aat ggg cag ccg gag aac aac tac aag acc acg cct ccc gtg ttg gac     920
```

```
Asn Gly Gln Pro Glu Asn Asn Tyr Lys Thr Thr Pro Pro Val Leu Asp
            280                 285                 290 tcc gac ggc tcc ttc ttc ctc tac agc aag ctc acc gtg gac aag agc      968
Ser Asp Gly Ser Phe Phe Leu Tyr Ser Lys Leu Thr Val Asp Lys Ser
295                 300                 305                 310 agg tgg cag cag ggg aac gtc ttc tca tgc tcc gtg atg cat gag gct     1016
Arg Trp Gln Gln Gly Asn Val Phe Ser Cys Ser Val Met His Glu Ala
                315                 320                 325 ctg cac aac cac tac acg cag aag agc ctc tcc ctg tct ccg ggt aaa     1064
Leu His Asn His Tyr Thr Gln Lys Ser Leu Ser Leu Ser Pro Gly Lys
            330                 335                 340 tgagtgcgcg cggccgctct agagggccct attctatagt gtcacctaaa t            1115
```

<210> SEQ ID NO 234
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

```
Met Ala His Val Gly Asp Cys Thr Gln Thr Pro Trp Leu Pro Val Leu
1               5                   10                  15

Val Val Ser Leu Met Cys Ser Ala Arg Ala Glu Tyr Ser Asn Cys Gly
            20                  25                  30

Glu Asn Glu Tyr Tyr Asn Gln Thr Thr Gly Leu Cys Gln Glu Cys Pro
        35                  40                  45

Pro Cys Gly Pro Gly Glu Glu Pro Tyr Leu Ser Cys Gly Tyr Gly Thr
    50                  55                  60

Lys Asp Glu Asp Tyr Gly Cys Val Pro Cys Pro Ala Glu Lys Phe Ser
65                  70                  75                  80

Lys Gly Gly Tyr Gln Ile Cys Arg Arg His Lys Asp Cys Glu Gly Phe
                85                  90                  95

Phe Arg Ala Thr Val Leu Thr Pro Gly Asp Met Glu Asn Asp Ala Glu
            100                 105                 110

Cys Gly Val Asp Lys Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Asp Glu Leu Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
```

```
                    275                 280                 285
Thr Pro Val Leu Asp Ser Asp Gly Ser Phe Phe Leu Tyr Ser Lys
290                 295                 300
Leu Thr Val Asp Lys Ser Arg Trp Gln Gln Gly Asn Val Phe Ser Cys
305                 310                 315                 320
Ser Val Met His Glu Ala Leu His Asn His Tyr Thr Gln Lys Ser Leu
                325                 330                 335
Ser Leu Ser Pro Gly Lys
                340

<210> SEQ ID NO 235
<211> LENGTH: 448
<212> TYPE: PRT
<213> ORGANISM: Homo sapiens

<400> SEQUENCE: 235

Met Ala His Val Gly Asp Cys Thr Gln Thr Pro Trp Leu Pro Val Leu
1               5                   10                  15
Val Val Ser Leu Met Cys Ser Ala Arg Ala Glu Tyr Ser Asn Cys Gly
                20                  25                  30
Glu Asn Glu Tyr Tyr Asn Gln Thr Thr Gly Leu Cys Gln Glu Cys Pro
            35                  40                  45
Pro Cys Gly Pro Gly Glu Glu Pro Tyr Leu Ser Cys Gly Tyr Gly Thr
        50                  55                  60
Lys Asp Glu Asp Tyr Gly Cys Val Pro Cys Pro Ala Glu Lys Phe Ser
65                  70                  75                  80
Lys Gly Gly Tyr Gln Ile Cys Arg Arg His Lys Asp Cys Glu Gly Phe
                85                  90                  95
Phe Arg Ala Thr Val Leu Thr Pro Gly Asp Met Glu Asn Asp Ala Glu
            100                 105                 110
Cys Gly Pro Cys Leu Pro Gly Tyr Tyr Met Leu Glu Asn Arg Pro Arg
        115                 120                 125
Asn Ile Tyr Gly Met Val Cys Tyr Ser Cys Leu Leu Ala Pro Pro Asn
130                 135                 140
Thr Lys Glu Cys Val Gly Ala Thr Ser Gly Ala Ser Ala Asn Phe Pro
145                 150                 155                 160
Gly Thr Ser Gly Ser Ser Thr Leu Ser Pro Phe Gln His Ala His Lys
                165                 170                 175
Glu Leu Ser Gly Gln Gly His Leu Ala Thr Ala Leu Ile Ile Ala Met
            180                 185                 190
Ser Thr Ile Phe Ile Met Ala Ile Ala Ile Val Leu Ile Ile Met Phe
        195                 200                 205
Tyr Ile Leu Lys Thr Lys Pro Ser Ala Pro Ala Cys Cys Thr Ser His
    210                 215                 220
Pro Gly Lys Ser Val Glu Ala Gln Val Ser Lys Asp Glu Glu Lys Lys
225                 230                 235                 240
Glu Ala Pro Asp Asn Val Val Met Phe Ser Glu Lys Asp Glu Phe Glu
                245                 250                 255
Lys Leu Thr Ala Thr Pro Ala Lys Pro Thr Lys Ser Glu Asn Asp Ala
            260                 265                 270
Ser Ser Glu Asn Glu Gln Leu Leu Ser Arg Ser Val Asp Ser Asp Glu
        275                 280                 285
Glu Pro Ala Pro Asp Lys Gln Gly Ser Pro Glu Leu Cys Leu Leu Ser
    290                 295                 300
Leu Val His Leu Ala Arg Glu Lys Ser Ala Thr Ser Asn Lys Ser Ala
```

```
              305                 310                 315                 320
Gly Ile Gln Ser Arg Arg Lys Lys Ile Leu Asp Val Tyr Ala Asn Val
                    325                 330                 335

Cys Gly Val Val Glu Gly Leu Ser Pro Thr Glu Leu Pro Phe Asp Cys
                    340                 345                 350

Leu Glu Lys Thr Ser Arg Met Leu Ser Ser Thr Tyr Asn Ser Glu Lys
                    355                 360                 365

Ala Val Val Lys Thr Trp Arg His Leu Ala Glu Ser Phe Gly Leu Lys
                370                 375                 380

Arg Asp Glu Ile Gly Gly Met Thr Asp Gly Met Gln Leu Phe Asp Arg
385                 390                 395                 400

Ile Ser Thr Ala Gly Tyr Ser Ile Pro Glu Leu Leu Thr Lys Leu Val
                405                 410                 415

Gln Ile Glu Arg Leu Asp Ala Val Glu Ser Leu Cys Ala Asp Ile Leu
                420                 425                 430

Glu Trp Ala Gly Val Val Pro Pro Ala Ser Gln Pro His Ala Ala Ser
                435                 440                 445

<210> SEQ ID NO 236
<211> LENGTH: 448
<212> TYPE: PRT
<213> ORGANISM: Mus sp.

<400> SEQUENCE: 236

Met Ala His Val Gly Asp Cys Lys Trp Met Ser Trp Leu Pro Val Leu
1               5                   10                  15

Val Val Ser Leu Met Cys Ser Ala Lys Ala Glu Asp Ser Asn Cys Gly
                20                  25                  30

Glu Asn Glu Tyr His Asn Gln Thr Thr Gly Leu Cys Gln Gln Cys Pro
            35                  40                  45

Pro Cys Arg Pro Gly Glu Glu Pro Tyr Met Ser Cys Gly Tyr Gly Thr
        50                  55                  60

Lys Asp Asp Asp Tyr Gly Cys Val Pro Cys Pro Ala Glu Lys Phe Ser
65                  70                  75                  80

Lys Gly Gly Tyr Gln Ile Cys Arg Arg His Lys Asp Cys Glu Gly Phe
                85                  90                  95

Phe Arg Ala Thr Val Leu Thr Pro Gly Asp Met Glu Asn Asp Ala Glu
            100                 105                 110

Cys Gly Pro Cys Leu Pro Gly Tyr Tyr Met Leu Glu Asn Arg Pro Arg
        115                 120                 125

Asn Ile Tyr Gly Met Val Cys Tyr Ser Cys Leu Leu Ala Pro Pro Asn
    130                 135                 140

Thr Lys Glu Cys Val Gly Ala Thr Ser Gly Val Ser Ala His Ser Ser
145                 150                 155                 160

Ser Thr Ser Gly Gly Ser Thr Leu Ser Pro Phe Gln His Ala His Lys
                165                 170                 175

Glu Leu Ser Gly Gln Gly His Leu Ala Thr Ala Leu Ile Ile Ala Met
            180                 185                 190

Ser Thr Ile Phe Ile Met Ala Ile Ala Ile Val Leu Ile Ile Met Phe
        195                 200                 205

Tyr Ile Met Lys Thr Lys Pro Ser Ala Pro Ala Cys Cys Ser Ser Pro
    210                 215                 220

Pro Gly Lys Ser Ala Glu Ala Pro Ala Asn Thr His Glu Glu Lys Lys
225                 230                 235                 240

Glu Ala Pro Asp Ser Val Val Thr Phe Pro Glu Asn Gly Glu Phe Gln
```

```
            245                 250                 255
Lys Leu Thr Ala Thr Pro Thr Lys Thr Pro Lys Ser Glu Asn Asp Ala
            260                 265                 270

Ser Ser Glu Asn Glu Gln Leu Leu Ser Arg Ser Val Asp Ser Asp Glu
            275                 280                 285

Glu Pro Ala Pro Asp Lys Gln Gly Ser Pro Glu Leu Cys Leu Leu Ser
            290                 295                 300

Leu Val His Leu Ala Arg Glu Lys Ser Val Thr Ser Asn Lys Ser Ala
305                 310                 315                 320

Gly Ile Gln Ser Arg Arg Lys Lys Ile Leu Asp Val Tyr Ala Asn Val
                325                 330                 335

Cys Gly Val Val Glu Gly Leu Ser Pro Thr Glu Leu Pro Phe Asp Cys
                340                 345                 350

Leu Glu Lys Thr Ser Arg Met Leu Ser Ser Thr Tyr Asn Ser Glu Lys
                355                 360                 365

Ala Val Val Lys Thr Trp Arg His Leu Ala Glu Ser Phe Gly Leu Lys
                370                 375                 380

Arg Asp Glu Ile Gly Gly Met Thr Asp Gly Met Gln Leu Phe Asp Arg
385                 390                 395                 400

Ile Ser Thr Ala Gly Tyr Ser Ile Pro Glu Leu Leu Thr Lys Leu Val
                405                 410                 415

Gln Ile Glu Arg Leu Asp Ala Val Glu Ser Leu Cys Ala Asp Ile Leu
                420                 425                 430

Glu Trp Ala Gly Val Val Pro Pro Ala Ser Pro Pro Ala Ala Ser
                435                 440                 445

<210> SEQ ID NO 237
<211> LENGTH: 44
<212> TYPE: PRT
<213> ORGANISM: Homo sapiens

<400> SEQUENCE: 237

Ser Asn Cys Gly Glu Asn Glu Tyr Tyr Asn Gln Thr Thr Gly Leu Cys
1               5                   10                  15

Gln Glu Cys Pro Pro Cys Gly Pro Gly Glu Pro Tyr Leu Ser Cys
            20                  25                  30

Gly Tyr Gly Thr Lys Asp Glu Asp Tyr Gly Cys Val
            35                  40

<210> SEQ ID NO 238
<211> LENGTH: 43
<212> TYPE: PRT
<213> ORGANISM: Homo sapiens

<400> SEQUENCE: 238

Val Pro Cys Pro Ala Glu Lys Phe Ser Lys Gly Gly Tyr Gln Ile Cys
1               5                   10                  15

Arg Arg His Lys Asp Cys Glu Gly Phe Phe Arg Ala Thr Val Leu Thr
            20                  25                  30

Pro Gly Asp Met Glu Asn Asp Ala Glu Cys Gly
            35                  40

<210> SEQ ID NO 239
<211> LENGTH: 86
<212> TYPE: PRT
<213> ORGANISM: Homo sapiens

<400> SEQUENCE: 239
```

```
Ser Asn Cys Gly Glu Asn Glu Tyr Tyr Asn Gln Thr Thr Gly Leu Cys
1               5                   10                  15

Gln Glu Cys Pro Pro Cys Gly Pro Gly Glu Pro Tyr Leu Ser Cys
            20                  25                  30

Gly Tyr Gly Thr Lys Asp Glu Asp Tyr Gly Cys Val Pro Cys Pro Ala
            35                  40                  45

Glu Lys Phe Ser Lys Gly Gly Tyr Gln Ile Cys Arg Arg His Lys Asp
        50                  55                  60

Cys Glu Gly Phe Phe Arg Ala Thr Val Leu Thr Pro Gly Asp Met Glu
65                  70                  75                  80

Asn Asp Ala Glu Cys Gly
                85
```

<210> SEQ ID NO 240
<211> LENGTH: 44
<212> TYPE: PRT
<213> ORGANISM: Mus sp.

<400> SEQUENCE: 240

```
Ser Asn Cys Gly Glu Asn Glu Tyr His Asn Gln Thr Thr Gly Leu Cys
1               5                   10                  15

Gln Gln Cys Pro Pro Cys Arg Pro Gly Glu Pro Tyr Met Ser Cys
            20                  25                  30

Gly Tyr Gly Thr Lys Asp Asp Tyr Gly Cys Val
            35                  40
```

<210> SEQ ID NO 241
<211> LENGTH: 43
<212> TYPE: PRT
<213> ORGANISM: Mus sp.

<400> SEQUENCE: 241

```
Val Pro Cys Pro Ala Glu Lys Phe Ser Lys Gly Gly Tyr Gln Ile Cys
1               5                   10                  15

Arg Arg His Lys Asp Cys Glu Gly Phe Phe Arg Ala Thr Val Leu Thr
            20                  25                  30

Pro Gly Asp Met Glu Asn Asp Ala Glu Cys Gly
            35                  40
```

<210> SEQ ID NO 242
<211> LENGTH: 86
<212> TYPE: PRT
<213> ORGANISM: Mus sp.

<400> SEQUENCE: 242

```
Ser Asn Cys Gly Glu Asn Glu Tyr His Asn Gln Thr Thr Gly Leu Cys
1               5                   10                  15

Gln Gln Cys Pro Pro Cys Arg Pro Gly Glu Pro Tyr Met Ser Cys
            20                  25                  30

Gly Tyr Gly Thr Lys Asp Asp Asp Tyr Gly Cys Val Pro Cys Pro Ala
            35                  40                  45

Glu Lys Phe Ser Lys Gly Gly Tyr Gln Ile Cys Arg Arg His Lys Asp
        50                  55                  60

Cys Glu Gly Phe Phe Arg Ala Thr Val Leu Thr Pro Gly Asp Met Glu
65                  70                  75                  80

Asn Asp Ala Glu Cys Gly
                85
```

<210> SEQ ID NO 243

```
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Lys, Glu or Gln

<400> SEQUENCE: 243
```

Glu Val Xaa Leu Glu Glu Ser Gly Gly Gly Leu Val Lys Pro Gly Gly
1               5                   10                  15

Ser Arg Lys Leu Ser Cys Ala Ala Ser Gly Phe Thr Phe Ser Asp His
            20                  25                  30

Gly Met His Trp Val Arg Gln Ala Pro Glu Lys Gly Leu Glu Trp Ile
        35                  40                  45

Ala Tyr Ile Ser Ser Gly Ser Ser Asn Val Tyr Tyr Ser Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Glu Leu Leu Arg Phe Tyr Phe Asp Val Trp Gly Ala Gly
            100                 105                 110

Thr Thr Val Thr Val Ser Ser Ala Lys Thr Thr Pro Pro Ser Val
        115                 120                 125

```
<210> SEQ ID NO 244
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Lys, Glu or Gln

<400> SEQUENCE: 244
```

Glu Val Xaa Leu Glu Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ala Ile Tyr Tyr Ala Asp Thr Val
    50                  55                  60

Lys Gly Arg Phe Thr Ile Ser Arg Asp Asn Ala Lys Ser Thr Leu Phe
65                  70                  75                  80

Leu Gln Met Thr Ser Leu Arg Ser Glu Asp Thr Ala Met Tyr Tyr Cys
                85                  90                  95

Ala Arg Arg Glu Ile Leu Arg Tyr Tyr Phe Asp Val Trp Gly Ala Gly
            100                 105                 110

Thr Thr Val Thr Val Ser Ser Ala Lys Thr Thr Pro Pro Ser Val
        115                 120                 125

```
<210> SEQ ID NO 245
<211> LENGTH: 128
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Lys, Glu or Gln

<400> SEQUENCE: 245

Glu Val Xaa Leu Glu Glu Ser Gly Gly Gly Leu Val Gln Pro Gly Gly
1               5                   10                  15

Ser Leu Ser Leu Ser Cys Ala Thr Ser Gly Phe Pro Phe Ser Asp Tyr
            20                  25                  30

Tyr Met Thr Trp Ile Arg Gln Pro Pro Gly Lys Ala Leu Glu Trp Leu
        35                  40                  45

Ala Leu Ile Arg Asn Lys Ala Asn Gly Tyr Thr Thr Glu Asp Ser Pro
    50                  55                  60

Ser Val Lys Gly Arg Phe Ile Ile Ser Arg Asp Asp Ser Gln Arg Ile
65                  70                  75                  80

Leu Tyr Leu Gln Met Asn Ala Leu Arg Asp Glu Asp Ser Ala Thr Tyr
                85                  90                  95

Tyr Cys Ala Thr Val Gly Gly Tyr Tyr Arg Phe Pro Ser Trp Gly Gln
            100                 105                 110

Gly Thr Leu Val Thr Val Ser Ala Ala Lys Thr Thr Pro Pro Ser Val
        115                 120                 125

<210> SEQ ID NO 246
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Glu Val Pro Leu Glu Glu Ser Gly Gly Gly Leu Val Lys Pro Gly Gly
1               5                   10                  15

Ser Arg Lys Leu Ser Cys Ala Ala Ser Gly Phe Thr Phe Ser Asp His
            20                  25                  30

Gly Met His Trp Val Arg Gln Ala Pro Glu Lys Gly Leu Glu Trp Ile
        35                  40                  45

Ala Tyr Ile Ser Ser Gly Ser Ser Asn Val Tyr Tyr Ser Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Glu Leu Leu Arg Phe Tyr Phe Asp Val Trp Gly Gln Gly
            100                 105                 110

Thr Ser Val Thr Val Ser Ser Ala Lys Thr Thr Pro Pro Ser Val Tyr
        115                 120                 125

<210> SEQ ID NO 247
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Ile Glu Trp Ile
        35                  40                  45

Gly Glu Ile Asp Pro Ser Asp Ser Tyr Thr Tyr Tyr Asn Gln Lys Phe
    50                  55                  60

Lys Gly Lys Ala Thr Leu Thr Ile Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ser Arg Lys Asn Tyr Tyr Arg Gly Met Asp Tyr Trp Gly Gln Gly Thr
            100                 105                 110

Ser Val Thr Val Ser Ser Ala Lys Thr Thr Pro Pro Ser Val Tyr
            115                 120                 125
```

<210> SEQ ID NO 248
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

```
Glu Val Pro Leu Glu Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ala Ile Tyr Tyr Ala Asp Thr Val
    50                  55                  60

Lys Gly Arg Phe Thr Ile Ser Arg Asp Asn Ala Lys Ser Thr Leu Phe
65                  70                  75                  80

Leu Gln Met Thr Ser Leu Arg Ser Glu Asp Thr Ala Met Tyr Tyr Cys
                85                  90                  95

Ala Arg Arg Glu Ile Leu Arg Tyr Tyr Phe Asp Val Trp Gly Ala Gly
            100                 105                 110

Thr Thr Val Thr Val Ser Ser Ala Lys Thr Thr Pro Pro Ser Val Tyr
            115                 120                 125
```

<210> SEQ ID NO 249
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ser Asn Tyr
            20                  25                  30

Gly Val His Trp Ile Arg Gln Ser Pro Gly Lys Gly Leu Glu Trp Leu
        35                  40                  45
```

```
Gly Val Ile Trp Gly Gly Ser Thr Asp Tyr Asn Ala Ala Phe Ile
         50                  55                  60

Ser Arg Leu Ser Ile Ser Lys Asp Asn Ser Lys Ser Gln Val Phe
 65                  70                  75                  80

Lys Met Asn Ser Leu Gln Ala Asp Asp Thr Ala Ile Tyr Tyr Cys Ala
                 85                  90                  95

Ser Tyr Tyr Gly Tyr Tyr Asp Trp Phe Ala Tyr Trp Gly Gln Gly Thr
                100                 105                 110

Leu Val Thr Val Ser Ala Ala Lys Thr Thr Pro Pro Ser Val Tyr
            115                 120                 125

<210> SEQ ID NO 250
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Ser Phe Thr Gly Tyr
                20                  25                  30

Asn Met His Trp Val Lys Gln Ser His Gly Lys Ser Leu Glu Trp Ile
             35                  40                  45

Gly Tyr Ile Asp Pro Tyr Asn Gly Ala Thr Ser Lys Asn Gln Lys Phe
         50                  55                  60

Lys Gly Lys Ala Thr Leu Thr Val Asp Lys Ser Ser Thr Thr Ala Tyr
 65                  70                  75                  80

Ile Gln Leu Asn Ser Leu Thr Ser Glu Asp Ser Ala Val Tyr Tyr Cys
                 85                  90                  95

Ala Arg Tyr Tyr Tyr Gly Asp Tyr His Trp Tyr Phe Asp Val Trp Gly
                100                 105                 110

Ala Gly Thr Thr Val Thr Val Ser Ser Ala Lys Thr Thr Ala Pro Ser
            115                 120                 125

Val Tyr
    130

<210> SEQ ID NO 251
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid

<400> SEQUENCE: 251

Glu Val Xaa Leu Glu Glu Ser Gly Gly Gly Leu Val Gln Pro Gly Gly
 1               5                  10                  15

Ser Leu Ser Leu Ser Cys Ala Thr Ser Gly Phe Pro Phe Ser Asp Tyr
                20                  25                  30

Tyr Met Thr Trp Ile Arg Gln Pro Pro Gly Lys Ala Leu Glu Trp Leu
             35                  40                  45

Ala Leu Ile Arg Asn Lys Ala Asn Gly Tyr Thr Thr Glu Asp Ser Pro
         50                  55                  60
```

```
Ser Val Lys Gly Arg Phe Ile Ile Ser Arg Asp Asp Ser Gln Arg Ile
 65                  70                  75                  80

Leu Tyr Leu Gln Met Asn Ala Leu Arg Asp Glu Asp Ser Ala Thr Tyr
                 85                  90                  95

Tyr Cys Ala Thr Val Gly Gly Tyr Tyr Arg Phe Pro Ser Trp Gly Gln
                100                 105                 110

Gly Thr Thr Val Thr Val Ser Ala Ala Lys Thr Thr Pro Pro Ser Val
            115                 120                 125

Tyr
```

<210> SEQ ID NO 252
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid

<400> SEQUENCE: 252

```
Glu Val Xaa Leu Glu Glu Ser Gly Gly Gly Leu Val Lys Pro Gly Gly
 1               5                  10                  15

Ser Arg Lys Leu Ser Cys Ala Ala Ser Gly Phe Thr Phe Ser Asp Tyr
                20                  25                  30

Gly Met His Trp Val Arg Gln Ala Pro Glu Lys Gly Leu Glu Trp Val
            35                  40                  45

Ala Tyr Ile Ser Ser Gly Ser Ser Thr Ile Tyr Tyr Ala Asp Thr Val
 50                  55                  60

Lys Gly Arg Phe Thr Ile Ser Arg Asp Asn Ala Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Arg Glu Leu Leu Arg Tyr Tyr Phe Glu Tyr Trp Gly Gln Gly
                100                 105                 110

Thr Thr Leu Thr Val Ser Ser Ala Lys Thr Thr Pro Pro Ser Val Tyr
            115                 120                 125
```

<210> SEQ ID NO 253
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(6)
<223> OTHER INFORMATION: Any amino acid

<400> SEQUENCE: 253

```
Glu Val Gln Leu Xaa Xaa Ser Gly Ala Glu Leu Val Arg Pro Gly Thr
 1               5                  10                  15

Ser Val Lys Met Ser Cys Arg Ala Ala Gly Tyr Thr Phe Thr Asn Tyr
                20                  25                  30

Trp Ile Gly Trp Val Lys Gln Arg Pro Gly His Gly Leu Glu Trp Ile
            35                  40                  45

Gly Asp Ile Tyr Pro Gly Gly Leu Tyr Thr Asn Tyr Asn Glu Lys Phe
 50                  55                  60
```

```
Lys Asp Lys Ala Thr Leu Thr Ala Asp Thr Ser Ser Thr Ala Tyr
 65                  70                  75                  80

Met Gln Leu Ser Ser Leu Thr Ser Glu Asp Ser Ala Ile Tyr Tyr Cys
                 85                  90                  95

His Phe Tyr Asp Gly Asp Gln Tyr Ala Met Asp Tyr Trp Gly Gln Gly
                100                 105                 110

Thr Ser Val Thr Val Ser Ser Ala Lys Thr Thr Pro Pro Ser Val Tyr
            115                 120                 125

<210> SEQ ID NO 254
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(6)
<223> OTHER INFORMATION: Any amino acid

<400> SEQUENCE: 254

Glu Val Gln Leu Xaa Xaa Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Met Lys Gln Ser His Gly Lys Ser Leu Glu Trp Ile
        35                  40                  45

Gly Asn Ile Asn Pro Tyr Tyr Gly Ser Thr Asn Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ala Arg Gly Gly Val Arg Glu Leu Pro Gly Trp Phe Thr Tyr Trp Gly
                100                 105                 110

Gln Gly Thr Leu Val Thr Val Ser Ser Ala Ala Lys Thr Thr Pro Pro Ser
            115                 120                 125

Val Tyr
    130

<210> SEQ ID NO 255
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(6)
<223> OTHER INFORMATION: Any amino acid

<400> SEQUENCE: 255

Glu Val Gln Leu Xaa Xaa Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Met Lys Gln Ser His Gly Lys Ser Leu Glu Trp Ile
        35                  40                  45

Gly Asn Ile Asn Pro Tyr Tyr Gly Ser Thr Asn Tyr Asn Gln Lys Phe
 50                  55                  60
```

```
Lys Gly Lys Ala Thr Leu Thr Val Asp Lys Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ala Arg Gly Gly Val Arg Glu Leu Pro Gly Trp Phe Thr Tyr Trp Gly
            100                 105                 110

Gln Gly Thr Leu Val Thr Val Ser Ala Ala Lys Thr Thr Pro Pro Ser
            115                 120                 125

Val Tyr
    130

<210> SEQ ID NO 256
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(6)
<223> OTHER INFORMATION: Any amino acid

<400> SEQUENCE: 256

Glu Val Gln Leu Xaa Xaa Ser Gly Pro Glu Leu Val Lys Pro Gly Ala
1               5                   10                  15

Ser Val Lys Met Ser Cys Lys Ala Ser Gly Pro Ala Phe Thr Thr Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Tyr Thr Lys Tyr Asp Glu Lys Phe
    50                  55                  60

Arg Gly Lys Ala Thr Leu Thr Ser Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Ser Lys Ala Ala Tyr Tyr Val Gly Asn Ala Met Asp Ser Trp Gly
            100                 105                 110

Gln Gly Thr Ser Ile Thr Val Ser Ser Ala Lys Thr Thr Pro Pro Ser
            115                 120                 125

Val Tyr
    130

<210> SEQ ID NO 257
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(6)
<223> OTHER INFORMATION: Any amino acid

<400> SEQUENCE: 257

Glu Val Gln Leu Xaa Xaa Ser Gly Pro Glu Leu Val Lys Pro Gly Ala
1               5                   10                  15

Ser Val Lys Met Ser Cys Lys Ala Ser Gly Tyr Ser Phe Thr Gly Tyr
            20                  25                  30

Asn Met His Trp Val Lys Gln Ser His Gly Lys Ser Leu Glu Trp Ile
```

```
            35                  40                  45
Gly Tyr Ile Asp Pro Tyr Asn Gly Ala Thr Ser Asn Asn Gln Arg Phe
    50                  55                  60

Lys Gly Lys Ala Thr Leu Thr Ala Asp Lys Ser Ser Ser Thr Ala Tyr
65                  70                  75                  80

Ile Gln Leu Asn Ser Leu Thr Ser Glu Asp Ser Ala Phe Tyr Tyr Cys
                85                  90                  95

Val Arg Tyr Tyr Tyr Gly Asp Tyr His Trp Tyr Phe Asp Val Trp Gly
            100                 105                 110

Ala Gly Thr Thr Val Thr Val Ser Ser Ala Lys Thr Thr Pro Pro Ser
        115                 120                 125

Val Tyr
    130

<210> SEQ ID NO 258
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Glu Val Gln Leu Glu Glu Ser Gly Pro Glu Leu Val Lys Pro Gly Ala
1               5                   10                  15

Ser Val Arg Ile Ser Cys Lys Ala Ser Gly Tyr Ser Phe Thr Asp Tyr
            20                  25                  30

Trp Met His Trp Val Lys Gln Gly Pro Glu Lys Ser Leu Glu Trp Ile
        35                  40                  45

Gly Glu Ile Asn Pro Ser Thr Gly Gly Ile Ile Tyr Asn Gln Lys Phe
    50                  55                  60

Glu Ala Lys Ala Thr Leu Thr Val Asp Ile Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Thr Arg Ser Gly Gly Phe Pro Tyr Trp Gly Gln Gly Thr Leu Val Thr
            100                 105                 110

Val Ser Ala Ala Lys Thr Thr Pro Pro Ser Val Tyr
        115                 120

<210> SEQ ID NO 259
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(6)
<223> OTHER INFORMATION: Any amino acid

<400> SEQUENCE: 259

Xaa Val Gln Leu Xaa Xaa Ser Gly Ala Glu Leu Val Arg Pro Gly Thr
1               5                   10                  15

Ser Val Lys Met Ser Cys Lys Ala Gly Tyr Thr Phe Thr Asn Tyr
            20                  25                  30
```

```
Trp Ile Gly Trp Val Lys Gln Arg Pro Gly His Gly Leu Glu Trp Ile
            35                  40                  45

Gly Asn Ile Tyr Pro Gly Gly Tyr Thr Asn Tyr Asn Glu Lys Phe
 50                  55                  60

Lys Gly Lys Ala Thr Leu Thr Ala Asp Thr Ser Ser Ser Thr Ala Tyr
 65                  70                  75                  80

Met Gln Leu Ser Ser Leu Thr Ser Glu Asp Ser Ala Ile Tyr Tyr Cys
                 85                  90                  95

Ala Arg Arg Arg Gly Tyr Phe Asp Val Trp Gly Ala Gly Thr Thr Cys
                100                 105                 110

Thr Val Ser Ser Ala Lys Thr Thr Pro Pro Ser Val Tyr
            115                 120                 125
```

<210> SEQ ID NO 260
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 260

```
Cys His Phe Tyr Asp Gly Asp Gln Tyr Ala Met Asp Tyr Trp
 1               5                  10
```

<210> SEQ ID NO 261
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 261

```
Cys Ala Arg Arg Arg Gly Tyr Phe Asp Val Trp
 1               5                  10
```

<210> SEQ ID NO 262
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 262

```
Cys Ser Arg Lys Asn Tyr Tyr Arg Gly Met Asp Tyr Trp
 1               5                  10
```

<210> SEQ ID NO 263
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 263

```
Cys Ala Ser Lys Ala Ala Tyr Tyr Val Gly Asn Ala Met Asp Ser Trp
 1               5                  10                  15
```

<210> SEQ ID NO 264
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 264

Cys Thr Arg Ser Gly Gly Phe Pro Tyr Trp
1               5                   10

<210> SEQ ID NO 265
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Cys Ala Arg Gly Gly Val Arg Glu Leu Pro Gly Trp Phe Thr Tyr Trp
1               5                   10                  15

<210> SEQ ID NO 266
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Cys Ala Arg Gly Gly Val Arg Glu Leu Pro Gly Trp Phe Thr Tyr Trp
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Cys Ala Arg Tyr Tyr Tyr Gly Asp Tyr His Trp Tyr Phe Asp Val Trp
1               5                   10                  15

<210> SEQ ID NO 268
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Cys Val Arg Tyr Tyr Tyr Gly Asp Tyr His Trp Tyr Phe Asp Val Trp
1               5                   10                  15

<210> SEQ ID NO 269
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Cys Ala Arg Arg Glu Leu Leu Arg Phe Tyr Phe Asp Val Trp
1               5                   10

<210> SEQ ID NO 270

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Cys Ala Arg Arg Glu Ile Leu Arg Tyr Tyr Phe Asp Val Trp
1               5                   10

<210> SEQ ID NO 271
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Cys Ala Arg Arg Glu Leu Leu Arg Tyr Tyr Phe Glu Tyr Trp
1               5                   10

<210> SEQ ID NO 272
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Cys Ala Thr Val Gly Gly Tyr Tyr Arg Phe Pro Ser Trp
1               5                   10

<210> SEQ ID NO 273
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Cys Ala Ser Tyr Tyr Gly Tyr Tyr Asp Trp Phe Ala Tyr Trp
1               5                   10

<210> SEQ ID NO 274
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Cys Phe Gln Gly Ser His Val Pro Phe Thr Phe
1               5                   10

<210> SEQ ID NO 275
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Cys Gln His His Tyr Gly Thr Pro Tyr Thr Phe
```

<210> SEQ ID NO 276
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Cys Phe Gln Val Ser His Val Pro Tyr Thr Phe
1               5                   10

<210> SEQ ID NO 277
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Cys Leu Gln Ser Asp Asn Val Pro Leu Thr Phe
1               5                   10

<210> SEQ ID NO 278
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Cys Gln Gln Tyr Ser Lys Leu Pro Tyr Thr Phe
1               5                   10

<210> SEQ ID NO 279
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Cys Gln Gln Trp Ser Ser Tyr Pro Leu Thr Phe
1               5                   10

<210> SEQ ID NO 280
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Cys Gln Gln Tyr Ser Lys Leu Pro Pro Thr Phe
1               5                   10

<210> SEQ ID NO 281
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 281

Cys Ser Gln His Thr His Val Pro Pro Thr Phe
1               5                   10

<210> SEQ ID NO 282
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Cys Ser Gln Asn Thr His Val Pro Pro Thr Phe
1               5                   10

<210> SEQ ID NO 283
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Cys Gln Gln Gly Asn Thr Leu Pro Trp Thr Phe
1               5                   10

<210> SEQ ID NO 284
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Cys His Gln Gly Lys Thr Leu Pro Tyr Thr Phe
1               5                   10

<210> SEQ ID NO 285
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Cys Gln Gln Gly Asn Thr Leu Pro Tyr Thr Phe
1               5                   10

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gln Tyr Ser Asp Tyr Pro Leu Thr Phe
1               5

<210> SEQ ID NO 287
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 287

Cys Gln Gln Gly Ser Ser Ile Pro Arg Thr Phe
1               5                   10

<210> SEQ ID NO 288
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Cys Phe Gln Val Ser His Val Pro Tyr Thr Phe
1               5                   10
```

PREPARATION OF ISOLATED AGONIST ANTI-EDAR MONOCLONAL ANTIBODIES

CROSS REFERENCE TO RELATED APPLICATIONS

This application is continuation-in-part of U.S. application Ser. No. 13/260,937 filed Sep. 29, 2011 and which is a 35 U.S.C. §371 National Phase Entry Application of International Application No. PCT/IB2010/051385 filed Mar. 30, 2010, which designates the United States, and which claims benefit under 35 U.S.C. §119(a) of the prior International Application No. PCT/IB2009/05118 filed Mar. 30, 2009, the contents of which are incorporated herein by reference in their entirety.

SEQUENCE LISTING

The instant application contains a Sequence Listing which has been submitted via EFS-Web and is hereby incorporated by reference in its entirety. Said ASCII copy, named REVISED0216536942US, was filed with U.S. application Ser. No. 13/260,937 filed on Feb. 16, 2012 and is 219,917 bytes in size.

FIELD OF THE INVENTION

The present invention concerns the preparation of substantially purified agonist anti-EDAR monoclonal antibodies or isolated monoclonal antibody fragments or antigen binding portions or fragments thereof. The invention further relates to isolated agonist anti-EDAR monoclonal antibodies or isolated monoclonal antibody fragments or antigen binding portions or fragments thereof as well as their use in the treatment of X-linked hypohidrotic ectodermal dysplasia and tooth agenesis. The invention also relates to a pharmaceutical composition comprising said isolated agonist anti-EDAR monoclonal antibodies or isolated monoclonal antibody fragments or antigen binding portions or fragments thereof and to a method of treating X-linked hypohidrotic ectodermal dysplasia and tooth agenesis. Finally, the present invention concerns a pharmaceutical kit comprising said isolated agonist anti-EDAR monoclonal antibodies or isolated monoclonal antibody fragments or antigen binding portions or fragments thereof.

BACKGROUND OF THE INVENTION

The ectodermal dysplasias (EDs) are congenital, diffuse, and nonprogressive. The EDs comprise a large, heterogeneous group of inherited disorders that share primary defects in the development of 2 or more tissues derived from embryonic ectoderm. To date, more than 192 distinct disorders have been described. The most common EDs are X-linked hypohidrotic ectodermal dysplasia (Christ-Siemens-Touraine syndrome) and hidrotic ectodermal dysplasia (Clouston syndrome). The X-linked hypohidrotic ectodermal dysplasia is also known and hereinafter referred to as XLHED.

The tissues primarily involved are the skin, hair, nails, eccrine glands, and teeth. A reduction in the number of hair follicles in conjunction with structural hair shaft abnormalities may be seen.

Structural hair shaft abnormalities may result from aberrations in hair bulb formation and include longitudinal grooving, hair shaft torsion, and cuticle ruffling. Hair bulbs may be distorted, bifid, and small.

Eccrine sweat glands may be absent or sparse and rudimentary, particularly in patients with hypohidrotic ED.

Hypoplasia of the salivary and lacrimal glands may occur. In some patients, mucous glands may be absent in the upper respiratory tract and in the bronchi, esophagus, and duodenum.

Abnormal morphogenesis or absence of teeth may occur.

Abnormal nail plate formation may result in brittle, thin, ridged, or grossly deformed nails.

The mortality rate in early infancy (below 2 years old) approaches 30%. Morbidity and mortality is related to the absence or dysfunction of eccrine and mucous glands. Beyond early childhood, life expectancy ranges from normal to slightly reduced.

An activator protein, the ectodysplasin isoform A1 (Eda-A1, hereinafter referred to as EDA1) which is required for normal development of several ectodermally derived organs in humans and mice has been identified. This molecule is coded by the ectodysplasin gene (EDA) and belongs to the tumor necrosis factor family. The ectodysplasin gene codes for 2 proteins isoforms, EDA1 and EDA2, which bind to and activate two different receptors, EDA1 receptor (EDAR) and X-linked EDA1 receptor (XEDAR), respectively. The EDA1 receptor is hereinafter referred to as EDAR.

XLHED is characterized by the absence or the functional deficiency of EDA1, the ligand of EDAR.

Studies have been performed to characterize the origin of XLHED and to find appropriate treatments. Most of these studies have been done on Tabby mice which share many symptoms with human XLHED patients. The phenotype of Tabby mice, like in human XLHED patients, is caused by mutations in the EDA gene located on the X chromosome.

Different approaches have been studied to treat XLHED.

One of these approaches is the use of recombinant proteins containing the receptor-binding domain of Eda-A1 fused to the C-terminus of an IgG1 Fc domain. The publication "Permanent correction of an inherited ectodermal dysplasia with recombinant EDA", O. Gaide et al., Nature Medicine, vol. 9, number 5, pp 614-618, May 2003, describes the administration of recombinant EDA1 to developing embryos and newborn Tabby mice in order to correct the phenotype and provide a basis for a possible treatment of XLHED.

Such an approach is also described in US Patent 2005/152, 872 (Gaide et al.). In particular this document discloses a recombinant fusion protein containing an amino-acid sequence which comprises: (a) the Fc section or part of an Fc section of an immunoglobulin as component (A) or a functional variant of component (A); (b) the extracellular part of a TNF ligand or a partial sequence of the extracellular part of a TNF ligand as component (B) or a functional variant of component (B); and optionally (c) a transition area between component (A) and component (B), containing a linker.

Another approach is disclosed in U.S. Pat. No. 6,355,782 (Zonana et al.) and U.S. Pat. No. 7,115,555 (Zonana et al.). In these documents a nucleic acid sequence encoding a human EDA1, methods and compositions for increasing or decreasing the development of cells or tissues of ectodermal origin, such as hair, teeth, skin, and/or sweat glands, by altering EDA1 activity in a cell or tissue are described. EDA1 activity can be increased or decreased using the EDA1, dl and DL gene, cDNA and protein sequences (and variants, polymorphisms and mutants thereof), as well as anti-sense molecules and specific binding agents disclosed herein alone or with a pharmaceutical carrier.

Considering that antibodies are the most widely used type of therapeutic proteins, that the safety, long half-life, good bio-availability, ease of production and controlled cost of manufacturing for the antibodies are apparently well established, such an approach was envisioned in US 2003/0023991 (Zonana et al.). In particular this document describes DNA and amino acid sequences for the protein ligand (EDA1-II) and receptors (dl and DL) involved in ectodermal dysplasia. Also disclosed are variant DNA and amino acid sequences, and therapeutic applications of the ligands and receptors. Also described are different potential applications in which administration of antibody against EDAR (dl/DL) may be used. This application in particular describes the use of antagonists against dl/DL (EDAR receptor). According to this application, these antagonists can be used to reduce hair growth, for example in the treatment of hirsutism, to inhibit tooth development, such as ectopic teeth, to selectively eliminate sweat glands, for example on the upper lip or under the arm, and to inhibit breast epithelial cell proliferation, for example in the treatment of breast cancer or other trauma of the skin. Finally, the production and use of monoclonal or polyclonal antibodies are envisioned. However, no specific sequences of antibodies against EDAR either agonists or antagonists are described in this document. No working examples are provided in order to evidence that monoclonal or polyclonal antibodies are biologically active, effective and functional.

It might be stated that the selection of monoclonal antibodies is a routine work for a person skilled in the art. However, one cannot acknowledge that the preparation and obtainment of isolated agonist anti-EDAR monoclonal antibodies was routine and does not involve inventive step. For example, the CH11 monoclonal antibody directed against human Fas, another TNF receptor family member, was obtained by immunization of mice with membranes of FS-7 human fibroblasts (Yonehara et al, 1989, J. Exp. Med 169. 1747-1756). CH11 is an IgM. When an IgG1 recognizing the exact same epitope (mAb ZB4) or a divalent Fab'2 of CH11 was used, there was no agonist activity (Fadeel et al, 1997, Int Immunol 9, 201-209). A second example of an agonist monoclonal antibody against human Fas is APO-1. The APO-1 monoclonal antibody against human Fas was obtained by immunizing mice with plasma membrane of the human SKW 6.4 cell line (Trauth et al, 1989, Science 245, 301-305). This antibody is an IgG3. Upon isotype switch, this antibody looses its agonist activity (Dhein et al, 1992, J. Immunol 149, 3166-3173), although the Fas-binding portion of the antibody remains the same. This result was tentatively explained by the propensity of IgG3 to self-aggregate. These two examples indicate that the obtainment of agonist monoclonal antibodies against a TNF receptor family member is absolutely not trivial to a skilled in the art.

In the context of the present invention, Applicants had to face several problems as follows:

Commercial polyclonal anti-EDAR antibodies (raised in the goat, from R&D Systems) failed to induce death of EDAR:Fas-transduced Jurkat cells. One could believe that the polyclonal antibody preparations were made of a mixture of antibodies with various activities (agonist, antagonist, etc.). It was therefore Applicant's disappointment to observe that the cell-based assay did not reveal any agonist activity, even when using a large quantity of antibody. These results were not encouraging for the development of agonist anti-EDAR monoclonal antibodies.

The development of an EDA1-dependent biological assay was found difficult for several reasons. First, there are only few cell lines, which endogenously express EDAR (one example is the human keratinocyte cell line HaCat). Several human, mouse and rat keratinocyte cell lines were screened for EDAR expression. This was done by staining cells with Fc-EDA1 and the anti-EDAR mAb, as detected by flow cytometry. None of the cell lines was found to express detectable levels of EDAR. Second, an NF-κB-dependent read-out system was found not satisfying (phosphorylation and degradation of IκBα), because it was neither quantitative, nor fully reproducible. In order to overcome these limitations, it was finally attempted to introduce in EDAR-transfected fibroblasts a reporter gene (e.g. luciferase) under the control of the NF-κB promoter. However, this system was also found not to result in a biological activity assay working properly (low signal to noise ratio and low sensitivity). Therefore the use of the techniques known to the skilled in the art was not found satisfactory.

The naturally occurring soluble EDA1 protein is probably a multimer of trimers (Swee et al, J. Biol. Chem. 284: 27267-76, 2009), and Fc-EDA1 is an hexameric ligand. As it has been extensively documented for Fas, the Applicants have obtained evidence that the simultaneous engagement and clustering of multiple EDAR receptors was necessary for biological activity (Swee et al, J. Biol. Chem. 284:27267-76, 2009). By contrast, anti-EDAR antibodies are only divalent. It was therefore not likely that this molecular format would be as biologically active as Fc-EDA1.

No convenient animal model was available. Without the identification of a convenient strain of mice (EDAR-deficient mice), the development of antibodies according to the invention would have been considerably hampered. It is assumed that in the absence of Applicant's proposed animal model and specific preparation process, anti-EDAR monoclonal antibodies with agonist properties would have not been obtained (i.e. because they would have had distinct binding sites on EDAR).

However, there is a need for more effective treatment for XLHED and for increasing the quality of life of those suffering from this disease. In particular no curative treatment of children, young adults or adults suffering from ectodermal dysplasia such as XLHED or tooth agenesis is presently available.

The aim of the present invention is to provide a new process for the preparation of substantially purified and isolated agonist anti-EDAR monoclonal antibodies that are biologically active, effective and functional. The present invention also allows to rapidly discriminating the best agonist anti-EDAR monoclonal antibodies. The present invention also demonstrates that the use of agonist anti-EDAR monoclonal antibodies represent drug candidates for the treatment of the XLHED or related diseases.

These and other objects as will be apparent from the foregoing have been achieved by the present invention.

SUMMARY OF THE INVENTION

In a first embodiment, the present invention concerns a method for producing agonist anti-EDAR monoclonal antibodies or isolated monoclonal antibody fragments or antigen binding portions or fragments thereof comprising the steps of:
a) producing EDAR antigen, or EDAR fragment, or EDAR fusion protein of mouse and/or human and/or vertebrate species
b) immunizing EDAR-deficient mice with said EDAR antigen or EDAR fragment, or EDAR fusion protein c) detection of anti-EDAR antibodies in the serum of said EDAR antigen or EDAR fragment, or EDAR fusion protein-immunized EDAR-deficient mice d) producing hybridomas between lymph node cells from EDAR antigen or EDAR fragment, or EDAR fusion protein-immunized, EDAR-deficient mice and myeloma cells e) identifying agonist anti-EDAR antibodies or isolated monoclonal antibody fragments or antigen binding portions or fragments thereof recognizing human and/or mouse EDAR and/or EDAR from vertebrate species
  i. by binding assays designed to detect binding between the said agonist anti-EDAR antibodies or isolated monoclonal antibody fragments or antigen binding portions or fragments thereof and human and/or mouse EDAR antigen or EDAR fragment, or EDAR fusion protein; and
  ii. for their ability to induce a biological response in vitro in cells or tissues expressing EDAR or an EDAR fusion protein.
  iii. for their ability to induce a biological response in vivo in organisms expressing EDAR or EDAR fusion proteins.

f) selecting hybridomas lines for the agonist anti-EDAR monoclonal antibodies they produce on the basis of steps e) ii and e) iii g) cloning and sub-cloning of said selected hybridoma lines h) purifying the resulting agonist anti-EDAR monoclonal antibodies or isolated monoclonal antibody fragments or antigen binding portions or fragments thereof.

In a second embodiment, the present invention provides isolated agonist anti-EDAR monoclonal antibodies or isolated monoclonal antibody fragments or antigen binding portions or fragments thereof obtainable by this process, and wherein said isolated agonist anti-EDAR monoclonal antibodies or isolated monoclonal antibody fragments or antigen binding portions or fragments thereof bind to human and/or mouse EDAR with an affinity (KD) of at least $10^{-8}$ M for the Fab fragment. In addition, the said isolated agonist anti-EDAR monoclonal antibodies or isolated monoclonal antibody fragments or antigen binding portions or fragments thereof that cross-react with mouse EDAR induce tail hair formation and/or sweat gland formation with an EC50 of less than 20 mg/kg when administered to newborn Tabby mice, as described in example 7.

Also disclosed are the isolated nucleic acid molecules encoding the isolated agonist anti-EDAR monoclonal antibodies or isolated monoclonal antibody fragments or antigen binding portions or fragments thereof of the invention as well as an expression vector comprising at least one copy of said nucleic acid molecules.

Host cells comprising the expression vector of the invention, hybridoma secreting the isolated agonist anti-EDAR monoclonal antibodies or isolated monoclonal antibody fragments or antigen binding portions or fragments thereof and transgenic non-human animals having a genome comprising said isolated nucleic acid molecule and/or the expression vector are also disclosed.

Furthermore, the present invention relates to a pharmaceutical composition comprising the isolated agonist anti-EDAR monoclonal antibodies or isolated monoclonal antibody fragments or antigen binding portions or fragments thereof of the present invention, and a pharmaceutically acceptable carrier.

A further object of the invention concerns the use of the isolated agonist anti-EDAR monoclonal antibodies or isolated monoclonal antibody fragments or antigen binding portions or fragments thereof or the pharmaceutical composition, for the preparation of a medication for modulating the development of cells or tissues of ectodermal origin, such as hair, teeth, skin, sweat glands, sebaceous glands, larynx and trachea mucus-producing cells, Meibomian glands, preputial glands, mammary glands and salivary glands.

Another object of the invention comprises the use of the isolated agonist anti-EDAR monoclonal antibodies or isolated monoclonal antibody fragments or antigen binding portions or fragments thereof or the pharmaceutical composition, in the manufacture of a medicament for the reconstitution of the skin or for modifying hair morphology.

Also provided is a method of increasing the development of one or more hair follicle, tooth, sweat gland, sebaceous glands, larynx and trachea mucus-producing cells, Meibomian glands, preputial glands, mammary glands and salivary glands in a tissue, comprising administering to a subject in need thereof, the isolated agonist anti-EDAR monoclonal antibodies or isolated monoclonal antibody fragments or antigen binding portions or fragments thereof or the pharmaceutical composition of the invention.

Finally, the present invention concerns a pharmaceutical kit comprising at least an effective amount of the isolated agonist anti-EDAR monoclonal antibodies or isolated monoclonal antibody fragments or antigen binding portions or fragments thereof or the pharmaceutical composition of the invention, together with instructions for use.

Other objects and advantages will become apparent to those skilled in the art from a review of the ensuing detailed description, which proceeds with reference to the following illustrative drawings, and the attendant claims.

BRIEF DESCRIPTION OF THE FIGURES

FIG. 3. Determination of the amino acid sequences and nucleotide sequences of the variable domain of the heavy chains of anti-EDAR monoclonal antibodies mAbEDAR1, 2, 3, 5, 6, 7, 8, 9, 10, 11, 12, 13, 14 and 15. Sequences start at the mature N-terminus of the heavy chain. The CDR are shown in bold and underlined.

Figure 4A:
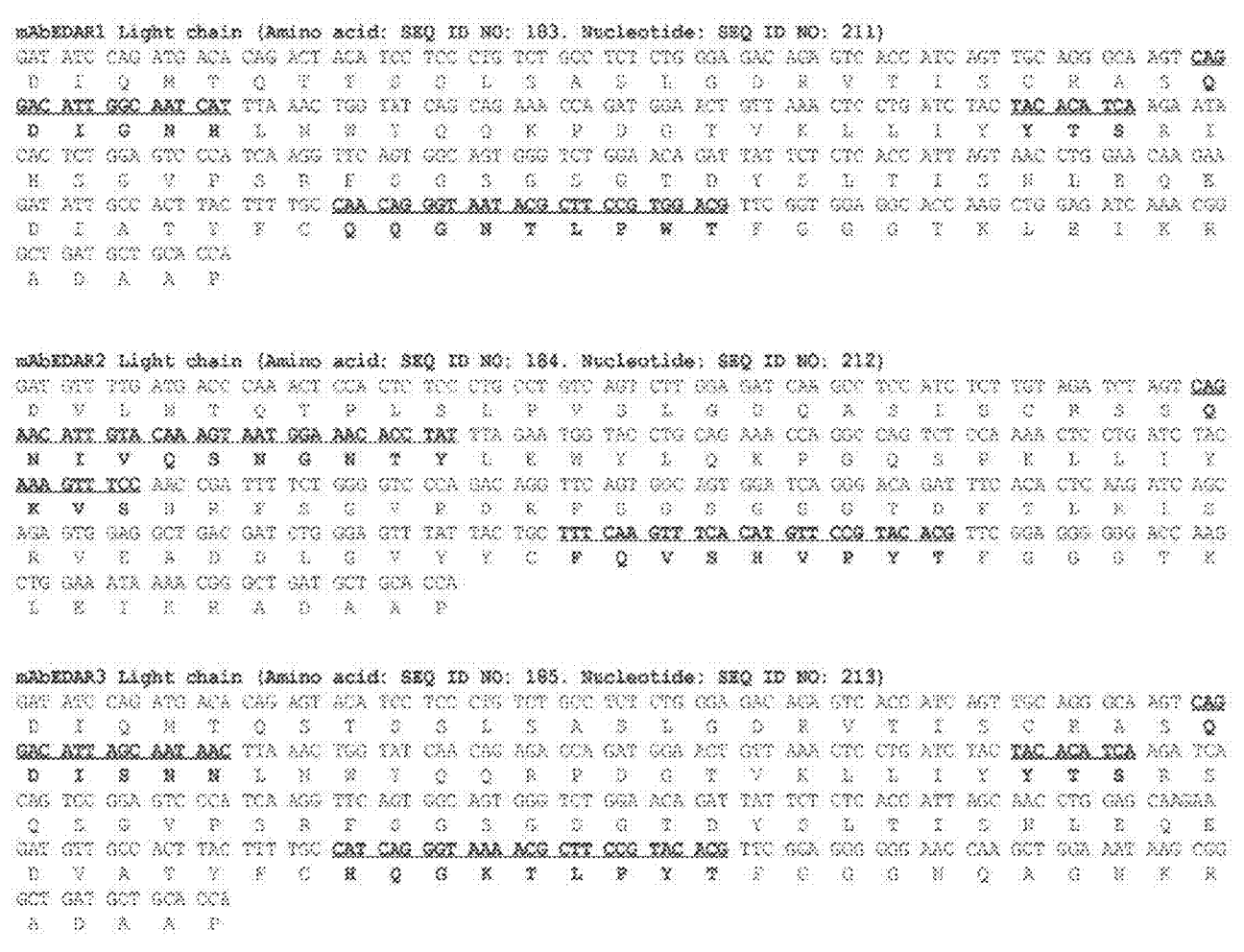
Figure 4B:
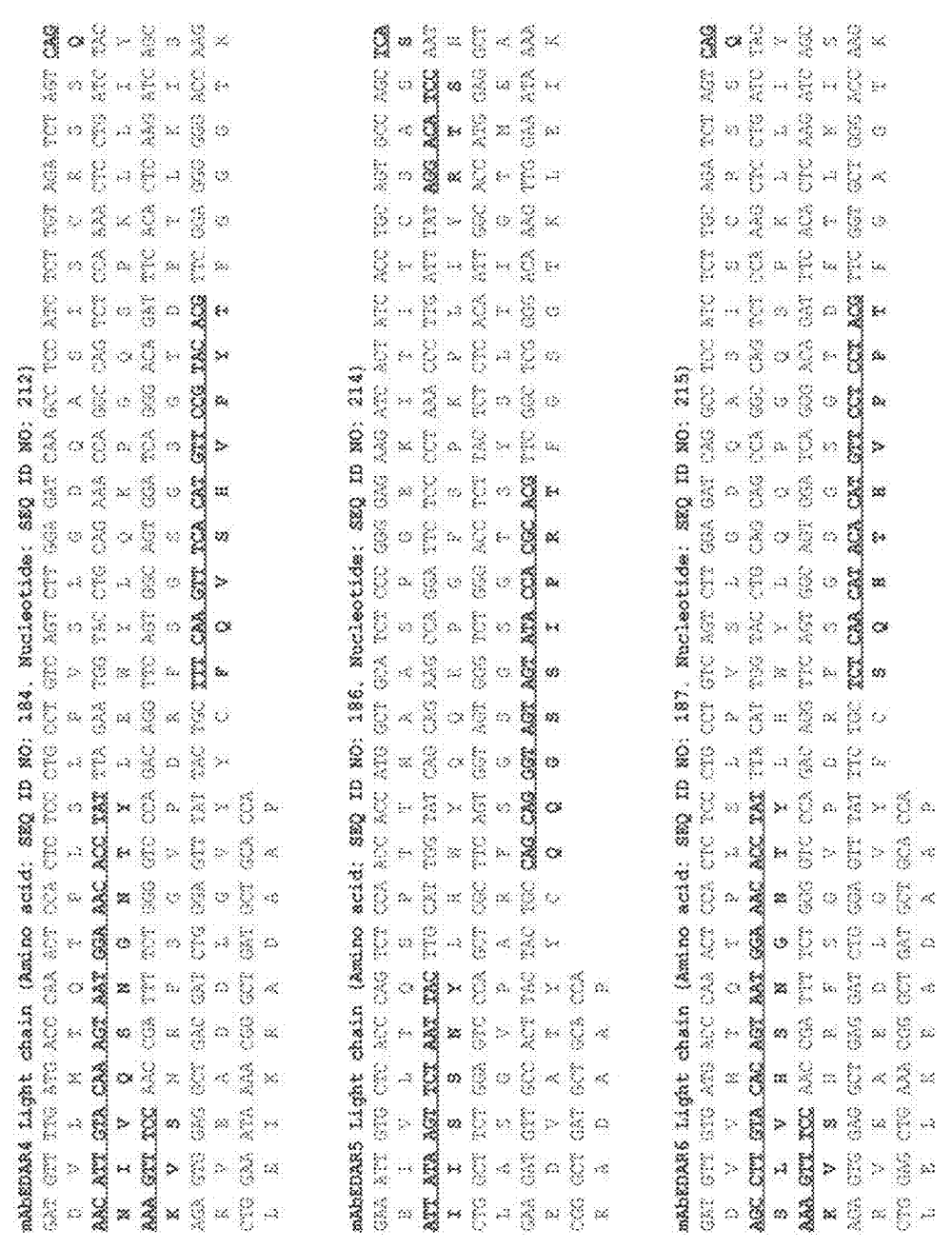
Figure 4C:
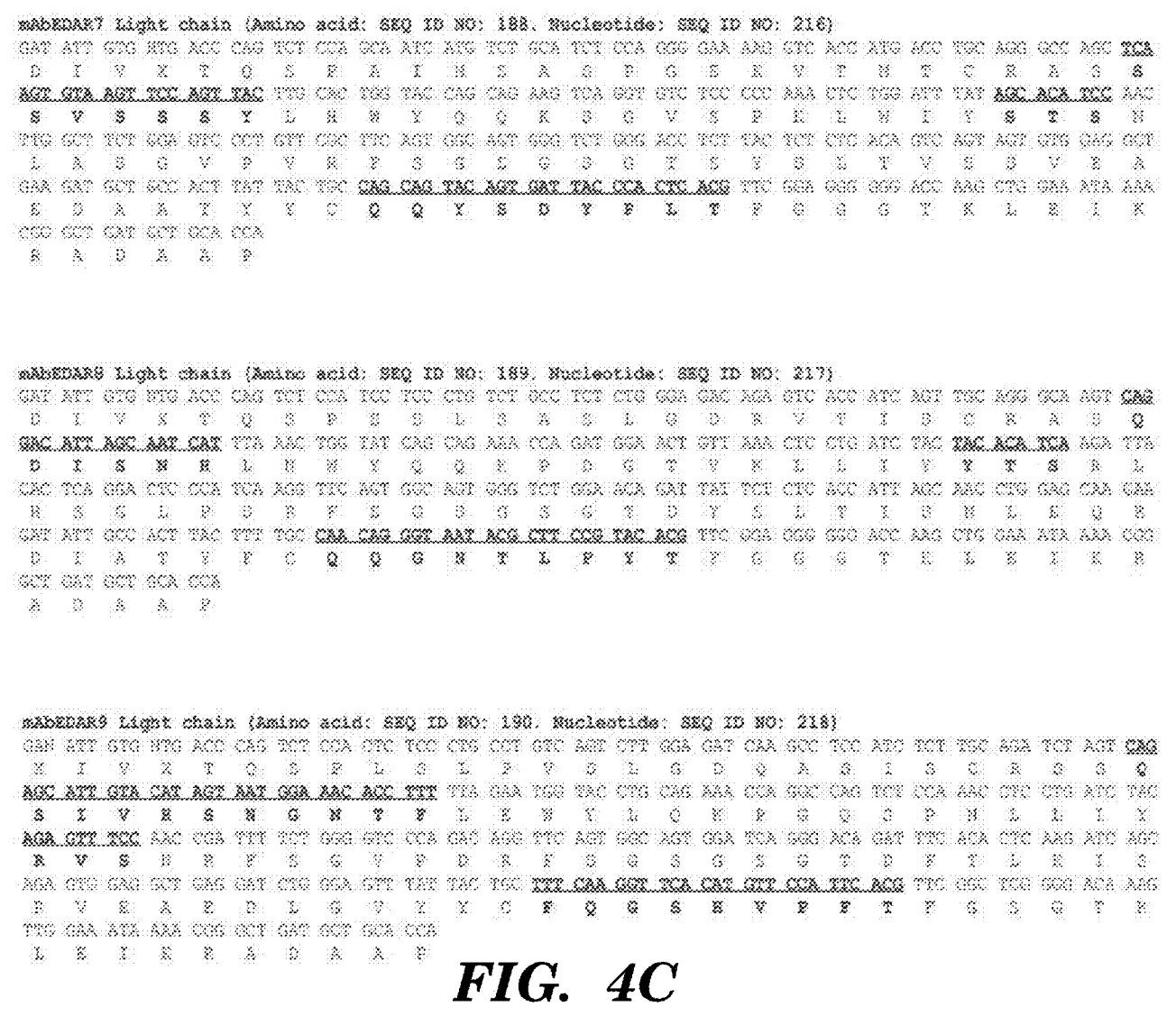
Figure 4D:
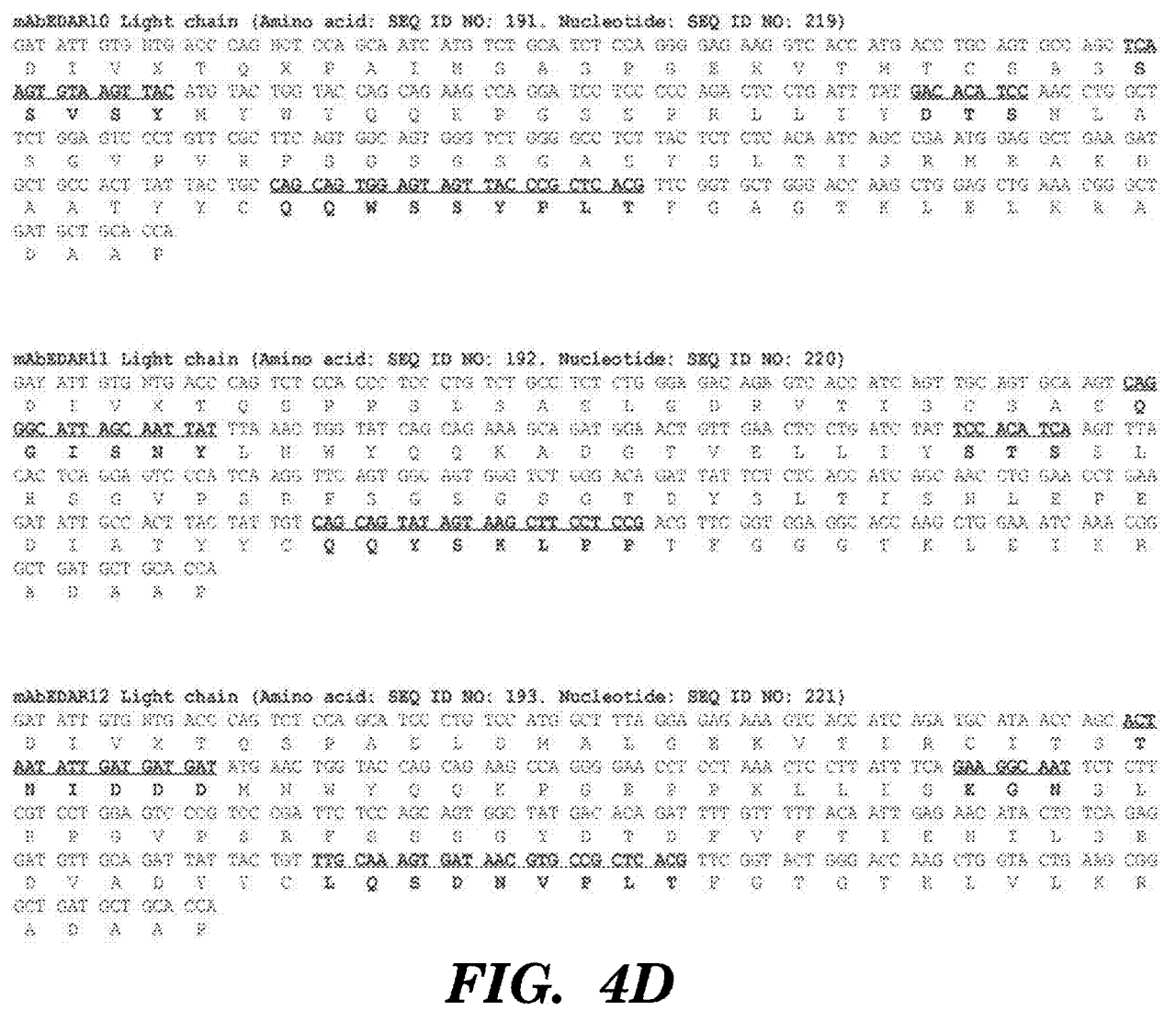
Figure 4E:
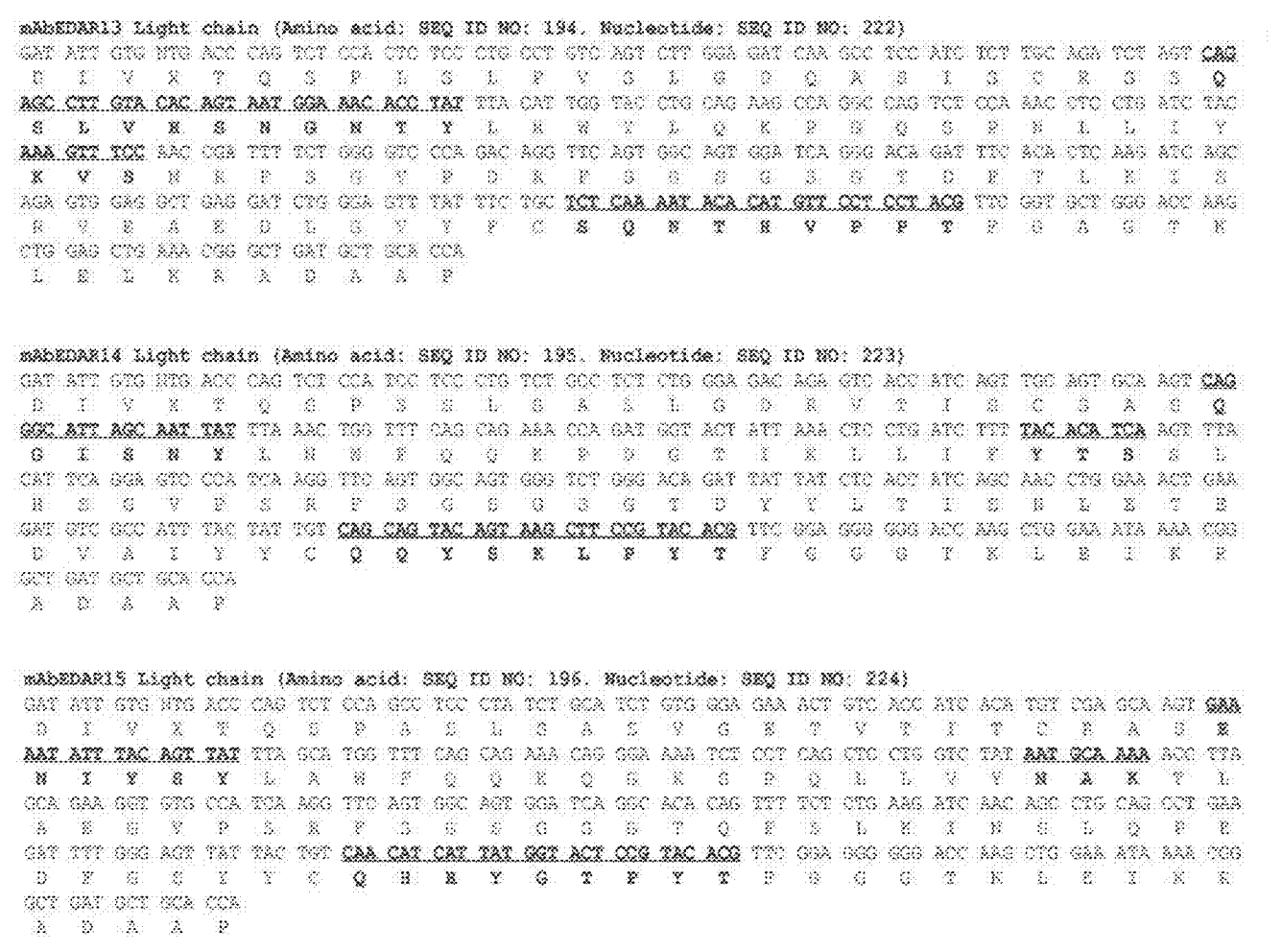

FIG. 4. Determination of the amino acid sequences and nucleotide sequences of the variable domain of the light chains of anti-EDAR monoclonal antibodies mAbEDAR1, 2, 3, 4, 5, 6, 7, 8, 9, 10, 11, 12, 13, 14 and 15. Sequences start at the mature N-terminus of the light chain. The CDR are shown in bold and underlined.

FIG. 5. Alignment of the amino acid sequences of heavy and light chains of anti-EDAR monoclonal antibodies mAbEDAR1 (heavy chain SEQ ID NO: 246, light chain SEQ ID NO: 183), 2 (heavy chain SEQ ID NO: 247, light chain SEQ ID NO: 18, 3 (heavy chain 248, light chain SEQ ID NO: 185, 4 (light chain SEQ ID NO: 184), 5 (heavy chain SEQ ID NO: 249, light chain SEQ ID NO: 186), 6 (heavy chain SEQ ID NO: 250, light chain SEQ ID NO: 187), 7 (heavy chain SEQ ID NO: 251, light chain SEQ ID NO: 188), 8 (heavy chain SEQ ID NO: 252, light chain SEQ ID NO: 189), 9 (heavy chain SEQ ID NO: 253, light chain SEQ ID NO: 190), 10 (heavy chain SEQ ID NO: 254, light chain SEQ ID NO: 191), 11 (heavy chain SEQ ID NO: 255, light chain SEQ ID NO: 192), 12 (heavy chain SEQ ID NO: 256, light chain SEQ ID NO: 193), 13 (heavy chain SEQ ID NO: 257, light chain SEQ ID NO: 195), 14 (heavy chain SEQ ID NO: 258, light chain SEQ ID NO: 195) and 15 (heavy chain SEQ ID NO: 259, light chain SEQ ID NO: 196). Sequences start at the mature N-terminus. CDRs are highlighted in large boxes. Putative junctions of the protein sections encoded by the V, D and J genes, or by randomly added nucleotides (N) are indicated. The junction with the constant region (C) is also shown. Heavy and light chains of mAbEDARs 1, 2, 3, 4, 5 and 6 were resolved by SDS-PAGE, digested with 20 trypsin and analyzed by liquid chromatography coupled to mass-spectrometry (LC-msms). Peptides identified by LC-ms-ms are indicated. mAbEDAR1, 2, 3, 4, 7, 8, 9, 10, 11, 12, 13, 14 and 15 are IgG1, mAbEDAR5 is an IgG2b, mAbEDAR6 is an IgG2a.

Figure 1:
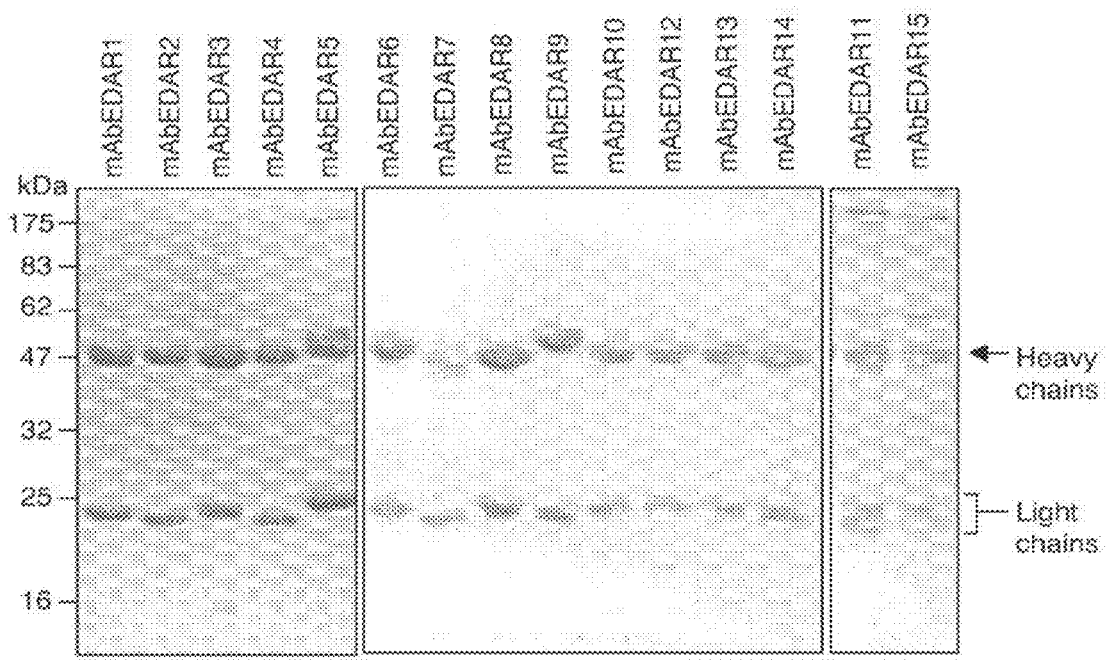
FIG. 1. Sodium dodecyl sulphate polyacrylamide gel electrophoresis (SDS-PAGE) analysis of anti-EDAR mAb purified by protein G affinity chromatography. Anti-EDAR mAb were purified by protein G affinity chromatography from culture supernatant in serum-free medium (mAbEDARs1-4, 6-10, 12-14) or in serum-containing medium (mabEDAR5, 11 and 15). Purified material (10 μg/lane) was analyzed by Coomassie Blue staining of SDS-PAGE run under reducing conditions. Molecular weight standards were run on the far left lane, with their corresponding sizes indicated in kDa. It shows that the purified anti-EDAR mAb have classical characteristics of mAb (it was purified on protein G and it was made of a heavy and a light chain with the expected sizes of about 50 and 25 kDa).
Figure 2:
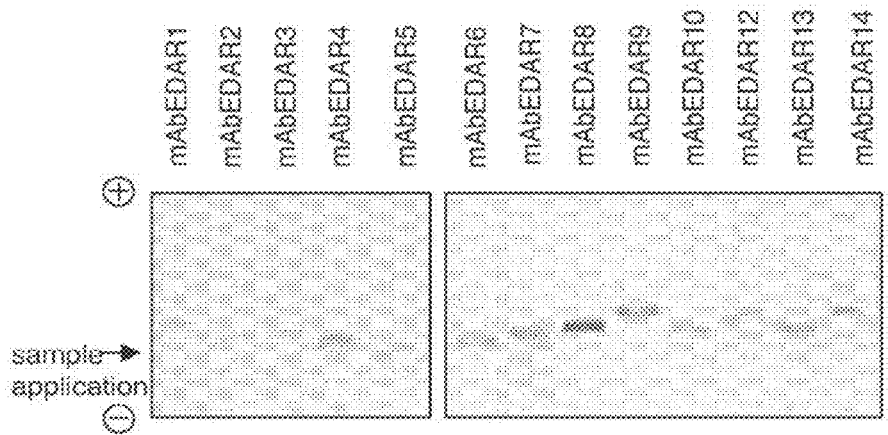
FIG. 2. Native gel electrophoresis of anti-EDAR mAb. 4 μg of protein G-purified anti-EDAR antibodies were analyzed by native gel electrophoresis (BIOMIDI, Ref KGMP) and stained with amidoblack according to manufacturer's instructions, except that the electrophoresis was performed for 1 h. This shows that the various mAbEDARs differ in their isoelectric points.

This figure shows that mabEDAR1-15 are all different, although the light chains of mAbEDAR2 and mAbEDAR4 are identical, and the heavy chains of mAbEDAR10 and mAbEDAR11 are identical. mAbEDAR1, mAbEDAR3 and mAbEDAR8 have similar heavy chains, most probably originating from the same $V_H$ gene, and similar light chains, most probably originating from the same $V_L$ gene.

FIG. 6. Specific binding of the anti-EDAR mAb to both mouse and human EDAR. Graded concentrations of mAbEDAR1-4 or of a control mAb (Aprily 5) were added to wells of a 96-well ELISA plate coated with 100 µl of 1 µg/ml of human EDAR-Fc, mouse EDAR-Fc, human Fas-Fc or Flag-human APRIL. Bound antibodies were revealed by the addition of anti-mouse IgG coupled to HRP, followed by substrate. The absorbance was measured at 490 nm.

This figure shows that the four anti-EDAR mAb bind to both human EDAR (panel A) and mouse EDAR (panel B). In addition, their binding specificity is established by showing that they fail to bind human Fas-Fc (panel C). An irrelevant, isotype matched mAb, Aprily-5, recognizes APRIL but none of the EDAR-Fc molecules (panel D). Samples of the EDAR-Fc and Fas-Fc (5 µg) used for the experiment were submitted to non-reducing SDS-PAGE and Coomassie Blue staining (panel E).

FIG. 7. Use of anti-EDAR mAb in Western blotting. (A) Purified human EDAR-Fc, mouse EDAR-Fc, human Fas-Fc (see FIG. 6E) and Flag-human April were run on a 12% SDS-PAGE under reducing or non-reducing conditions, transferred onto nitrocellulose membrane and probed with mAbEDAR1-4 or with Aprily5 as indicated.

It shows that the anti-EDAR mAb mAbEDAR1, 2, 3 and 4 recognized both human and mouse EDAR immobilized on nitrocellulose, but only under non-reducing conditions, suggesting that intact disulfide bonds are required for EDAR recognition. The weaker signal obtained with mouse EDAR might be explained by the lower amount of mouse EDAR-Fc loaded on the gel. Binding specificity is established by showing that none of the mAbEDARs does bind to Fas-Fc and Flag-human APRIL (while Flag-human APRIL is recognized by an anti-APRIL mAb). (B) Bovine serum albumin (BSA, 2 µg), purified human EDAR-Fc (20 ng) and purified hFas-Fc (20 ng) were resolved on a 12% SDS-PAGE under reducing or non-reducing conditions, transferred onto nitrocellulose membrane and probed with mAbEDAR1-15. The band recognized by mAbEDAR5 in the BSA lane is probably due to a cross-contamination of EDAR-Fc in the neighboring lane.

These figures show that all mAbEDARs specifically recognize human EDAR-Fc and not Fas-Fc under non-reducing conditions. It further shows that mAbEDAR5, 6 and 12 also recognize reduced EDAR.

FIG. 8. Anti-EDAR mAb do not compete with Fc-EDA1 for binding to EDAR. (A, B, C) Wells of ELISA plates were coated with hEDAR-Fc, blocked with milk, and incubated with graded concentrations of mAbEDAR1, 2, 3, 4, Aprily5 or Fc-EDA1 used as competitors, as indicated. Thereafter, a constant amount of biotinylated mAbEDAR1, 2, 3 or 4, (A) or of Flag tagged-EDA1 (B) was added as indicated. The binding of biotinylated mAbEDARs was revealed with horseradish peroxydase-coupled streptavidin, and the binding of Fc-EDA1 was revealed with biotinylated anti-Flag antibody (M2) and horseradish peroxydase-coupled streptavidin. The binding of mAbEDAR1, 2, 3 and 4 was also revealed directly using horseradish peroxydase-coupled anti-mouse antibody (C). Following substrate addition, the absorbance was monitored at 490 nm.

This figure shows that there is no competition between anti-EDAR mAb and Fc-EDA1 for binding to EDAR, meaning that the anti-EDAR mAb and Fc-EDA1 bind to different sites on EDAR. The figure also shows that mAbEDAR1, 2, 3 and 4 compete with each other for EDAR binding, with mAbEDAR1 having the greatest binding efficacy.

Figure 9A:
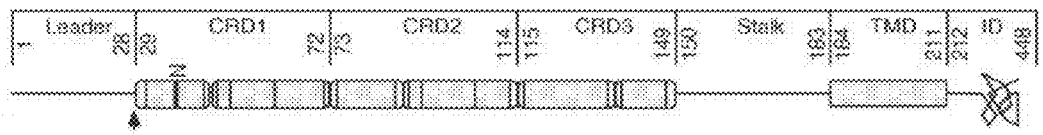
Figure 9B:
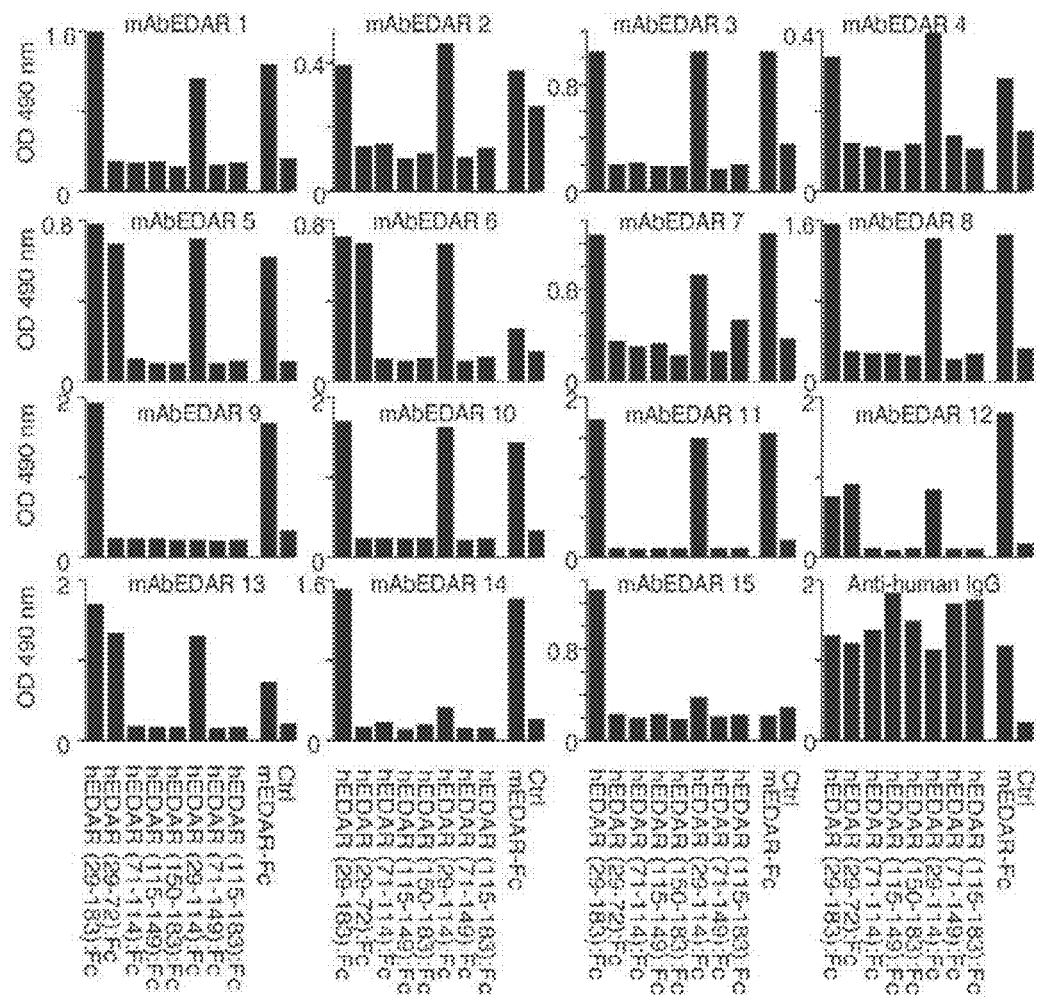

FIG. 9. Epitope mapping of anti-EDAR monoclonal antibodies on recombinant human EDAR by ELISA. (A) Schematic linear representation of human EDAR showing the position of cystein residues (thin horizontal lines), of the putative N-linked glycosylation site (thick horizontal line, N), of the six structural modules (rectangles with rounded corners) composing the three cystein-rich domains (CRD1, CRD2, CRD3), of the transmembrane domain (rectangle, TMD), of the signal peptide (Leader), of the stalk and of the intracellular domain (ID). Amino acid numbers at the junctions of interest are indicated. The arrow indicates the predicted cleavage site of the signal peptide. The scheme is drawn to scale, except for the intracellular domain. (B) Wells of ELISA plates were coated with goat anti-human IgG antibody, blocked, and further incubated with human EDAR-Fc, mouse EDAR-Fc or the indicated human EDAR-Fc truncation proteins in cell supernatants of transfected cells. One well was also left without cell supernatant (Ctrl). The efficient capture of the various EDAR-Fc proteins was controlled using horseradish peroxydase-coupled donkey anti-human IgG antibody. Binding of mAbEDARs were monitored with horseradish peroxydase-coupled anti-mouse IgG antibody.

This figure shows that mAbEDAR1, 2, 3, 4, 7, 8, 10 and 11 recognize an epitope in CRD1 and CRD2 (but not CRD1 or CRD2 taken alone), that mAbEDAR5, 6, 12 and 13 recognize an epitope that is entirely comprised in CRD1, and that mAbEDAR9, 14, and 15 recognize the full extracellular domain of EDAR, but not fusion proteins containing any combination of two adjacent CRDs. All mAbEDARs recognize both human and mouse EDAR, with the exception of mAbEDAR15 that recognizes human EDAR but not mouse EDAR.

Figure 10:
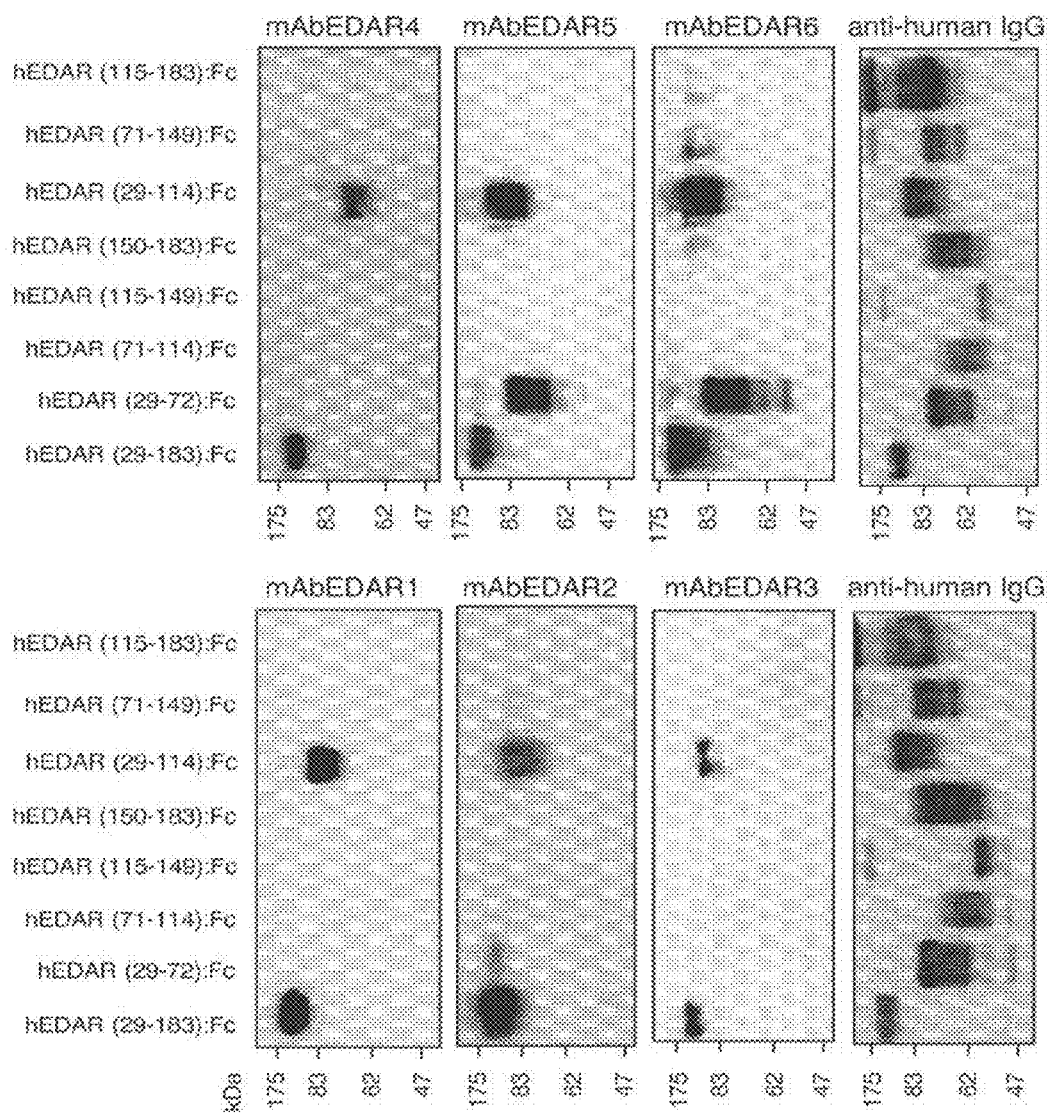

FIG. 10. Epitope mapping of anti-EDAR monoclonal antibodies on recombinant human EDAR by Western blot. The indicated EDAR-Fc truncation proteins present in supernatants of transfected cells were resolved by 12% SDS-PAGE under non-reducing conditions and transferred onto nitrocellulose. After saturation with irrelevant milk proteins, membranes were revealed with mAbEDAR1, 2, 3, 4, 5 or 6 at 1 µg/ml followed by horseradish peroxydase-coupled anti-mouse IgG antibody or with horseradish peroxydase-coupled anti-human IgG antibody. Positions of molecular weight standards (in kDa) are indicated on the left.

This figure shows that the EDAR-Fc truncation mutants are present on the membrane in roughly comparable amounts. mAbEDAR1, 2, 3 and 4 recognize an epitope overlapping CRD1 and CRD2, whereas mAbEDAR5 and 6 recognize an epitope that is entirely comprised in CRD1.

Figure 11:
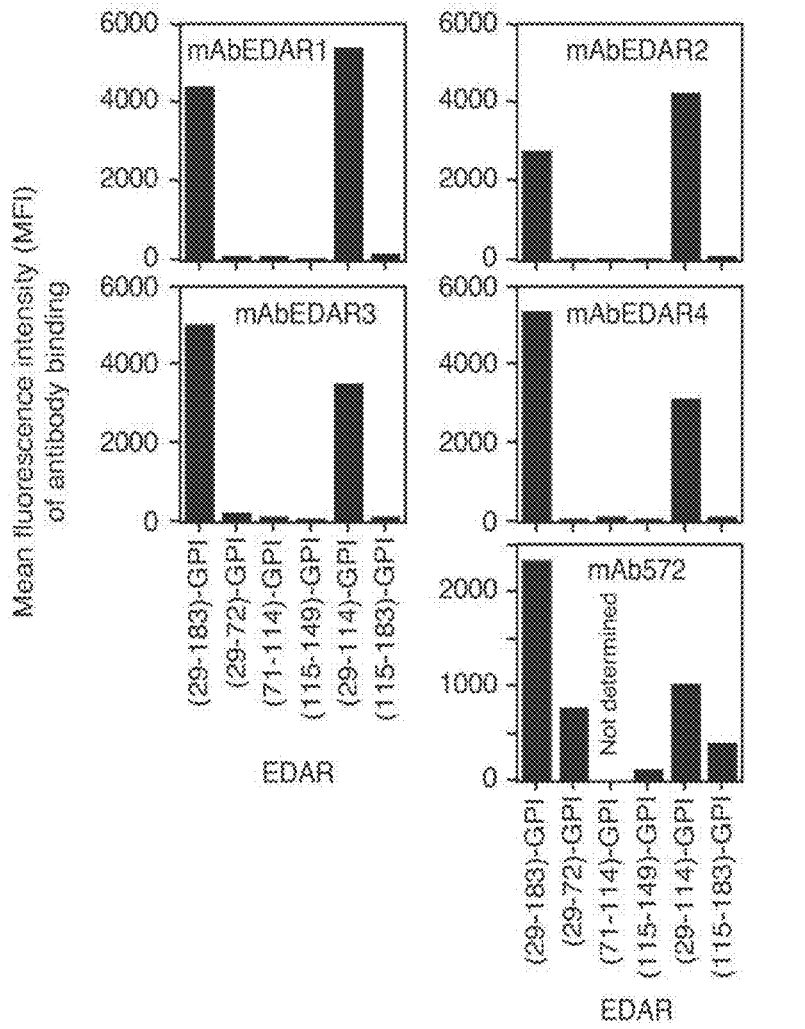

FIG. 11. Epitope mapping of anti-EDAR monoclonal antibodies by FACS. Plasmids encoding the indicated portions of human EDAR fused to the C-terminal portion of TRAIL-R3, including its glycosylphosphatidylinositol (GPI)-addition sequence, were transfected in 293T cells together with a tracer plasmid encoding enhanced green fluorescent protein (EGFP). Two days after transfection, cells were stained with mAbEDAR1, 2, 3, or 4 followed by PE-coupled anti-mouse IgG antibody. Cells were also stained with the rat monoclonal antibody mAb572 that recognizes TRAIL-R3, followed by PE-coupled anti-rat IgG antibody. Cells were analyzed by two colors FACS. EGFP is detected on FL1, and correlated with the expression of the GPI-anchored EDAR fragments. Antibody binding is detected in FL2. Antibody binding is quantified by the mean FL2 fluorescence intensity of transfected cells (i.e. cells with a FL1 fluorescence intensity of 50 to 1000).

This figure shows that mAbEDAR1, 2, 3 and 4 recognize an epitope of human EDAR overlapping CRD1 and CRD2. The figure also shows that the antibodies can recognize native EDAR-GPI proteins expressed on the cell surface.

Figure 12A:
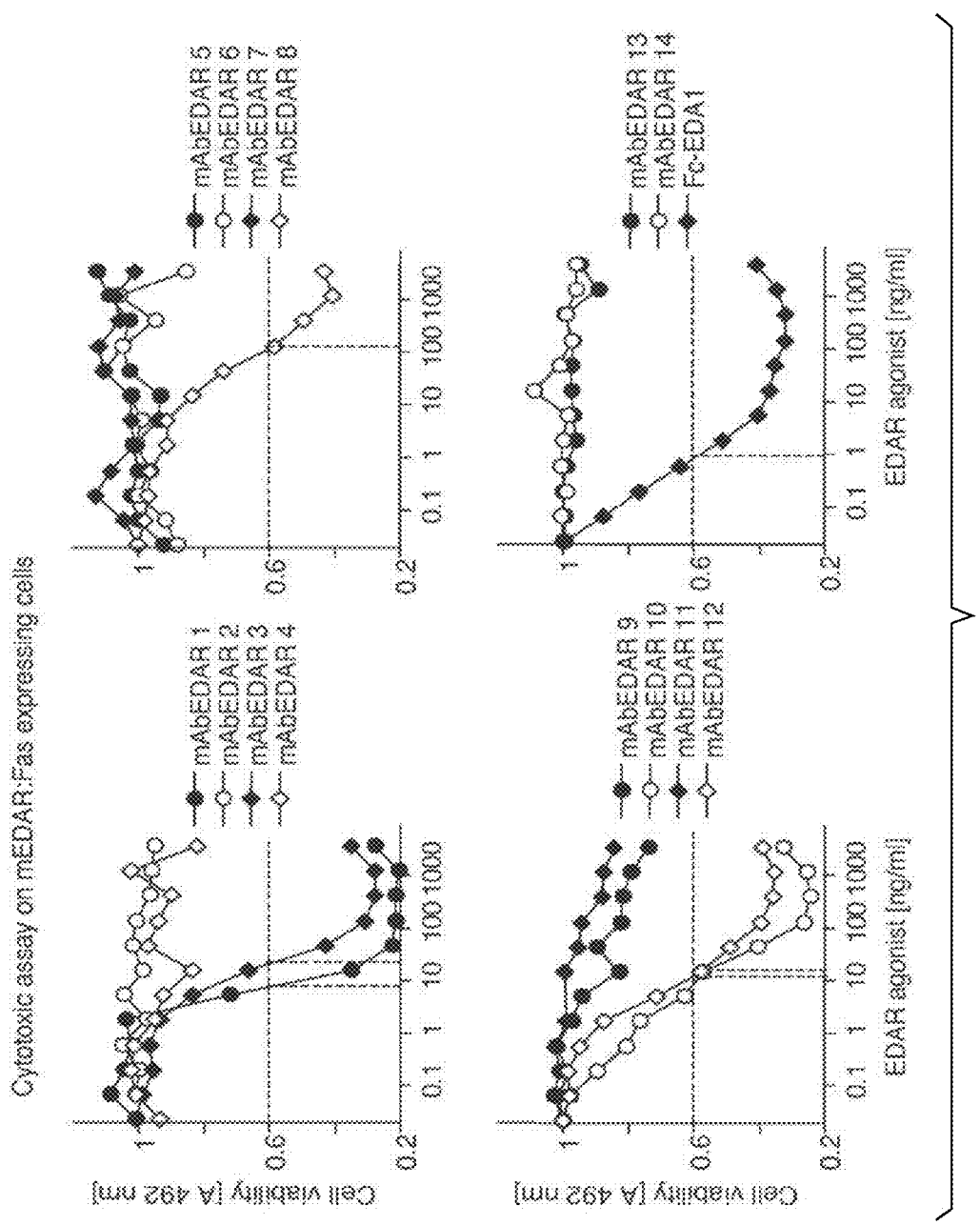
Figure 12B:
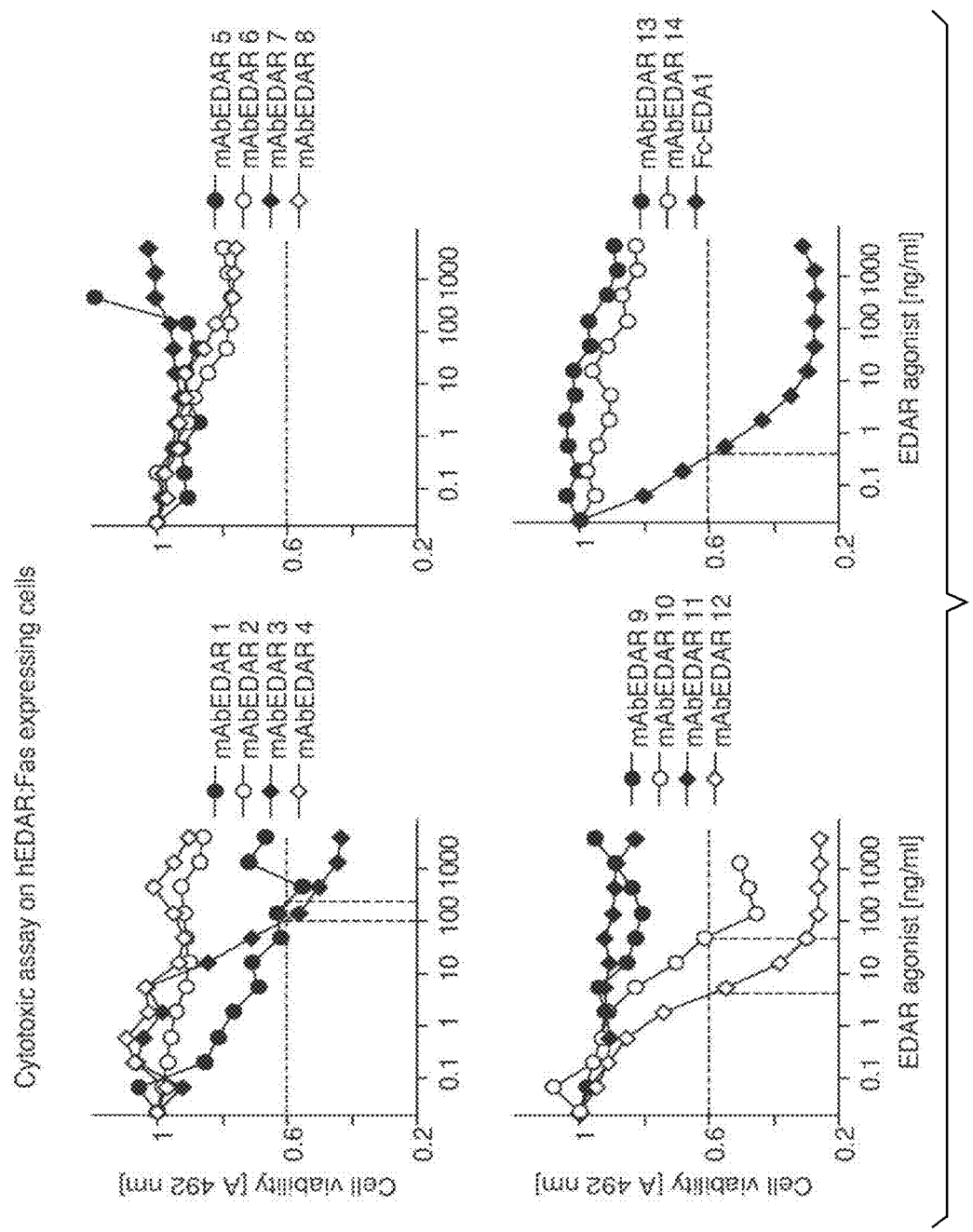

FIG. 12. Killing of EDAR-Fas-expressing Jurkat cells by anti-EDAR monoclonal antibodies. (A, B) Serial dilutions of purified anti-EDAR monoclonal antibodies mAbEDAR1 to mAbEDAR14 and purified Fc-EDA1 were tested for their capacity to induce apoptosis of mEDAR-Fas-expressing, Fas-deficient Jurkat cells (A) or hEDAR-Fas-expressing, Fas-deficient cells (B). After overnight culture, cell viability was determined by PMS/MTS staining. The EC50 (concentration of agonist inducing half maximal decrease of cell viability) of Fc-EDA was about 1 ng/ml, whereas the EC50 of mAbEDAR1, 3, 8, 10 and 12 were between 5 and 500 ng/ml, depending on the antibody and on the cell line. mAbEDAR2, 4, 5, 6, 7, 9, 11, 13 and 14 had no or little activity in this assay.

These results show that some but not all anti-EDAR antibodies can promote signaling through an EDAR-Fas fusion protein in cell culture in vitro, but that they are less potent than Fc-EDA 1.

Figures 13A, 13B:
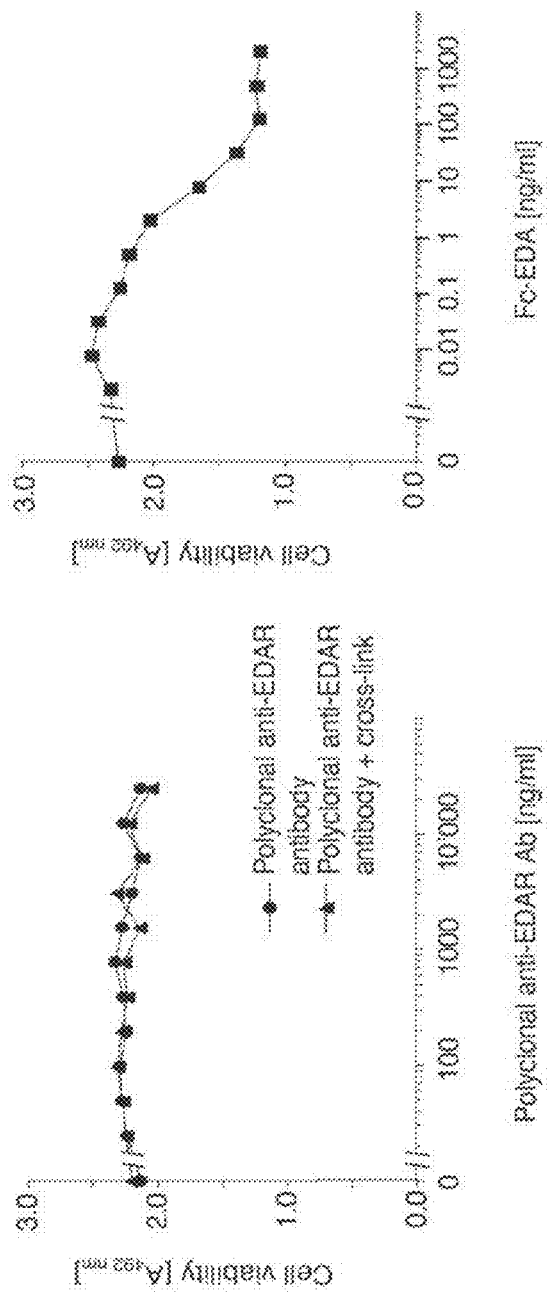

FIG. 13. Failure of polyclonal anti-EDAR antibodies to induce killing of EDAR-Fas-expressing Jurkat cells. Serial dilutions of goat polyclonal anti-mouse EDAR antibodies, in the presence or the absence of anti-goat IgG (A), and purified Fc-EDA (B) were tested for their capacity to induce apoptosis of EDAR-Fas-expressing, Fas-deficient Jurkat cells. After overnight culture, cell viability was determined by PES/MTS staining. The $EC_{50}$ (concentration of agonist inducing half maximal decrease of cell viability) of APO200 was between 3 to 9 ng/ml, while the polyclonal anti-EDAR antibodies failed to induce cell death.

These results show that the polyclonal anti-mouse EDAR antibodies exhibited no agonist activity in vitro. Similar findings were obtained with polyclonal anti-human EDAR antibodies. Altogether, these results support the argument that the development of agonist anti-EDAR mAb is not obvious.

Figure 14A:
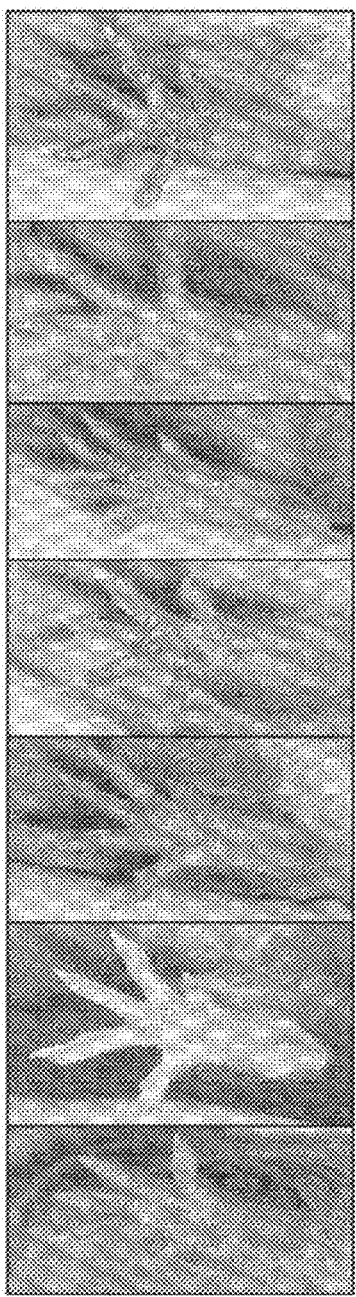
Figure 14B:
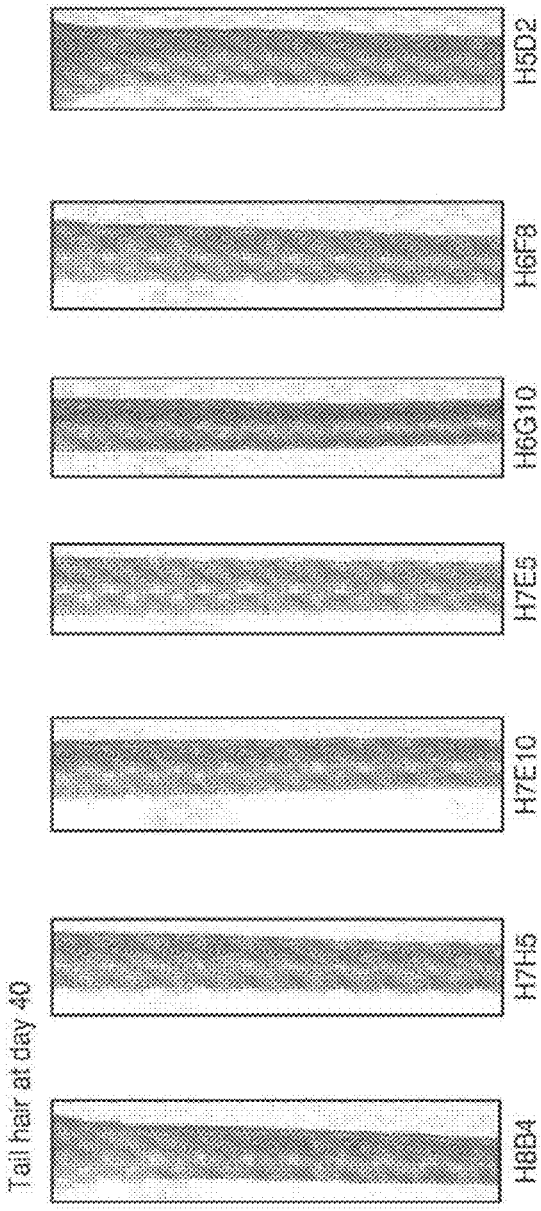

FIG. 14. Identification of anti-EDAR mAb capable of correcting the Tabby phenotype following their injection in newborn mice. Supernatant samples from forty positive hybridomas were intraperitoneally injected into one day-old Tabby mice. Six weeks later, the presence of functional sweat glands on the footpads and of hair on the tail was determined. Examples of results obtained with seven hybridoma supernatant samples are presented.

These results showed that more than half of the hybridoma supernatants were found capable of inducing the development of functional sweat glands on the footpads and the growth of hair on the tail, indicating that a large proportion of the anti-EDAR mAb had agonist properties mimicking the activity of the naturally occurring protein EDA1.

Figure 15A:
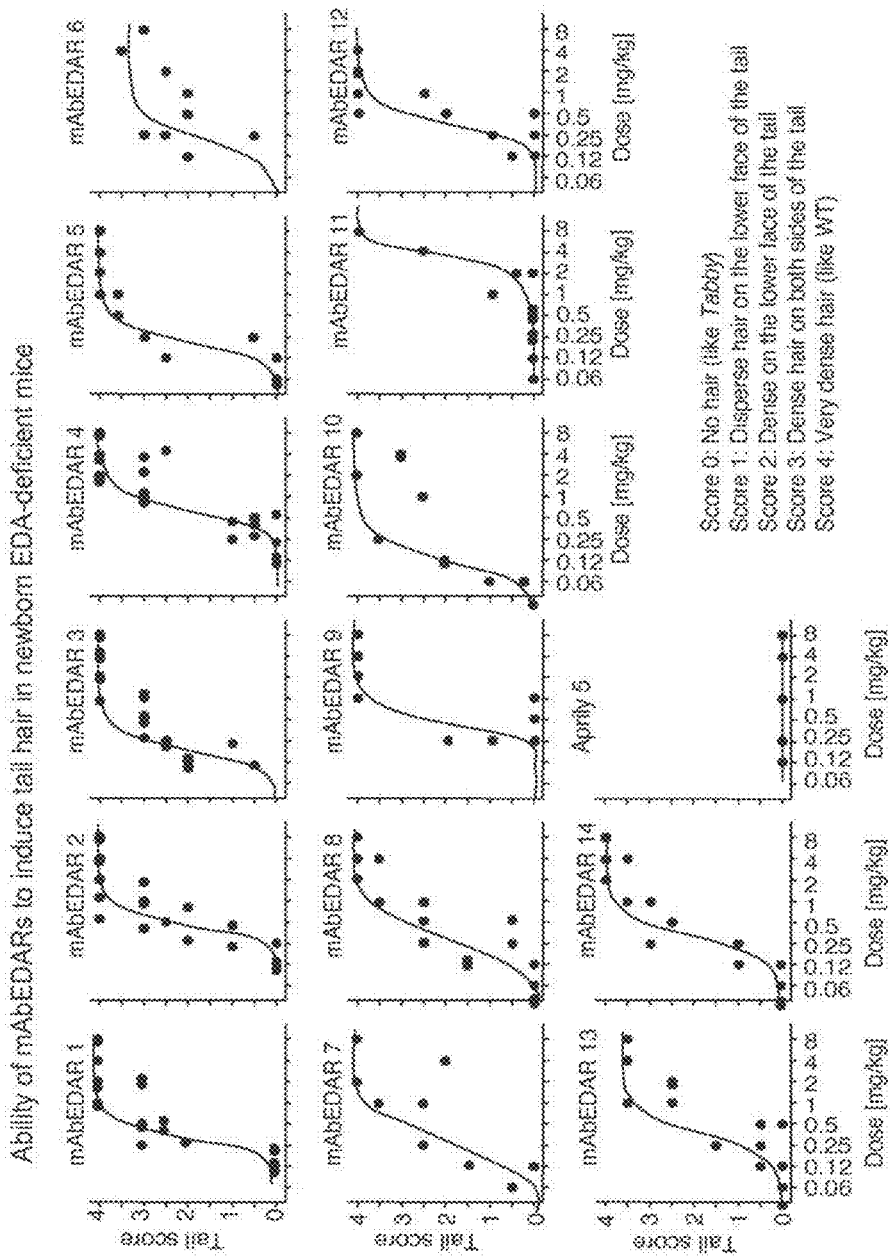
Figure 15B:
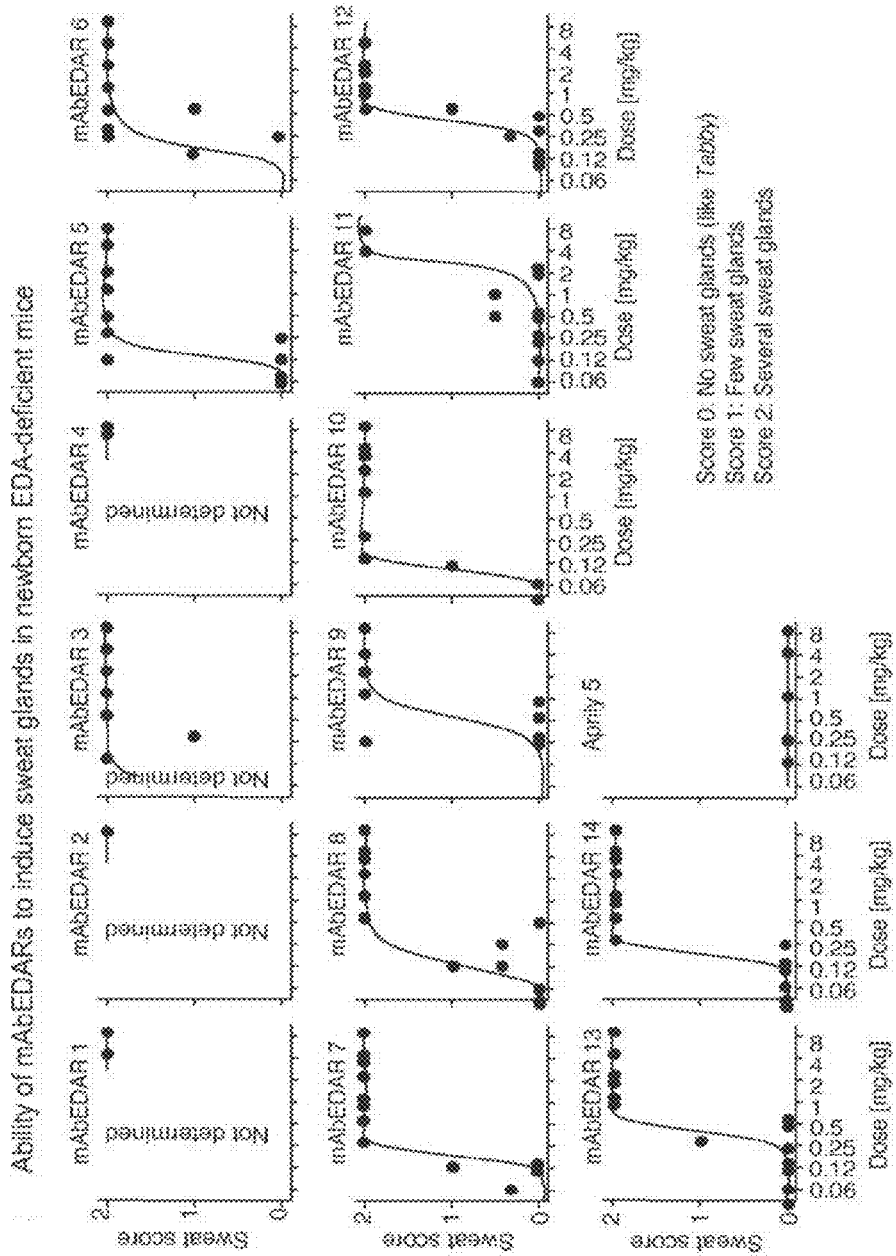

FIG. 15. Therapeutic dose of the anti-EDAR mAb in newborn Tabby mice. Newborn Tabby mice were intraperitoneally injected during the first 24 h of life with graded doses of protein G-affinity chromatographed anti-EDAR mAb. Four to six weeks later (mAbEDAR1, 2, 3 and 4) or 3 weeks later (mAbEDAR4 to 14 and Aprily5), hair density on the tail was scored (A). In addition, mice were submitted to starch-iodine sweat tests, and the presence of functional sweat glands was scored (B).

These results show that the dose producing half-maximal effects in newborn Tabby mice was in the 0.1-0.5 µg range for most mAbEDARs, which is similar to what was obtained with Fc-EDA1. Albeit 10- to more than 1000-fold less efficient in vitro, the anti-EDAR mAb were as efficient as Fc-EDA1 when used in vivo.

Figures 16A, 16B:
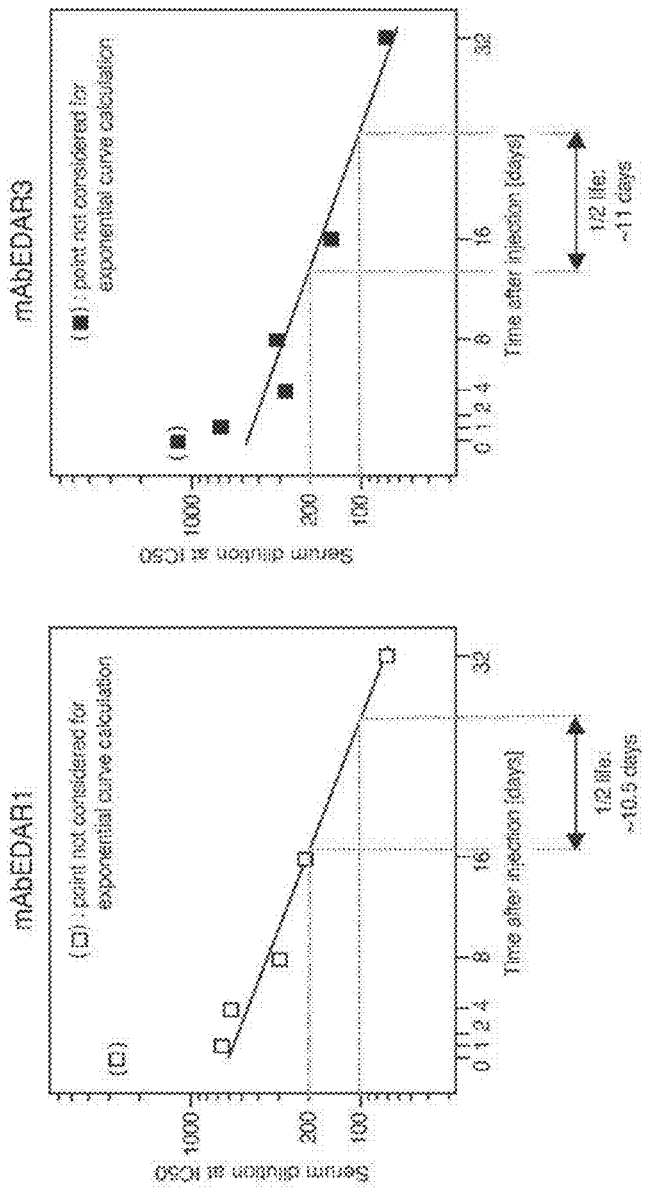

FIG. 16. Half-life of the anti-EDAR mAb in wild type mice. Wild type mice were intravenously injected with 200 µl of 1 mg/ml of mAbEDAR1 or mAbEDAR3. Serum samples were collected after 20 minutes, 1, 2, 8, 16 and 32 days. The concentration of the anti-EDAR mAb was determined by incubating serial dilutions of serum in wells coated with human EDAR-Fc at 1 µg/ml, followed by horseradish peroxidase-coupled anti-mouse IgG and OPD substrate. For analysis, the serum dilutions giving OD=1 (considered to represent the $IC_{50}$) for each time points were plotted as a function of time. An exponential curve was fitted on the series of points except the time point 20 minutes. A half-life for mAbEDAR1 and mAbEDAR3 of 10 to 11 days was thus determined.

A half-life of 10-11 days is a classical value in such an experimental setting. These results further document that these mAb have the classical attributes for this class of molecules. It also illustrates that the mAb have likely better pharmacological properties than Fc-EDA1, which has a short in vivo half-life (10 hours).

FIG. 17-23. Correction of the Tabby phenotype following injection of anti-EDAR mAb in pregnant mice. Pregnant Tabby mice were treated at day 13 and 20 (E13/E20) or 9 and 17 (E9/E17) of gestation with 400 µg anti-EDAR mAb mAbEDAR3. Offspring was analyzed at 6 months of age. Age-matched wild-type and EDA-deficient Tabby mice were similarly analyzed for comparison.

Figure 22:
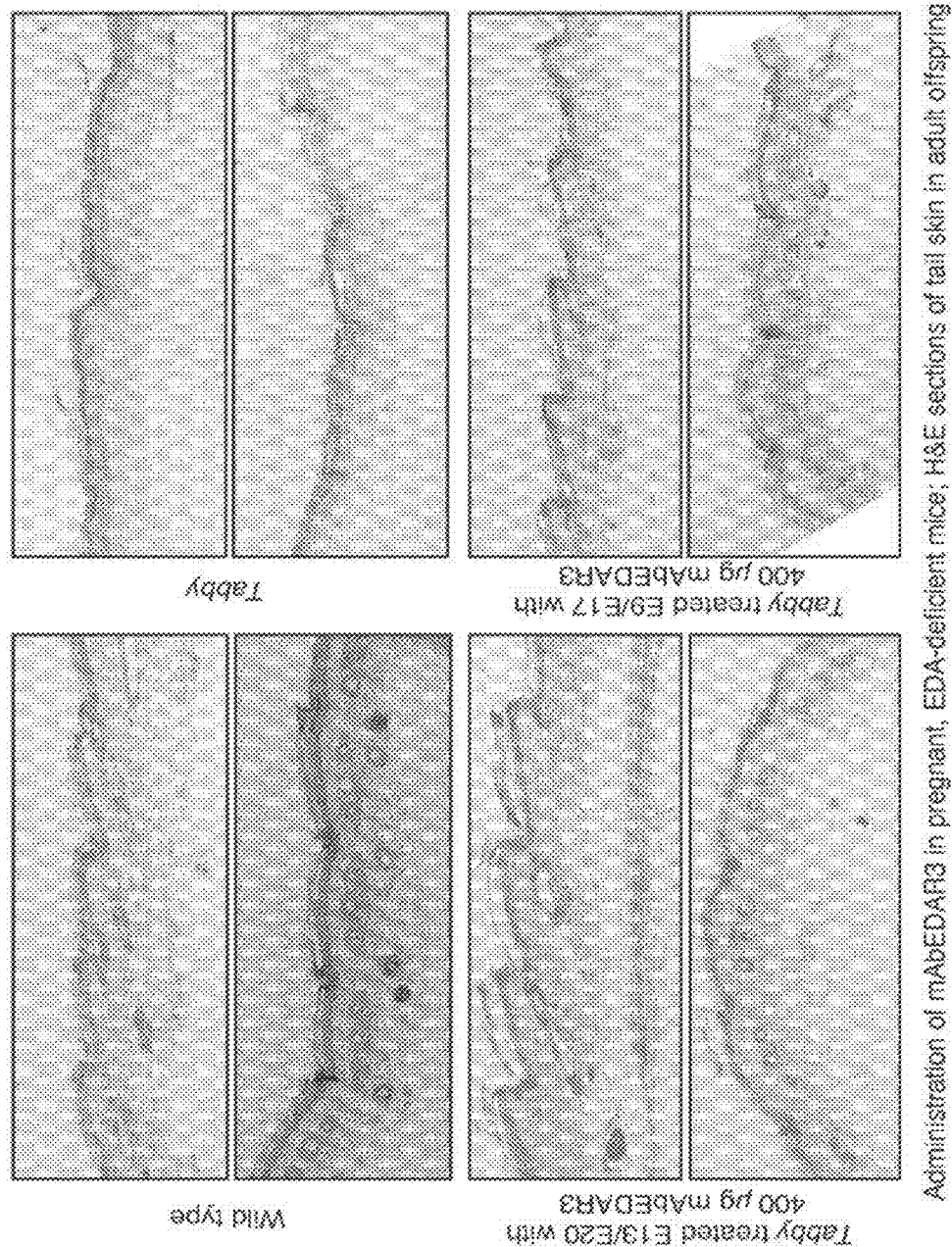
Figure 23:
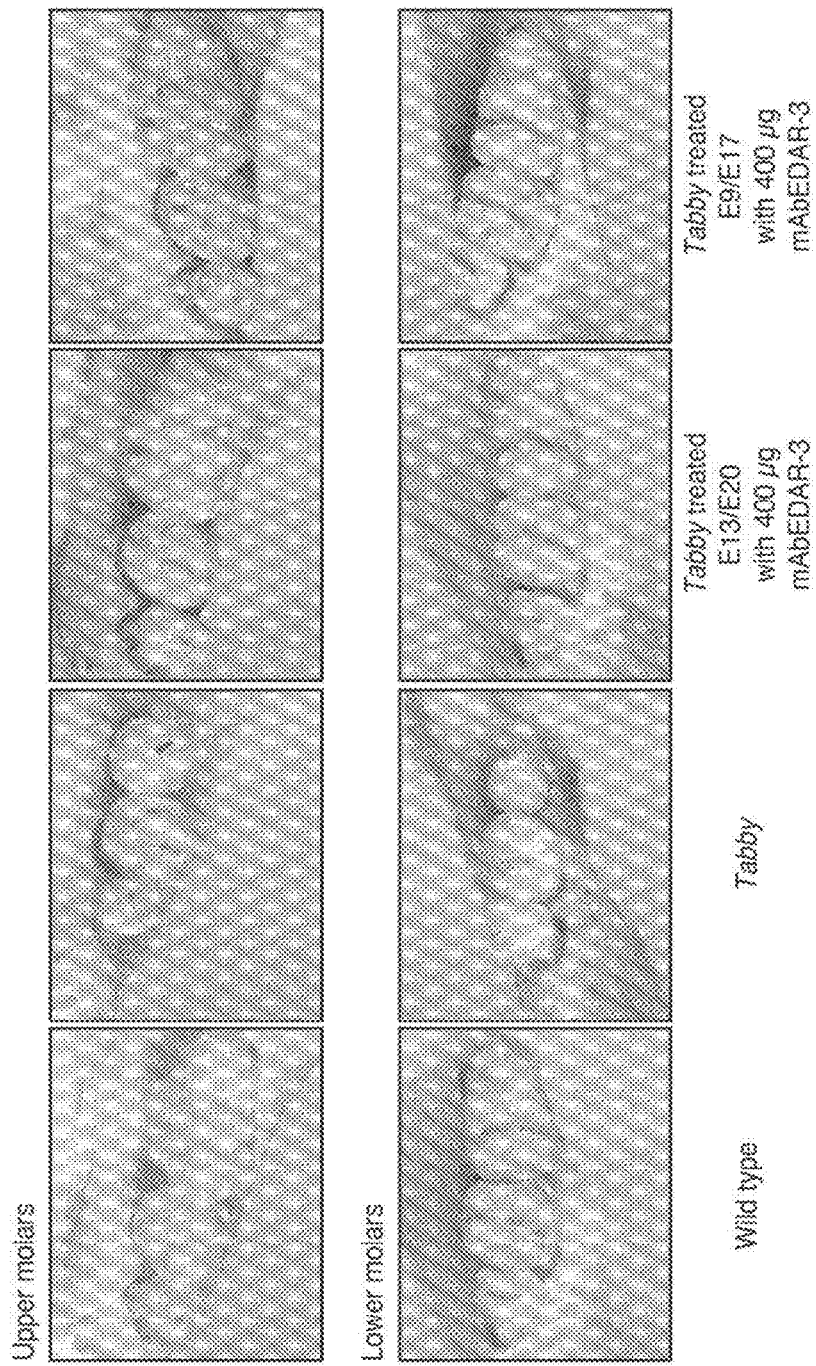

Front view of the animals, tail phenotype and starch iodine sweat tests (FIG. 17), appearance of the belly (FIG. 18), top view of the head showing the presence of hair behind the ears (FIG. 19), H&E sections of foot pads showing the presence of glandular structures of sweat glands (FIG. 20), sections of the trachea stained with Alcian blue to reveal mucus-secreting glands (FIG. 21), longitudinal and transversal sections of tail skin showing the presence of hair follicles (FIG. 22), and pictures of the jaw carrying the upper and lower molars (FIG. 23).

These figures illustrate the in vivo biological activities of the anti-EDAR mAb. In particular, these results established that these mAb are at least as therapeutically active as Fc-EDA1. The presence of functional mucus-producing cells (FIG. 21) was previously not reported in Fc-EDA1-treated Tabby mice (this result expands the scope of the therapeutic activities exhibited by anti-EDAR mAb, but it did not constitute a surprise).

Figure 24:
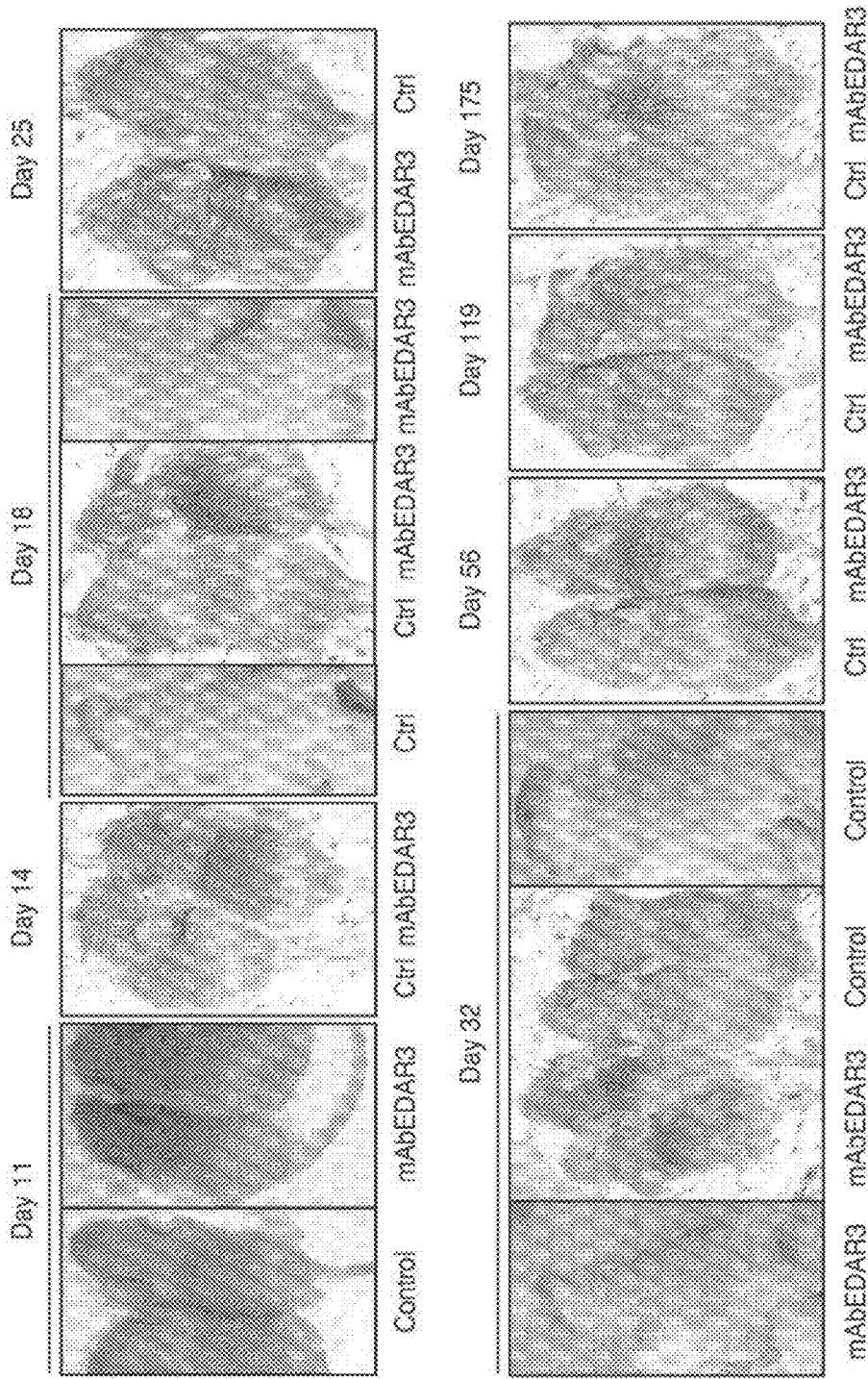

FIG. 24. Modified fur appearance following injection of anti-EDAR mAb in newborn wild type mice. mAbEDAR3 was administered intraperitoneally in newborn wildtype mice at days 0, 4, 7, 11, 14 and at 5 mg/kg. Control littermates were treated with PBS. Pictures of the mice were taken at the indicated time points.

Figure 25:
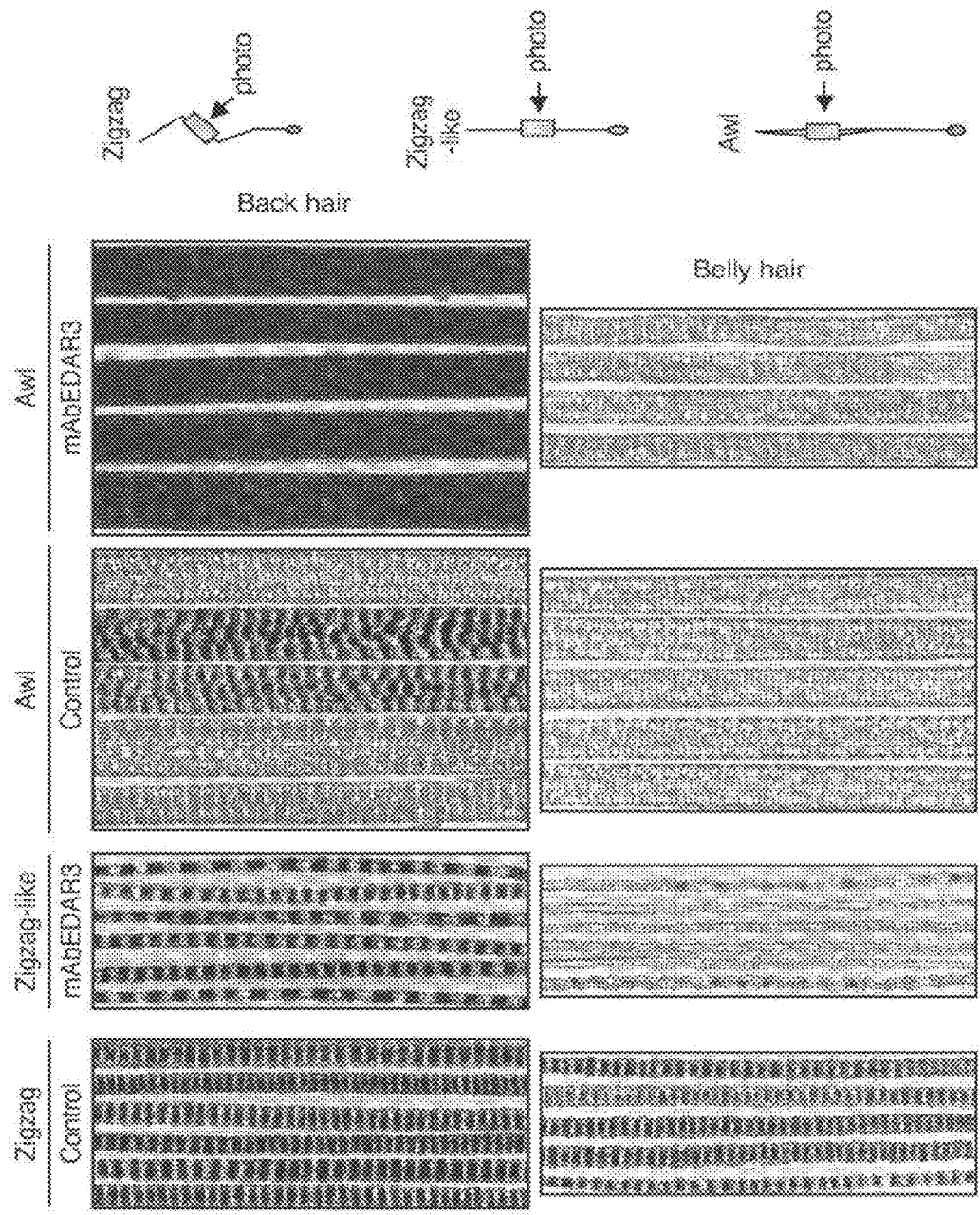

FIG. 25. Modified hair morphology following injection of anti-EDAR mAb in newborn wild type mice. Hair was taken at day 18 from the back and belly of the mice shown in FIG. 24, and photographed under the microscope. The scheme on the right indicates the portion of the zigzag and awl hair that is shown. Kinks found in wild-type zigzag hairs are no longer present in mAbEDAR3-treated mice (and these hairs are called zigzag-like).

Figure 26:
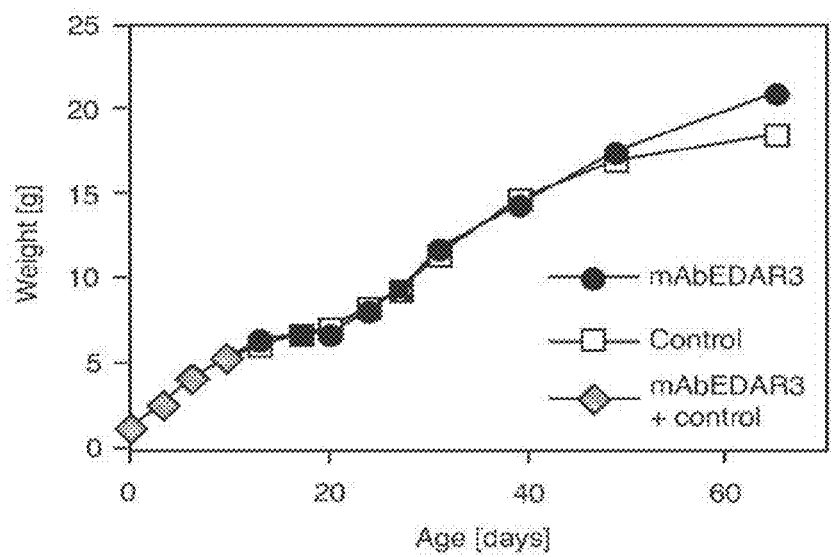

FIG. 26. Administration of anti-EDAR mAb in newborn wild type mice does not affect weight gain. mAbEDAR3 was administered intraperitoneally in newborn wildtype mice at days 0, 4, 7, 11, 14 and at 1 mg/kg. Control littermates were treated with PBS. Weight is plotted as a function of time and represents the average of 6 mice (up to day 11), the average of 3 mice per group (1 male and 2 females) (up to day 32) and the average of 2 mice per group (1 male and one female, from day 40).

Figure 27:
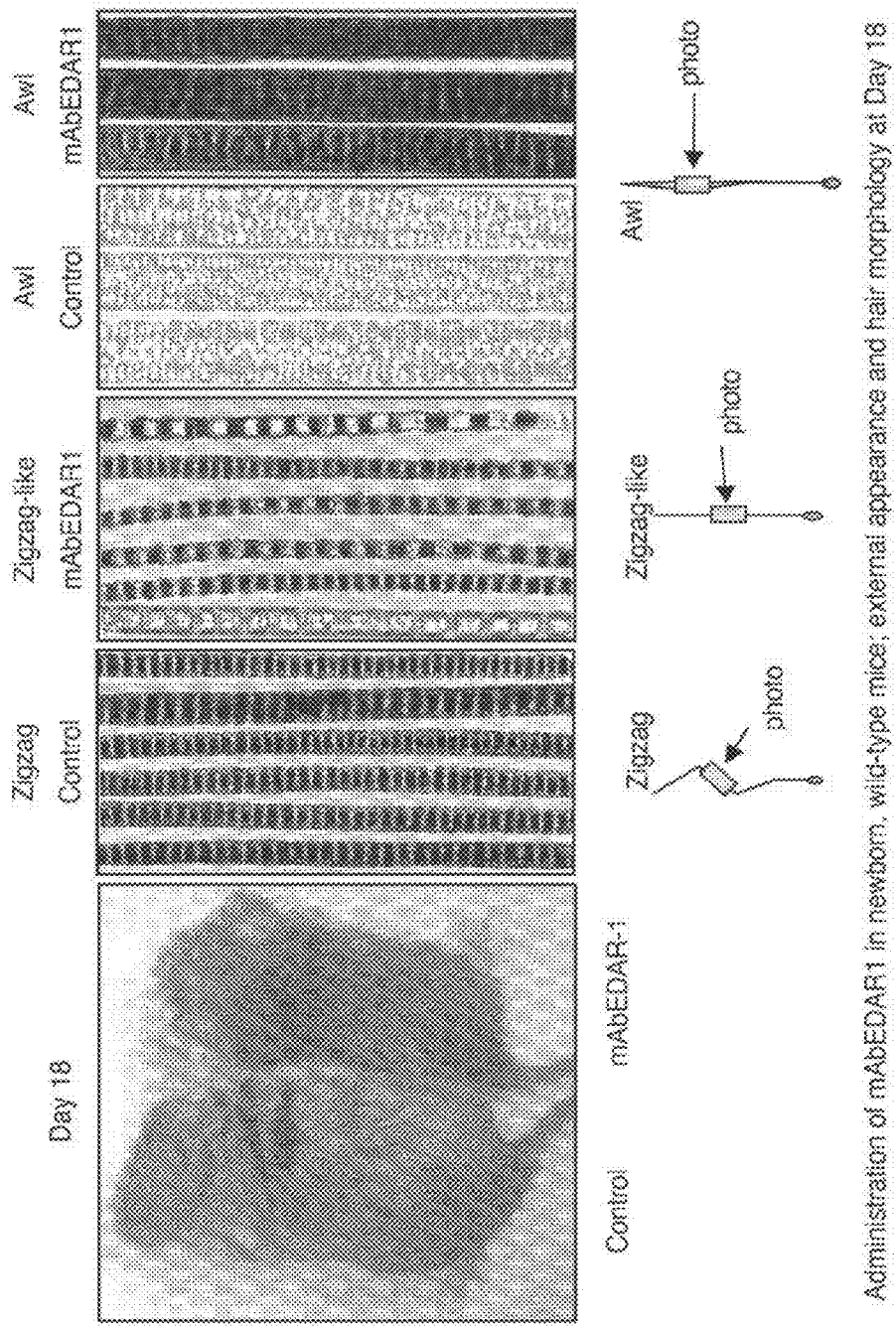

FIG. 27. Modified fur appearance and hair morphology following injection of anti-EDAR mAb in newborn wild type mice. mAbEDAR1 was administered intraperitoneally in newborn wildtype mice at days 0, 4, 7, 11 and 14, and at 5 mg/kg. Control littermates were treated with PBS. Pictures of the mice were taken at day 18. Hair was collected at day 18 for morphological analysis.

Figure 28:
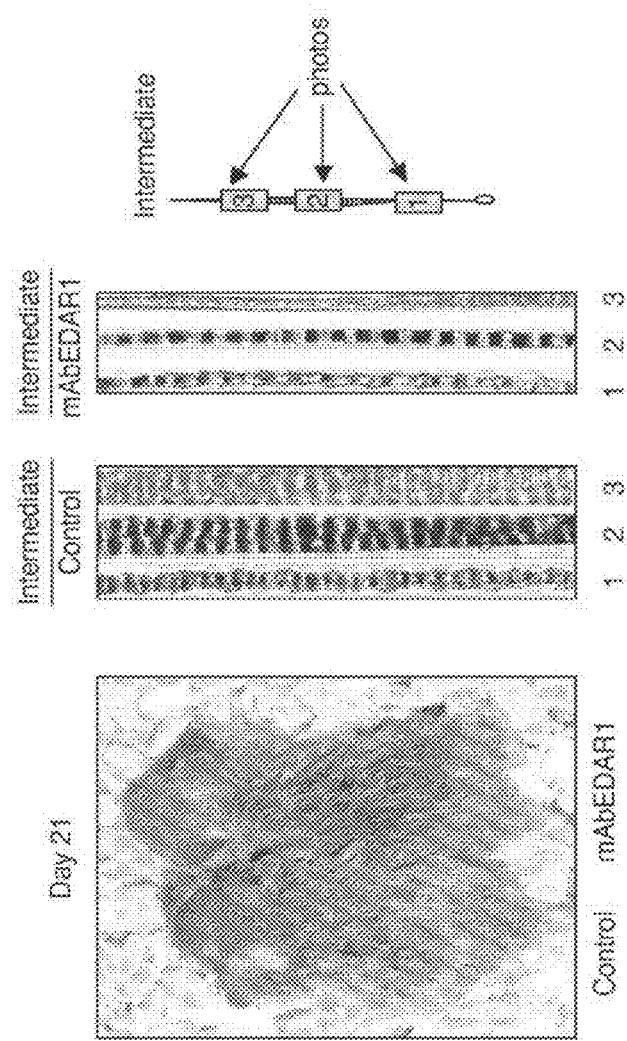

FIG. 28. Modified fur appearance and hair morphology following injection of anti-EDAR mAb in newborn EDA-deficient mice. mAbEDAR1 was administered intraperitoneally in newborn EDA-deficient mice at days 0, 4, 7, 11 and 14, and at 5 mg/kg. Control littermates were treated with PBS. Pictures of mice were taken at day 21. Hair was collected at day 21 for morphological analysis. EDA-deficient mice have a single hair type called "intermediate".

Figure 29:
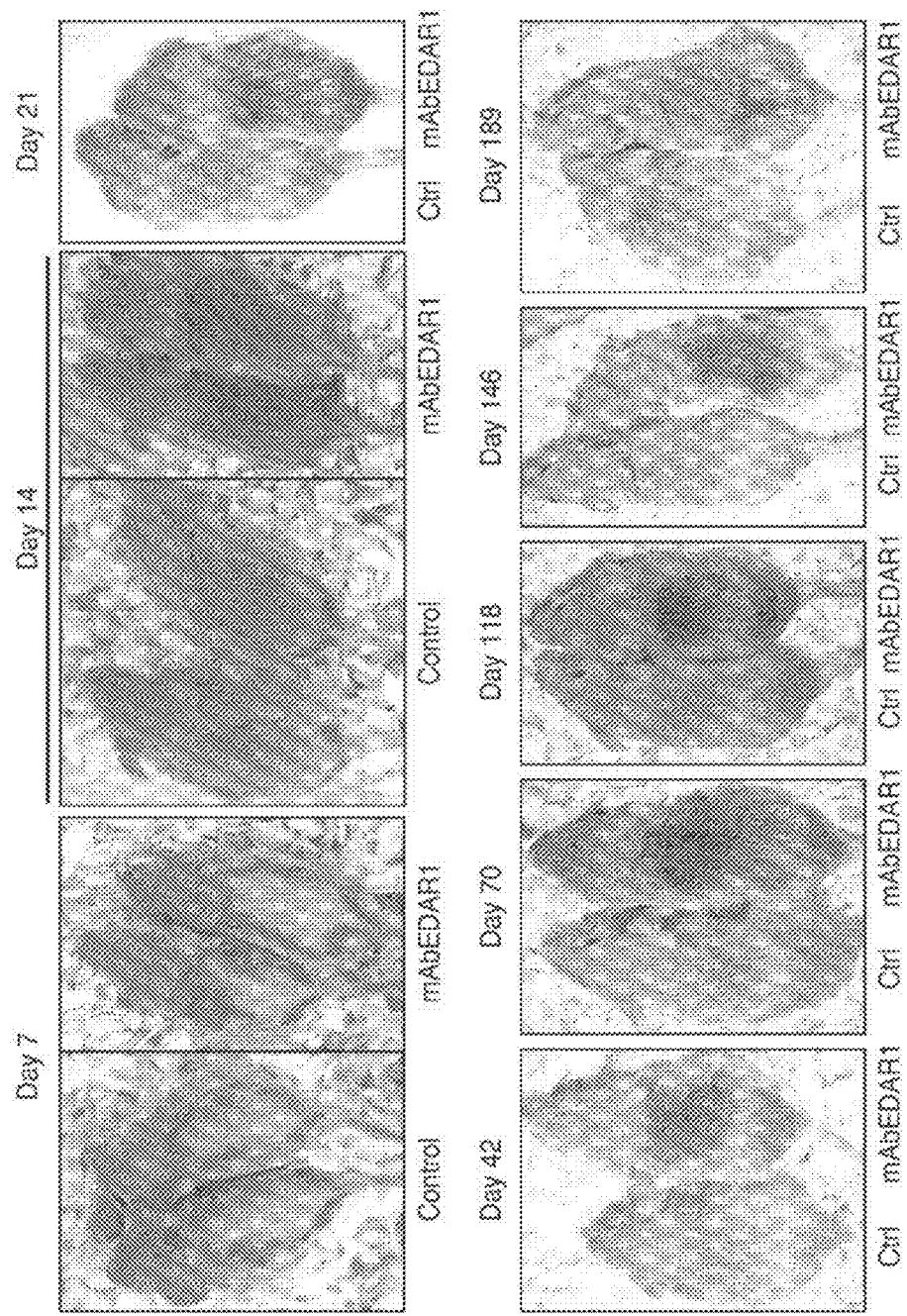

FIG. 29. Modified fur appearance and colour following injection of anti-EDAR mAb in adult wild type mice. The backs of 3 weeks-old wild-type mice were depilated, and the mice received a single intraperitoneal injection of mAbEDAR1 at 5 mg/kg immediately after depilation. Control littermates were treated with PBS. Pictures of the mice were taken at the indicated time points.

Figure 30:
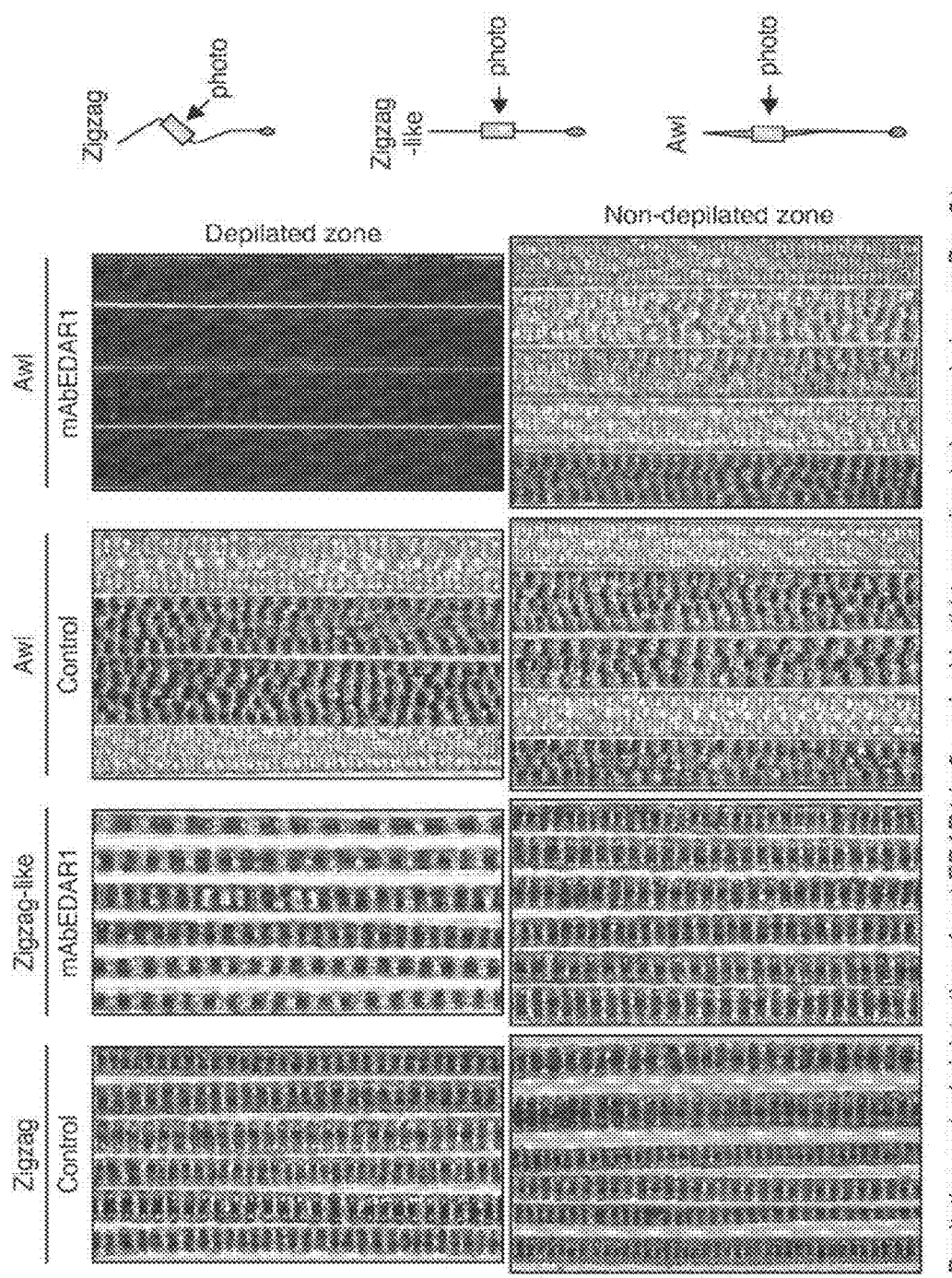

FIG. 30. Modified hair morphology following injection of anti-EDAR mAb in adult wild type mice. Hair was taken at day 21 post-depilation from the back of the mice shown in FIG. 29, in the depilated or non-depilated zones, and photographed under the microscope.

Figure 31:
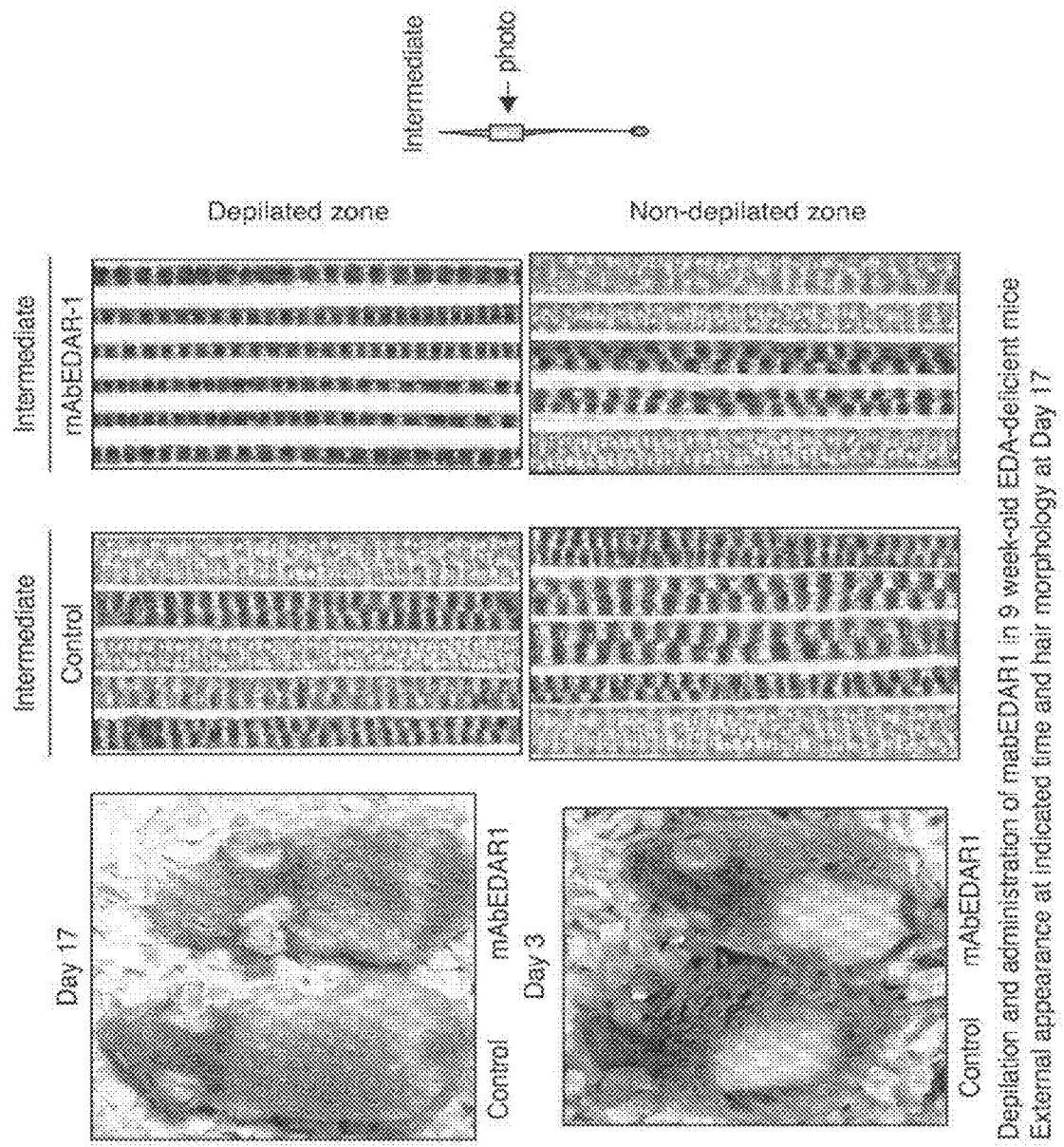

FIG. 31. Modified fur appearance and hair morphology following injection of anti-EDAR mAb in adult EDA-deficient mice. The backs of 9 weeks-old wild-type mice were depilated, and the mice received a single intraperitoneal injection of mAbEDAR1 at 5 mg/kg immediately after depilation. Control littermates were treated with PBS. Pictures of the mice were taken at the indicated time points, and hair morphology was analyzed by microscopy at day 17 post-depilation.

Figure 32:
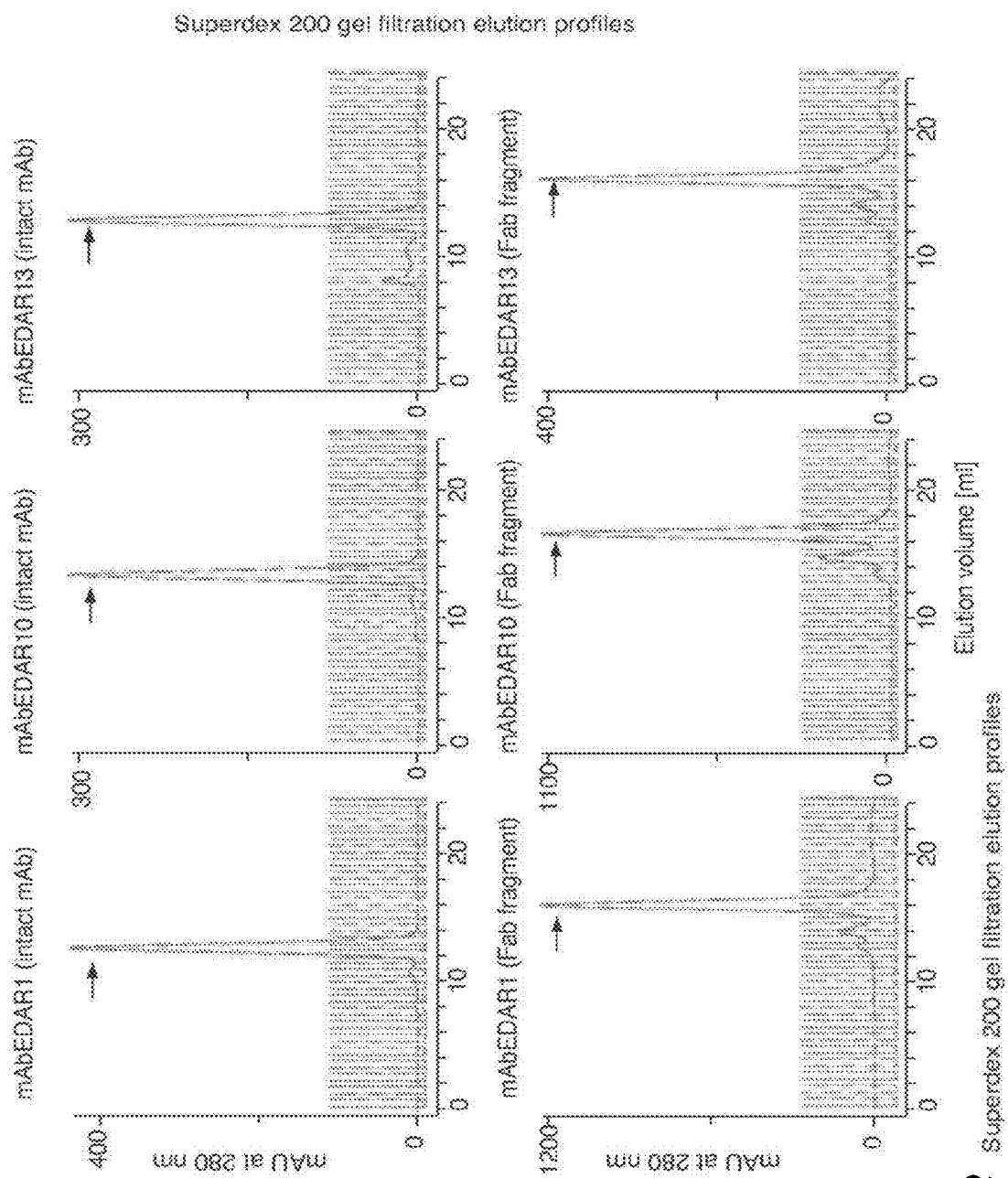

FIG. 32. Gel permeation chromatography elution profiles of anti-EDAR antibodies and Fab fragments thereof. Purified anti-EDAR antibodies mAbEDAR1, 10 and 13 were left untreated or digested for 72 h at 37° C. with immobilized ficin. In the digested antibodies, Fc fragments and undigested antibodies were removed by chromatography on Protein A. The flow through, containing the Fab fragment, was concentrated and applied onto a Superdex-200 gel permeation chromatography column eluted in PBS. Absorbance was recorded at 280 nm. Undigested antibodies were also size-fractionated in a similar way. Similar results were obtained with mAbEDAR2, 4, 5, 6, 7, 8, 9, 12 and 14 (data not shown).

This indicates that monomeric Fab fragments of anti-EDAR antibodies can be obtained by a combination of ficin digestion and gel filtration chromatography.

Figure 33:
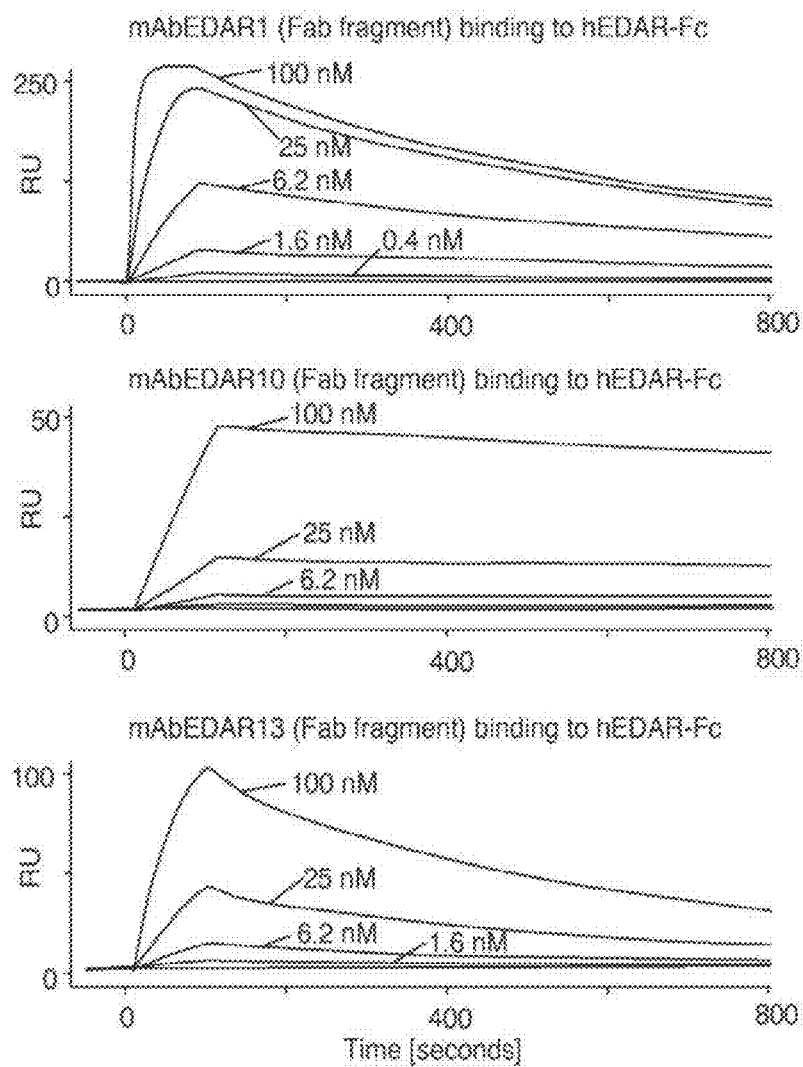

FIG. 33. Binding and dissociation kinetics of anti-EDAR Fab fragments to hEDAR-Fc. Human EDAR-Fc was captured on anti-human IgG Fc-derivatized CM5 chips in a Biacore T100. Fab solutions of anti-EDAR antibodies at the indicated concentration were applied for 90 sec, and subsequently washed with buffer. Similar experiments were also performed for Fab fragments of mAbEDAR2, 4, 5, 6, 7, 8, 9, 12 and 14 (data not shown).

These data indicate that anti-EDAR antibodies differ in their binding and dissociation constants.

Figure 34:
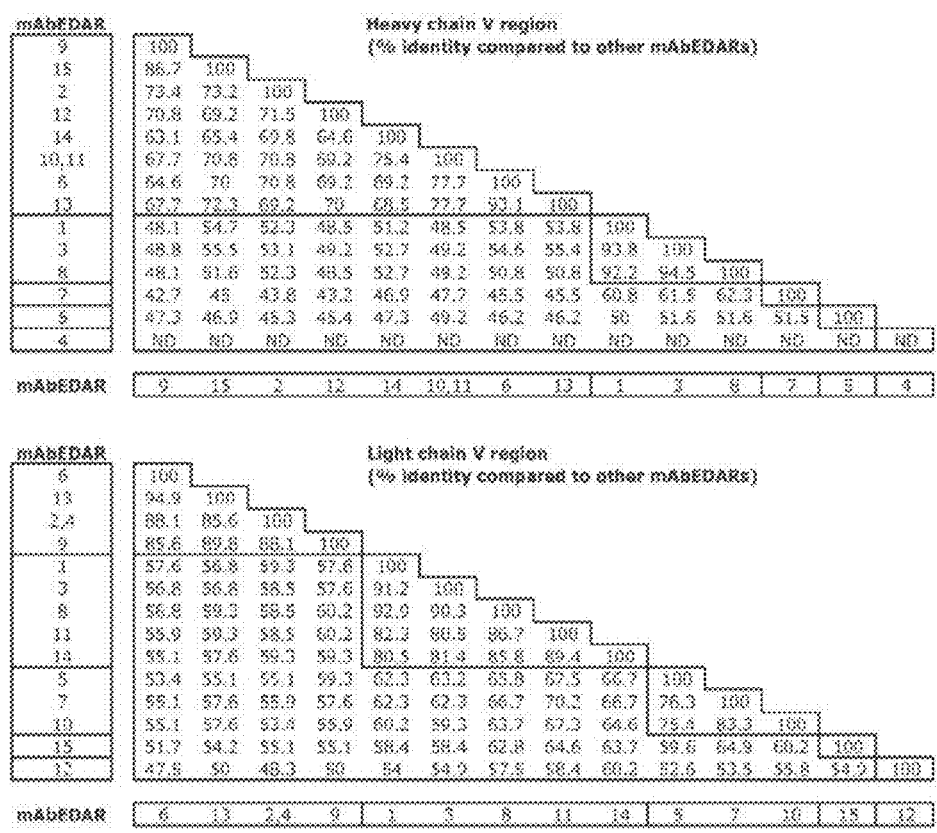

FIG. 34. Sequence comparison of the variable region of heavy and light chains of anti-EDAR antibodies. Amino acid sequences of the variable portions of heavy and light chains of anti-EDAR mAb were aligned with the ClustalW alignment option of the program MacVector. Percentage of identity at the amino acid level between various anti-EDAR antibodies are shown.

FIG. 35. Characteristics and properties of anti-EDAR antibodies. This figure summarizes some characteristics of the mAbEDARs: most likely used genes, amino acid sequence at the VDJ (SEQ ID NOS 260-273, respectively, in order or appearance) and VJ (SEQ ID NOS: 274-288, respectively, in order of appearance) junctions, antigen used for immunization, isotype, epitope recognized and EDAR species. IGHV, D, J, IGLV genes: genes most likely used by the hybridoma (nomenclature of the international immunogenetics information system); V-D-J and V-J junctions: amino acid sequence at junctions; Antigen: protein used for immunization (mEDAR: mouse EDAR-Fc. hEDAR: human EDAR-Fc); Epitope: portion of hEDAR required for recognition by ELISA (full: entire extracellular domain. I+II: cystein-rich domains I and II I: cystein-rich domain I; Cross-reaction: EDAR species recognized by ELISA (h: human. m: mouse); ND: not determined.

Figure 36:
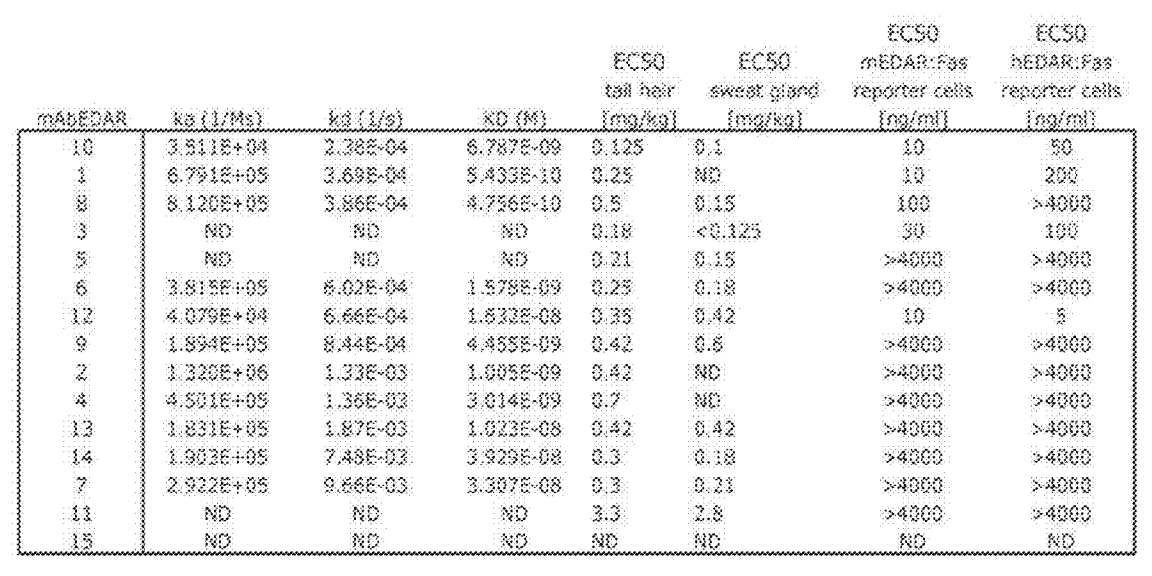

FIG. 36. Characteristics and properties of anti-EDAR antibodies This figure summarizes physical and biological properties of the mAbEDARs: association and dissociation constants of the Fab fragments, affinity of the Fab fragments, in vivo activity to induce tail hair formation and sweat gland formation in newborn EDA-deficient Tabby mice, in vitro activity on EDAR:Fas, Fas-deficient reporter Jurkat cells. These data show that mAbEDAR1-14 are agonists in vivo (mAbEDAR15 that does not recognize mouse EDAR was not tested). It also shows a correlation between antibodies with the lowest affinity constant, and in particular with the lowest dissociation constant, and antibodies with the best activities in the in vitro activity assay. All of the antibodies with activity in vitro performed well in vivo. As used in Figue, ka: association constant of monomeric mAbEDAR Fab fragments to immobilized hEDAR-Fc; kd: dissociation constant of monomeric mAbEDAR Fab fragments to immobilized hEDAR-Fc; KD: affinity constant of monomeric mAbEDAR Fab fragments to immobilized hEDAR-Fc; EC50 tail hair: dose to obtain half maximal reversion score of tail hair in newborn EDA-deficient mice; EC50 sweat gland: dose to obtain half maximal reversion score of sweat gland in newborn EDA-deficient mice; EC50 mEDAR:Fas reporter cells: Antibody concentration required to kill half of the reporter cells; EC50 hEDAR:Fas reporter cells: Antibody concentration required to kill half of the reporter cells; ND: not determined.

Figure 37:
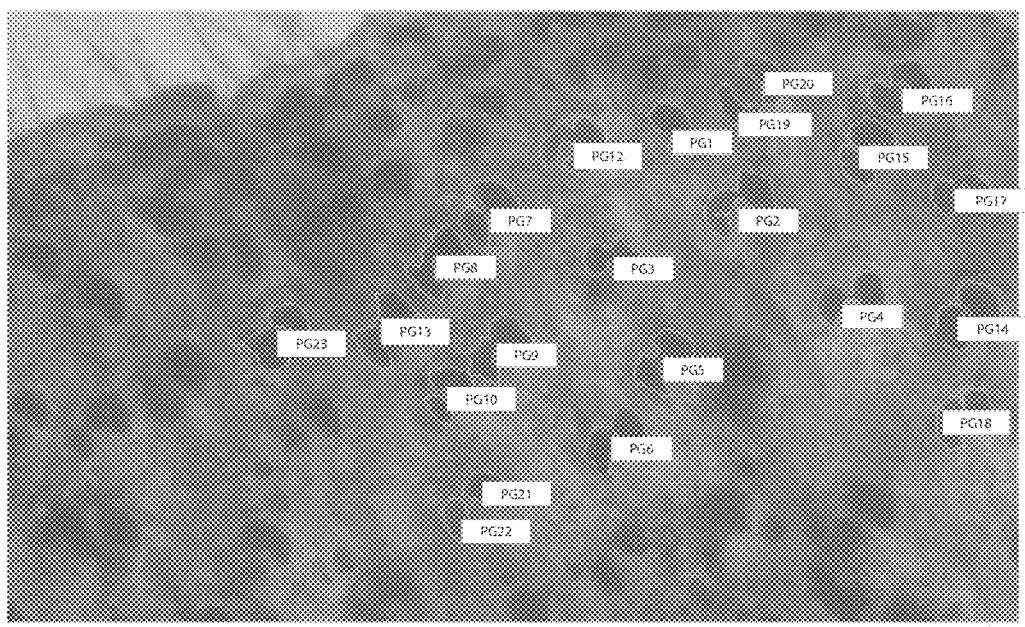

FIG. 37. Photograph of an ear section of a Tabby mouse with 22 sebaceous glands labeled and marked for size and area measurements. Measurement data obtained from this photograph are provided in Table 3 (Example 12).

Figure 38:
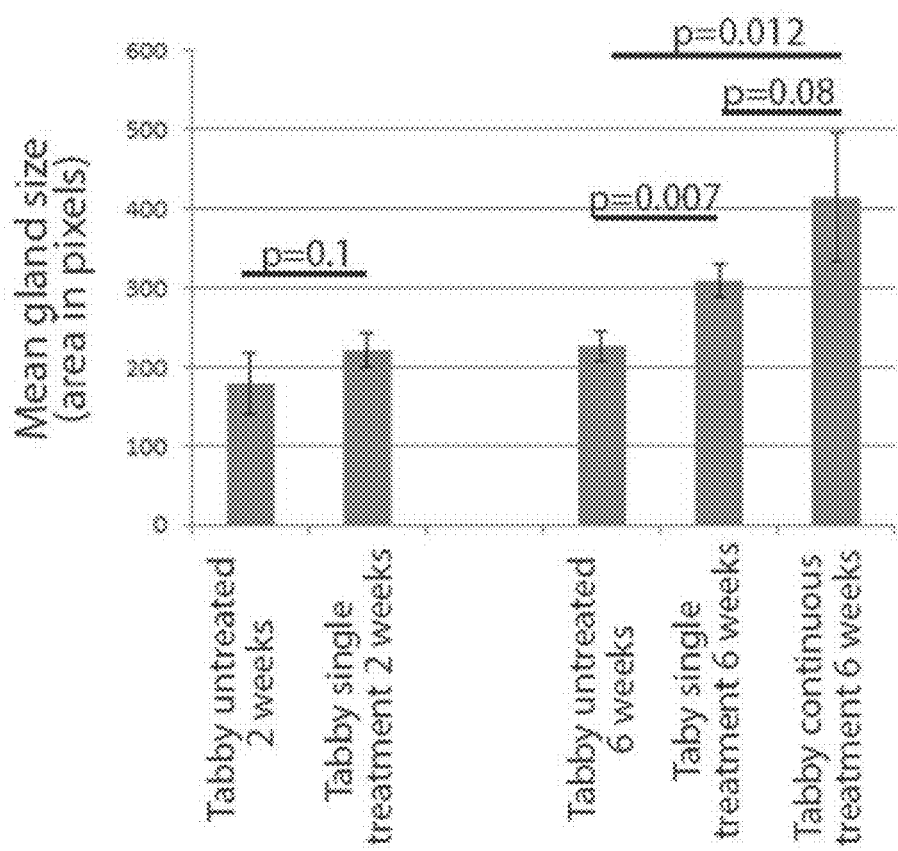

FIG. 38. Plot of sebaceous gland sizes in ear sections of Tabby mice according to mAbEDAR1 treatment regimen. Error bars indicate standard deviation (n=3 or 4 per treatment condition).

Figure 39:
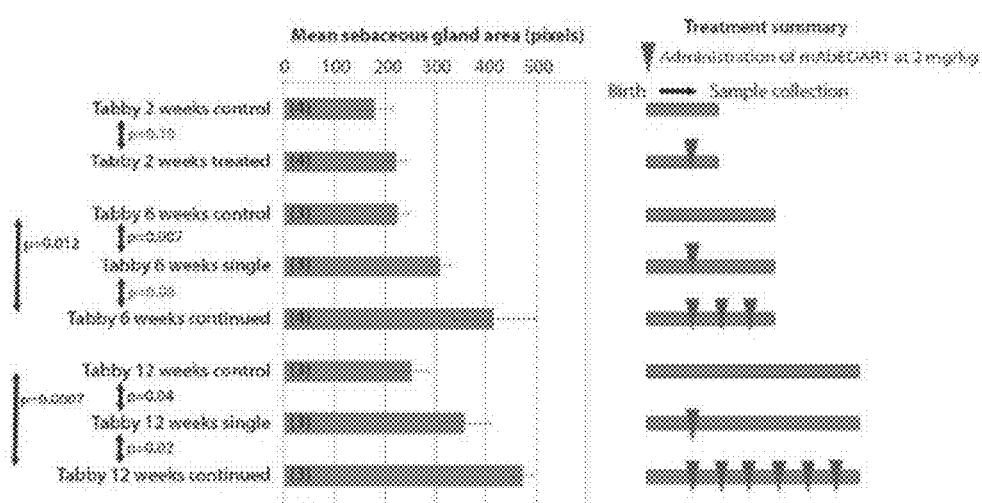

FIG. 39. Plot of sebaceous gland sizes in ear sections of Tabby mice according to mAbEDAR1 treatment regimen. Error bars indicate standard deviation. The number of animals per treatment is shown in parentheses within the corresponding bar. The P-values obtained from the 2-tailed test are shown in the chart labels on the left. Error bars indicate standard deviation (n=3 or 4 per treatment condition—indicated at the bottom of each bar).

Figure 40A:
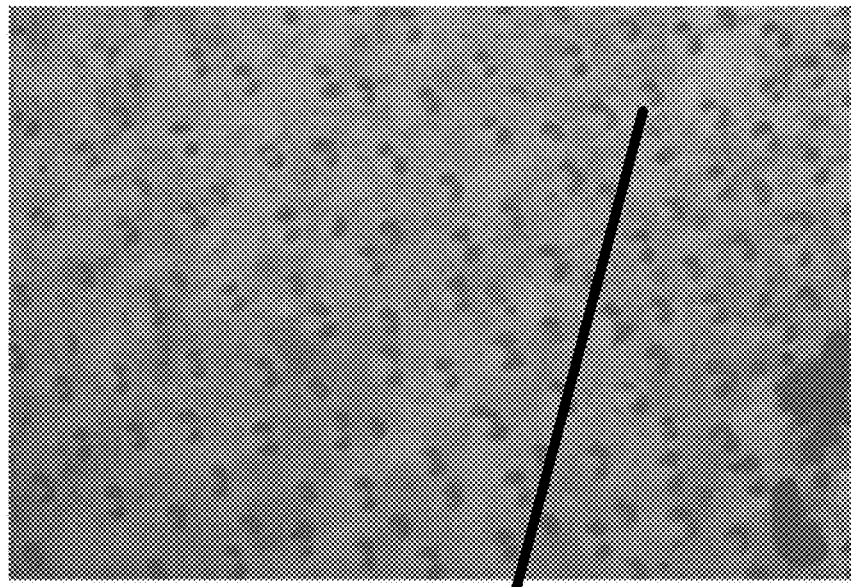
Figure 40B:
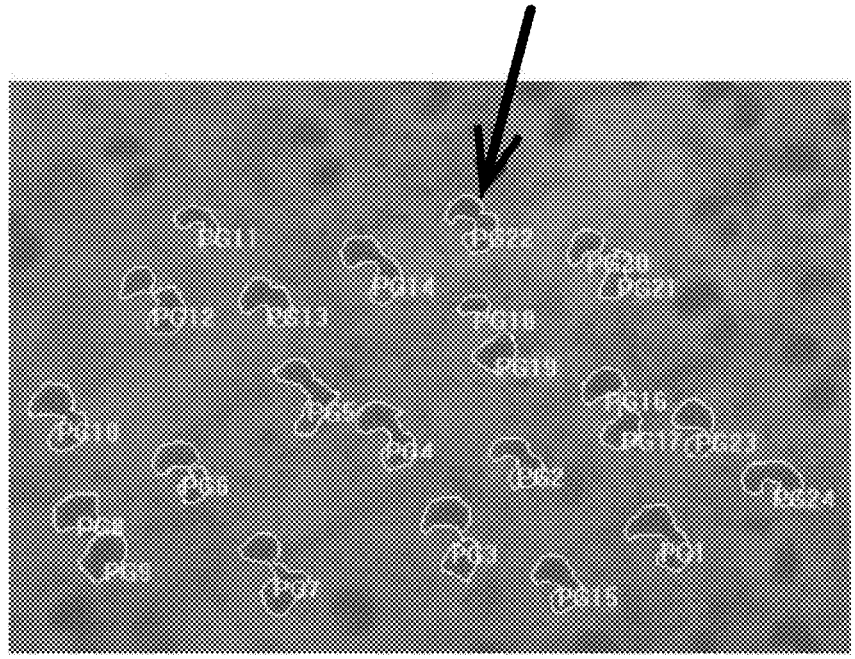

FIG. 40. Photographs of an ear section of a Tabby mouse showing sebaceous glands. Panel A: Photograph of a section of an ear of a Tabby mouse including visible sebaceous glands. Panel B: A magnification of a portion of the ear section of panel A with 23 sebaceous glands labeled and marked for measurements.

Figure 41:
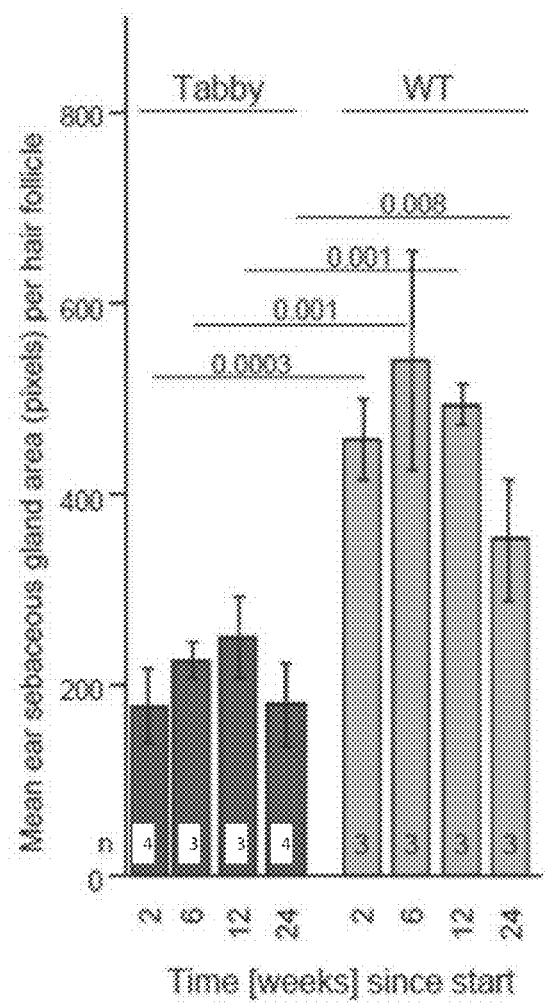

FIG. 41. Plot indicating changes in sebaceous gland area as a function of time in untreated Tabby and wild type mice. Error bars indicate standard deviation (n=3 or 4 per treatment condition—indicated at the bottom of each bar).

Figure 42:
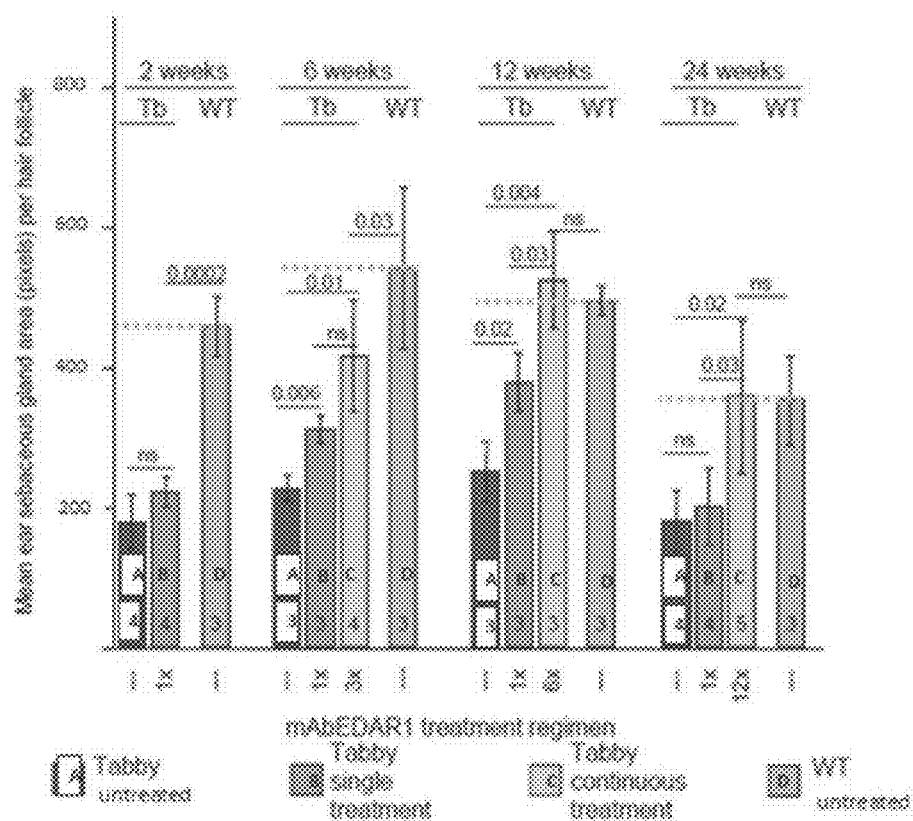

FIG. 42. Plot of sebaceous gland area according to mAbEDAR1 treatment regimen in Tabby and wild type mice. Multiplication factors shown on the x-axis indicate the number of treatments. Error bars indicate standard deviation (n=3, 4 or 5 per treatment condition—indicated at the botom of each bar).

Figure 43:
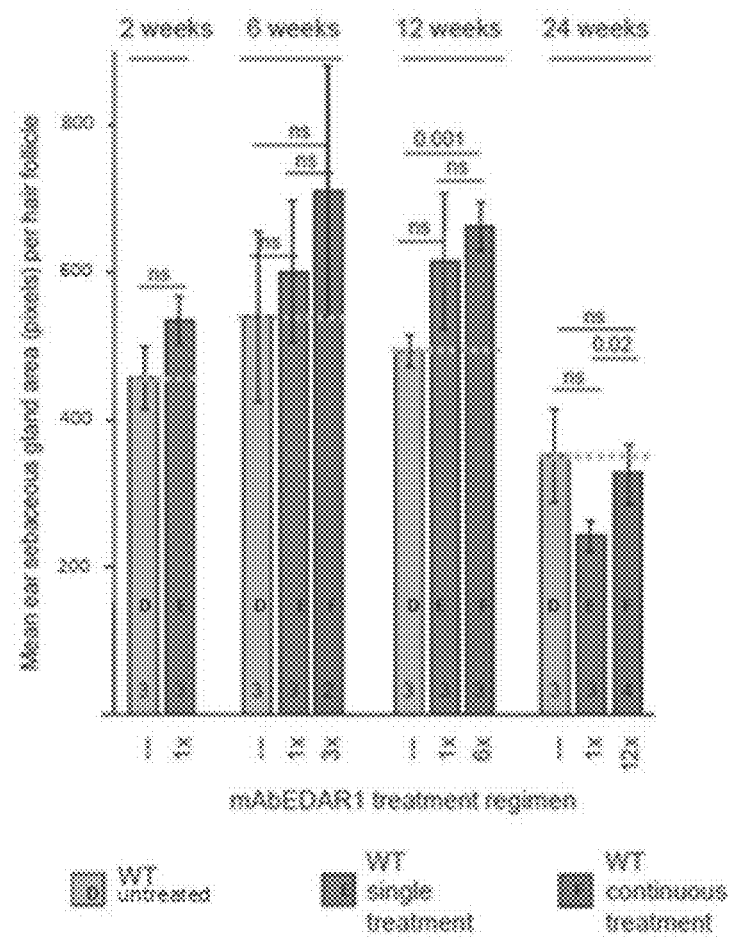

FIG. 43. Plot indicating the changes in sebaceous gland size as a function of time in treated and untreated wild type mice. Multiplication factors shown on the x-axis indicate the number of treatments. Error bars indicate standard deviation (n=2, 3 or 4 per treatment condition—indicated at the bottom of each bar).

Figure 44:
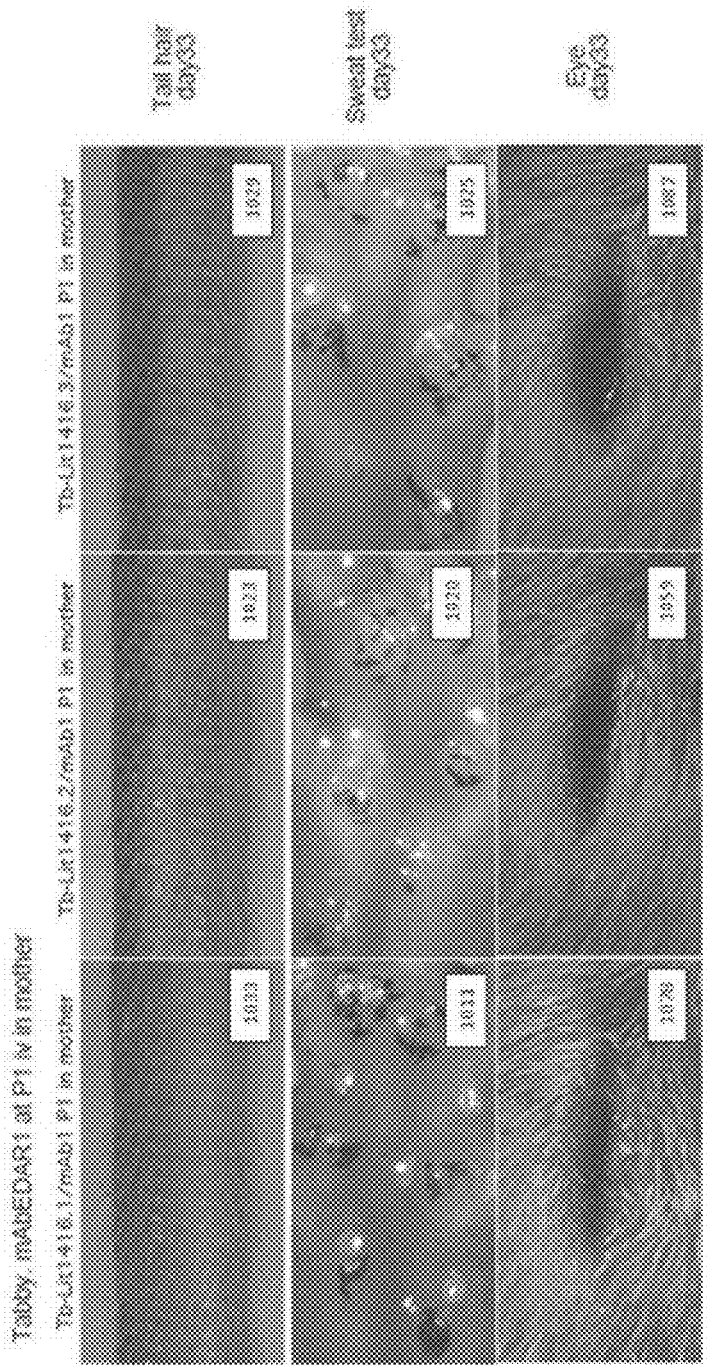

FIG. 44. Photographs of tail hair, sweat glands and an eye obtained from three individual Tabby mouse litter mates taken 33 days after birth. The identifier of each litter mate is indicated above each vertical series of photographs. The mother was injected intravenously with mAbEDAR1 at 5 mg/kg within 24 hours after delivery and the litter mates were allowed to nurse naturally.

Figure 45:
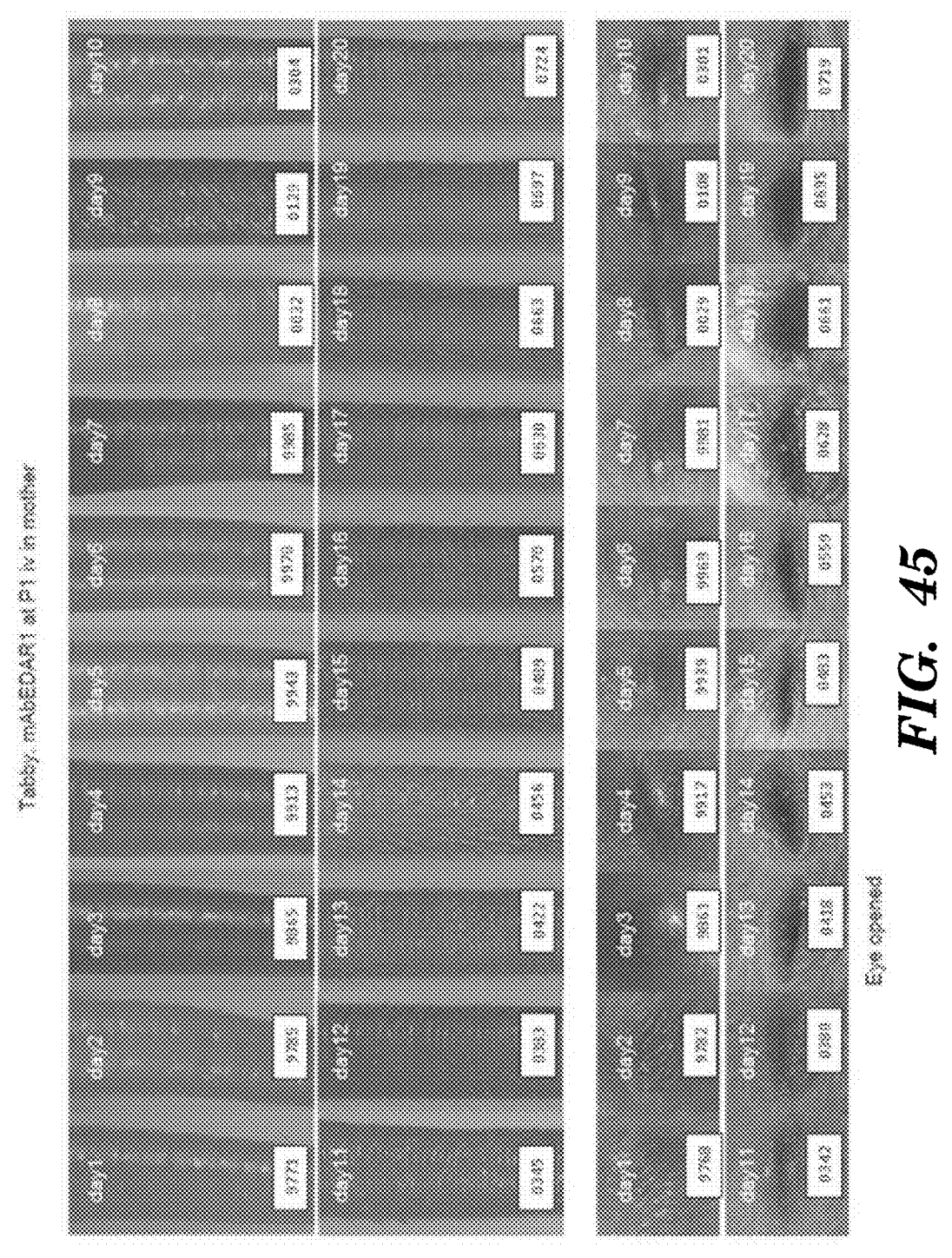

FIG. 45. Photographs taken daily (for 20 days) of tail hairs and eye of a Tabby mouse pup. The pup was nursed naturally by a mother injected intravenously with mAbEDAR1 at 5 mg/kg within 24 hours after delivery.

Figure 46:
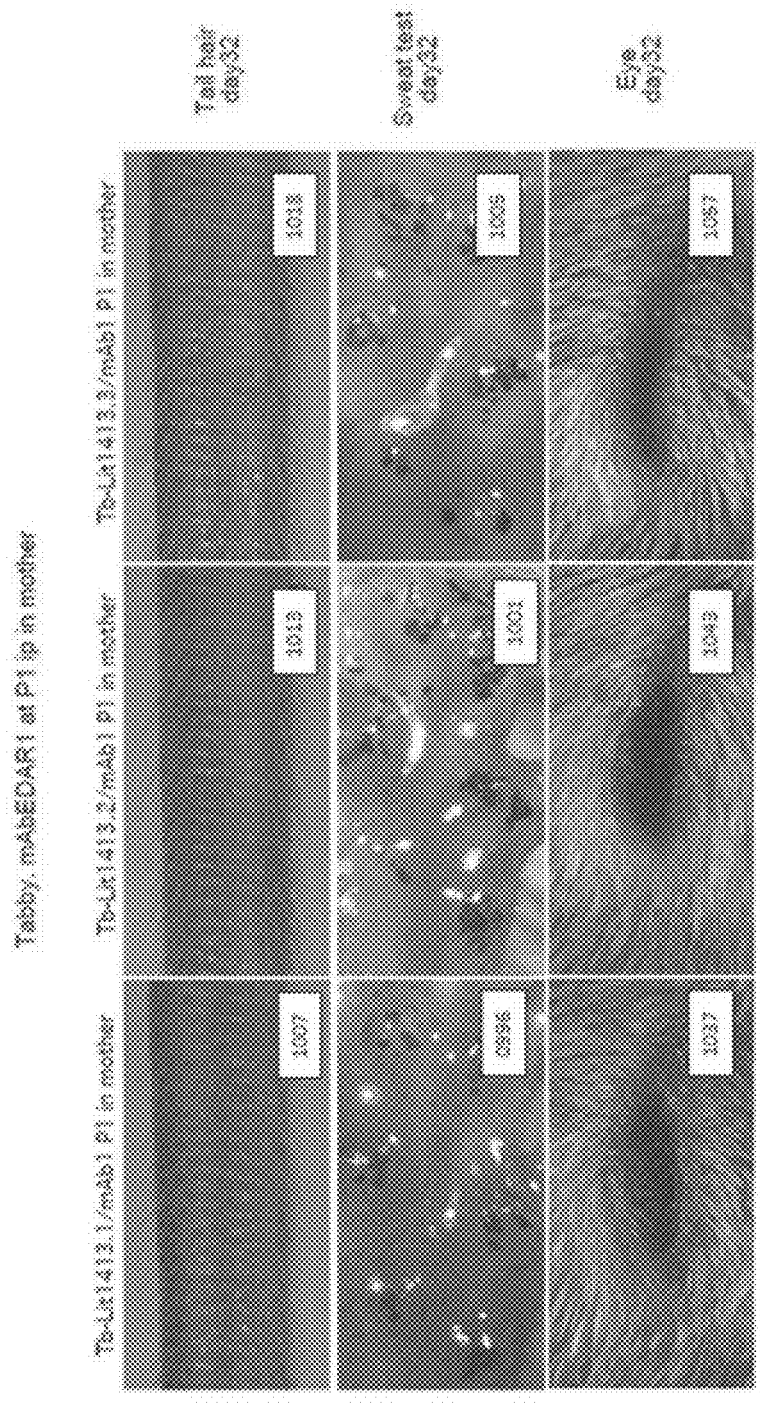

FIG. 46. Photographs of tail hair, sweat glands and eye obtained from three Tabby mouse litter mates taken 32 days after birth. The identifier of each litter mate is indicated above each vertical series of photographs. The mother was injected intraperitoneally with mAbEDAR1 at 5 mg/kg within 24 hours after delivery and the litter mates were allowed to nurse naturally.

Figure 47:
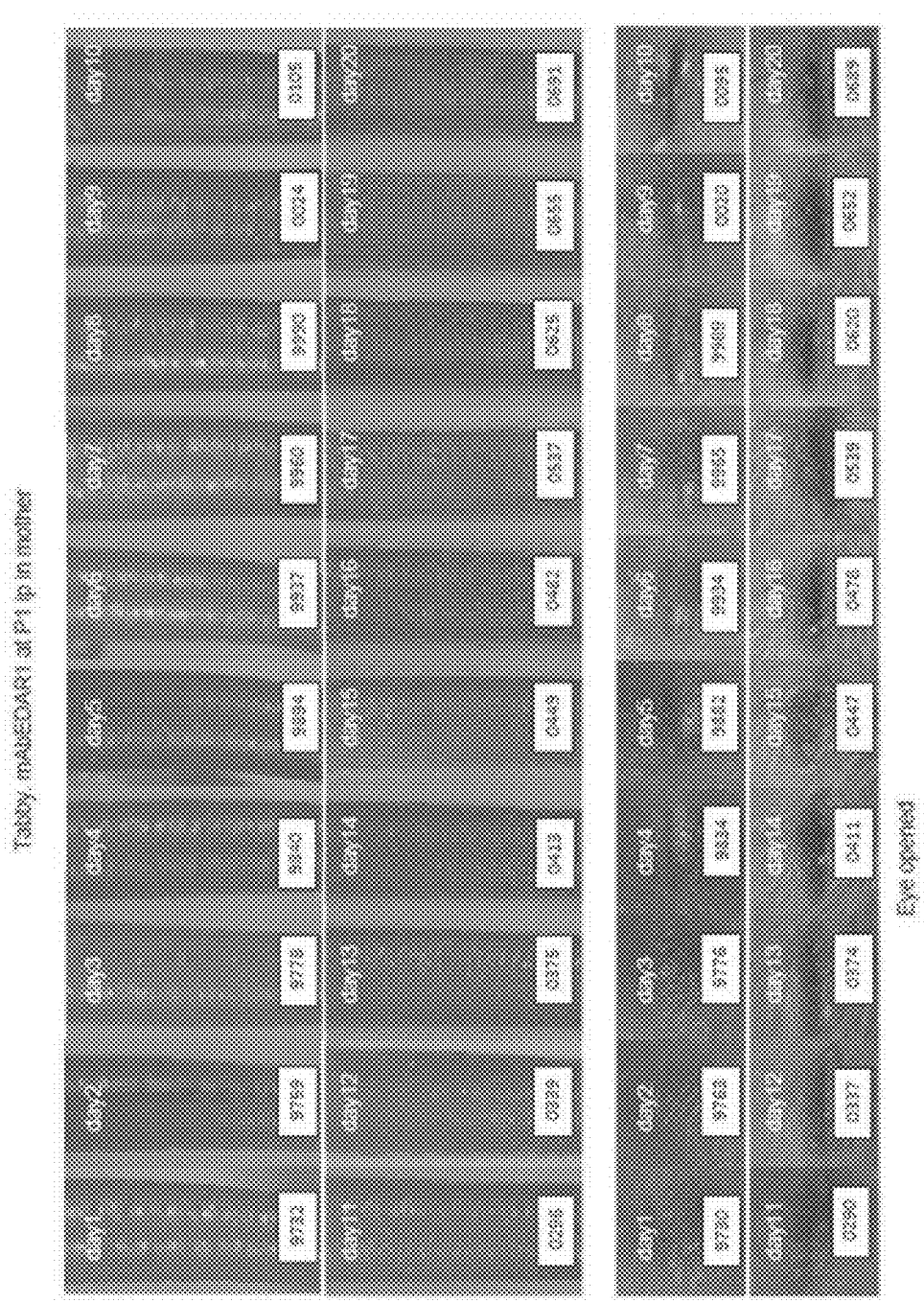

FIG. 47. Photographs taken daily (for 20 days) of tail hairs and eye of a Tabby mouse pup. The pup was nursed naturally by a mother injected intraperitoneally with mAbEDAR1 at 5 mg/kg within 24 hours after delivery.

Figure 48:
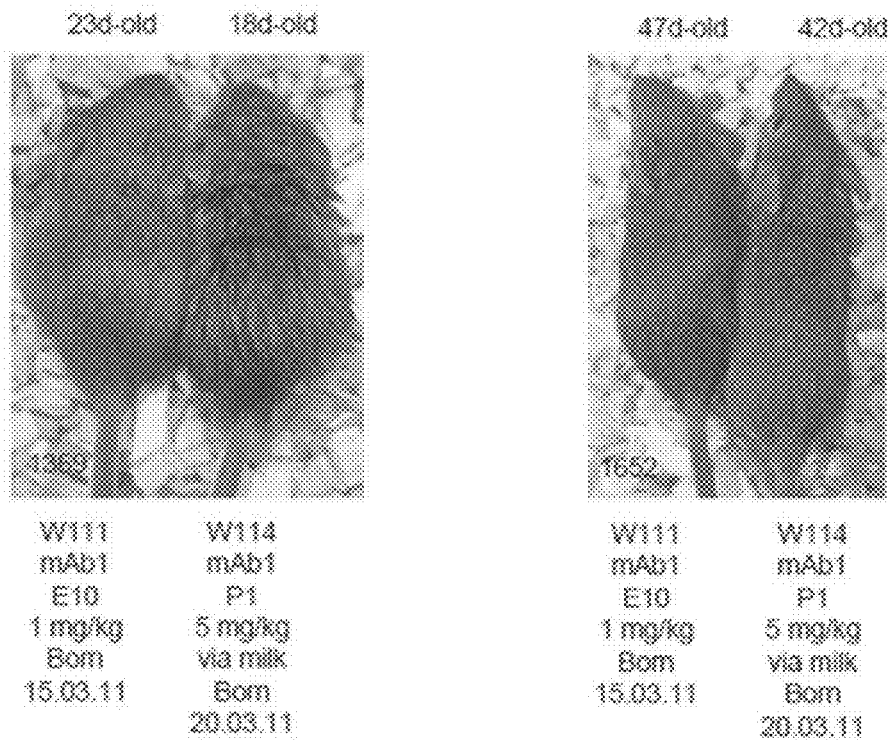

FIG. 48. Photographs of wild type mice nursed by mothers injected with mAbEDAR1 at 1 mg/kg or 5 mg/kg on the same day as delivery of pups. The mouse designated W111 mAb1 E10 was nursed by a mother injected intravenously with 1 mg/kg of mAbEDAR1 and the mouse designated W114 mAb1 P1 was injected intraperitoneally with 5 mg/kg of mAbEDAR1.

SEQUENCE LISTING

The instant application contains a Sequence Listing which has been submitted via EFS-Web and is hereby incorporated by reference in its entirety. Said ASCII copy, created on Mar. 29, 2010, is named 17321PCT.txt and is 160,961 bytes in size.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1-84 show the amino acid sequences of the CDR1, CDR2 and CDR3 of the heavy chains and light chains of fourteen agonist anti-EDAR monoclonal antibodies, namely mAbEDAR1, mAbEDAR2, mAbEDAR3, mAbEDAR5, mAbEDAR6, mAbEDAR7, mAbEDAR8, mAbEDAR9, mAbEDAR10, mAbEDAR11, mAbEDAR12, mAbEDAR13, mAbEDAR14 and mAbEDAR15. In addition, the light chain of mAbEDAR4 is identical to that of mAbEDAR2 (see Table 1).

SEQ ID NO: 85-168 show the nucleotide sequences of the CDR1, CDR2 and CDR3 of the heavy chains and light chains of the fourteen previous agonist anti-EDAR monoclonal antibodies, namely mAbEDAR1, mAbEDAR2, mAbEDAR3, mAbEDAR5, mAbEDAR6, mAbEDAR7, mAbEDAR8, mAbEDAR9, mAbEDAR10, mAbEDAR11, mAbEDAR12, mAbEDAR13, mAbEDAR14 and mAbEDAR15 (see Table 2).

Figure 3C:
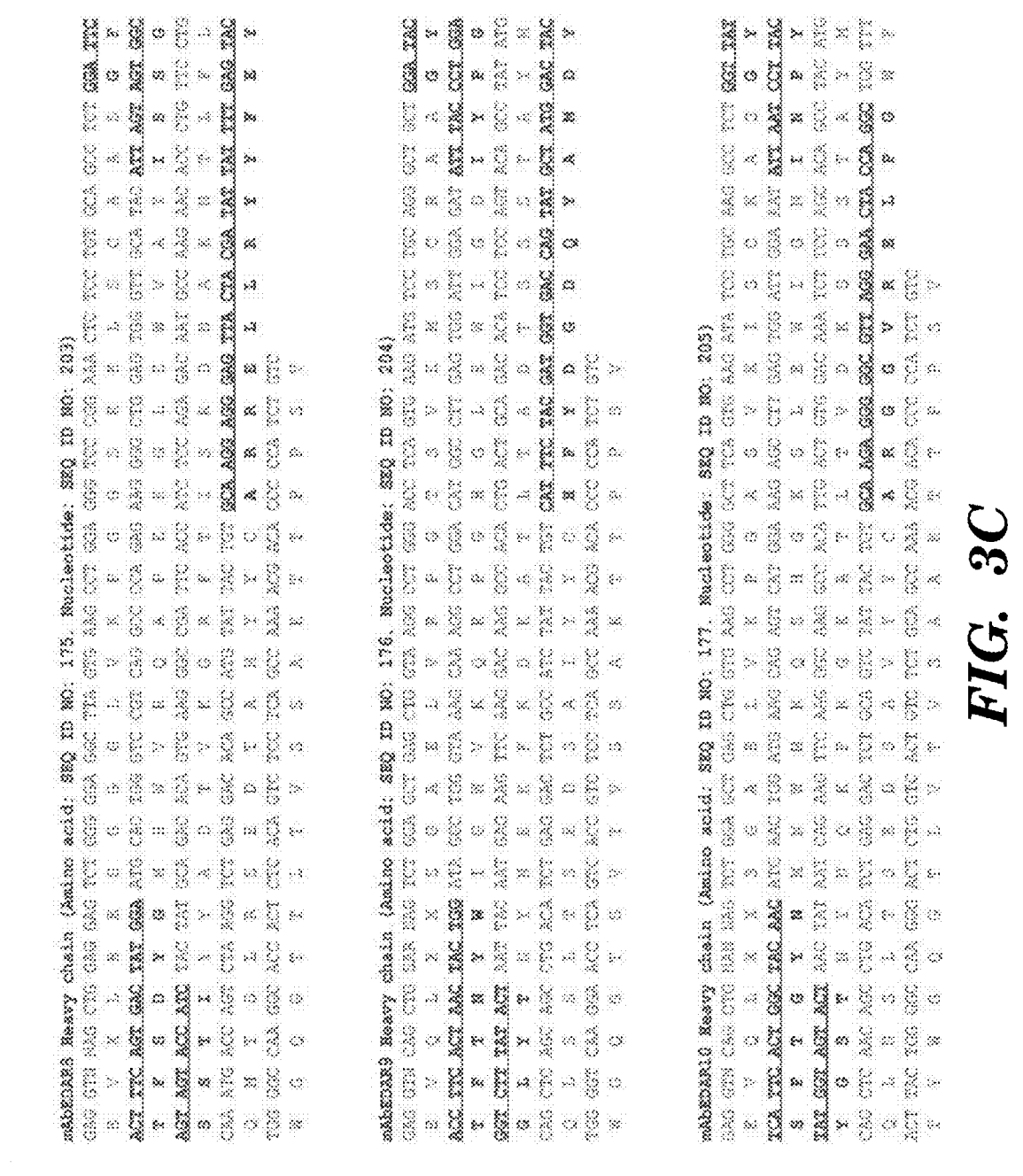
Figure 3D:
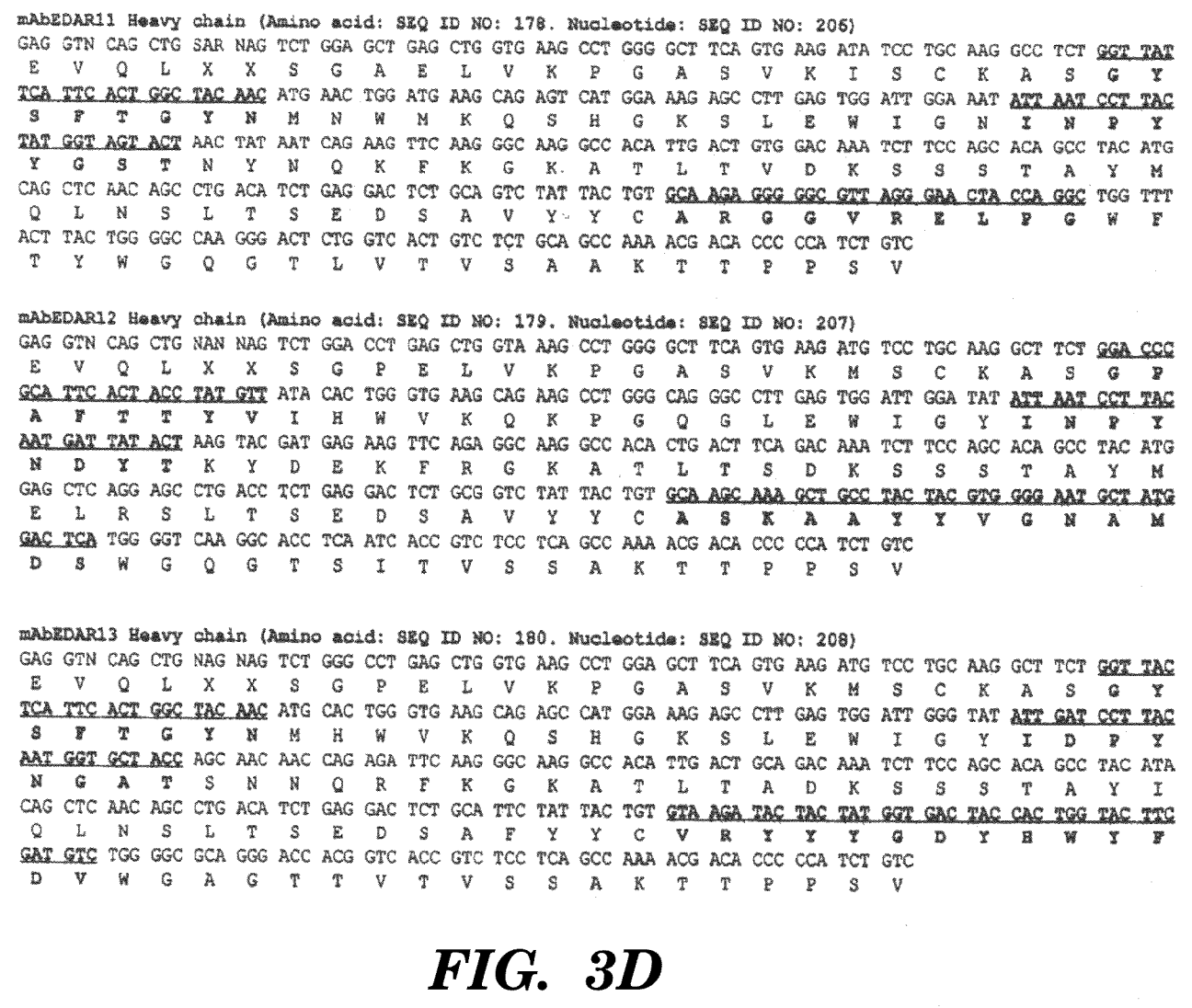
Figure 3E:
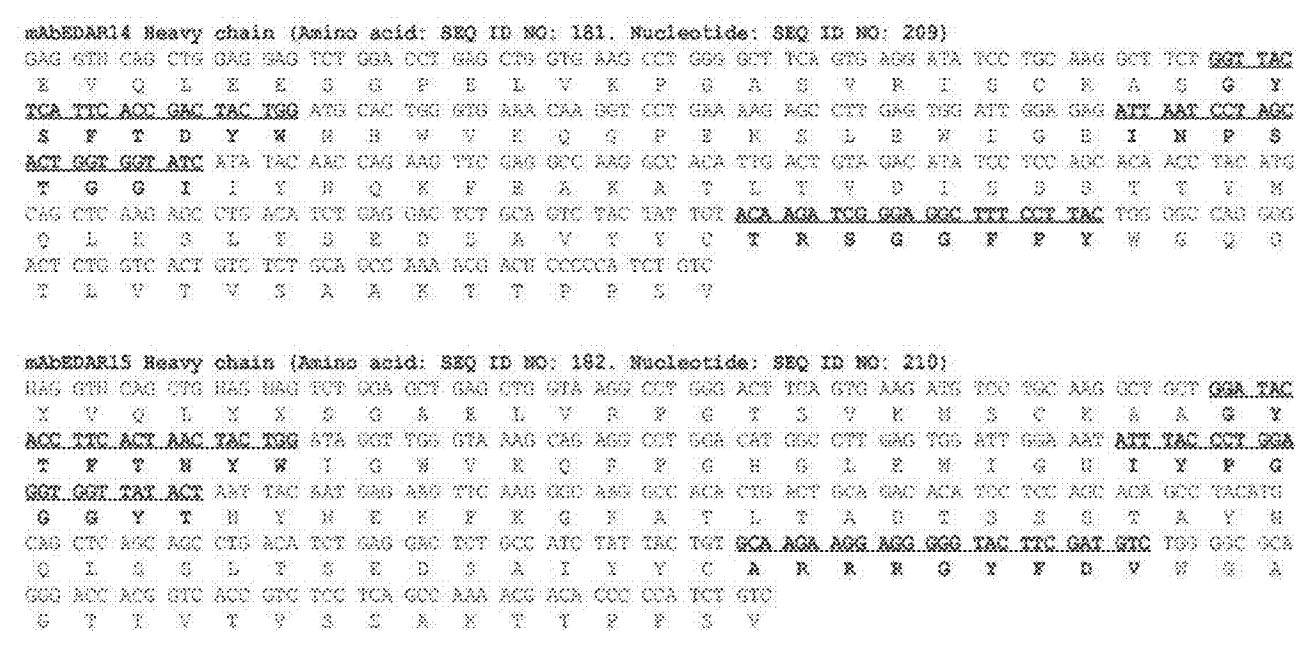

SEQ ID NO: 169-182 show the amino acid sequence of variable regions of the heavy chain of mAbEDAR1, mAbEDAR2, mAbEDAR3, mAbEDAR5, mAbEDAR6, mAbEDAR7, mAbEDAR8, mAbEDAR9, mAbEDAR10, mAbEDAR11, mAbEDAR12, mAbEDAR13, mAbEDAR14 and mAbEDAR15 (FIG. 3).

SEQ ID NO: 183-196: show the amino acid sequences of variable regions of the light chain of mAbEDAR1, mAbEDAR2 (identical to mAbEDAR4), mAbEDAR3, mAbEDAR5, mAbEDAR6, mAbEDAR7, mAbEDAR8, mAbEDAR9, mAbEDAR10, mAbEDAR11, mAbEDAR12, mAbEDAR13, mAbEDAR14 and mAbEDAR15 (FIG. 4).

SEQ ID NO: 197-210 shows the nucleotide sequence of variable regions of the heavy chain of mAbEDAR1, mabEDAR2, mAbEDAR3, mAbEDAR5, mAbEDAR6, mAbEDAR7, mAbEDAR8, mAbEDAR9, mAbEDAR10, mAbEDAR11, mAbEDAR12, mAbEDAR13, mAbEDAR14 and mAbEDAR15 (FIG. 3).

SEQ ID NO: 211-224: show the nucleotide sequences of variable regions of the light chain of mAbEDAR1, mAbEDAR2 (identical to mAbEDAR4), mAbEDAR3, mAbEDAR5, mAbEDAR6, mAbEDAR7, mAbEDAR8, mAbEDAR9, mAbEDAR10, mAbEDAR11, mAbEDAR12, mAbEDAR13, mAbEDAR14 and mAbEDAR15 (FIG. 4).

SEQ ID NO: 225, 227, 229, 231, 233: show the nucleotide sequences (from T7 to Sp6 sites of the mammalian expression vector PCR3 from Invitrogen) of various EDAR constructs. SEQ ID NO 225: mouse EDAR (1-183)-Fc. SEQ ID NO 227: human EDAR (1-183)-Fc. SEQ ID NO 229: full length human EDAR (1-448). SEQ ID NO 229: human EDAR (1-72)-Fc. SEQ ID NO 231: human EDAR (1-114)-Fc SEQ ID NO: 226, 228, 230, 232, 234: show the amino acid sequence coded by SEQ ID NO: 225, 227, 229, 231, 233.

SEQ ID NO: 235-242: show the amino acid sequences of full length human and mouse EDAR, and of fragments of human and mouse EDAR. SEQ ID NO 235: full length human EDAR (1-448). SEQ ID NO 236: full length mouse EDAR (1-448). SEQ ID NO 237: human EDAR (29-72). SEQ ID NO 238: human EDAR (71-114). SEQ ID NO 239: human EDAR (29-114). SEQ ID NO 240: mouse EDAR (29-72). SEQ ID NO 241: mouse EDAR (71-114). SEQ ID NO 242: mouse EDAR (29-114).

DETAILED DESCRIPTION OF THE INVENTION

As used herein, the following definitions are supplied in order to facilitate the understanding of the present invention.

"A" or "an" means "at least one" or "one or more."

The term "comprise" is generally used in the sense of include, that is to say permitting the presence of one or more features or components.

As used herein, the terms "protein", "polypeptide", "polypeptidic", "peptide" and "peptidic" or "peptidic chain" are used interchangeably herein to designate a series of amino acid residues connected to the other by peptide bonds between the alpha-amino and carboxy groups of adjacent residues.

"Amino acid residue" means any amino acid residue known to those skilled in the art. This encompasses naturally occurring amino acids (including for instance, using the three-letter code, Ala, Arg, Asn, Asp, Cys, Gln, Glu, Gly, His, Ile, Leu, Lys, Met, Phe, Pro, Ser, Thr, Trp, Tyr, Val), as well as rare and/or synthetic amino acids and derivatives thereof (including for instance Aad, Abu, Acp, Ahe, Aib, Apm, Dbu, Des, Dpm, Hyl, McLys, McVal, Nva, and the like).

Said amino acid residue or derivative thereof can be any isomer, especially any chiral isomer, e.g. the L- or D-isoform.

By amino acid derivative, we hereby mean any amino acid derivative as known in the art. For instance, amino acid derivatives include residues derivable from natural amino acids bearing additional side chains, e.g. alkyl side chains, and/or heteroatom substitutions.

The term "purified" does not require absolute purity; rather, it is intended as a relative term. Thus, for example, a purified agonist anti-EDAR monoclonal antibody preparation is one in which the protein is more pure than the protein in its natural environment within a cell. Preferably, a preparation of agonist anti-EDAR monoclonal antibody is purified such that the protein represents at least 50% of the total protein content of the preparation.

As used herein, the expression "substantially pure" refers to material that is at least 50% pure, preferably at least 90% pure, more preferably at least 95% pure, even more preferably at least 98% pure and most preferably 99% pure, or with greater purity.

An "isolated antibody", as used herein, is intended to refer to an antibody which is substantially free of other antibodies having different antigenic specificities (e. g., an isolated antibody that specifically binds to EDAR is substantially free of antibodies that specifically bind antigens other than EDAR). An isolated antibody that specifically binds to an epitope, isoform or variant of human EDAR may, however, have cross-reactivity to other related antigens, e. g., from other species (e. g., EDAR species homologues). Moreover, an isolated antibody may be substantially free of other cellular material and/or chemicals. In one embodiment of the invention, a combination of "isolated" monoclonal antibodies having different specificities are combined in a well defined composition.

"Disease", as used herein, refers to a pathological condition of a part, organ, or system of an organism resulting from various causes, such as infection, genetic defect, or environmental stress, and characterized by an identifiable group of signs or symptoms.

The term "subject" refers to patients of human or other vertebrates in particular mammal and includes any individual it is desired to examine or treat using the methods according to the present invention. However, it will be understood that "patient" does not automatically imply that symptoms or diseases are present. As used herein, the term "patient" preferably refers to a human in need of treatment to treat XLHED.

"Mammal" for purposes of treatment refers to any animal classified as a mammal, including humans, domestic and farm animals, and zoo, sports, or pet animals, such as dogs, horses, cats, cows, monkeys etc. Preferably, the mammal is a human.

"Vertebrate" for purposes of treatments refers to any animal classified as a vertebrate, including birds, amphibians and fishes. Preferably, the vertebrate is a human.

"Treatment" refers to both therapeutic treatment and prophylactic or preventive measures. Those in need of treatment include those already with the disorder as well as those in which the disorder is to be prevented. Hence, the mammal to be treated herein may have been diagnosed as having the disorder or may be predisposed or susceptible to the disorder. Thus the term "treatment" or "treating" herein encompasses curative treatment, preventive treatment as well as palliative treatment, more specifically palliative treatment and curative treatment. For the purpose of this invention, the "treatment" is an approach for obtaining beneficial results including, but not limited to, one or more of the following: reducing or totally destroying of the symptoms of the XLHED disease and decreasing the frequency of mortality by patients.

The phrase "pharmaceutically acceptable" refers to molecular entities and compositions that are physiologically tolerable and do not typically produce an allergic or similar untoward reaction, such as gastric upset, dizziness and the like, when administered to a patient in particular to a human.

The expression "effective amount" is an amount sufficient to effect beneficial or desired results including, without limitation, clinical results, preventing or attenuating symptoms resulting from the disease, decreasing the dose of other medicaments required to treat the disease. An effective amount can be administered in one or more administrations of the active substance. For the purpose of this invention, the active substance is a molecular composition inducing a biological activity when interacting with EDAR (EDAR modulator).

In the present invention, the term "receptor" refers to a structure on the surface of a cell (or inside a cell) that selectively receives and binds a specific molecule which affects the activities of the cell.

The term "antigen" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes.

The term "antibody", as used herein, refers to a protein produced by the immune system that protects the organism against an antigen. But, as used herein, the term encompasses not only intact monoclonal antibodies but also fragments thereof, single chains, mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity. An intact "antibody" comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4.

The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "agonist" refers to a drug/ligand/antibody which binds to a receptor and activates it, producing a pharmacological response (e.g. contraction, relaxation, secretion, enzyme activation, etc.).

The terms "monoclonal antibody" (mAb) or "monoclonal antibody composition" as used herein refer to a preparation of antibody molecules of single molecular composition. A monoclonal antibody composition displays a single binding specificity and affinity for a particular epitope. The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics.

The phrases "an antibody recognizing an antigen" and "an antibody specific for an antigen" are used interchangeably herein with the term "an antibody which binds specifically to an antigen."

The term "antigen-binding portion" of an antibody (or simply "antibody portion"), as used herein, refers to one or more fragments of an intact antibody that retain the ability to specifically bind to an antigen (e.g., EDAR). It has been shown that the antigen-binding function of an antibody can be performed by fragments of a full-length antibody. Examples of binding include (i) a Fab fragment, a monovalent fragment consisting of the VL, VH, CL and CH1 domains; (ii) a F (ab)'2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341: 544-546), which consists of a VH domain; and (vi) an isolated complementarity determining region (CDR); and (vii) a nanobody, a heavy chain variable region containing a single variable domain and two constant domains. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Huston et al (1988) Proc. Natl. Acad. Sc USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

"Fragments" refer to sequences sharing at least 40% amino acids in length with the respective sequence of the intact or full length agonist anti-EDAR monoclonal antibodies (native). These sequences can be used as long as they exhibit the same properties as the native sequence from which they derive. Preferably these sequences share more than 70%, preferably more than 80%, in particular more than 90% amino acids in length with the respective sequence the intact or full length agonist anti-EDAR monoclonal antibodies.

In the case of an agonist anti-EDAR monoclonal antibody of the invention, useful fragments include, but are not limited to: a CDR region, especially a CDR3 region of the heavy or light chain; a variable domain of a heavy or light chain; a portion of an antibody chain or just its variable region including two CDRs; and the like.

Suitable agonist anti-EDAR monoclonal antibody fragments of the invention are immunologically functional immunoglobulins. The term "immunologically functional immunoglobulin fragment" as used herein refers to a polypeptide fragment that contains at least the CDRs of the immunoglobulin heavy and light chains. An immunologically functional immunoglobulin fragment of the invention is capable of specifically binding to EDAR. Most preferably, the fragment binds specifically to and/or modulates the biological activity of EDAR.

In a first embodiment, the present invention concerns a method for producing agonist anti-EDAR monoclonal antibodies or isolated monoclonal antibody fragments or antigen binding portions or fragments thereof comprising the steps of:
  a) producing EDAR antigen, or EDAR fragment, or EDAR fusion protein of mouse and/or human and/or vertebrate species
  b) immunizing EDAR-deficient mice with said EDAR antigen or EDAR fragment, or EDAR fusion protein
  c) detection of anti-EDAR antibodies in the serum of said EDAR antigen or EDAR fragment, or EDAR fusion protein-immunized EDAR-deficient mice
  d) producing hybridomas between lymph node cells from EDAR antigen or EDAR fragment, or EDAR fusion protein-immunized, EDAR-deficient mice and myeloma cells
  e) identifying agonist anti-EDAR antibodies or isolated monoclonal antibody fragments or antigen binding portions or fragments thereof recognizing human and/or mouse EDAR and/or EDAR from any vertebrate species
    i. by binding assays designed to detect binding between the said agonist anti-EDAR antibodies or isolated monoclonal antibody fragments or antigen binding portions or fragments thereof and human and/or mouse EDAR antigen or EDAR fragment, or EDAR fusion protein; and
    ii. for their ability to induce a biological response in vitro in cells or tissues expressing EDAR or an EDAR fusion protein.
    iii. for their ability to induce a biological response in vivo in organisms expressing EDAR or EDAR fusion proteins.

f) selecting hybridomas lines for the agonist anti-EDAR monoclonal antibodies they produce on the basis of steps e) ii and e) iii
g) cloning and sub-cloning of said selected hybridoma lines
h) purifying the resulting agonist anti-EDAR monoclonal antibodies or isolated monoclonal antibody fragments or antigen binding portions or fragments thereof.

Preferably, the EDAR antigen of step a) is human EDAR, or mouse EDAR, or EDAR from another mammalian species, or EDAR from another vertebrate species.

Preferably, the EDAR antigen of step a) is a cell line naturally expressing full length EDAR or transfected with full length EDAR, or the EDAR antigen is a soluble EDAR fragment, or the EDAR antigen is a fusion protein between the extracellular domain of EDAR and another protein, or the EDAR antigen is part of a virus-like particle.

More preferably, the EDAR antigen is expressed in a cell line syngenic with mice of step b), or the EDAR antigen is fused to the Fc portion of an IgG.

Even more preferably, the EDAR antigen is human or mouse EDAR fused to the Fc portion of human IgG1.

As an alternative to steps b), c) and d), anti-EDAR antibodies, or fragment thereof such as single chain Fv can be obtained by selecting antibody sequences by phage display on the antigen of step a).

Preferably, the binding assays of step e) is carried out by applying visualizing methods comprising ELISA, dot blot, Western blot, RIA, immunoprecipitation, flow cytometry, fluorescence microscopy, electron microscopy, confocal microscopy, calorimetry, plasmon resonance, test of Ouchterlony, complement-mediated lysis of red blood cells, antibody-dependent cell cytotoxicity and the like.

More preferably, the binding assays of step e) i is carried out by direct or capture ELISA.

Preferably, the biological in vitro assay of step e) ii is the measure of placode formations in embryonic skin of Tabby mouse embryos ex vivo (Mustonen et al. Ectodysplasin A1 promotes placodal fate during early morphogenesis of ectodermal appendages, Development 131:4907-4919, 2004), the measure of NF-kB activation in EDAR-positive cells, or the measure of apoptosis of Fas-deficient Jurkat cells transduced with chimeric human and/or mouse EDAR-Fas receptor.

More preferably, the biological in vitro assay of step e) ii is the measure of apoptosis of Fas-deficient Jurkat cells transduced with chimeric human and/or mouse EDAR-Fas receptor.

Preferably, the biological in vivo assay of step e) iii is the measure of tail hair formation and/or the measure of functional sweat glands formation upon administration to newborn EDA-deficient Tabby mice.

In particular, the purification of step h) is carried out by protein A or G affinity chromatography or by protein L, anti-mouse IgG antibody-based affinity chromatography, ion exchange, ethanol or ammonium sulfate precipitation and the like.

Methods for preparing an immunogen and immunizing an animal are well-known in the art (Kohler and Milstein 1975 Nature 256:495-497; Brown et al. 1981 J Immunol 127:539-46; Brown et al., 1980 J Biol Chem 255:4980-83; Yeh et al., 1976 Proc Natl Acad Sci USA 76:2927-31; Yeh et al., 1982 Int J Cancer 29:269-75; Kozbor et al., 1983 Immunol Today 4:72; Cole et al., 1985 Monoclonal Antibodies and Cancer Therapy, Alan R. Liss, Inc., pp. 77-96; U.S. Pat. No. 4,816,567; Clackson, et al., 1991 Nature 352:624-628; Marks, et al., 1991 J Mol Biol 222:581-597).

One of the preferred embodiments for obtaining agonist anti-EDAR antibodies is as follows:
a) produce human EDAR-Fc and mouse EDAR-Fc fusion proteins.
b) immunize OVE1B EDAR-deficient mice with human EDAR-Fc fusion protein and immunize OVE1B EDAR-deficient mice with mouse EDAR-Fc fusion protein.
c) detect anti-EDAR antibodies in the serum of immunized EDAR-deficient mice.
d) produce hybridomas between lymph node cells from EDAR-Fc-immunized, EDAR-deficient mice and myeloma cells.
e) identify hybridoma of interest for their ability to specifically recognize human and mouse EDAR-Fc, but not an irrelevant Fc fusion protein by ELISA.
f) identify hybridoma of point e) producing agonist anti-EDAR antibodies by administering unpurified supernatants to newborn Tabby mice, and select those that induce tail hair formation and/or sweat gland formation.
g) sub-clone and amplify hybridoma selected in point f), transfer them in serum-free medium and purify antibodies from serum-free supernatants by protein G affinity chromatography. Dose purified antibodies by their absorbance at 280 nm.
h) titrate purified anti-EDAR antibodies of point g) on Fas-deficient Jurkat cells transduced with chimeric human EDAR-Fas receptor and on Fas-deficient Jurkat cells transduced with chimeric human EDAR-Fas receptor. Determine their EC50 of apoptosis induction.
i) titrate purified anti-EDAR antibodies of point g) in newborn Tabby mice and determine the EC50 of their ability to induce tail hair formation and/or sweat gland formation.
j) select anti-EDAR antibodies with the lowest EC50 in tests of points h) and i). Antibody sequences obtained by this process are those of mAbEDAR1-15 (SEQ ID #169-196), preferably those of mAbEDAR1, 3, 5, 6, 7, 8, 9, 10, 12, 13 and 14 (SEQ ID#169, 171-177, 179-181, 183, 185, 186-191 and 193-195), even more preferably those of mAbEDAR1, 3, 10 and 12 (SEQ ID#169, 171, 177, 179, 183, 185, 191 and 193).

A preferred method for producing agonist anti-EDAR monoclonal antibodies or isolated monoclonal antibody fragments or antigen binding portions or fragments thereof is illustrated in example 1.

Surprisingly, Applicants have observed some unanticipated results obtained with the process according to the invention.

In particular, in order to develop an EDA1-dependent biological activity assay, which was sensitive and specific for the multimerized form of EDA1, cell lines were developed (EDAR-Fas-transduced and Fas-negative Jurkat cell lines). The use of a Fas-negative recipient cell line might be needed, as Fas-positive cells would result in cell lines with an inappropriate sensitivity to EDAR agonists. It was then found that the cell lines, which were working properly for this assay, expressed low levels of the transduced EDAR-Fas fusion protein. If selection of the cell lines would have been based on the expression of the transgene, one could expect that one would have selected the cells expressing high levels of the transgene. One could predict that this would have not resulted in the successful identification of suitable cell lines. These unanticipated results can be now rationalized by explaining that a high level of transgene causes apoptosis, even in the absence of ligand. These cells are thus rapidly eliminated before selection. The cells that nevertheless expressed high levels of the EDAR-Fas fusion protein were insensitive, most probably because they had mutated downstream elements in the signaling pathway.

Another important point is that EDAR-Fas-expressing cells allowed to rapidly sorting agonist anti-EDAR antibodies into two categories: those that displayed, and those that did not displayed in vitro activity on these cells. Those antibodies able to activate EDAR-Fas expressing cells were also very often those with the lowest affinity constants, and the lowest dissociation constants. It may be anticipated that these antibodies will also be those with the best activity on toot development. EDA signals required for proper tooth development are indeed believed to be stronger or of better quality than those required for the development of other ectodermal appendages (Mues et al., Eur. J. Hum. Gen. 18:19-25, 2010).

A third important point of interest is that the classical approach for the development of monoclonal antibodies consists in the immunization of wild type mice with the human protein antigens. In this situation, antibodies specific for determinants differing between the mouse and the human proteins are obtained. In order to generate agonist anti-EDAR monoclonal antibodies cross-reacting with both mouse and human EDAR, Applicants have used the EDAR-deficient mice OVEB1 (the EDAR signaling-defective mice downless and sleek would not have been suitable, as they still express the extracellular region of the EDAR polypeptide). This approach is believed to have maximized the diversity of anti-EDAR antibodies Applicants have generated. The OVEB 1 mouse strain is not commercially available. This situation renders this approach problematic for most people who would like to develop agonist anti-EDAR antibodies. At the beginning, Applicants attempted to develop anti-EDA1 antibodies by immunizing wild type mice with recombinant EDA1 protein (the portion which is 100% identical between human and mouse). No useful antibodies were obtained. By contrast, when Tabby mice (EDA-deficient mice) were immunized with EDA1, anti-EDA1 monoclonal antibodies were obtained. Applicants further note that following in vitro screening, the agonist anti-EDAR monoclonal antibodies were screened in vivo by injecting them in newborn Tabby mice. This in vivo assay is certainly not a standard test, which can be easily performed by scientists without experience in the field.

Another object of the invention is to provide an isolated agonist anti-EDAR monoclonal antibodies or isolated monoclonal antibody fragments or antigen binding portions or fragments thereof obtainable by the above-described process and wherein said isolated agonist anti-EDAR monoclonal antibodies or isolated monoclonal antibody fragments or antigen binding portions or fragments thereof bind to human and/or mouse EDAR with an affinity constant (KD) of at least $10^{-8}$ M for the Fab fragment. The specific binding according to the invention presents a high affinity. In addition, the said isolated agonist anti-EDAR monoclonal antibodies or isolated monoclonal antibody fragments or antigen binding portions or fragments thereof that cross-react with mouse EDAR induce tail hair formation and/or sweat gland formation with an EC50 of less than 20 mg/kg when administered to newborn Tabby mice, as described in example 7.

As used herein, "specific binding" refers to antibody binding to a predetermined antigen. Typically, the antibody binds with a affinity constant (KD) of $10^{-8}$ M or less for the Fab fragment, and binds to the predetermined antigen with a KD that is at least ten-fold less than its KD for binding to a non-specific antigen (e. g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

The term "Kassoc" or "Ka", as used herein, is intended to refer to the association rate of a particular antibody-antigen interaction, whereas the term "KdiS" or "Kd" is intended to refer to the dissociation rate of a particular antibody-antigen interaction. The term "high affinity" for an IgG antibody refers to an affinity constant (KD) for the Fab fragment of at least about $10^{-8}$ M, at least about $10^{-9}$ M, at least about $10^{-10}$ M, at least about $10^{-11}$ M, or at least about $10^{-12}$ M or greater, e. g., up to $10^{-13}$ M or $10^{-14}$ M or greater. However, "high affinity" binding can vary for other antibody isotypes.

Preferably, the isolated agonist anti-EDAR monoclonal antibodies or isolated monoclonal antibody fragments or antigen binding portions or fragments thereof, that specifically bind human and mouse EDAR, comprise: a heavy chain variable region comprising the complementary determining region amino acid sequences of SEQ ID NO: 1, SEQ ID NO: 2, SEQ ID NO: 3, or SEQ ID NO: 7, SEQ ID NO: 8, SEQ ID NO: 9, or SEQ ID NO: 13, SEQ ID NO: 14, SEQ ID NO: 15, or SEQ ID NO: 19, SEQ ID NO: 20, SEQ ID NO: 21, or SEQ ID NO: 25, SEQ ID NO: 26, SEQ ID NO: 27, or SEQ ID NO: 31, SEQ ID NO: 32, SEQ ID NO: 33, or SEQ ID NO: 37, SEQ ID NO: 38, SEQ ID NO: 39, or SEQ ID NO: 43, SEQ ID NO: 44, SEQ ID NO: 45, or SEQ ID NO: 49, SEQ ID NO: 50, SEQ ID NO: 51, or SEQ ID NO: 55, SEQ ID NO: 56, SEQ ID NO: 57, or SEQ ID NO: 61, SEQ ID NO: 62, SEQ ID NO: 63, or SEQ ID NO: 67, SEQ ID NO: 68, SEQ ID NO: 69, or SEQ ID NO: 73, SEQ ID NO: 74, SEQ ID NO: 75, or SEQ ID NO: 79, SEQ ID NO: 80, SEQ ID NO: 81 and a light chain variable region comprising the complementary determining region amino acid sequences of SEQ ID NO: 4, SEQ ID NO: 5, SEQ ID NO: 6 or SEQ ID NO: 10, SEQ ID NO: 11, SEQ ID NO: 12, or SEQ ID NO: 16, SEQ ID NO: 17, SEQ ID NO: 18, or SEQ ID NO: 22, SEQ ID NO: 23, SEQ ID NO: 24, or SEQ ID NO: 28, SEQ ID NO: 29, SEQ ID NO: 30, or SEQ ID NO: 34, SEQ ID NO: 35, SEQ ID NO: 36, or SEQ ID NO: 40, SEQ ID NO: 41, SEQ ID NO: 42, or SEQ ID NO: 46, SEQ ID NO: 47, SEQ ID NO: 48, or SEQ ID NO: 52, SEQ ID NO: 53, SEQ ID NO: 54, or SEQ ID NO: 58, SEQ ID NO: 59, SEQ ID NO: 60, or SEQ ID NO: 64, SEQ ID NO: 65, SEQ ID NO: 66, or SEQ ID NO: 70, SEQ ID NO: 71, SEQ ID NO: 72, or SEQ ID NO: 76, SEQ ID NO: 77, SEQ ID NO: 78, or SEQ ID NO: 82, SEQ ID NO: 83, SEQ ID NO: 84 and or combinations thereof and wherein said isolated monoclonal antibodies or isolated monoclonal antibody fragments or antigen binding portions or fragments thereof are agonists of human and mouse EDAR.

CDR amino acid sequences of the obtained agonist anti-EDAR monoclonal antibodies or isolated monoclonal antibody fragments or antigen binding portions or fragments thereof that specifically bind human (mAbEDAR1-15) and mouse EDAR (mAbEDAR1-14) are shown in Table 1.

TABLE 1

| SEQ ID | mAb | Chain | CDR | Amino acid sequence |
|---|---|---|---|---|
| SEQ ID#1 | mAbEDAR1 | Heavy | CDR1 | GFTFSDHG |
| SEQ ID#2 | mAbEDAR1 | Heavy | CDR2 | ISSGSSNV |
| SEQ ID#3 | mAbEDAR1 | Heavy | CDR3 | ARRELLRFYFDV |
| SEQ ID#4 | mAbEDAR1 | Light | CDR1 | QDIGNH |
| SEQ ID#5 | mAbEDAR1 | Light | CDR2 | YTS |

TABLE 1-continued

| SEQ ID | mAb | Chain | CDR | Amino acid sequence |
|---|---|---|---|---|
| SEQ ID#6 | mAbEDAR1 | Light | CDR3 | QQGNTLPWT |
| SEQ ID#7 | mAbEDAR2 | Heavy | CDR1 | GYTFTSYW |
| SEQ ID#8 | mAbEDAR2 | Heavy | CDR2 | IDPSDSYT |
| SEQ ID#9 | mAbEDAR2 | Heavy | CDR3 | SRKNYYRGMDY |
| SEQ ID#10 | mAbEDAR2 and 4 | Light | CDR1 | QNIVQSNGNTY |
| SEQ ID#11 | mAbEDAR2 and 4 | Light | CDR2 | KVS |
| SEQ ID#12 | mAbEDAR2 and 4 | Light | CDR3 | FQVSHVPYT |
| SEQ ID#13 | mAbEDAR3 | Heavy | CDR1 | GFTFSDYG |
| SEQ ID#14 | mAbEDAR3 | Heavy | CDR2 | ISSGSSAI |
| SEQ ID#15 | mAbEDAR3 | Heavy | CDR3 | ARREILRYYFDV |
| SEQ ID#16 | mAbEDAR3 | Light | CDR1 | QDISNN |
| SEQ ID#17 | mAbEDAR3 | Light | CDR2 | YTS |
| SEQ ID#18 | mAbEDAR3 | Light | CDR3 | HQGKTLPYT |
| SEQ ID#19 | mAbEDAR5 | Heavy | CDR1 | GFSLSNYG |
| SEQ ID#20 | mAbEDAR5 | Heavy | CDR2 | IWGGGST |
| SEQ ID#21 | mAbEDAR5 | Heavy | CDR3 | ASYYGYYDWFAY |
| SEQ ID#22 | mAbEDAR5 | Light | CDR1 | SIISSNY |
| SEQ ID#23 | mAbEDAR5 | Light | CDR2 | RTS |
| SEQ ID#24 | mAbEDAR5 | Light | CDR3 | QQGSSIPRT |
| SEQ ID#25 | mAbEDAR6 | Heavy | CDR1 | GYSFTGYN |
| SEQ ID#26 | mAbEDAR6 | Heavy | CDR2 | IDPYNGAT |
| SEQ ID#27 | mAbEDAR6 | Heavy | CDR3 | ARYYYGDYHWYFDV |
| SEQ ID#28 | mAbEDAR6 | Light | CDR1 | QSLVHSNGNTY |
| SEQ ID#29 | mAbEDAR6 | Light | CDR2 | KVS |
| SEQ ID#30 | mAbEDAR6 | Light | CDR3 | SQHTHVPPT |
| SEQ ID#31 | mAbEDAR7 | Heavy | CDR1 | GFPFSDYY |
| SEQ ID#32 | mAbEDAR7 | Heavy | CDR2 | IRNKANGYTT |
| SEQ ID#33 | mAbEDAR7 | Heavy | CDR3 | ATVGGYYRFPS |
| SEQ ID#34 | mAbEDAR7 | Light | CDR1 | SSVSSSY |
| SEQ ID#35 | mAbEDAR7 | Light | CDR2 | STS |
| SEQ ID#36 | mAbEDAR7 | Light | CDR3 | QQYSDYPLT |
| SEQ ID#37 | mAbEDAR8 | Heavy | CDR1 | GFTFSDYG |
| SEQ ID#38 | mAbEDAR8 | Heavy | CDR2 | ISSGSSTI |
| SEQ ID#39 | mAbEDAR8 | Heavy | CDR3 | ARRELLRYYFLY |
| SEQ ID#40 | mAbEDAR8 | Light | CDR1 | QDISNH |
| SEQ ID#41 | mAbEDAR8 | Light | CDR2 | YTS |
| SEQ ID#42 | mAbEDAR8 | Light | CDR3 | QQGNTLPYT |
| SEQ ID#43 | mAbEDAR9 | Heavy | CDR1 | GYTFTNYW |
| SEQ ID#44 | mAbEDAR9 | Heavy | CDR2 | IYPGGLYT |
| SEQ ID#45 | mAbEDAR9 | Heavy | CDR3 | HFYDGDQYAMDY |
| SEQ ID#46 | mAbEDAR9 | Light | CDR1 | QSIVHSNGNTF |
| SEQ ID#47 | mAbEDAR9 | Light | CDR2 | RVS |
| SEQ ID#48 | mAbEDAR9 | Light | CDR3 | FQGSHVPFT |
| SEQ ID#49 | mAbEDAR10 | Heavy | CDR1 | GYSFTGYN |
| SEQ ID#50 | mAbEDAR10 | Heavy | CDR2 | INPYYGST |
| SEQ ID#51 | mAbEDAR10 | Heavy | CDR3 | ARGGVRELPG |
| SEQ ID#52 | mAbEDAR10 | Light | CDR1 | SSVSY |
| SEQ ID#53 | mAbEDAR10 | Light | CDR2 | DTS |
| SEQ ID#54 | mAbEDAR10 | Light | CDR3 | QQWSSYPLT |
| SEQ ID#55 | mAbEDAR11 | Heavy | CDR1 | GYSFTGYN |
| SEQ ID#56 | mAbEDAR11 | Heavy | CDR2 | INPYYGST |
| SEQ ID#57 | mAbEDAR11 | Heavy | CDR3 | ARGGVRELPG |
| SEQ ID#58 | mAbEDAR11 | Light | CDR1 | QGISNY |
| SEQ ID#59 | mAbEDAR11 | Light | CDR2 | STS |
| SEQ ID#60 | mAbEDAR11 | Light | CDR3 | QQYSKLPP |
| SEQ ID#61 | mAbEDAR12 | Heavy | CDR1 | GPAFTTYV |
| SEQ ID#62 | mAbEDAR12 | Heavy | CDR2 | INPYNDYT |
| SEQ ID#63 | mAbEDAR12 | Heavy | CDR3 | ASKAAYYVGNAMDS |
| SEQ ID#64 | mAbEDAR12 | Light | CDR1 | TNIDDD |
| SEQ ID#65 | mAbEDAR12 | Light | CDR2 | EGN |
| SEQ ID#66 | mAbEDAR12 | Light | CDR3 | LQSDNVPLT |
| SEQ ID#67 | mAbEDAR13 | Heavy | CDR1 | GYSFTGYN |
| SEQ ID#68 | mAbEDAR13 | Heavy | CDR2 | IDPYNGAT |
| SEQ ID#69 | mAbEDAR13 | Heavy | CDR3 | VRYYYGDYHWYFDV |
| SEQ ID#70 | mAbEDAR13 | Light | CDR1 | QSLVHSNGNTY |
| SEQ ID#71 | mAbEDAR13 | Light | CDR2 | KVS |
| SEQ ID#72 | mAbEDAR13 | Light | CDR3 | SQNTHVPPT |
| SEQ ID#73 | mAbEDAR14 | Heavy | CDR1 | GYSFTDYW |
| SEQ ID#74 | mAbEDAR14 | Heavy | CDR2 | INPSTGGI |
| SEQ ID#75 | mAbEDAR14 | Heavy | CDR3 | TRSGGFPY |
| SEQ ID#76 | mAbEDAR14 | Light | CDR1 | QGISNY |
| SEQ ID#77 | mAbEDAR14 | Light | CDR2 | YTS |
| SEQ ID#78 | mAbEDAR14 | Light | CDR3 | QQYSKLPYT |
| SEQ ID#79 | mAbEDAR15 | Heavy | CDR1 | GYTFTNYW |
| SEQ ID#80 | mAbEDAR15 | Heavy | CDR2 | IYPGGGYT |

TABLE 1-continued

| SEQ ID | mAb | Chain | CDR | Amino acid sequence |
|---|---|---|---|---|
| SEQ ID#81 | mAbEDAR15 | Heavy | CDR3 | ARRRGYFDV |
| SEQ ID#82 | mAbEDAR15 | Light | CDR1 | ENIYSY |
| SEQ ID#83 | mAbEDAR15 | Light | CDR2 | NAK |
| SEQ ID#84 | mAbEDAR15 | Light | CDR3 | QHHYGTPYT |

More preferably, the isolated agonist anti-EDAR monoclonal antibodies or isolated monoclonal antibody fragments or antigen binding portions or fragments thereof, comprise: a heavy chain variable region that comprises CDR1, CDR2, CDR3 sequences and a light chain variable region that comprises CDR1, CDR2, CDR3 sequences wherein:
  (a) the heavy chain variable region CDR1 sequence comprises the amino acid sequence of SEQ ID NOs: 1, 7, 13, 19, 25, 31, 37, 43, 49, 55, 61, 67, 73 or 79 and conservative modifications thereof;
  (b) the heavy chain variable region CDR2 sequence comprises the amino acid sequence of SEQ ID NOs: 2, 8, 14, 20, 26, 32, 38, 44, 50, 56, 62, 68, 74 or 80 and conservative modifications thereof;
  (c) the heavy chain variable region CDR3 sequence comprises the amino acid sequence of SEQ ID NOs: 3, 9, 15, 21, 27, 33, 39, 45, 51, 57, 63, 69, 75 or 81 and conservative modifications thereof;
  (d) the light chain variable region CDR1 sequence comprises an amino acid sequence selected from the group consisting of amino acid sequences of SEQ ID NOs: 4, 10, 16, 22, 28, 34, 40, 46, 52, 58, 64, 70, 76 or 82 and conservative modifications thereof;
  (e) the light chain variable region CDR2 sequence comprises an amino acid sequence selected from the group consisting of amino acid sequences of SEQ ID NOs: 5, 11, 17, 23, 29, 35, 41, 47, 53, 59, 65, 71, 77 or 83 and conservative modifications thereof;
  (f) the light chain variable region CDR3 sequence comprises an amino acid sequence selected from the group consisting of amino acid sequences of SEQ ID NOs: 6, 12, 18, 24, 30, 36, 42, 48, 54, 60, 66, 72, 78 or 84 and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. Conservative amino acid substitutions are herein defined as exchanges within one of the following five groups:
  I. Small aliphatic, nonpolar or slightly polar residues: Ala, Ser, Thr, Pro, Gly
  II. Polar, positively charged residues: His, Arg, Lys
  III. Polar, negatively charged residues: and their amides: Asp, Asn, Glu, Gln
  IV. Large, aromatic residues: Phe, Tyr, Trp
  V. Large, aliphatic, nonpolar residues: Met, Leu, Ile, Val, Cys. (see, e.g., Creighton, Proteins (1984)).

According to certain embodiments, amino acid substitutions are those that: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides.

The isolated agonist anti EDAR monoclonal antibody according to the present invention is not limited to the whole molecule, and may be a fragment of the antibody or the modified product thereof, as long as it still binds to EDAR (or fragment or variant thereof) and has retained the capacity of being EDAR agonist.

Multivalent, preferably bivalent, antibody and a monovalent antibody are included Examples of the fragment of an antibody include Fab, F(ab)'2, Fv, Fab/c having one Fab and a complete Fc, and a single chain Fv (scFv) wherein the Fv of the H-chain or the L-chain is ligated with an appropriate linker. Specifically, an antibody fragment is synthesized by treating the antibody with an enzyme such as papain, pepsin or ficin, or genes encoding these antibody fragments are constructed, the genes are introduced into expression vectors, and the genes are then expressed by appropriate host cells (see e g, Rousseaux, J et al, Methods in Enzymology (1989) 121, 663-669, and Bird, R E et al, TIBTECH (1991)9, 132-137).

scFv is obtained by linking the H-chain V-region and the L-chain V-region of antibodies. In the scFv, the H-chain V-region and the L-chain V-region are linked via a linker, or preferably a peptide linker (Huston, J. S. et al., Proc. Natl. Acad. Sci. U.S.A. (1988) 85, 5879-5883). The H-chain V-region and the L-chain V-region in scFv may be derived from any of those described as antibodies in this specification. As a peptide linker to link the V-regions, for example, any single-stranded peptide comprising 12 to 19 amino acid residues is used.

Most preferably, the isolated agonist anti-EDAR monoclonal antibodies or isolated monoclonal antibody fragments or antigen binding portions or fragments thereof, consist of:
  (a) a heavy chain variable region CDR1 comprising SEQ ID NO: 1, 7, 13, 19, 25, 31, 37, 43, 49, 55, 61, 67, 73 or 79;
  (b) a heavy chain variable region CDR2 comprising SEQ ID NO: 2, 8, 14, 20, 26, 32, 38, 44, 50, 56, 62, 68, 74 or 80;
  (c) a heavy chain variable region CDR3 comprising SEQ ID NO: 3, 9, 15, 21, 27, 33, 39, 45, 51, 57, 63, 69, 75 or 81;
  (d) a light chain variable region CDR1 comprising SEQ ID NO: 4, 10, 16, 22, 28, 34, 40, 46, 52, 58, 64, 70, 76 or 82;
  (e) a light chain variable region CDR2 comprising SEQ ID NO: 5, 11, 17, 23, 29, 35, 41, 47, 53, 59, 65, 71, 77 or 83; and
  (f) a light chain variable region CDR3 comprising SEQ ID NO: 6, 12, 18, 24, 30, 36, 42, 48, 54, 60, 66, 72, 78 or 84.

According to an embodiment of the invention, the isolated agonist anti-EDAR monoclonal antibodies or isolated monoclonal antibody fragments or antigen binding portions or fragments thereof may present an antibody heavy chain selected among: IgG, IgM, IgA, IgE, single chain antibody and other immunoglobulin-derived constructs or non antibody binding proteins.

As used herein, "isotype" refers to the antibody class (e. g., IgM, IgA, IgE or IgG) that is encoded by heavy chain constant region genes.

Usually, the non antibody binding proteins comprise adnectins (fibronectin-based reagents), Affibody (protein A-based reagents), DARPins (ankyrin-based reagents), avimers (cysteine rich cell surface receptor proteins), anticalins (lipocalin-derived reagents), and nucleotide-based reagents and the like (see for example Nutall & Walsh 2008 *Curr Op Pharmacol* 8:609).

When the isolated agonist anti-EDAR monoclonal antibodies or isolated monoclonal antibody fragments or antigen binding portions or fragments thereof may present a IgG antibody heavy chain the latter may be selected among: IgG1, IgG2, IgG3 or IgG4, mutated IgG1 that is no longer recognized by FcR; mutated IgG4 sequence that no longer undergoes heavy chain swapping; mutated IgG to modify glycosylation; PEGylated IgG and the like. It is acknowledged that all possible "isotype switching" known to the person skilled in the art may be envisioned in the context of the present invention.

As used herein, "isotype switching" refers to the phenomenon by which the class, or isotype, of an antibody changes from one Ig class to one of the other Ig classes.

Among the list of antibody-based scaffolds, $V_{NAR}$, which are lamprey-derived single domain antibodies may be advantageously used.

The present invention further provides isolated agonist anti-EDAR monoclonal antibodies or isolated monoclonal antibody fragments or antigen binding portions or fragments thereof, comprising an amino acid sequence selected from the group consisting of:
(a) the amino acid sequences of variable region of the heavy chain shown in SEQ ID NO 169, 170, 171, 172, 173, 174, 175, 176, 177, 178, 179, 180, 181 or 182 and the variable regions of the light chain shown in SEQ ID NO 183, 184, 185, 186, 187, 188, 189, 190, 191, 192, 193, 194, 195 or 196;
(b) amino acid sequences that differ from those specified in (a) by one or more conservative amino acid substitutions;
(c) amino acid sequences having at least 95% sequence identity to the sequences specified in (a), or (b);
(d) biological active fragments of amino acid sequences specified in (a) or (b) or (c) being agonists of human and mouse EDAR; and
(e) biological active variants or modifications of amino acid sequences specified in (a) or (b) or (c) or (d) being agonists of human and mouse EDAR.

The term "sequence identity/similarity" has its ordinary meaning in the field. The terms "identical" or percent "identity" in the context of two or more polypeptide sequences, refer to two or more sequences that are the same, or have a specified percentage of amino acid residues that are the same (i.e., at least 70% identity, preferably at least 75%, 80%, 85%, 90%, even more preferably at least 95% or 98% or even 99% identity over a specified region), when compared and aligned for maximum correspondence. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (e.g., human and mouse sequences), compared to species more distantly related (e.g., human and *C. elegans* sequences).

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:23744, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol Biol. 215: 403-10, 1990, presents a detailed consideration of sequence alignment methods and homology calculations. The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, 75%, 80%, 85%, 90%, 92%, 95%, 98%, 99% sequence identity. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site. Homologs of the disclosed agonist anti-EDAR monoclonal antibodies are typically characterized by possession of at least 70%, preferably of at least 95%, and more preferably of at least 98% sequence identity sequence identity counted over the full-length alignment with the disclosed amino acid sequences using the NCBI Blast 2.0, or using the manual alignment as described above. Proteins with even greater similarity to the agonist anti-EDAR monoclonal antibody sequences will show increasing percentage identities when assessed by this method, such as at least 75%, 80%, 85%, 90%, 95% or even 98% sequence identity. When less than the entire sequence is being compared for sequence identity, homologs will typically possess at least 75% sequence identity over short windows of 10-20 amino acids, and can possess sequence identities of at least 85%, 90%, 95% or even 98% depending on their similarity to the reference sequence. One of skill in the art will appreciate that these sequence identity ranges are provided for guidance only; it is possible that strongly significant homologs could be obtained that fall outside the ranges provided.

The present invention also includes variants of the agonist anti-EDAR monoclonal antibodies. The term "variants" or derivatives or equivalents of the agonist anti-EDAR monoclonal antibody sequences refer to polypeptides having amino acid sequences that differ to some extent from a native sequence polypeptide that is amino acid sequences that vary from the native sequence by conservative amino acid substitutions, whereby one or more amino acids are substituted by another with same characteristics and conformational roles. The amino acid sequence variants possess substitutions, deletions, and/or insertions at certain positions within the amino acid sequence of the native amino acid sequence. Typically, such variants possess at least 90%, preferably at least 95%, and very particularly preferably at least 98%, sequence identity with the native sequence. Variants which are particularly preferred in this connection are replacement variants which typically contain less than 10, preferably less than 5, and very particularly preferably less than 3, replacements as compared with the respective disclosed sequences.

In addition or alternative to modifications made within the framework or CDR regions, agonist anti EDAR monoclonal antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified {e.g., one or more chemical moieties can be attached to the antibody) or be modified to alter its glycosylation, again to alter one or more functional properties of the antibody.

Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such a glycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express agonist anti-EDAR monoclonal antibodies of the invention to thereby produce an antibody with altered glycosylation. Alternatively, the fucose residues of the antibody may be cleaved off using a fucosidase enzyme.

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is a glycosylated antibody. Methods for pegylating proteins are known in the art and can be applied to the antibodies of the invention. See for example, EP 0 154 316 by Nishimura et al. and EP 0 401 384 by Ishikawa et al.

In a particular embodiment, the agonist anti-EDAR monoclonal antibodies of the present invention do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain.

In a preferred embodiment, antibodies are selected that do not rapidly degrade. Fragmentation of a monoclonal anti-EDAR antibody may be measured using capillary electrophoresis (CE) and MALDI-MS, as is well understood in the art (Alexander A J and Hughes D E (1995) Anal Chem 67:3626-32). In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Figure 5A:
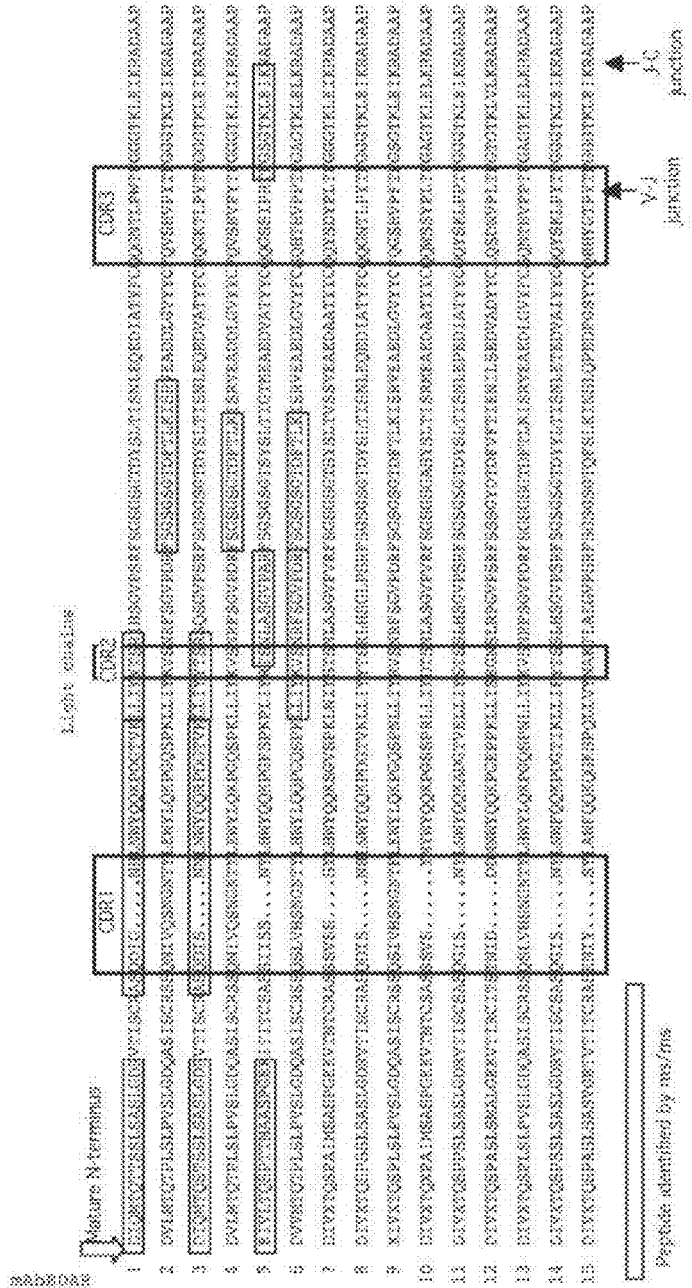
Figure 5B:
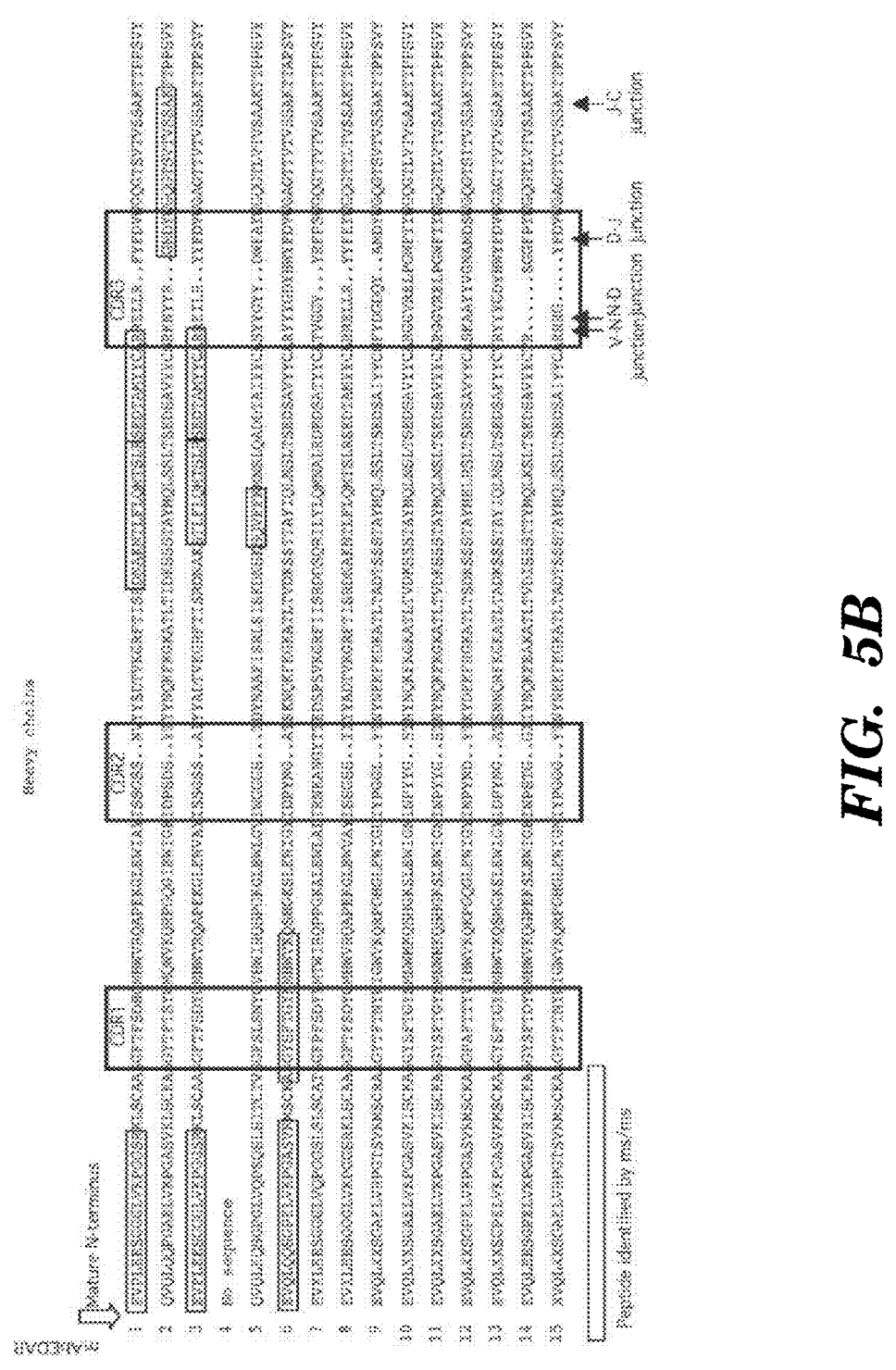

FIG. 5 shows the amino acid sequences of the variable regions of the light chains and heavy chains in respect of fourteen agonist anti-EDAR monoclonal antibodies, namely mAbEDAR1, mAbEDAR2, mAbEDAR3, mAbEDAR5, mAbEDAR6, mAbEDAR7, mAbEDAR8, mAbEDAR9, mAbEDAR10, mAbEDAR11, mAbEDAR12, mAbEDAR13, mAbEDAR14 and mAbEDAR15.

Some additional unanticipated results are in favor of the non obviousness nature of the present invention.

Following some preliminary results, Applicants observed that agonist anti-EDAR mAb of the invention were found 10- to more than 1000-fold less potent than Fc-EDA1 (see US Patent 2005/152,872; Gaide et al.) in the in vitro assay using EDAR-Fas-transduced Jurkat cells. Based on this low in vitro potency, at the time of their first in vivo evaluation, it was not anticipated to observe that the anti-EDAR mAb would be as active as Fc-EDA1. These results might be explained by the 10- to 20-times longer half-life of the antibodies than of the Fc-EDA1 fusion protein, or by the fact that the activation pathway in the in vitro system used by the Applicants, or in cells in vivo is different.

Apart from this, the naturally occurring soluble EDA1 likely is a multimer of trimers and Fc-EDA1 is a hexameric ligand. It was well documented that the simultaneous engagement and clustering of multiple Fas receptors is necessary for biological activity (Schneider et al., J. Exp. Med. 187:1205-13, 1998; Holler et al., Mol. Cell. Biol. 23:1428-40, 2003) and strongly suspected that simultaneous engagement and clustering of multiple EDAR receptors was necessary for biological activity (Schneider et al., J. Biol. Chem. 276:18819-27, 2001; Swee et al, J. Biol. Chem. 284:27267-76, 2009). By contrast, anti-EDAR antibodies are only divalent. It was therefore not likely that this molecular format would be as biologically active as Fc-EDA1.

In addition, it was not expected that anti-EDAR monoclonal antibodies that would have binding specificities other than the one of Fc-EDA1 (different binding sites on EDAR) would have agonist properties. Since there is no simple way of controlling antigen specificity of antibodies (unless using short antigen fragments covering the desired region of antigen specificity; with the risk of losing conformation determinants), Applicants results were totally surprising.

Finally, antibodies from some isotypes might exhibit toxicity activities (e.g. ADCC or antibody-dependent cytotoxicity, CDC or complement-dependent cytotoxicity and FcR-mediated activation of myeloid cells), which could have made the use of these antibodies not practical in vivo.

Another object of the invention is to provide an isolated nucleic acid molecule encoding the isolated agonist anti-EDAR monoclonal antibodies or isolated monoclonal antibody fragments or antigen binding portions or fragments thereof as defined above.

The term "nucleic acid molecule", as used herein, is intended to include DNA molecules and RNA molecules. A nucleic acid molecule may be single-stranded or double-stranded, but preferably is double-stranded DNA.

In addition to the above described monoclonal antibodies, artificially altered gene recombinant antibodies such as chimeric antibodies or humanized antibodies can be used for, for example, lowering heteroantigenicity against a human. These altered antibodies can be produced using a known method.

Chimeric antibodies can e.g., be obtained by ligating the DNA encoding the antibody V-region to a DNA encoding a human antibody C-region, incorporating the product into an expression vector, and then introducing the vector into a host to cause the host to produce the antibodies. Using this known method, chimeric agonist anti EDAR monoclonal antibodies useful in the present invention can be obtained.

Humanized antibodies are also referred to as reshaped human antibodies, which are prepared by grafting an antibody CDR (complementarity determining region) of a mammal other than a human, such as a mouse, to the CDR of a human antibody. The general gene recombination technique thereof is also known (see European Patent Application Publication EP 125023 and WO 96/02576, or any one of their US counterparts, such as e g U.S. Pat. No. 6,068,040).

The term "humanized antibody" is intended to refer to antibodies in which CDR sequences derived from the germline of another mammalian species, such as a mouse, have been grafted onto human framework sequences. Additional framework region modifications may be made within the human framework sequences.

Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al). To create a humanized monoclonal antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al). In a preferred embodiment, the antibodies of the invention are human monoclonal antibodies.

CDR nucleotide sequences encoding for the obtained agonist anti-EDAR monoclonal antibodies or isolated monoclonal antibody fragments or antigen binding portions or fragments thereof that specifically bind human (mAbEDAR1-15) and mouse (mAbEDAR1-14) EDAR are shown in Table 2.

TABLE 2

| SEQ ID | mAb | Chain | CDR | Nucleotide sequence |
|---|---|---|---|---|
| SEQ ID#85 | mAbEDAR1 | Heavy | CDR1 | GGATTCACTTTCAGTGACCATGGA |
| SEQ ID#86 | mAbEDAR1 | Heavy | CDR2 | ATTAGTAGTGGCAGTAGTAATGTC |
| SEQ ID#87 | mAbEDAR1 | Heavy | CDR3 | GCAAGGAGGGAATTGCTACGATTTTACTTCGATGTC |
| SEQ ID#88 | mAbEDAR1 | Light | CDR1 | CAGGACATTGGCAATCAT |
| SEQ ID#89 | mAbEDAR1 | Light | CDR2 | TACACATCA |
| SEQ ID#90 | mAbEDAR1 | Light | CDR3 | CAACAGGGTAATACGCTTCCGTGGACG |
| SEQ ID#91 | mAbEDAR2 | Heavy | CDR1 | GGATACACCTTCACTAGCTACTGG |
| SEQ ID#92 | mAbEDAR2 | Heavy | CDR2 | ATTGATCCTTCTGATAGTTATACT |
| SEQ ID#93 | mAbEDAR2 | Heavy | CDR3 | TCGAGAAAGAATTACTATAGGGGTATGGACTAC |
| SEQ ID#94 | mAbEDAR2 and 4 | Light | CDR1 | CAGAACATTGTACAAAGTAATGGAAACACCTAT |
| SEQ ID#95 | mAbEDAR2 and 4 | Light | CDR2 | AAAGTTTCC |
| SEQ ID#96 | mAbEDAR2 and 4 | Light | CDR3 | TTTCAAGTTTCACATGTTCCGTACACG |
| SEQ ID#97 | mAbEDAR3 | Heavy | CDR1 | GGATTCACTTTCAGTGACTATGGA |
| SEQ ID#98 | mAbEDAR3 | Heavy | CDR2 | ATTAGTAGTGGCAGTAGTGCCATC |
| SEQ ID#99 | mAbEDAR3 | Heavy | CDR3 | GCAAGGCGGGAGATACTGCGCTACTACTTCGATGTC |
| SEQ ID#100 | mAbEDAR3 | Light | CDR1 | CAGGACATTAGCAATAAC |
| SEQ ID#101 | mAbEDAR3 | Light | CDR2 | TACACATCA |
| SEQ ID#102 | mAbEDAR3 | Light | CDR3 | CATCAGGGTAAAACGCTTCCGTACACG |

TABLE 2-continued

| SEQ ID | mAb | Chain | CDR | Nucleotide sequence |
|---|---|---|---|---|
| SEQ ID#103 | mAbEDAR5 | Heavy | CDR1 | GGTTTCTCATTATCTAACTATGGT |
| SEQ ID#104 | mAbEDAR5 | Heavy | CDR2 | ATATGGGGTGGTGGAAGCACA |
| SEQ ID#105 | mAbEDAR5 | Heavy | CDR3 | GCCAGCTATTATGGTTACTACGACTGGTTTGCTTAC |
| SEQ ID#106 | mAbEDAR5 | Light | CDR1 | TCAATTATAAGTTCTAATTAC |
| SEQ ID#107 | mAbEDAR5 | Light | CDR2 | AGGACATCC |
| SEQ ID#108 | mAbEDAR5 | Light | CDR3 | CAGCAGGGTAGTAGTATACCACGCACG |
| SEQ ID#109 | mAbEDAR6 | Heavy | CDR1 | GGTTACTCATTCACTGGCTACAAC |
| SEQ ID#110 | mAbEDAR6 | Heavy | CDR2 | ATTGATCCTTACAATGGTGCTACT |
| SEQ ID#111 | mAbEDAR6 | Heavy | CDR3 | GCAAGATACTACTATGGTGACTACCACTGGTACTTCGATGTC |
| SEQ ID#112 | mAbEDAR6 | Light | CDR1 | CAGAGCCTTGTACACAGTAATGGAAACACCTAT |
| SEQ ID#113 | mAbEDAR6 | Light | CDR2 | AAAGTTTCC |
| SEQ ID#114 | mAbEDAR6 | Light | CDR3 | TCTCAACATACACATGTTCCTCCTACG |
| SEQ ID#115 | mAbEDAR7 | Heavy | CDR1 | GGATTCCCCTTCAGTGATTACTAC |
| SEQ ID#116 | mAbEDAR7 | Heavy | CDR2 | ATTAGAAACAAAGCTAATGGTTACACAACA |
| SEQ ID#117 | mAbEDAR7 | Heavy | CDR3 | GCAACAGTGGGAGGTTACTACAGGTTTCCTTCC |
| SEQ ID#118 | mAbEDAR7 | Light | CDR1 | TCAAGTGTAAGTTCCAGTTAC |
| SEQ ID#119 | mAbEDAR7 | Light | CDR2 | AGCACATCC |
| SEQ ID#120 | mAbEDAR7 | Light | CDR3 | CAGCAGTACAGTGATTACCCACTCACG |
| SEQ ID#121 | mAbEDAR8 | Heavy | CDR1 | GGATTCACTTTCAGTGACTATGGA |
| SEQ ID#122 | mAbEDAR8 | Heavy | CDR2 | ATTAGTAGTGGCAGTAGTACCATC |
| SEQ ID#123 | mAbEDAR8 | Heavy | CDR3 | GCAAGGAGGGAGTTACTACGATATTATTTTGAGTAC |
| SEQ ID#124 | mAbEDAR8 | Light | CDR1 | CAGGACATTAGCAATCAT |
| SEQ ID#125 | mAbEDAR8 | Light | CDR2 | TACACATCA |
| SEQ ID#126 | mAbEDAR8 | Light | CDR3 | CAACAGGGTAATACGCTTCCGTACACG |
| SEQ ID#127 | mAbEDAR9 | Heavy | CDR1 | GGATACACCTTCACTAACTACTGG |
| SEQ ID#128 | mAbEDAR9 | Heavy | CDR2 | ATTTACCCTGGAGGTCTTTATACT |
| SEQ ID#129 | mAbEDAR9 | Heavy | CDR3 | CATTTCTACGATGGTGACCAGTATGCTATGGACTAC |
| SEQ ID#130 | mAbEDAR9 | Light | CDR1 | CAGAGCATTGTACATAGTAATGGAAACACCTTT |
| SEQ ID#131 | mAbEDAR9 | Light | CDR2 | AGAGTTTCC |
| SEQ ID#132 | mAbEDAR9 | Light | CDR3 | TTTCAAGGTTCACATGTTCCATTCACG |
| SEQ ID#133 | mAbEDAR10 | Heavy | CDR1 | GGTTATTCATTCACTGGCTACAAC |
| SEQ ID#134 | mAbEDAR10 | Heavy | CDR2 | ATTAATCCTTACTATGGTAGTACT |
| SEQ ID#135 | mAbEDAR10 | Heavy | CDR3 | GCAAGAGGGGCGTTAGGGAACTACCAGGC |
| SEQ ID#136 | mAbEDAR10 | Light | CDR1 | TCAAGTGTAAGTTAC |
| SEQ ID#137 | mAbEDAR10 | Light | CDR2 | GACACATCC |
| SEQ ID#138 | mAbEDAR10 | Light | CDR3 | CAGCAGTGGAGTAGTTACCCGCTCACG |
| SEQ ID#139 | mAbEDAR11 | Heavy | CDR1 | GGTTATTCATTCACTGGCTACAAC |
| SEQ ID#140 | mAbEDAR11 | Heavy | CDR2 | ATTAATCCTTACTATGGTAGTACT |
| SEQ ID#141 | mAbEDAR11 | Heavy | CDR3 | GCAAGAGGGGCGTTAGGGAACTACCAGGC |

TABLE 2-continued

| SEQ ID | mAb | Chain | CDR | Nucleotide sequence |
|---|---|---|---|---|
| SEQ ID#142 | mAbEDAR11 | Light | CDR1 | CAGGGCATTAGCAATTAT |
| SEQ ID#143 | mAbEDAR11 | Light | CDR2 | TCCACATCA |
| SEQ ID#144 | mAbEDAR11 | Light | CDR3 | CAGCAGTATAGTAAGCTTCCTCCG |
| SEQ ID#145 | mAbEDAR12 | Heavy | CDR1 | GGACCCGACTTCACTACCTATGTT |
| SEQ ID#146 | mAbEDAR12 | Heavy | CDR2 | ATTAATCCTTACAATGATTATACT |
| SEQ ID#147 | mAbEDAR12 | Heavy | CDR3 | GCAAGCAAAGCTGCCTACTACGTGGGGAATGCTATGGACTCA |
| SEQ ID#148 | mAbEDAR12 | Light | CDR1 | ACTAATATTGATGATGAT |
| SEQ ID#149 | mAbEDAR12 | Light | CDR2 | GAAGGCAAT |
| SEQ ID#150 | mAbEDAR12 | Light | CDR3 | TTGCAAAGTGATAACGTGCCGCTCACG |
| SEQ ID#151 | mAbEDAR13 | Heavy | CDR1 | GGTTACTCATTCACTGGCTACAAC |
| SEQ ID#152 | mAbEDAR13 | Heavy | CDR2 | ATTGATCCTTACAATGGTGCTACC |
| SEQ ID#153 | mAbEDAR13 | Heavy | CDR3 | GTAAGATACTACTATGGTGACTACCACTGGTACTTCGATGTC |
| SEQ ID#154 | mAbEDAR13 | Light | CDR1 | CAGAGCCTTGTACACAGTAATGGAAACACCTAT |
| SEQ ID#155 | mAbEDAR13 | Light | CDR2 | AAAGTTTCC |
| SEQ ID#156 | mAbEDAR13 | Light | CDR3 | TCTCAAAATACACATGTTCCTCCTACG |
| SEQ ID#157 | mAbEDAR14 | Heavy | CDR1 | GGTTACTCATTCACCGACTACTGG |
| SEQ ID#158 | mAbEDAR14 | Heavy | CDR2 | ATTAATCCTAGCACTGGTGGTATC |
| SEQ ID#159 | mAbEDAR14 | Heavy | CDR3 | ACAAGATCGGGAGGCTTTCCTTAC |
| SEQ ID#160 | mAbEDAR14 | Light | CDR1 | CAGGGCATTAGCAATTAT |
| SEQ ID#161 | mAbEDAR14 | Light | CDR2 | TACACATCA |
| SEQ ID#162 | mAbEDAR14 | Light | CDR3 | CAGCAGTACAGTAAGCTTCCGTACACG |
| SEQ ID#163 | mAbEDAR15 | Heavy | CDR1 | GGATACACCTTCACTAACTACTGG |
| SEQ ID#164 | mAbEDAR15 | Heavy | CDR2 | ATTTACCCTGGAGGTGGTTATACT |
| SEQ ID#165 | mAbEDAR15 | Heavy | CDR3 | GCAAGAAGGAGGGGGTACTTCGATGTC |
| SEQ ID#166 | mAbEDAR15 | Light | CDR1 | GAAAATATTTACAGTTAT |
| SEQ ID#167 | mAbEDAR15 | Light | CDR2 | AATGCAAAA |
| SEQ ID#168 | mAbEDAR15 | Light | CDR3 | CAACATCATTATGGTACTCCGTACACG |

In addition, FIGS. 3 and 4 show the determination of the nucleotide sequences of the anti-EDAR monoclonal antibodies mAbEDAR1, 2, 3, 5, 6, 7, 8, 9, 10, 11, 12, 13, 14 and 15.

Another object of the invention concerns an expression vector comprising at least one copy of the nucleic acid molecule as described above.

The term "vector" as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e. g., bacterial vectors having a bacterial origin of replication and episomal mammalian vectors). Other vectors (e. g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e. g. replication defective retroviruses, adenoviruses and adeno-associated viruses), which serve equivalent functions.

The invention also concerns host cells comprising the above described expression vector. The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells and lymphocytic cells.

Expression vectors and host cells suitable for expression of recombinant antibodies and humanized antibodies in particular, are well known in the art. The following references are representative of methods and vectors suitable for expression of recombinant immunoglobulins which may be utilized in carrying out the present invention: Weidle et al., Gene, 51: 21-29 (1987); Dorai et al., J. Immunol., 13 (12): 4232-4241 (1987); De Waele et al., Eur. J. Biochem., 176: 287-295 (1988); Colcher et al., Cancer Res., 49: 1738-1745 (1989); Wood et al., J. Immunol., 145 (9): 3011-3016 (1990); Bulens et al., Eur. J. Biochem., 195: 235-242 (1991); Beldsington et al., Biol. Technology, 10: 169 (1992); King et al., Biochem. J., 281: 317-323 (1992); Page et al., Biol. Technology, 9: 64 (1991); King et al., Biochem. J., 290: 723-729 (1993); Chaudhary et al., Nature, 339: 394-397 (1989); Jones et al., Nature, 321: 522-525 (1986); Morrison and Oi, Adv. Immunol., 44: 65-92 (1989); Benhar et al., Proc. Natl. Acad. Sci. USA, 91: 12051-12055 (1994); Singer et al., J. hnunol., 150: 2844-2857 (1993); Couto et al., Hybridoma, 13 (3): 215-219 (1994); Queen et al., Proc. Natl. Acad. Sci. USA, 86: 10029-10033 (1989); Caron et al., Cancer Res., 52: 6761-6767 (1992); Coloura et al, J. Immunol. Meth., 152: 89-109 (1992). Moreover, vectors suitable for expression of recombinant antibodies are commercially available. The vector may, e. g. be a bare nucleic acid segment, a carrier-associated nucleic acid segment, a nucleoprotein, a plasmid, a virus, a viroid, or a transposable element.

Host cells known to be capable of expressing functional immunoglobulins include, e. g.: mammalian cells such as Chinese Hamster Ovary (CHO) cells; COS cells; myeloma cells, such as NSO and SP2/0 cells; insect cells, bacteria such as *Escherichia coli*; yeast cells such as *Saccharomyces cerevisiae*; and other host cells. Of these, CHO cells are used by many researchers given their ability to effectively express and secrete immunoglobulins. NSO cells are one of the preferred types of host cells useful in the present invention.

Host cells are transformed following techniques that are known to the person skilled in the art. A "transformed" cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, calcium phosphate precipitation, and particle gun acceleration.

In particular, the present invention also relates to a hybridoma secreting the isolated agonist anti-EDAR monoclonal antibodies or isolated monoclonal antibody fragments or antigen binding portions or fragments thereof according to the present invention.

The thus prepared hybridomas producing monoclonal antibodies can be passage-cultured in a standard culture solution, or can be stored for a long period in liquid nitrogen. One example of a method employed to obtain monoclonal antibodies from the hybridomas involves culturing the hybridomas and obtaining monoclonal antibodies in the culture supernatant according to a standard method. The former method is suitable for the mass production of antibodies.

A monoclonal antibody that can be used in the present invention can be a recombinant monoclonal antibody that is prepared by cloning the antibody gene from the hybridoma, incorporating the gene into an appropriate vector, introducing the vector into a host, and then causing the host to produce the recombinant monoclonal antibodies by genetic engineering techniques (e.g., see Vandamme, A. M. et al., Fur. J. Biochem, (1990) 192, 767-775, 1990).

In addition to the above host cell, a transgenic animal or plant can also be used to produce a recombinant antibody.

Thus a further object of the invention concerns a transgenic non-human animal having a genome comprising the isolated nucleic acid molecule and/or the expression vector according to the present invention.

In another aspect, the present invention concerns a pharmaceutically composition comprising the isolated agonist anti-EDAR monoclonal antibodies or isolated monoclonal antibody fragments or antigen binding portions or fragments thereof according to the present invention and a pharmaceutically acceptable carrier. According to the present invention, the pharmaceutically composition comprises at least a therapeutically effective quantity or amount of the substantially purified and isolated agonist anti-EDAR monoclonal antibodies or isolated monoclonal antibody fragments or antigen binding portions or fragments thereof according to the present invention.

The isolated agonist anti-EDAR monoclonal antibodies or isolated monoclonal antibody fragments or antigen binding portions or fragments thereof described herein as the "compound" may be administered with a physiologically acceptable carrier. A physiologically acceptable carrier is a formulation to which the compound can be added to dissolve it or otherwise facilitate its administration. An important factor in choosing an appropriate physiologically acceptable carrier is selecting a carrier in which the compound remains active or the combination of the carrier and the compound produces an active compound. Usually, the pharmaceutically acceptable carrier can be a solvent or dispersion medium. Examples of suitable aqueous and nonaqueous carriers which may be employed in the pharmaceutical composition of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of emulsifying agents such as lecithin, by the maintenance of the required particle size in the case of dispersions, and by the use of surfactants, such as Tween 20.

The pharmaceutical composition may also contain adjuvants such as preservatives, wetting agents, emulsifying agents, pharmaceutically-acceptable antioxidants and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutically acceptable salts of the isolated agonist anti-EDAR monoclonal antibodies or isolated monoclonal antibody fragments or antigen binding portions or fragments thereof according to the present invention may also be envisioned.

A "pharmaceutically acceptable salt" refers to a salt that retains the desired biological activity of the parent compound and does not impart any undesired toxicological effects (see e. g., Berge, S. M., et al. (1977) J. Pharm. Sci. 66: 1-19).

In a preferred embodiment, the pharmaceutical composition of the invention is formulated for parenteral, intravenous, oral, subcutaneous, intradermal, intramuscular or topical, administration.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

Preferred routes of administration for the isolated agonist anti-EDAR monoclonal antibodies or isolated monoclonal antibody fragments or antigen binding portions or fragments thereof according to the present invention are intravenously, intramuscularly and intraperitoneally. Preferred modes of delivery are by injection and infusion.

Injectable forms may include sterile aqueous solutions or dispersions. Furthermore, form of sterile powders may be prepared for the extemporaneous preparation of such sterile injectable solutions or dispersions. In all cases, the final injectable form must be sterile and must be effectively fluid for easy syringability. The pharmaceutical composition must be stable under the conditions of manufacture and storage; thus, preferably should be preserved against the contaminating action of microorganisms such as bacteria and fungi.

Parenteral administration may be prepared as solutions or suspensions of the combined components in physiological solution. A suitable surfactant can be included such as, for example, hydroxypropylcellulose. Dispersions can also be prepared in glycerol, liquid polyethylene glycols, and mixtures thereof in oils.

Further, a preservative can be included to prevent the detrimental growth of microorganisms.

In preparing oral dosage forms, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or non-aqueous techniques.

A tablet may be prepared by compression or molding, optionally with one or more accessory ingredients or adjuvants.

Compressed tablets may be prepared by compressing, in a suitable machine, the combined components in a free-flowing form such as powder or granules, optionally mixed with a binder, lubricant, inert diluent, surface active or dispersing agent.

Molded tablets may be made by molding in a suitable machine, a mixture of the powdered compound moistened with an inert liquid diluent.

Effective dosage regimens are adjusted to provide the optimum desired response (e. g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Regardless of the route of administration selected, the isolated agonist anti-EDAR monoclonal antibodies or isolated monoclonal antibody fragments or antigen binding portions or fragments thereof according to the present invention, which may be used in a suitable hydrated form, and/or the pharmaceutical composition of the present invention, are formulated into pharmaceutically acceptable dosage forms by conventional methods known to those of skill in the art.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the salt or amide thereof, the route of administration, the time of administration, the duration of the treatment, other drugs, compounds and/or materials used in combination with the particular compositions employed, the age, sex, weight, condition, general health and prior medical history of the patient being treated, and like factors.

A physician or veterinarian can start doses of the compounds of the invention-employed in the pharmaceutical composition at levels lower than that required to achieve the desired therapeutic effect and gradually increase the dosage until the desired effect is achieved. In general, a suitable daily dose of a composition of the invention is that amount of the compound which is the lowest dose effective to produce a therapeutic effect. Such an effective dose generally depends upon the factors described above. It is preferred that administration be intravenous, intramuscular, intraperitoneal, or subcutaneous, or administered proximal to the site of the target. If desired, the effective daily dose of a therapeutic composition can be administered as two; three, four, five, six or more sub-doses administered separately at appropriate intervals throughout the day, optionally, in unit dosage forms.

While it is possible for the isolated agonist anti-EDAR monoclonal antibodies or isolated monoclonal antibody fragments or antigen binding portions or fragments thereof according to the present invention to be administered alone, it is preferable to administer the latter as a pharmaceutical formulation (composition).

Effective doses of the compositions of the present invention, for the treatment of immune-related conditions and diseases described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy.

For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1 to 10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to EDAR in the patient. In some methods, dosage is adjusted to achieve a plasma antibody concentration of 0.001-1000 μg/ml. Alternatively, antibody can be administered as a sustained release formulation, in which case less frequent administration is required.

Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The dosage ranges of the isolated agonist anti-EDAR monoclonal antibodies or isolated monoclonal antibody fragments or antigen binding portions or fragments thereof according to the present invention may vary with the administration routes, as well as the state of the patient (age, sex, body weight, extent of the disease etc.). Ideally, the isolated agonist anti-EDAR monoclonal antibodies or isolated monoclonal antibody fragments or antigen binding portions or fragments thereof is administered to a patient in need thereof at a dosage unit from 0.1 mg/kg of body weight to 100 mg/kg of body weight.

It was unexpectedly found that the administration (for example application, injection, delivery, contact etc.) of the pharmaceutical composition according to the invention results in an improved therapeutic effect in particular in the treatment of X-linked hypohidrotic ectodermal dysplasia (XLHED) or tooth agenesis.

It was demonstrated that the present invention has important implications for the design of novel treatment strategies of patients suffering in the development of cells or tissues of ectodermal origin. More specifically, the present invention has important implications for the design of novel treatment strategies of patients with XLHED or tooth agenesis.

The present invention also concerns the use of the isolated agonist anti-EDAR monoclonal antibodies or isolated monoclonal antibody fragments or antigen binding portions or fragments thereof or the pharmaceutical composition of the invention, for the preparation of a medicament for modulating the development of cells or tissues of ectodermal origin, such as hair, teeth, skin, sweat glands, sebaceous glands, larynx and trachea mucus-producing cells, Meibomian glands, preputial glands, mammary glands and salivary glands.

In the present invention, the term "modulating" refers to a molecule which is capable to interact with a specific receptor and to modify or control its activity.

The medicament according to the invention can be used for the treatment of diseases such as ectodermal dysplasia, or disturbances or anomalies of ectodermal structures that are not caused by mutations in EDA1, such as anomalies of the hair, of the teeth or of the glands, in particular for treating alopecia, sebaceous gland malfunction or a deficiency of sweat glands or sebaceous glands or for wound healing.

Preferably, the medicament of the invention can be used for the treatment of X-linked hypohidrotic ectodermal dysplasia or tooth agenesis.

In a first embodiment, the medicament may be administered to the mother/the mother animal during pregnancy. Injection of the medicament to the fetus, may be carried out either directly, following the same routes as identified above (parenterally, intravenously, orally, subcutaneously, intradermally, intramuscularly or topically) or alternatively through the umbilical vein.

In a second embodiment of the invention, the medicament may be administered to a pre-term newborn, a newborn, a child, a young adult or an adult. Considering the results reported in the study of Gaide and Schneider (Nature Medicine 2003), the assumption was that a few days after birth, Fc-EDA1 had no longer biological activity. It thus came as a surprise that administration of the isolated agonist anti-EDAR monoclonal antibodies or isolated monoclonal antibody fragments or antigen binding portions or fragments thereof or the pharmaceutical composition of the invention in adult Tabby mice and adult wild type mice would still be therapeutically active.

The half-lives of immunoglobulins are measured in days to weeks. Not surprisingly, the presence of monoclonal anti-EDAR antibody of the invention was still detectable in the serum one week following injection. The long in vivo half-life of the antibodies opens the possibility to expose patients such as adolescent and adult Tabby mice or humans to these therapeutic agents for extended periods of time. Therefore this long term treatment brings unexpected therapeutic benefit, even after the post-natal period.

Beside the use of monoclonal anti-EDAR antibodies as drug candidates for the treatment of XLHED and the like, these antibodies also constitute invaluable analytical tools. Most of these antibodies show cross-reactivity with mouse and human EDAR. Monoclonal anti-EDAR antibodies of the invention are also able to detect rat, rabbit and dog EDAR. These antibodies were successfully tested in flow cytometry and Western blotting applications. The use of these reagents in immunohistochemistry is of real importance as a diagnostic tool.

Alternatively, a further aspect of the present invention also concerns a method of treating XLHED in a patient in need thereof. According to the present invention, the method of treating XLHED comprises administering to the patient the isolated agonist anti-EDAR monoclonal antibodies or isolated monoclonal antibody fragments or antigen binding portions or fragments thereof in an amount which is therapeutically effective.

It is also another aspect of the invention to use the isolated agonist anti-EDAR monoclonal antibodies or isolated monoclonal antibody fragments or antigen binding portions or fragments thereof or the pharmaceutical composition of the invention, for the manufacture of a medicament involved in the reconstitution of the skin.

Preferably, the reconstitution of the skin comprises burns, ulcers or scares such as bedsores, cosmetic reconstruction after surgery such as tumour ablation.

Another object of the invention is the use of the isolated agonist anti-EDAR monoclonal antibodies or isolated monoclonal antibody fragments or antigen binding portions or fragments thereof or the pharmaceutical composition of the invention, for the manufacture of a medicament for modifying hair morphology.

If it was reasonable to predict that the injection of the isolated agonist anti-EDAR monoclonal antibodies or isolated monoclonal antibody fragments or antigen binding portions or fragments thereof or the pharmaceutical composition of the invention would have similar effects to Fc-EDA1, it was not anticipated that these antibodies would so dramatically modify hair coloration (Gaide and Schneider, Nature Medicine 2003 says "The coat of treated animals was often darker in color, probably because of an increased number of hair-associated melanocytes").

It was also not anticipated that the morphology (the structure) of the hairs would be modified by anti-EDAR antibodies. It was more believed that the number of hair follicles or their cycle would be altered.

Furthermore, it was demonstrated that the administration of the isolated agonist anti-EDAR monoclonal antibodies or isolated monoclonal antibody fragments or antigen binding portions or fragments thereof or the pharmaceutical composition of the invention in adult Tabby mice and adult wild type mice modified hair structure and color.

The invention also provides a method of increasing the development of one or more hair follicle, tooth, sweat gland, sebaceous glands, larynx and trachea mucus-producing cells, Meibomian glands, preputial glands, mammary glands and salivary glands in a tissue, comprising administering to a subject in need thereof, the isolated agonist anti-EDAR monoclonal antibodies or isolated monoclonal antibody fragments or antigen binding portions or fragments thereof or the pharmaceutical composition of the invention.

Preferably this method comprises administering to said subject in need thereof an amount of the isolated agonist anti-EDAR monoclonal antibodies or isolated monoclonal antibody fragments or antigen binding portions or fragments thereof or the pharmaceutical composition of the invention, sufficient to promote the development of one or more hair follicle, tooth, sweat gland, sebaceous glands, larynx and trachea mucus-producing cells, Meibomian glands, preputial glands, mammary glands and salivary glands in a tissue of said subject in need thereof.

In particular, the subject is suffering from an ectodermal disease and preferably the ectodermal disease is XLHED, tooth agenesis or alopecia.

Additionally, the present invention pertains to a pharmaceutical kit comprising at least an effective amount of the isolated agonist anti-EDAR monoclonal antibodies or isolated monoclonal antibody fragments or antigen binding portions or fragments thereof or the pharmaceutical composition of the invention, together with instructions for use and in particular instructions directed to the treatment of XLHED.

The pharmaceutical kit according to the present invention may comprise a container comprising at least said isolated agonist anti-EDAR monoclonal antibodies or isolated monoclonal antibody fragments or antigen binding portions or fragments thereof.

Generally, the Kit comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The label or package insert indicates that the composition is used for treating the condition of choice, such as XLHED.

Alternatively, or additionally, the Kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Agonist anti-EDAR antibodies that cross-react with mouse and human EDAR can also cross-react with EDAR of most mammalian species, and also with EDAR of other vertebrate species. If the agonist antibodies do not cross-react with EDAR of a given mammalian or vertebrate species, it is possible to generate them according to the process described in this application by immunizing EDAR-deficient mice with an EDAR antigen in which the EDAR sequence corresponds to that of the species of interest.

Finally, another object of the invention is the use of the isolated agonist anti-EDAR monoclonal antibodies or isolated monoclonal antibody fragments or antigen binding portions or fragments thereof or the pharmaceutical composition of the invention, for the manufacture of a medicament for use in veterinary applications in any mammal or vertebrate species. The medicament can be utilized in utero (for mammals) or in ovo (for birds, reptiles, egg-layer fishes, etc. . . . ), or in young animals, or in adult animals. The treatment can be used to modulate the development of cells or tissues of ectodermal origin, such as hair, feathers, scales, horns, claws, beaks, teeth, skin, sweat glands, sebaceous glands, larynx and trachea mucus-producing cells, Meibomian glands, preputial glands, mammary glands and salivary glands, In particular, the treatment can be used to temporarily or permanently modify hair, scale or feathers color and/or morphology.

Given a specific variable domain region sequence, one of ordinary skill can easily screen for complementary variable domain region sequences using methods well known in the art. See, for example, Klimka et al., British Journal of Cancer (2000) 93: 252-260; Beboer et al., J. Mol. Biol. (2000) 296: 833-849; Radar et al., PNAS (1998) 95:8910-8915; Portolano et al, J. Immuno. (193) 150: 880-887; and Clarkson et al., Nature (1991) 352: 624-628, contents of all of which is herein incorporated by reference. For example, a heavy chain variable domain sequence comprising 1, 2, or 3 of the heavy chain CDR amino acid sequences described herein can be screened against a library of light chain variable domain sequences to obtain antibodies that bind human and/or mouse EDAR. Alternatively, a light chain variable domain sequence comprising 1, 2, or 3 of the light chain CDRs described herein can be screened against a library of heavy chain variable domain sequences to obtain antibodies that bind human and/or mouse EDAR. Without wishing to be bound by theory, this methodology can be used to humanize any known antibody. For example, a non-human variable domain sequence can be screened against human variable domain sequences and then the identified human variable domain sequences screened against a second set of human variable domain sequences.

Accordingly, in some embodiments, the antibody, antibody fragment, or antigen binding portion or fragment thereof comprises a heavy chain variable region and a light chain variable region, the heavy chain variable region comprising the complementary determining region (CDR) amino acid sequences of SEQ ID NO: 1, SEQ ID NO: 2, and SEQ ID NO: 3; or SEQ ID NO: 7, SEQ ID NO: 8, and SEQ ID NO: 9; or SEQ ID NO: 13, SEQ ID NO: 14, and SEQ ID NO: 15; or SEQ ID NO: 19, SEQ ID NO: 20, and SEQ ID NO: 21; or SEQ ID NO: 25, SEQ ID NO: 26, and SEQ ID NO: 27; or SEQ ID NO: 31, SEQ ID NO: 32, and SEQ ID NO: 33; or SEQ ID NO: 37, SEQ ID NO: 38, and SEQ ID NO: 39; or SEQ ID NO: 43, SEQ ID NO: 44, and SEQ ID NO: 45; or SEQ ID NO: 49, SEQ ID NO: 50, and SEQ ID NO: 51; or SEQ ID NO: 55, SEQ ID NO: 56, and SEQ ID NO: 57; or SEQ ID NO: 61, SEQ ID NO: 62, and SEQ ID NO: 63; or SEQ ID NO: 67, SEQ ID NO: 68, and SEQ ID NO: 69; or SEQ ID NO: 73, SEQ ID NO: 74, and SEQ ID NO: 75; or SEQ ID NO: 79, SEQ ID NO: 80, and SEQ ID NO: 81.

In some embodiments, the antibody, antibody fragment, or antigen binding portion or fragment thereof comprises a heavy chain variable region and a light chain variable region, the heavy chain variable region comprising an amino acid sequence selected from the group consisting of: (a) SEQ ID NO: 169, 170, 171, 172, 173, 174, 175, 176, 177, 178, 179, 180, 181 and 182; (b) amino acid sequences that differ from those sequences specified in (a) by 1, 2, 3, 4, 5, 6, 7, 8, 9, 10 or more conservative amino acid substitution; and (c) amino acid sequences having at least 95% sequence identity to the sequences specified in (a) or (b).

In some embodiments, the antibody, antibody fragment, or antigen binding portion or fragment thereof comprises a light chain variable region and a heavy chain variable region, the light chain variable region comprising the complementary determining region (CDR) amino acid sequences of SEQ ID NO: 4, SEQ ID NO: 5, and SEQ ID NO: 6; or SEQ ID NO: 10, SEQ ID NO: 11, and SEQ ID NO: 12; or SEQ ID NO: 16, SEQ ID NO: 17, and SEQ ID NO: 18; or SEQ ID NO: 22, SEQ ID NO: 23, and SEQ ID NO: 24; or SEQ ID NO: 28, SEQ ID NO: 29, and SEQ ID NO: 30; or SEQ ID NO: 34, SEQ ID NO: 35, and SEQ ID NO: 36; or SEQ ID NO: 40, SEQ ID NO: 41, and SEQ ID NO: 42; or SEQ ID NO: 46, SEQ ID NO: 47, and SEQ ID NO: 48; or SEQ ID NO: 52, SEQ ID NO: 53, and SEQ ID NO: 54; or SEQ ID NO: 58, SEQ ID NO: 59, and SEQ ID NO: 60; or SEQ ID NO: 64, SEQ ID NO: 65, and SEQ ID NO: 66; or SEQ ID NO: 70, SEQ ID NO: 71, and SEQ ID NO: 72; or SEQ ID NO: 76, SEQ ID NO: 77, and SEQ ID NO: 78; or SEQ ID NO: 82, SEQ ID NO: 83, and SEQ ID NO: 84.

In some embodiments, the antibody, antibody fragment, or antigen binding portion or fragment thereof comprises a light chain variable region and a heavy chain variable region, the light chain variable region comprising an amino acid sequence selected from the group consisting of: (a) SEQ ID NO 183, 184, 185, 186, 187, 188, 189, 190, 191, 192, 193, 194, 195 and 196; (b) amino acid sequences that differ from those sequences specified in (a) by 1, 2, 3, 4, 5, 6, 7, 8, 9, 10 or more conservative amino acid substitutions; and (c) amino acid sequences having at least 80%, 85%, 90%, or 95% sequence identity to the sequences specified in (a) or (b).

Generally, amino acid sequences having at least 80%, 85%, 90%, or 95% sequence identity to the variable domain region sequences will differ from the variable domain region sequence at substitutable positions. A "substitutable position" is a particular position of the variable domain region sequence that can be substituted by different amino acid(s) without significantly decreasing the binding activity of the antibody. A substitutable position may also be referred to as "variation tolerant position." Substitutable positions of variable domain sequence are revealed by aligning the heavy chain or light chain variable domain sequences and determining which amino acid occurs at which position. A substitutable position of a variable domain sequence disclosed herein is identified by virtue of the fact that the identity of the amino acid at the substitutable position varies between the individual variable domain sequences of related antibodies, e.g., antibodies exemplified herein. Once identified, the amino acid at the substitutable position of an individual variable domain sequence can be substituted for a different amino acid without significantly decreasing the binding affinity of the antibody. Generally to obtain antibodies, antibodies fragments, or antigen binding portions or fragments thereof substitutable positions outside the CDRs are preferred. However, one, two, three, four, or five or more positions in the CDRs can also be used. Preferably when substitutable positions within CDRs are used no more than one, two, three, four or five such positions may be used as substitutable positions. U.S. Pat. App. Publ. No. 2006/0099204, contents of which is herein incorporated by reference, describes methods for identifying substitutable positions.

In some embodiments, the antibody, antibody fragment, or antigen binding portion or fragment thereof comprises a heavy chain variable region and a light chain variable region, the heavy chain variable region comprising the complementary determining region (CDR) amino acid sequences of SEQ ID NO: 1, SEQ ID NO: 2, and SEQ ID NO: 3; or SEQ ID NO: 7, SEQ ID NO: 8, and SEQ ID NO: 9; or SEQ ID NO: 13, SEQ ID NO: 14, and SEQ ID NO: 15; or SEQ ID NO: 19, SEQ ID NO: 20, and SEQ ID NO: 21; or SEQ ID NO: 25, SEQ ID NO: 26, and SEQ ID NO: 27; or SEQ ID NO: 31, SEQ ID NO: 32, and SEQ ID NO: 33; or SEQ ID NO: 37, SEQ ID NO: 38, and SEQ ID NO: 39; or SEQ ID NO: 43, SEQ ID NO: 44, and SEQ ID NO: 45; or SEQ ID NO: 49, SEQ ID NO: 50, and SEQ ID NO: 51; or SEQ ID NO: 55, SEQ ID NO: 56, and SEQ ID NO: 57; or SEQ ID NO: 61, SEQ ID NO: 62, and SEQ ID NO: 63; or SEQ ID NO: 67, SEQ ID NO: 68, and SEQ ID NO: 69; or SEQ ID NO: 73, SEQ ID NO: 74, and SEQ ID NO: 75; or SEQ ID NO: 79, SEQ ID NO: 80, and SEQ ID NO: 81, and the light chain variable region comprising the complementary determining region (CDR) amino acid sequences of SEQ ID NO: 4, SEQ ID NO: 5, and SEQ ID NO: 6; or SEQ ID NO: 10, SEQ ID NO: 11, and SEQ ID NO: 12; or SEQ ID NO: 16, SEQ ID NO: 17, and SEQ ID NO: 18; or SEQ ID NO: 22, SEQ ID NO: 23, and SEQ ID NO: 24; or SEQ ID NO: 28, SEQ ID NO: 29, and SEQ ID NO: 30; or SEQ ID NO: 34, SEQ ID NO: 35, and SEQ ID NO: 36; or SEQ ID NO: 40, SEQ ID NO: 41, and SEQ ID NO: 42; or SEQ ID NO: 46, SEQ ID NO: 47, and SEQ ID NO: 48; or SEQ ID NO: 52, SEQ ID NO: 53, and SEQ ID NO: 54; or SEQ ID NO: 58, SEQ ID NO: 59, and SEQ ID NO: 60; or SEQ ID NO: 64, SEQ ID NO: 65, and SEQ ID NO: 66; or SEQ ID NO: 70, SEQ ID NO: 71, and SEQ ID NO: 72; or SEQ ID NO: 76, SEQ ID NO: 77, and SEQ ID NO: 78; or SEQ ID NO: 82, SEQ ID NO: 83, and SEQ ID NO: 84.

As disclosed herein, the inventors have identified the novel antigenic portion of the human and mouse EDAR to which the antibodies described herein bind. Thus, the antibodies, antibody fragments, or antigen binding portions or fragments thereof described herein that bind to human and/or mouse EDAR sequence fragments corresponding to amino acids 29-114 of SEQ ID NO. 235 (identified as SEQ ID NO: 239 SNCGENEYYNQTTGLCQECPPCGPGEEPYLSCGYGT-KDEDYGCVPCPAEKFSKGGYQICRR HKDCEGF-FRATVLTPGDMENDAECG) and SEQ ID NO. 236 (identified as SEQ ID NO: 242, SNCGENEYHNQTTGLCQQCPPCRP-GEEPYMSCGYGTKDDDYGCVP CPAEKFSKGGYQI-CRRHKDCEGFFRATVLTPGDMENDAECG) but do not significantly bind to the EDAR sequence fragments corresponding to amino acids 29-72 of SEQ ID NO: 235 (identified as SEQ ID NO. 237, SNCGENEYYNQTT GLCQECPPCGP GEEPYLSCGYGTKDEDYGCV) and/or amino acids 29-72 of SEQ ID NO: 236 (identified as SEQ ID NO: 240, SNC-GENEYHNQTTGLCQQCPPCRPGEEPYMSCGYG TKD-DDYGCV) are also subject of the invention disclosed herein. As used herein, the term "does not significantly bind" indicates that the affinity constant of the antibody, antibody fragment, or antigen binding portion or fragment thereof for binding to SEQ ID NO: 239 and/or SEQ ID NO: 242 is more than $10^{-7}$M, $10^{-6}$M, $10^{-5}$M, $10^{-4}$M, $10^{-3}$M, $10^{-2}$M, $10^{-1}$M, or 1M. In some further embodiments of this, the antibody, antibody fragment, or antigen binding portion or fragment therefore does not significantly bind to the EDAR sequence fragments corresponding to amino acids 71-114 of SEQ ID NO: 235 (identified as SEQ ID NO. 238, VPCPAEKFSKG-GYQICRRHKDCEGFFRATVLTPGDMENDA ECG) and/or amino acids 71-114 of SEQ ID NO: 236 (identified as SEQ ID NO. 241, VPCPAEKFSKGGYQICRRHKDCEGF-FRATVLTPGD MENDAECG).

In some embodiments, the antibody, antibody fragment, or antigen binding portion or fragments thereof bind to human and/or mouse EDAR bind to human and/or mouse EDAR sequence fragments corresponding to SEQ ID NO: 2441 and/or SEQ ID NO: 243, but do not significantly bind to the EDAR sequence fragment SEQ ID NO: 239 in absence of SEQ ID NO. 238 and/or do not bind to the EDAR sequence fragment SEQ ID NO. 242 in the absence of SEQ ID NO 241.

In some embodiments, the antibody, antibody fragment, or antigen binding portion or fragment binds to the same antigenic determinant as does: (a) an antibody comprising a heavy chain variable region comprising the complementary determining region amino acid sequences of: SEQ ID NO: 1, SEQ ID NO: 2, and SEQ ID NO: 3; or SEQ ID NO: 7, SEQ ID NO: 8, and SEQ ID NO: 9; or SEQ ID NO: 13, SEQ ID NO: 14, and SEQ ID NO: 15; or SEQ ID NO: 19, SEQ ID NO: 20, and SEQ ID NO: 21; or SEQ ID NO: 25, SEQ ID NO: 26, and SEQ ID NO: 27; or SEQ ID NO: 31, SEQ ID NO: 32, and SEQ ID NO: 33; or SEQ ID NO: 37, SEQ ID NO: 38, and SEQ ID NO: 39; or SEQ ID NO: 43, SEQ ID NO: 44, and SEQ ID NO: 45; or SEQ ID NO: 49, SEQ ID NO: 50, and SEQ ID NO: 51; or SEQ ID NO: 55, SEQ ID NO: 56, and SEQ ID NO: 57; or SEQ ID NO: 61, SEQ ID NO: 62, and SEQ ID NO: 63; or SEQ ID NO: 67, SEQ ID NO: 68, and SEQ ID NO: 69; or SEQ ID NO: 73, SEQ ID NO: 74, and SEQ ID NO: 75; or SEQ ID NO: 79, SEQ ID NO: 80, and SEQ ID NO: 81; and/or (b) an antibody comprising a light chain variable region comprising the complementary determining region amino acid sequences of: SEQ ID NO: 4, SEQ ID NO: 5, and SEQ ID NO: 6; or SEQ ID NO: 10, SEQ ID NO: 11, and SEQ ID NO: 12; or SEQ ID NO: 16, SEQ ID NO: 17, and SEQ ID NO: 18; or SEQ ID NO: 22, SEQ ID NO: 23, and SEQ ID NO: 24; or SEQ ID NO: 28, SEQ ID NO: 29, and SEQ ID NO: 30; or SEQ ID NO: 34, SEQ ID NO: 35, and SEQ ID NO: 36; or SEQ ID NO: 40, SEQ ID NO: 41, and SEQ ID NO: 42; or SEQ ID NO: 46, SEQ ID NO: 47, and SEQ ID NO: 48; or SEQ ID NO: 52, SEQ ID NO: 53, and SEQ ID NO: 54; or SEQ ID NO: 58, SEQ ID NO: 59, and SEQ ID NO: 60; or SEQ ID NO: 64, SEQ ID NO: 65, and SEQ ID NO: 66; or SEQ ID NO: 70, SEQ ID NO: 71, and SEQ ID NO: 72; or SEQ ID NO: 76, SEQ ID NO: 77, and SEQ ID NO: 78; or SEQ ID NO: 82, SEQ ID NO: 83, and SEQ ID NO: 84, and wherein the isolated antibody, antibody fragment, or antigen binding portion or fragment thereof competes with the antibody of (a) or (b) for binding at that antigenic determinant.

According to the invention, the isolated monoclonal antibody or isolated monoclonal antibody fragment or antigen binding portion or fragment thereof, wherein the antibody, antibody fragment, or antigen binding portion or fragment thereof is an agonist of human and/or mouse EDAR. Preferably, said antibody, antibody fragment, or antigen binding portion or fragment thereof binds to human and/or mouse EDAR with an affinity constant (KD) of at least $10^{-8}$M.

According to an embodiment of the invention, said antibody, antibody fragment, or antigen binding portion or fragment thereof is a humanized antibody, antibody fragment, or antigen binding portion or fragment thereof.

In a preferred embodiment of the invention said antibody, antibody fragment, or antigen binding portion or fragment thereof is a monovalent. According to another embodiment of the invention, said antibody, antibody fragment, or antigen binding portion or fragment thereof is multivalent.

In some embodiments, the antibody, antibody fragment, or antigen binding portion or fragment thereof is a single chain antibody, antibody fragment, or antigen binding portion or fragment thereof.

According to one embodiment, said antibody, antibody fragment, or antigen binding portion or fragment thereof is a Fab, F(ab)'2, Fv, Fab/c, Fv, single chain Fv (scFv), or Fd fragment.

According to another embodiment, the antibody, antibody fragment, or antigen binding portion or fragment thereof is a chimeric antibody, antibody fragment, or antigen binding portion or fragment thereof.

Yet according to another embodiment of the invention, the antibody, antibody fragment, or antigen binding portion or fragment thereof is a fusion protein.

In some embodiment, the heavy chain of the isolated monoclonal antibody or isolated monoclonal antibody fragment or antigen binding portion or fragment thereof of the invention is selected from the group consisting of heavy chain of IgG, IgM, IgA, IgE, single chain antibody, immunoglobulin-derived constructs, and non antibody binding proteins. Preferably, the IgG is selected from the group consisting of IgG1, IgG2, IgG3, IgG4, mutated IgG1 that is no longer recognized by FcR, and mutated IgG4 that no longer undergoes heavy chain swapping.

According to another embodiment, the non antibody binding protein of the isolated monoclonal antibody or isolated monoclonal antibody fragment or antigen binding portion or fragment thereof is selected from the group consisting of adnectins, Affibody, DARPins, avimers, anticalins, and nucleotide based reagents.

As used herein, the term "antigenic determinant" refers to that portion of an antigen that makes contact with a particular antibody, antibody fragment, or antigen binding portion or fragment thereof (i.e., an epitope). When a protein or fragment of a protein is used to immunize a host animal, numerous regions of the protein may induce the production of antibodies which bind specifically to a given region or three dimensional structure on the protein; these regions or structures are referred to as antigenic determinants. An antigenic determinant may compete with the intact antigen (i.e., the immunogen used to elicit the immune response) for binding to an antibody, antibody fragment, or antigen binding portion or fragment thereof.

As used herein, the phrase "competes for binding at that antigenic determinant" refers to the ability of an antibody, antibody fragment, or antigen binding portion or fragment thereof to increase the affinity constant, for binding to same antigenic determinant, of a second antibody, antibody fragment, or antigen binding portion or fragment thereof by at least 5%, 10%, 20%, 30%, 40%, 50%, 60%, 70%, 80%. 90%, 100%, 1.1 fold, 1.25 fold, 1.5 fold, 5 fold, 10, fold, 50 fold, 100 fold or more in a competition binding assay. One of ordinary skill is well aware of methods for determining binding constants. One method for measuring binding constants is the commercially available Biacore assay apparatus as described in Example 1. In some embodiments, the binding affinity of an antibody, antibody fragment, or antigen binding portion or fragment thereof is higher than $10^{-7}$M, $10^{-6}$M, $10^{-5}$M, $10^{-4}$M, $10^{-3}$M, $10^{-2}$M, $10^{-1}$M, or 1M in the presence of the competing antibody, antibody fragment, or antigen binding portion or fragment thereof.

Chimeric antibodies are antibodies whose light and heavy chain genes have been constructed, typically by genetic engineering, from antibody variable and constant region genes belonging to different species. For example the variable region of the genes from a mouse monoclonal antibody may be joined to human constant regions, such as gamma 1, gamma 2, gamma 3 and gamma 4.

The term "fusion protein" as used herein refers to a polypeptide which comprises protein domains from at least two different proteins. For example, a fusion protein may comprise an antigen-binding portion or fragment of an antibody and a non-antibody protein.

In one embodiment of the invention, the antibody, antibody fragment, or antigen binding portion or fragment thereof is conjugated to a ligand and/or a tag.

In one example, the heavy chain of said antibody, antibody fragment, or antigen binding portion thereof is conjugated to the ligand and/or tag.

In another example, the light chain of said antibody, antibody fragment, or antigen binding portion or fragment thereof is conjugated to the ligand and/or tag.

Conjugation of Antibodies with Ligand/Tags

A wide variety of ligands or tags can be coupled (i.e. linked) with the antibodies described herein. Without wishing to be bound by theory, the antibodies of the invention can be conjugated to either other peptides or other molecules to tailor, for example, the bioavailability, serum half-life or shelf-life of the antibodies, immunogenicity, tolerance by human body, or to affect the solubility of the antibodies in pharmaceutically acceptable carriers. Although, conjugation with ligands and tags is discussed in reference to antibodies herein, it is to be understood that antibody fragments and antigen binding portions and fragments are also amenable to conjugation with ligands and tags. In some embodiments, ligands include naturally occurring molecules, in some embodiments recombinant or synthetic molecules. Exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), poly-ethylene glycol (PEG, e.g., PEG-2K, PEG-5K, PEG-10K, PEG-12K, PEG-15K, PEG-20K, PEG-40K), MPEG, [MPEG]$_2$, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B 12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), bovine serum albumin (BSA), ovalbumin, keyhole limpet hemocyanin (KLH), and a cell-permeation agent (e.g., a.helical cell-permeation agent).

Ligands can be used for any number of reasons including, but no limited to, targeting, PK modulation, and labeling/tagging. A targeting ligand can provide enhanced affinity for a selected target, e.g., a cell, cell type, tissue, organ, region of the body, or a compartment, e.g., a cellular, tissue or organ compartment. A PK modulating ligand can modulate pharmacokinetics of an antibody in vivo.

In some embodiments, the antibody of the invention is conjugated with a label/tag, such as a fluorescent label or a biotin label. Without wishing to be bound by theory, such labeling allows one to easily track the antibody, if necessary or to assist in purification of the antibody.

One can also design the ligand in such a way that is can be removed after purification of the antibody is complete. For example, the ligand can be attached to the antibody via a linker that can be is easily cleavable under the appropriate conditions. Such conditions can include acid or basic pH, heating, sonication, enzymatic cleavage, and the like.

As used herein, the term "label" refers to a composition capable of producing a detectable signal indicative of the presence of a target. Suitable labels include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means needed for the methods and devices described herein. For example, the antibody can be labeled with a detectable tag which can then be detected using an antibody specific to the label.

Exemplary fluorescent labels include, but are not limited to, Hydroxycoumarin, Succinimidyl ester, Aminocoumarin, Succinimidyl ester, Methoxycoumarin, Succinimidyl ester, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5 or Cy7.

The ligands can be conjugated, either directly or through a linker, to the N-terminal, C-terminal, or the amino acid side chains of the heavy and/or light chain of the antibody. A ligand can be present on an amino acid when said amino acid is incorporated into the antibody heavy and/or light during synthesis. In some embodiments, the ligand can be incorporated via coupling to a "precursor" amino acid after said "precursor" amino acid has been incorporated into the antibody heavy and/or light chain. For example, a ligand having an electrophilic group, e.g., a pentafluorophenyl ester or aldehyde group, can be conjugated to the N-terminal of heavy and/or light chain of the antibody.

In another example, a monomer having a chemical group suitable for taking part in Click Chemistry reaction can be incorporated, e.g., an azide or alkyne group. In a subsequent operation, i.e., after incorporation of the precursor monomer antibody heavy and/or light chain, a ligand having complementary chemical group, e.g., an alkyne or azide can be attached to the precursor monomer by coupling the alkyne and the azide together.

In some embodiments, the covalent linkages between the antibody and a ligand is mediated by a linker. This linker can be cleavable linker or non-cleavable linker, depending on the application. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In some embodiments, a cleavable linker can be used to release the antibody after transport to the desired target. The intended nature of the conjugation or coupling interaction, or the desired biological effect, will determine the choice of linker group.

As used herein, the term "non-peptide linker" means an organic moiety that connects two parts of the peptide and such a moiety is not a peptide. Linkers typically comprise a direct bond or an atom such as oxygen or sulfur, a unit such as $NR^1$, $C(O)$, $C(O)NH$, $SO$, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic. The two parts of the compound can be linked together by providing on each part of the molecule complementary chemical functionalities that undergo a coupling reaction.

In some embodiments, linkers can be non-covalent coupling of two parts of a compound or two different molecules. Such non-covalent coupling can be achieved through, for example, ionic interactions, H-bonding, van der Waals interactions and affinity of one molecule for another. When non-covalent coupling is used, each part of the compound can be conjugated with a moiety that has complementary to another moiety that is conjugated to the second part of the compound. One example of such complementary coupling is the biotin/avidin coupling. Other examples include affinity of an oligonucleotide for its complementary strand, receptor/ligand binding, aptamer/ligand binding and antibody/antigen binding.

Many strategies are known in the art for conjugating peptides to peptides and other molecules. For example, Hermanson, G. T., *Bioconjugate Techniques*, $2^{nd}$ Ed., Academic Press (2008) and Niemeyr, C. M., *Bioconjugation Protocols: Strategies and Methods (Methods in Molecular Biology)*, Humana Press (2004) provide a number of methods and techniques for conjugating peptides to other molecules. Contents of both of these are herein incorporated by reference in their entirety for all purposes. For a review of site-specific introduction of non-natural amino acids into peptides for conjugation see A. J. de Graaf, et al., Biocojugate Chemistry (2009) 20(7):1281-1295, contents of which are herein incorporated in its entirety. Int. Pat. App. Pub. No.: WO92/13095, contents of which are herein incorporated in its entirety, describes methods for PEGylation of peptides.

One conjugation strategy is the biotin-sandwich method (Davis, et al., *Proc. Natl. Acad. Sci. USA* 103:8155-8160 (2006)) in which a peptide is biotinylated and bound to biotinylated ligand using tetravalent streptavidin as a linker. To accomplish this, the peptide may be coupled to the 15 amino acid sequence of an acceptor peptide for biotinylation (referred to as AP; Chen, et al., *Nat. Methods* 2:99-104 (2005)). The fusion proteins can be made by incorporating the extra sequences at the N- or the C-terminus of the peptide. The acceptor peptide sequence allows site-specific biotinylation by the *E. coli* enzyme biotin ligase (BirA; Chen, et al., *Nat. Methods* 2:99-104 (2005)). A ligand peptide can be similarly biotinylated for conjugation with a peptide described herein.

Many commercial kits are available for biotinylating proteins. Non-peptidyl ligands agents can also be conjugated with biotin using methods well known in the art for conjugating biotin to non-peptide molecules, e.g. small organic molecules. In order to prevent steric interference between the biotin/avidin groups and the peptides or the ligands, a spacer may be included between them.

The linkers and linking methods described herein can also be used for linking together heavy chain and light chain of an antibody, two or more Fv domains, and fragments thereof.

For simplicity, chemical moieties are defined and referred to throughout can be univalent chemical moieties (e.g., alkyl, aryl, etc.) or multivalent moieties under the appropriate structural circumstances clear to those skilled in the art.

The term "alkyl" refers to saturated non-aromatic hydrocarbon chains that may be a straight chain or branched chain, containing the indicated number of carbon atoms (these include without limitation methyl, ethyl, propyl, allyl, or propargyl), which may be optionally inserted with N, O, S, SS, $SO_2$, C(O), C(O)O, OC(O), C(O)N or NC(O). For example, $C_1$-$C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "aryl" refers to monocyclic, bicyclic, or tricyclic aromatic ring system wherein 0, 1, 2, 3, or 4 atoms of each ring may be substituted by a substituent. Examplary aryl groups include, but are not limited to, phenyl, naphthyl, anthracenyl, azulenyl, fluorenyl, indanyl, indenyl, naphthyl, phenyl, tetrahydronaphthyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "cyclyl", "cyclic" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heterocyclyl", "heterocycle" or "heterocyclic" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examplary heterocyclyl groups include, but are not limited to piperazinyl, pyrrolidinyl, dioxanyl, morpholinyl, tetrahydrofuranyl, and the like.

The term "optionally substituted" means that the specified group or moiety, such as an alkyl, aryl group, heteroaryl group and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, heteroaryl, acyl, amino group at any atom of that group. Suitable substituents include, without limitation, halo, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkylthio, $CF_3$, N-morphilino, phenylthio, alkanesulfonyl, arenesulfonyl, alkanesulfonamido, arenesulfonamido, aralkylsulfonamido, alkylcarbonyl, acyloxy, cyano or ureido. In some embodiments, substituent can itself be optionally substituted. In some cases, two substituents, together with the carbons to which they are attached to can form a ring.

The term "halo" refers to any radical of fluorine, chlorine, bromine or iodine.

The term "acyl" refers to an alkylcarbonyl, cycloalkylcarbonyl, arylcarbonyl, heterocyclylcarbonyl, or heteroarylcarbonyl substituent, any of which may be further substituted by substituents. Exemplary acyl groups include, but are not limited to, ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions.

The term "alkoxy" refers to an —O-alkyl radical.

The term "aminoalkyl" refers to an alkyl substituted with an amino.

The term "mercapto" refers to an —SH radical.

The term "thioalkoxy" refers to an —S-alkyl radical.

The term "haloalkyl" refers to an alkyl group having one, two, three or more halogen atoms attached thereto. Exemplary haloalkyl groups include, but are not limited to chloromethyl, bromoethyl, trifluoromethyl, and the like.

According to another object of the invention, the antibody, antibody fragment, or antigen binding portion or fragment thereof is obtained by the method of the invention.

Another object of the invention is to provide an isolated nucleic acid molecule encoding isolated monoclonal antibody or isolated monoclonal antibody fragment or antigen binding portion or fragment thereof as disclosed above.

It is also an object of the invention to provide an expression vector comprising at least one copy of the nucleic acid molecule of the invention.

A host cell comprising said expression vector and transgenic non-human animal having a genome comprising the isolated nucleic acid molecule of the invention and/or the expression vector as described above are also encompassed by the present invention.

The invention further provides for a hybridoma secreting isolated monoclonal antibody or isolated monoclonal antibody fragment or antigen binding portion or fragment thereof according to the invention.

Another object of the invention is a pharmaceutical composition comprising the isolated monoclonal antibody or isolated monoclonal antibody fragment or antigen binding portion or fragment thereof, and a pharmaceutically acceptable carrier. Preferably, the isolated monoclonal antibody or isolated monoclonal antibody fragment or antigen binding portion or fragment thereof is administered to a patient in need thereof at a dosage unit from 0.1 mg/kg of body weight to 100 mg/kg of body weight.

The pharmaceutical composition of the invention is suitable in treating X-linked hypohidrotic ectodermal dysplasia (XLHED) or tooth agenesis.

In one embodiment of the invention, the pharmaceutical composition of the invention is formulated for parenteral, intravenous, oral, subcutaneous, intradermal, intramuscular or topical, administration.

Also encompassed is the use of isolated monoclonal antibody or isolated monoclonal antibody fragment or antigen binding portion or fragment thereof or the pharmaceutical composition of the invention, for the preparation of a medicament for modulating the development of cells or tissues of ectodermal origin, such as hair, teeth, skin, sweat glands, sebaceous glands, larynx and trachea mucus-producing cells, Meibomian glands, preputial glands, mammary glands and salivary glands.

Preferably said medicament is used for the treatment of ectodermal dysplasia, or disturbances or anomalies of ectodermal structures that are not caused by mutations in EDA1, such as anomalies of the hair, of the teeth or of the glands, in particular for treating alopecia, sebaceous gland malfunction or a deficiency of sweat glands or sebaceous glands or for wound healing.

More preferably, the medicament is used for the treatment of X-linked hypohidrotic ectodermal dysplasia or tooth agenesis.

In one embodiment, the medicament is administered to the mother/the mother animal during pregnancy.

In particular, the medicament is administered to a subject in need thereof. According to some cases, the subject in need thereof is a fetus, a pre-term newborn, a newborn, a child, a young adult or an adult.

Another object of the invention is the use of the isolated monoclonal antibody or isolated monoclonal antibody fragment or antigen binding portion or fragment thereof or the pharmaceutical composition of the invention, for the manufacture of a medicament involved in the reconstitution of the skin. In accordance with the invention, the reconstitution of the skin may comprise burns, ulcers or scares such as bedsores, cosmetic reconstruction after surgery such as tumour ablation.

Yet another object of the invention is the use of the isolated monoclonal antibody or isolated monoclonal antibody fragment or antigen binding portion or fragment thereof or the pharmaceutical composition of the invention, for the manufacture of a medicament for modifying hair morphology.

The present invention also provides for a method of increasing the development of one or more hair follicle, tooth, sweat gland, sebaceous glands, larynx and trachea mucus-producing cells, Meibomian glands, preputial glands, mammary glands and salivary glands in a tissue, comprising administering to a subject in need thereof, the isolated monoclonal antibody or isolated monoclonal antibody fragment or antigen binding portion or fragment thereof or the pharmaceutical composition of the invention. Preferably said method comprises administering to said subject in need thereof an amount of the isolated monoclonal antibody or isolated monoclonal antibody fragment or antigen binding portion or fragment thereof or the pharmaceutical composition of the invention sufficient to promote the development of one or more hair follicle, tooth, sweat gland, sebaceous glands, larynx and trachea mucus-producing cells, Meibomian glands, preputial glands, mammary glands and salivary glands in a tissue of said subject in need thereof. Preferably, the subject in need thereof is suffering from an ectodermal disease. In particular, said ectodermal disease is XLHED or alopecia or tooth agenesis.

Furthermore, the invention also concerns a pharmaceutical kit comprising at least an effective amount of the isolated monoclonal antibody or isolated monoclonal antibody fragment or antigen binding portion or fragment thereof or the pharmaceutical composition according to the invention, together with instructions for use.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The foregoing description will be more fully understood with reference to the following Examples. Such Examples, are, however, exemplary of methods of practicing the present invention and are not intended to limit the scope of the invention.

Some embodiments of the technology described herein can be defined according to any of the following numbered paragraphs:

1. A method of producing milk that comprises a monoclonal anti-EDAR antibody or antigen-binding portion or fragment thereof that binds human and/or mouse EDAR, the method comprising contacting blood or tissue of a lactating mammal with an isolated monoclonal anti-EDAR antibody or antigen-binding portion or fragment thereof that binds human and/or mouse EDAR, wherein the antibody or antigen-binding portion or fragment thereof is transferred from the blood or tissue into the milk.
2. The method of paragraph 1 wherein the contacting step comprises parenteral, intravenous, oral, subcutaneous, intradermal, intramuscular, or topical administration.
3. The method of paragraph 1 wherein the lactating mammal is a human or a mouse.
4. The method of paragraph 1 wherein the isolated monoclonal anti-EDAR antibody or antigen-binding portion or fragment thereof comprises:
   a) a heavy chain variable region comprising the complementary determining region (CDR) amino acid sequences: SEQ ID NO: 1, SEQ ID NO: 2, and SEQ ID NO: 3; or SEQ ID NO: 7, SEQ ID NO: 8, and SEQ ID NO: 9; or SEQ ID NO: 13, SEQ ID NO: 14, and SEQ ID NO: 15; or SEQ ID NO: 19, SEQ ID NO: 20, and SEQ ID NO: 21; or SEQ ID NO: 25, SEQ ID NO: 26, and SEQ ID NO: 27; and/or
   (b) a light chain variable region comprising the complementary determining region (CDR) amino acid sequences of SEQ ID NO: 4, SEQ ID NO: 5, and SEQ ID NO: 6; or SEQ ID NO: 10, SEQ ID NO: 11, and SEQ ID NO: 12; or SEQ ID NO: 16, SEQ ID NO: 17, and SEQ ID NO: 18; or SEQ ID NO: 22, SEQ ID NO:

23, and SEQ ID NO: 24; or SEQ ID NO: 28, SEQ ID NO: 29, and SEQ ID NO: 30.

5. The method of paragraph 1 wherein the isolated monoclonal anti-EDAR antibody or antigen-binding portion or fragment thereof comprises: a heavy chain variable region comprising the complementary determining region (CDR) amino acid sequences: SEQ ID NO: 1, SEQ ID NO: 2, and SEQ ID NO: 3; and/or a light chain variable region comprising the complementary determining region (CDR) amino acid sequences: SEQ ID NO: 4, SEQ ID NO: 5, and SEQ ID NO: 6.

6. The method of paragraph 1 wherein the isolated monoclonal antibody or fragment or antigen binding portion or fragment thereof is capable of binding human EDAR or a fragment thereof comprising cysteine rich domain I (CRD1).

7. The method of paragraph 6 wherein the isolated monoclonal antibody or antigen binding portion or fragment thereof is capable of binding human EDAR or a fragment thereof comprising cysteine rich domain I (CRD1) in the absence of cysteine rich domain II (CRD2).

8. The method of paragraph 1 wherein the isolated monoclonal antibody or fragment or antigen binding portion or fragment thereof is an agonist of human and/or mouse EDAR.

9. The method of paragraph 8 wherein the isolated monoclonal antibody or fragment or antigen binding portion or fragment thereof has EC50 for inducing half maximal decrease of cell viability in EDAR-Fas-expressing Jurkat cells equal to or less than 200 ng/mL.

10. The method of paragraph 9 wherein the isolated monoclonal antibody or fragment or antigen binding portion or fragment thereof has EC50 for inducing half maximal decrease of cell viability in EDAR-Fas-expressing Jurkat cells equal to or less than 100 ng/mL.

11. The method of paragraph 1 wherein the isolated monoclonal antibody or fragment or antigen binding portion or fragment thereof binds to human and/or mouse EDAR with an affinity constant (KD) of at least $10^{-8}$ M.

12. The method of paragraph 1 wherein the isolated monoclonal antibody or fragment or antigen binding portion or fragment thereof is a humanized antibody, antibody fragment, or antigen binding portion or fragment thereof.

13. The method of paragraph 1 wherein the isolated monoclonal antibody or fragment or antigen binding portion or fragment thereof is monovalent.

14. The method of paragraph 1 wherein the isolated monoclonal antibody or fragment or antigen binding portion or fragment thereof is a single chain antibody, antibody fragment, or antigen binding portion or fragment thereof.

15. The method of paragraph 1 wherein the isolated monoclonal antibody or fragment or antigen binding portion or fragment thereof is a Fab, F(ab)'2, Fv, Fab/c, Fv, single chain Fv (scFv), or Fd fragment.

16. The method of paragraph 1 wherein the isolated monoclonal antibody or fragment or antigen binding portion or fragment thereof is a chimeric antibody, antibody fragment, or antigen binding portion or fragment thereof.

17. The method of paragraph 1 wherein the isolated monoclonal antibody or fragment or antigen binding portion or fragment thereof is a fusion protein.

18. The method of paragraph 12 wherein the isolated monoclonal antibody or fragment or antigen binding portion or fragment thereof has a heavy chain selected from the group consisting of heavy chain of IgG, IgM, IgA, IgE, single chain antibody, immunoglobulin-derived constructs, and non-antibody binding proteins.

19. The method of paragraph 18, wherein the non-antibody binding protein is selected from the group consisting of adnectins, Affibody, DARPins, avimers, anticalins, and nucleotide based reagents.

20. The method of paragraph 18, wherein the IgG is selected from the group consisting of IgG1, IgG2, IgG3, IgG4, mutated IgG1 that is no longer recognized by FcR, and mutated IgG4 that no longer undergoes heavy chain swapping.

21. The method of paragraph 1 wherein the isolated monoclonal antibody or fragment or antigen binding portion or fragment thereof is conjugated to a ligand and/or a tag.

22. The method of paragraph 21 wherein the isolated monoclonal antibody or fragment or antigen binding portion or fragment thereof has a heavy chain conjugated to the ligand and/or tag.

23. The method of paragraph 21, wherein the ligand and/or tag is polyethylene glycol (PEG) or a label.

24. A method of increasing the development of one or more structures in subject in need thereof, the method comprising feeding to the subject the milk produced according to the method of paragraph 1, wherein the one or more structures are selected from the group consisting of: hair follicle, tooth, sweat gland, sebaceous glands, larynx and trachea mucus-producing cells, Meibomian glands, preputial glands, mammary glands, and salivary glands.

25. The method of paragraph 24 wherein the subject is a newborn individual receiving the milk via natural nursing.

26. The method of paragraph 25 wherein the subject is the offspring of the lactating mammal.

27. The method of paragraph 24, wherein the subject has an ectodermal disease.

28. The method of paragraph 27, wherein the ectodermal disease is XLHED, alopecia or tooth agenesis.

29. The method of paragraph 24 wherein the lactating mammal is a human or a mouse.

30. The method of paragraph 24 wherein the isolated monoclonal anti-EDAR antibody or antigen-binding portion or fragment thereof comprises:
  a) a heavy chain variable region comprising the complementary determining region (CDR) amino acid sequences: SEQ ID NO: 1, SEQ ID NO: 2, and SEQ ID NO: 3; or SEQ ID NO: 7, SEQ ID NO: 8, and SEQ ID NO: 9; or SEQ ID NO: 13, SEQ ID NO: 14, and SEQ ID NO: 15; or SEQ ID NO: 19, SEQ ID NO: 20, and SEQ ID NO: 21; or SEQ ID NO: 25, SEQ ID NO: 26, and SEQ ID NO: 27; and/or
  (b) a light chain variable region comprising the complementary determining region (CDR) amino acid sequences of SEQ ID NO: 4, SEQ ID NO: 5, and SEQ ID NO: 6; or SEQ ID NO: 10, SEQ ID NO: 11, and SEQ ID NO: 12; or SEQ ID NO: 16, SEQ ID NO: 17, and SEQ ID NO: 18; or SEQ ID NO: 22, SEQ ID NO: 23, and SEQ ID NO: 24; or SEQ ID NO: 28, SEQ ID NO: 29, and SEQ ID NO: 30.

31. The method of paragraph 24 wherein the isolated monoclonal anti-EDAR antibody or antigen-binding portion or fragment thereof comprises: a heavy chain variable region comprising the complementary determining region (CDR) amino acid sequences: SEQ ID NO: 1, SEQ ID NO: 2, and SEQ ID NO: 3; and/or a light chain variable region comprising the complementary determining region (CDR) amino acid sequences: SEQ ID NO: 4, SEQ ID NO: 5, and SEQ ID NO: 6.

32. The method of paragraph 24 wherein the isolated monoclonal antibody or fragment or antigen binding portion or fragment thereof is capable of binding human EDAR or a fragment thereof comprising cysteine rich domain I (CRD1).

33. The method of paragraph 32 wherein the isolated monoclonal antibody or fragment or antigen binding portion or fragment thereof is capable of binding human EDAR or a fragment thereof comprising cysteine rich domain I (CRD1) in the absence of cysteine rich domain II (CRD2).

34. The method of paragraph 24 wherein the isolated monoclonal antibody or fragment or antigen binding portion or fragment thereof is an agonist of human and/or mouse EDAR.

35. The method of paragraph 34 wherein the isolated monoclonal antibody or fragment or antigen binding portion or fragment thereof has EC50 for inducing half maximal decrease of cell viability in EDAR-Fas-expressing Jurkat cells equal to or less than 200 ng/mL.

36. The method of paragraph 35 wherein the isolated monoclonal antibody or fragment or antigen binding portion or fragment thereof has EC50 for inducing half maximal decrease of cell viability in EDAR-Fas-expressing Jurkat cells equal to or less than 100 ng/mL.

37. The method of paragraph 24 wherein the isolated monoclonal antibody or fragment or antigen binding portion or fragment thereof binds to human and/or mouse EDAR with an affinity constant (KD) of at least $10^{-8}$ M.

38. The method of paragraph 24 wherein the isolated monoclonal antibody or fragment or antigen binding portion or fragment thereof is a humanized antibody, antibody fragment, or antigen binding portion or fragment thereof.

39. The method of paragraph 24 wherein the isolated monoclonal antibody or fragment or antigen binding portion or fragment thereof is monovalent.

40. The method of paragraph 24 wherein the isolated monoclonal antibody or fragment or antigen binding portion or fragment thereof is a single chain antibody, antibody fragment, or antigen binding portion or fragment thereof.

41. The method of paragraph 24 wherein the isolated monoclonal antibody or fragment or antigen binding portion or fragment thereof is a Fab, F(ab)'2, Fv, Fab/c, Fv, single chain Fv (scFv), or Fd fragment.

42. The method of paragraph 24 wherein the isolated monoclonal antibody or fragment or antigen binding portion or fragment thereof is a chimeric antibody, antibody fragment, or antigen binding portion or fragment thereof.

43. The method of paragraph 24 wherein the isolated monoclonal antibody or fragment or antigen binding portion or fragment thereof is a fusion protein.

44. The method of paragraph 38 wherein the isolated monoclonal antibody or fragment or antigen binding portion or fragment thereof has a heavy chain selected from the group consisting of heavy chain of IgG, IgM, IgA, IgE, single chain antibody, immunoglobulin-derived constructs, and non-antibody binding proteins.

45. The method of paragraph 44, wherein the non-antibody binding protein is selected from the group consisting of adnectins, Affibody, DARPins, avimers, anticalins, and nucleotide based reagents.

46. The method of paragraph 44, wherein the IgG is selected from the group consisting of IgG1, IgG2, IgG3, IgG4, mutated IgG1 that is no longer recognized by FcR, and mutated IgG4 that no longer undergoes heavy chain swapping.

47. The method of paragraph 24 wherein the isolated monoclonal antibody or fragment or antigen binding portion or fragment thereof is conjugated to a ligand and/or a tag.

48. The method of paragraph 47 wherein the isolated monoclonal antibody or fragment or antigen binding portion or fragment thereof has a heavy chain conjugated to the ligand and/or tag.

49. The method of paragraph 47, wherein the ligand and/or tag is polyethylene glycol (PEG) or a label.

50. A method for increasing the size and/or number of sebaceous glands in a subject in need thereof, the method comprising contacting blood or tissue of the subject with an isolated monoclonal anti-EDAR antibody or antigen-binding portion or fragment thereof that binds human and/or mouse EDAR.

51. The method of paragraph 50, wherein the subject has an ectodermal disease.

52. The method of paragraph 51, wherein the ectodermal disease is XLHED, alopecia or tooth agenesis.

53. The method of paragraph 50 wherein the contacting step comprises parenteral, intravenous, oral, subcutaneous, intradermal, intramuscular, or topical administration.

54. The method of paragraph 50 wherein the subject is a human or a mouse.

55. The method of paragraph 50 wherein the isolated monoclonal anti-EDAR antibody or antigen-binding portion or fragment thereof comprises:
   a) a heavy chain variable region comprising the complementary determining region (CDR) amino acid sequences: SEQ ID NO: 1, SEQ ID NO: 2, and SEQ ID NO: 3; or SEQ ID NO: 7, SEQ ID NO: 8, and SEQ ID NO: 9; or SEQ ID NO: 13, SEQ ID NO: 14, and SEQ ID NO: 15; or SEQ ID NO: 19, SEQ ID NO: 20, and SEQ ID NO: 21; or SEQ ID NO: 25, SEQ ID NO: 26, and SEQ ID NO: 27; and/or
   (b) a light chain variable region comprising the complementary determining region (CDR) amino acid sequences of SEQ ID NO: 4, SEQ ID NO: 5, and SEQ ID NO: 6; or SEQ ID NO: 10, SEQ ID NO: 11, and SEQ ID NO: 12; or SEQ ID NO: 16, SEQ ID NO: 17, and SEQ ID NO: 18; or SEQ ID NO: 22, SEQ ID NO: 23, and SEQ ID NO: 24; or SEQ ID NO: 28, SEQ ID NO: 29, and SEQ ID NO: 30.

56. The method of paragraph 50 wherein the isolated monoclonal anti-EDAR antibody or antigen-binding portion or fragment thereof comprises: a heavy chain variable region comprising the complementary determining region (CDR) amino acid sequences: SEQ ID NO: 1, SEQ ID NO: 2, and SEQ ID NO: 3; and/or a light chain variable region comprising the complementary determining region (CDR) amino acid sequences: SEQ ID NO: 4, SEQ ID NO: 5, and SEQ ID NO: 6.

57. The method of paragraph 50 wherein the isolated monoclonal antibody or fragment or antigen binding portion or fragment thereof is capable of binding human EDAR or a fragment thereof comprising cysteine rich domain I (CRD1).

58. The method of paragraph 57 wherein the isolated monoclonal antibody or fragment or antigen binding portion or fragment thereof is capable of binding human EDAR or a fragment thereof comprising cysteine rich domain I (CRD1) in the absence of cysteine rich domain II (CRD2).

59. The method of paragraph 50 wherein the isolated monoclonal antibody or fragment or antigen binding portion or fragment thereof is an agonist of human and/or mouse EDAR.

60. The method of paragraph 59 wherein the isolated monoclonal antibody or fragment or antigen binding portion or fragment thereof has EC50 for inducing half maximal decrease of cell viability in EDAR-Fas-expressing Jurkat cells equal to or less than 200 ng/mL.

61. The method of paragraph 60 wherein the isolated monoclonal antibody or fragment or antigen binding portion or fragment thereof has EC50 for inducing half maximal decrease of cell viability in EDAR-Fas-expressing Jurkat cells equal to or less than 100 ng/mL.

62. The method of paragraph 50 wherein the isolated monoclonal antibody or fragment or antigen binding portion or fragment thereof binds to human and/or mouse EDAR with an affinity constant (KD) of at least $10^{-8}$ M.

63. The method of paragraph 50 wherein the isolated monoclonal antibody or fragment or antigen binding portion or fragment thereof is a humanized antibody, antibody fragment, or antigen binding portion or fragment thereof.

64. The method of paragraph 50 wherein the isolated monoclonal antibody or fragment or antigen binding portion or fragment thereof is monovalent.

65. The method of paragraph 50 wherein the isolated monoclonal antibody or fragment or antigen binding portion or fragment thereof is a single chain antibody, antibody fragment, or antigen binding portion or fragment thereof.

66. The method of paragraph 50 wherein the isolated monoclonal antibody or fragment or antigen binding portion or fragment thereof is a Fab, F(ab)'2, Fv, Fab/c, Fv, single chain Fv (scFv), or Fd fragment.

67. The method of paragraph 50 wherein the isolated monoclonal antibody or fragment or antigen binding portion or fragment thereof is a chimeric antibody, antibody fragment, or antigen binding portion or fragment thereof.

68. The method of paragraph 50 wherein the isolated monoclonal antibody or fragment or antigen binding portion or fragment thereof is a fusion protein.

69. The method of paragraph 63 wherein the isolated monoclonal antibody or fragment or antigen binding portion or fragment thereof has a heavy chain selected from the group consisting of heavy chain of IgG, IgM, IgA, IgE, single chain antibody, immunoglobulin-derived constructs, and non-antibody binding proteins.

70. The method of paragraph 69, wherein the non-antibody binding protein is selected from the group consisting of adnectins, Affibody, DARPins, avimers, anticalins, and nucleotide based reagents.

71. The method of paragraph 69, wherein the IgG is selected from the group consisting of IgG1, IgG2, IgG3, IgG4, mutated IgG1 that is no longer recognized by FcR, and mutated IgG4 that no longer undergoes heavy chain swapping.

72. The method of paragraph 50 wherein the isolated monoclonal antibody or fragment or antigen binding portion or fragment thereof is conjugated to a ligand and/or a tag.

73. The method of paragraph 72 wherein the isolated monoclonal antibody or fragment or antigen binding portion or fragment thereof has a heavy chain conjugated to the ligand and/or tag.

74. The method of paragraph 72, wherein the ligand and/or tag is polyethylene glycol (PEG) or a label.

EXAMPLES

Example 1

Anti-EDAR Monoclonal Antibodies, Development, Identification and Characterization Preparation of Soluble EDAR
Development of the EDAR-Fc Expression Vector.

The EDAR-Fc gene construct was cloned into the PCR3 mammalian expression vector (Invitrogen) according to standard molecular biology techniques. Development of the vector for expression of EDAR-Fc has been described previously (Holler, N., Tardivel, A., Kovacsovics-Bankowski, M., Hertig, S., Gaide, O., Maranon, F., Tinel, A., Deperthes, D., Calderara, S., Schulthess, T., Engel, J., Schneider, P., and Tschopp, J. 2003 *Mol Cell Biol* 23, 1428-1440; Bossen, C., Ingold, K., Tardivel, A., Bodmer, J. L., Gaide, O., Hertig, S., Ambrose, C., Tschopp, J., and Schneider, P. 2006 *J Biol Chem* 281, 13964-13971; Schneider, P. 2000 *Meth. Enzymol.* 322, 322-345; Holler, N., Kataoka, T., Bodmer, J. L., Romero, P., Romero, J., Deperthes, D., Engel, J., Tschopp, J., and Schneider, P. 2000 *J Immunol Methods* 237, 159-173).

Development of Stably Expressing EDAR-Fc 293 Cells.

EDAR-Fc was produced in stably expressing EDAR-Fc 293 cells. For the generation of these cells, human embryonic kidney 293 cells (ATCC CRL 1573) were diluted twice weekly in DMEM and nutrient mix F12 media mixed in a 1 to 1 ratio (Life Technologies) supplemented with 2% FCS and antibiotics (293 medium). Two days before transfection, $5 \times 10^5$ confluent 293 cells were resuspended in 4 ml of 293 medium. These cells were seeded in a 25 cm² cell culture flask (Nunc). Ten µg of expression plasmid sterilized by ethanol precipitation were redissolved in 250 µl of sterile 250 mM CaCl₂. Once cells were adherent, they were washed once with PBS then 4 ml of DMEM supplemented with 10% FCS and antibiotics were added. Two hundred and fifty µl of 2×HeBS were added to the plasmid solution while vortexing gently. After 1 to 3 minutes, the solution was added to the cells and left overnight. The cells were then washed once with PBS and 4 ml of 293 medium were added and left for 1 to 3 days. The cells were subsequently resuspended and diluted 1 to 8 in 4 ml of selection medium (50 ml of 293 medium supplemented with 400 µl of a 100 mg/ml aqueous solution of G418, Life Technologies). After 4 to 7 days, the cells were diluted 1 to 8 in 4 ml of selection medium. When cells reached confluency after 4 to 7 days, they were resuspended and 10 µl of cell suspension were seeded in 8 ml of selection medium in a 9 cm diameter cell culture plate. After 10 to 15 days, when clones were macroscopically visible with bare eyes, they were picked and transferred in wells of flat bottom 96 well plates (Costar, Cambridge, Mass.) containing 200 µl of selection medium. After 7 to 10 d, and thereafter every 3 to 4 d, the clones were diluted 1 to 10 in selection medium. After 14 d, when medium in the initial wells had turned yellow, the presence of recombinant EDAR-Fc was assessed by Western blotting under non reducing conditions. For the detection of unreduced EDAR-Fc fusion protein, a 0.5 µg/ml solution of protein A-peroxidase (Sigma, St-Louis, Mo.) was used and revealed with ECL reagent (GE Healthcare). The selected clones were amplified by successive transfer from 96 well plates into 25 cm$^2$, 75 cm$^2$, 175 cm$^2$ cell culture flasks and, finally, 2 liter roller bottles (Falcon, Lincoln Park, N.Y.). After 14 d in roller bottles, the culture supernatant was cleared from cells by centrifugation (3000×g) and filtered using a 0.45 µm filter (Nalgene, Rochester, Ill.). The supernatant was supplemented with 0.02% NaN3 and stored at 4° C. or −20° C. until purification.

Purification of EDAR-Fc Recombinant Fusion Protein.

A one step purification procedure of EDAR-Fc chimeric protein was performed using HiTrap Protein A columns (GE Healthcare). Briefly, the column was equilibrated in PBS, loaded with 1 liter of supernatant at a flow rate of 4 ml/min, washed with 10 ml PBS and eluted with 4 ml of 0.1 M citrate-NaOH, pH 2.5. The eluate was neutralized with 1 ml of 1 M Tris-HCl, pH 8.5, concentrated in a Centricon-30 device down to less than 0.5 ml and washed twice with 2 ml of PBS to exchange buffer. Protein concentration was determined using the BCA reagent (Pierce, Rockford, Ill.) and bovine serum albumin as a standard. The purification yield was comprised between 0.5 and 5 mg of EDAR-Fc per liter. The purified EDAR-Fc protein was finally sterilized by 0.2 µm filtration using Millex-GV low protein binding filters (Millipore, Bedford, Mass.) and aliquots were stored at −20° C. Purity was checked by SDS-PAGE and Coomassie Blue staining.

Immunization of EDAR-Deficient Mice

Soluble EDAR-Fc (150 µg) in PBS (500 µl) was mixed to 500 µl of STIMUNE (Cedi-diagnostics, Lelystad, The Netherlands), briefly sonicated three times and kept at 4° C. until used. Female OVEB1 mice (Headon et al., Nature Genetics 22:370-4, 1999) were injected subcutaneously on the back with 150 µl of antigen preparation and intramuscularly in the tail with 100 µl of antigen preparation. Ten to fourteen days later, mice were intramuscularly injected with 100 µl of antigen in each back leg and subcutaneously with 150 µl of antigen subcutaneously in the back. Twenty-eight to thirty-two days after the first immunization, the mice were bled and serial dilutions of serum were tested by ELISA for the presence of anti-EDAR antibodies (see protocol below). On day forty to forty-five after the first antigen injection, mice found positive by ELISA were injected in the back and the back legs with 150 µg of antigen in PBS. Three days later, the cells from the lymph nodes were fused with myeloma cells.

Detection of Anti-EDAR Antibodies in the Serum of EDAR-Immunized Mice

The presence of anti-EDAR antibodies in the serum of EDAR-immunized mice was determined by ELISA. Briefly, ELISA plates (96 wells Maxisorp Immunoplate, Nunc) were coated for 2 h at 37° C. or overnight at room temperature with 100 µl of 1 µg/ml EDAR-Fc in PBS. The wells were blocked with 300 µl of blocking buffer (5% FCS in PBS) and incubated for 1 h at 37° C. The wells were then washed 3× with wash buffer (PBS+0.05% Tween 20) and 100 µl of serum diluted in incubation buffer (0.5% FCS in PBS) were added to each well. After an incubation of 1 h at 37° C., the wells were washed 3× with wash buffer. Bound antibodies were revealed by the addition of 100 µl of peroxydase-labeled goat anti-mouse IgG (Jackson ImmunoResearch) diluted 1 in 1000 in incubation buffer for 30 min at 37° C., followed by three repetitive washes with wash buffer and addition of 100 µl of o-phenylenediamine (OPD) reagent (Sigma). When developed, the reaction was stopped with 50 µl of 2 N HCl and the absorbance was measured at 490 nm.

Generation of Hybridoma Cells

Lymph nodes were homogenized in a sterile glass homogenizer in 10 ml of RPMI 1640 with 6 to 8 strokes using a borosilicated pestle. The suspension was transferred in a 50 mL Falcon tube and cells spin down at 300 g for 10 minutes at room temperature. Cells were resuspended in 10 mL RPMI 1640 medium and lymph node cells were counted. Ten to 20×10$^7$ lymph node cells and 10 to 20×10$^6$ myeloma cells (P3-X63Ag8 or NS1) were mixed at a 10 to 1 ratio for the fusion, and the cells were pelleted by centrifugation at 300×g for 10 min. Pre-warmed PEG 1500 (0.5 ml) was added to the pellet drop-wise along the tube wall, and the tube was kept for 3 minutes at 37° C. while shaking gently every minute. Five ml of RPMI 1640 medium (pre-warmed at 37° C.) were added along the tube wall over a period of 10 minutes (0.5 ml/min), followed by a 1 minute incubation at 37° C. Five ml of RPMI 1640 medium were added again over a period of 5 to 6 minutes. Cells were pelleted by centrifugation at 300×g for 10 minutes and at room temperature, re-suspended in 6 ml of complete RPMI 1640 medium, and incubated for 1 hour at 37° C. in a $CO_2$ incubator. The cell fusion suspension was laid gently (100 µl/well) over mouse macrophages (feeder layer) contained in 6 96 flat bottom well plates. Twenty four hours after the fusion, HAT (hypoxanthine, aminopterine and thymidine)-containing selection medium (RPMI 1640) was added to the cells. The supernatants of the 96 well plates were tested by ELISA for antibody secretion. Confluent, positive clones by ELISA were amplified by transferring the cells into 24 well plates containing a macrophage feeding layer plus 1×HAT medium. Positive clones underwent two rounds of sub-cloning by limiting dilution, and screened by ELISA for antibody secretion. The final sub-clones were slowly adapted to medium without macrophages and HAT supplement.

ELISA-Based Identification of Anti-EDAR Antibodies

The presence of anti-EDAR antibodies in the supernatants of hybridoma cultures was determined by ELISA. Briefly, microplates were coated overnight at 4° C. with 1 µg/ml of EDAR-Fc or with the indicated control antigens in PBS. Plates were blocked for 1 hour at room temperature with PBS, 0.05% Tween 20 and 1% BSA. Hybridoma supernatants diluted in PBS and 0.1% BSA were incubated for 4 hours at room temperature. Detection of bound antibodies was performed using horseradish peroxydase-conjugated goat anti-mouse IgG antibodies (Jackson Immunoresearch). Tetramethylbenzidine (Sigma) was used as substrate. Two washes with PBS and 0.05% Tween 20 were performed between each step.

Production and Purification of Monoclonal Antibodies

Hybridoma cells were amplified in complete RPMI 1640 medium, washed twice in sterile PBS and resuspended at 100'000 cells/ml in Opti MEM I serum free medium (Gibco BRL, Life Technology, Basel, Switzerland). T175 flasks or roller bottles were inoculated with 100 ml and 800 ml of cell cultures, respectively. Cells were grown for 10 to 14 days. Culture supernatant was filtered and stored at 4° C. or −20° C. with sodium azide. Alternatively, hybridoma cells were slowly adapted to Opti MEM I medium and cultured directly in this medium. Supernatants were loaded onto HighTrap protein-G columns (GE Healthcare), washed with PBS and eluted in 0.1 M of sodium citrate, pH 2.7. Eluted fractions were neutralized with 1 M Tris, pH 9. Fractions were concentrated and buffer exchanged for PBS using microconcentrators (Millipore), Production of Fab Fragments of Monoclonal Antibodies (FIG. 32)

Monoclonal antibodies (0.5 to 5 mg of each) were digested with immobilized ficin for 72 h at 37° C. under the conditions recommended by the provider (Pierce, Rockford, Ill. Product number 44881). Fab fragments were recovered in the flow through of a Protein A affinity column, concentrated to 250 µl using a microconcentrator, and loaded onto a Superdex-200 gel filtration column (GE Healthcare) eluted at 0.5 ml/ml in PBS. Fractions of 0.5 ml were collected. Peak fractions containing the Fab fragment were pooled, and the Fab was used for the determination of the affinity constant.

Determination of Binding and Dissociation Constants of Anti-EDAR Fab Fragments (FIG. 33)

Measurements were performed on a Biacore T100 apparatus equipped with the Biacore T100 Control Software. Anti-human IgG Fc antibodies were immobilized on CM5 chips. hEDAR-Fc at 2 µg/ml was then loaded on the chip for 60 sec at 2 µl/min. Fab fragments at various concentrations (100, 25, 6.25, 1.6, 0.4 and 0 nM) were applied for 90 sec at 50 µl/min and then washed for 900 sec with buffer. Chips were regenerated for 30 sec with 3 M $MgCl_2$ at 10 µl/min. Experimental curves were fitted with a 1:1 interaction model used to determine the rate of association (ka), the rate of dissociation (kd) and the equilibrium dissociation constant (KD=kd/ka), also known as the affinity of the Fab.

Generation of EDAR-Fas-Expressing Jurkat Cells

Retroviruses were produced essentially as described previously (Soneoka, Y., Cannon, P. M., Ramsdale, E. E., Griffiths, J. C., Romano, G., Kingsman, S. M., and Kingsman, A. J. 1995 *Nucleic Acids Res* 23, 628-633). Briefly, 293T cells were transiently transfected with pMSCVpuro-hEDAR-Fas or pMSCVpuro-mEDAR-Fas and co-transfected with the pHIT60 and VSV-G plasmids, containing the sequences for gag-pol and VSV-G, respectively. pMSCVpuro-EDAR-Fas encoded the extracellular domain of human EDAR (amino acids 1-183) or mouse EDAR (amino acids 1-183), amino acids VD and the transmembrane and intracellular domains of human Fas (amino acids 169-335). After transfection, 293T cells were incubated for 24 h in RPMI supplemented with 10% FCS. Fas-deficient Jurkat-JOM2 cells were a kind gift of Olivier Micheau (University of Dijon, France). Jurkat-JOM2 cells ($10^6$ cells in 1 ml) were mixed with virus-containing supernatants (3 ml) supplemented with 8 µg/ml of polybrene, left for 15 min at 37° C., and centrifuged for 1 h at 37° C. and at 450×g. Cells were selected with 5 µg/ml of puromycin and cloned. About 40 clones were tested for their sensitivity to Fc-EDA1, and one of the sensitive clones (Jurkat-2199 clone 23 for hEDAR-Fas, Jurkat-2260 clone 7 for mEDAR) was selected for further experimental work.

Anti-EDAR Antibody-Induced Apoptosis of EDAR-Fas-Expressing Jurkat Cells (FIG. 12, 13)

The cytotoxicity assay using EDAR-Fas Jurkat cells was performed as described for FasL on Jurkat cells (Schneider, P., Holler, N., Bodmer, J. L., Hahne, M., Frei, K., Fontana, A., and Tschopp, J. 1998 *J Exp Med* 187, 1205-1213).

In Vivo Identification of Agonist Anti-EDAR Antibodies (FIG. 14)

Tabby mice (Jackson Laboratories, Bar Harbour) were handled according to institutional and Swiss Federal Veterinary Office guidelines, with the authorization of the Office Veterinaire Cantonal du Canton de Vaud.

Pups were labeled by puncture of a footpad with a 30 Gauge needle dipped in Aramis tattoo ink (Braintree Scientific, Braintree, Mass.). Intraperitoneal injections of antibodies were performed within 24 h after birth with a maximal volume of 20 µl of hybridoma supernatant using 0.5 ml U-100 Insulin syringe (Becton Dickinson, Franklin Lakes, N.J.). Examination and photography of tail hairs were performed 3 to 4 weeks post injection. Six weeks later, the presence of hair on the tail was scored on a scale of 4 units (0: no hair and 4: hair density similar to that on the tail of wild type mice), and the presence of sweat glands on the footpads was determined using the starch and iodine assay (Gaide, O., and Schneider, P. 2003 *Nat Med* 9, 614-618).

Example 2

Binding of mAbEDAR1, 2, 3, 4, 5, 6, 7, 8, 9, 10, 11, 12, 13, 14 and 15 Monoclonal Antibodies to both Human and Mouse EDAR (FIG. 6, 9)

Immunization of mice with human antigens usually gives rise to antibodies that do not cross-react with the mouse homologous proteins. In order to obtain antibodies recognizing both human and mouse EDAR, a feature which would considerably facilitate pre-clinical development of drug candidates, EDAR-deficient mice were immunized with human EDAR. It was then assessed whether monoclonal antibodies generated from these mice indeed recognized EDAR from these two animal species. The wells of microtiter plates were coated with soluble human and mouse EDAR-Fc fusion protein and a negative control protein (human Fas-Fc), blocked and probed with serial dilutions of anti-EDAR monoclonal antibody (mAb) mAbEDAR1, 2, 3 and 4 and a negative control mAb (Aprily 5) (FIG. 6), or with a single dose of mAbEDAR1 to 15 (FIG. 9). The presence of bound antibodies was revealed by the addition of peroxydase-labeled goat anti-mouse IgG antibodies, followed by ortho-phenylenediamine (OPD) and measure of the absorbance at 490 nm. It was found that mAbEDAR1 to 14 recognized human and mouse EDAR, whereas mAbEDAR15 recognized human but not mouse EDAR. None of the fifteen anti-EDAR antibodies recognized control proteins (Fas-Fc, or human Fc fused to an irrelevant portion of EDAR), and the control mAb Aprily 5 did not bind either to mouse and human EDAR. Altogether, these results indicated that fourteen anti-EDAR mAb were specific for both human and mouse EDAR, and one recognized human EDAR only.

The capacity of these mAb to recognize the human EDAR and its mouse counterpart constitutes an important feature for further clinical development, as it makes pharmacological studies in animals possible.

Example 3

Mapping of the Region on EDAR Recognized by the Anti-EDAR mAb (FIGS. 9, 10 and 11)

EDAR is a transmembrane protein whose extracellular part is composed of three membrane distal cystein-rich domains (CRDs) and of a proximal membrane stalk domain (FIG. 9A). Constructs coding for the entire EDAR protein, domains I and II, domains II and III, domain III and the stalk domain, domains I, II and III alone and the stalk domain alone were assembled with the Fc region of human IgG1, inserted into a mammalian expression vector and transiently transfected in 293T cells. Culture supernatants were captured in an ELISA plate with an anti-human IgG antibody, and revealed using the anti-EDAR mAb mAbEDAR1 to 15 and a horseradish peroxydase-coupled anti-human IgG mAb to monitor that the various EDAR-Fc truncation mutants had been efficiently captured. mAbEDAR1, 2, 3, 4, 7, 8, 10 and 11 recognize the fragment made up of domains I and II. The other fragments were not recognized, in particular the fragments made up of either domain I or II alone. mAbEDAR5, 6, 12 and 13 specifically recognized domain I, alone or together with domain II. mAbEDAR9, 14 and 15 only recognized Fc constructs containing the entire EDAR extracellular domain. Similar conclusions were obtained for mAbEDAR1 to 6 using a Western blot and for mAbEDAR1 to 4 with a FACS-based assay.

Example 4

Lack of Competition Between APO200 and Anti-EDAR mAb for Binding to EDAR (FIG. 8)

It was evaluated whether Fc-EDA1 and the anti-EDAR mAb have overlapping binding sites on EDAR. Wells of microtiter plates were coated with EDAR-Fc, blocked and incubated with serial dilutions of mAbEDAR1, 2, 3 or 4 or Aprily5 or Fc-EDA1 (competitors). Thereafter, a constant amount of biotinlyated mAbEDAR1, 2, 3 or 4 or Flag-EDA1 were added in each well (revelators). The presence of bound revelators was revealed with peroxydase labeled streptavidin (for biotinylated mAbEDAR1, 2, 3 and 4) or biotinylated anti-Flag M2 antibody followed by peroxydase-labeled streptavidin (for Flag-EDA1). It was found that the addition of Fc-EDA1 prevented the binding of Flag-EDA1, but did not prevent binding of the biotinylated anti-EDAR mAb to EDAR-Fc, indicating that the anti-EDAR mAb and APO200 have non-overlapping binding sites. Conversely, the addition of anti-EDAR antibodies (especially mAbEDAR1) prevented the binding of biotinylated anti-EDAR antibodies, but did not prevent the binding of Flag-EDA1. These results indicate that anti-EDAR mAb can be endowed with agonist activity even though their binding sites on EDAR are distinct from the one of APO200.

Example 5

Polyclonal Anti-EDAR Antibodies without Agonist Activity (FIG. 13)

In order to assess whether anti-EDAR antibodies are usually endowed with agonist properties, it was tested whether polyclonal anti-mouse EDAR antibodies raised in the goat were capable of inducing apoptosis of EDAR-Fas-transduced Jurkat cells. Incubation of these cells with serial dilutions of goat anti-EDAR antibodies did not result in any significant cell death. Even the addition of anti-goat IgG cross-linking antibodies failed to confer killing activity to these anti-EDAR polyclonal antibodies. By contrast, APO200 induced apoptosis with an $ED_{50}$ between 1 and 10 ng/ml ($ED_{50}$: efficacy dose 50, the dose of agonist inducing half-maximal cell death). In addition, these goat anti-EDAR antibodies were successfully used to stain human and mouse EDAR-transfected cells. These results indicated that these antibodies indeed bound to EDAR. Together, these findings indicated that only a subset of the anti-EDAR antibodies has agonist properties.

Example 6

Half-Life of the Anti-EDAR Monoclonal Antibodies Following Injection in Mice (FIG. 16)

The pharmacokinetics of a protein largely controls its therapeutic activity. It was previously determined that Fc-EDA1 has a half-life of 7 to 9 hours in the mouse. It is likely that EDAR agonists with more extended half-lives might prove more therapeutically effective. The in vivo half-life of the anti-EDAR mAb mAbEDAR1 and 3 was therefore established. Wild type mice were intravenously injected with mAbEDAR1 or mAbEDAR3 (200 µl of 1 mg/ml). Serum samples were collected after 20 minutes and 1, 2, 8, 16 and 32 days. The concentration of the anti-EDAR mAb was then determined by ELISA. Briefly, serial dilutions of serum were incubated in wells coated with human EDAR-Fc at 1 µg/ml, followed by anti-mouse IgG coupled to horseradish peroxydase and ortho-phenylenediamine as substrate. The half-lives of the anti-EDAR mAb were calculated by plotting for each time point the serum dilution giving an absorbance of 1 at 490 nm. An exponential curve was then fitted on the series of points. The time point 20 minutes was not included, as this time point corresponded to the distribution phase of the antibodies. Half-lives of 11 days were determined for mAbEDAR1 and mAbEDAR3. The extended half-lives of the anti-EDAR mAb, as compared with Fc-EDA1, contribute to the therapeutic activity of these molecules.

Example 7

Therapeutic Dose of the Anti-EDAR mAb in Newborn Tabby Mice (FIG. 15)

In order to evaluate the capacity of the anti-EDAR mAb to revert the Tabby phenotype, one day-old Tabby mice were intraperitoneally injected with graded doses of protein G-affinity chromatographed anti-EDAR mAb mAbEDAR1, 2, 3, 4, 5, 6, 7, 8, 9, 10, 11, 12, 13 and 14 (1 to 5 mice per group). Three to six weeks later, hair density on the tail was blindly scored on a scale of 4. Scores of 0, 1, 2, 3 and 4 corresponded to the absence of hair, sparse hair on the ventral side, dense hair on the ventral side, dense hair on both sides and a hair density similar to wild type mice, respectively. In some cases, the presence of functional sweat glands in footpads was evidenced by the starch-iodine assay, and scored on a scale of 2. Scores of 0, 1 and 2 corresponded to no sweat glands, few sweat glands (typically between 1 and 4) and several sweat glands (more than 4), respectively. It was found that the dose producing half-maximal effects in newborn Tabby mice was in the 0.25-1 µg range, which is similar to what is obtained with Fc-EDA1. These findings are remarkable in the sense that the anti-EDAR mAb were 10- to more than 1000-fold less efficient in vitro than Fc-EDA1, indicating that the pharmacological features of immunoglobulin G are well suited to convey in vivo EDAR agonist properties.

Example 8

Correction of the Tabby Phenotype Following Injection of Anti-EDAR mAb in Pregnant Mice (FIG. 17-22)

Figure 17:
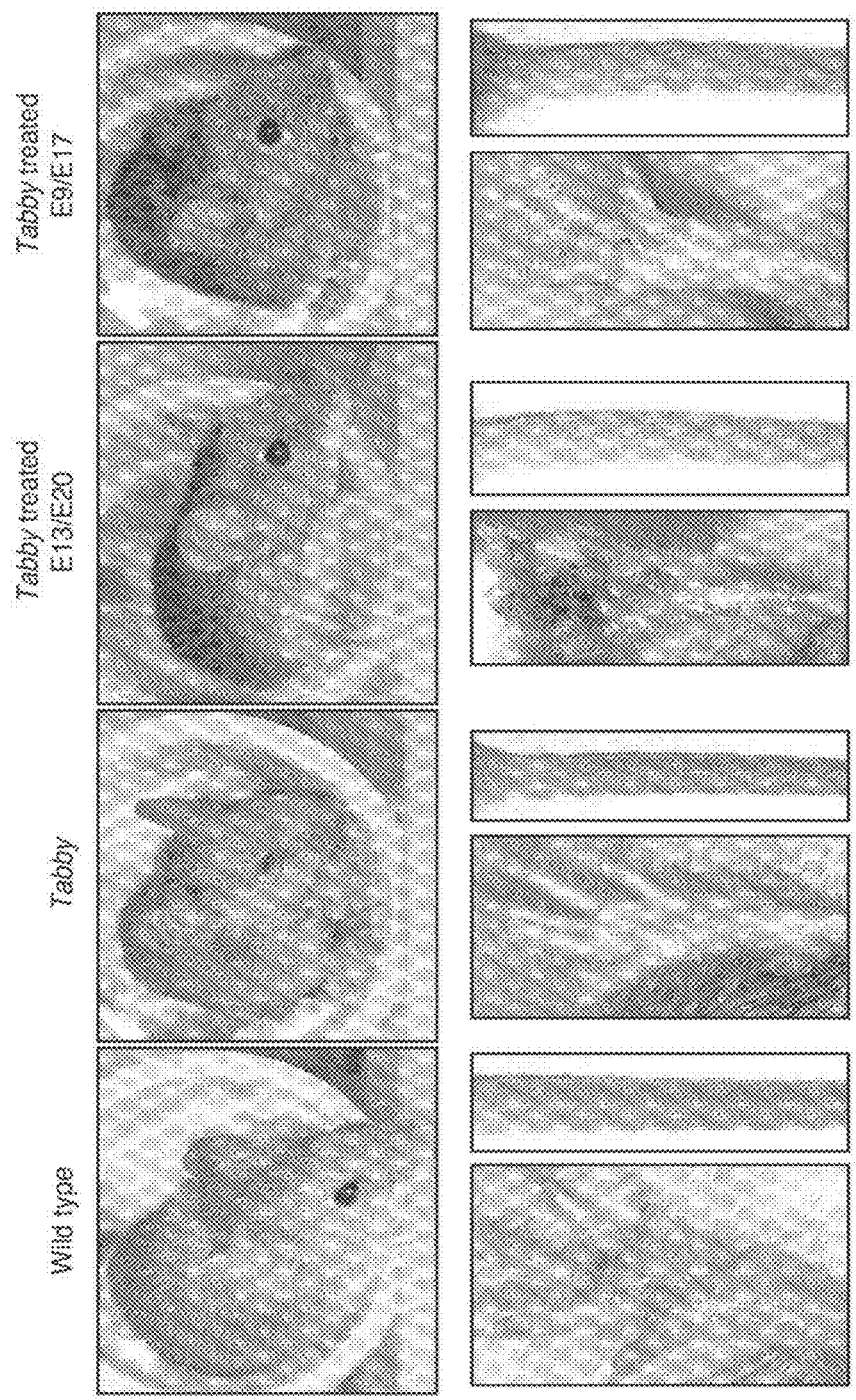
Figure 18:
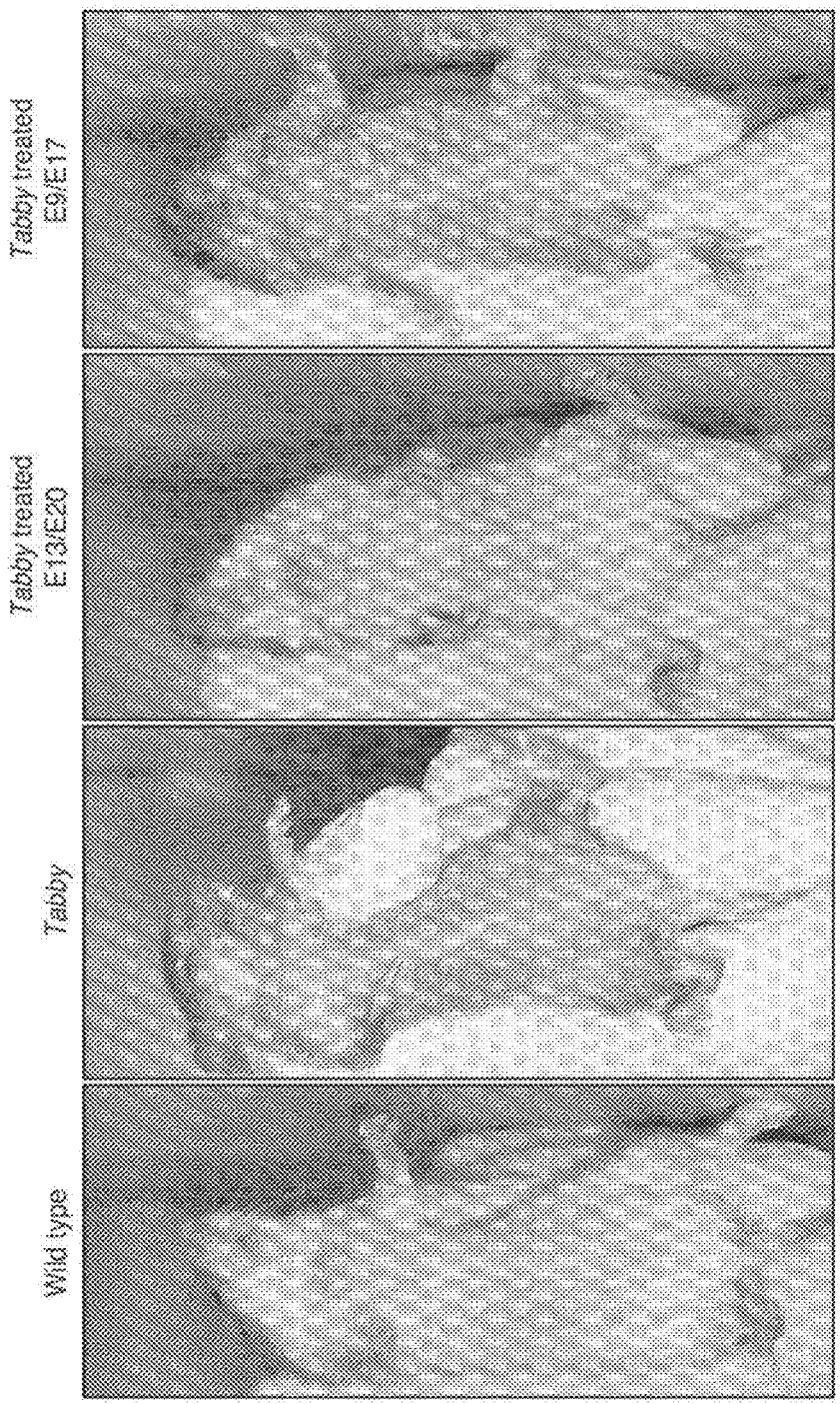

It was evaluated whether the intravenous administration of anti-EDAR mAb in pregnant Tabby mice had the capacity to correct the Tabby phenotype in the offspring. Gravid mice were treated at days 13 and 20 (E13/E20) or 9 and 17 (E9/E17) of gestation with 400 µg anti-EDAR mAb mAbEDAR3. Macroscopic and histological studies were then conducted on mice born from these mothers at six months of age. Many features of the Tabby phenotype were corrected in the mice treated with anti-EDAR mAb during their foetal life. The overall body appearance of the mice was modified. Specifically, the fur was darker and denser than in untreated Tabby mice, and the eyes were wide open. These features can be observed on the pictures of FIG. 17. Noticeably, the fur of the treated mice was also darker than in wild type mice (FIGS. 17 and 18). Similarly, fur of the ventral face of the treated animals was darker and denser than in Tabby mice (FIG. 18). Correction of features of the Tabby phenotype was further illustrated by the observation that in treated Tabby mice, hair was observed on the tail and functional sweat glands detected on the footpads using the starch and iodine test (FIG. 17).

Figure 19:
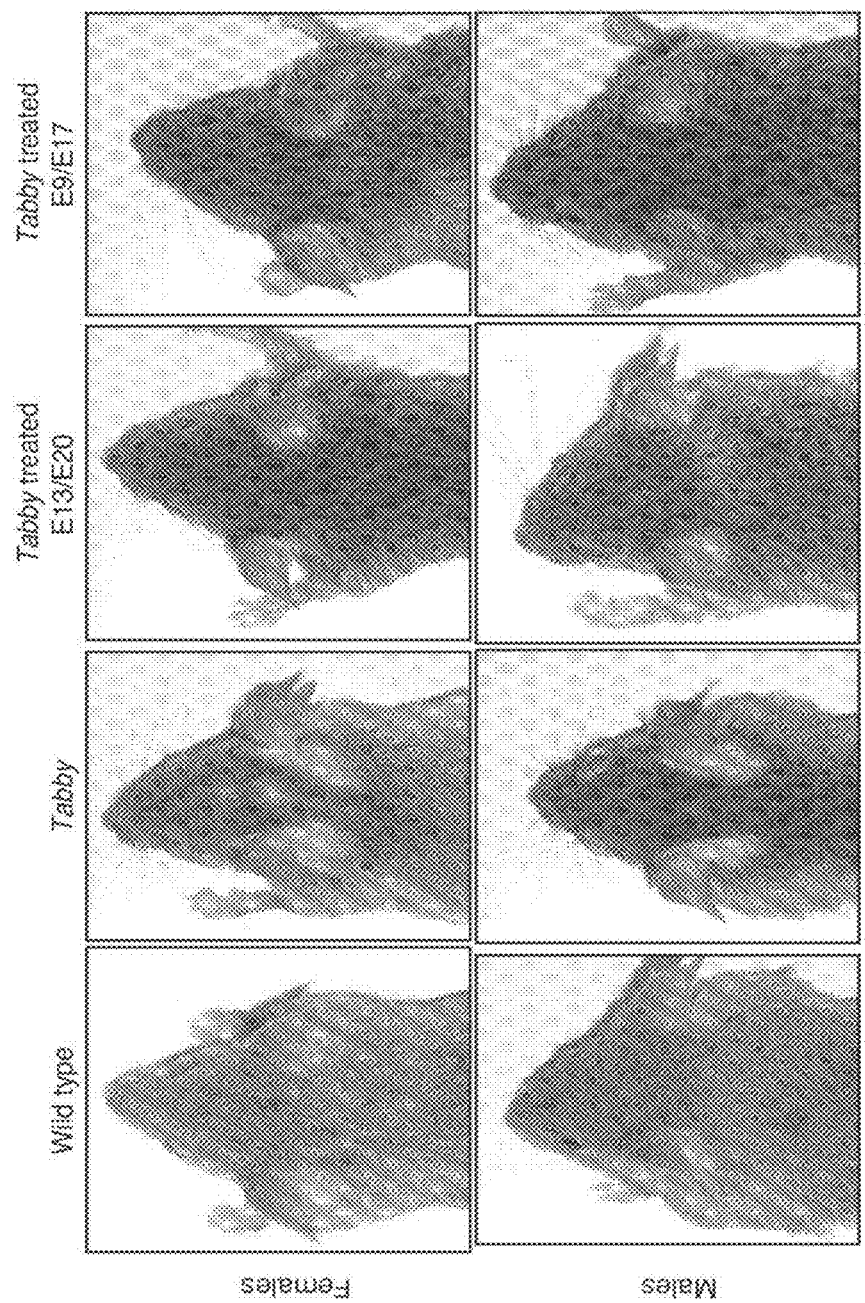

The absence of hair behind the ears is an additional macroscopic feature characterizing Tabby mice. Following exposure to anti-EDAR mAb during foetal development, the treated mice showed hair growth behind the ears to an extent similar to what is observed in wild type mice (FIG. 19).

Figure 20:
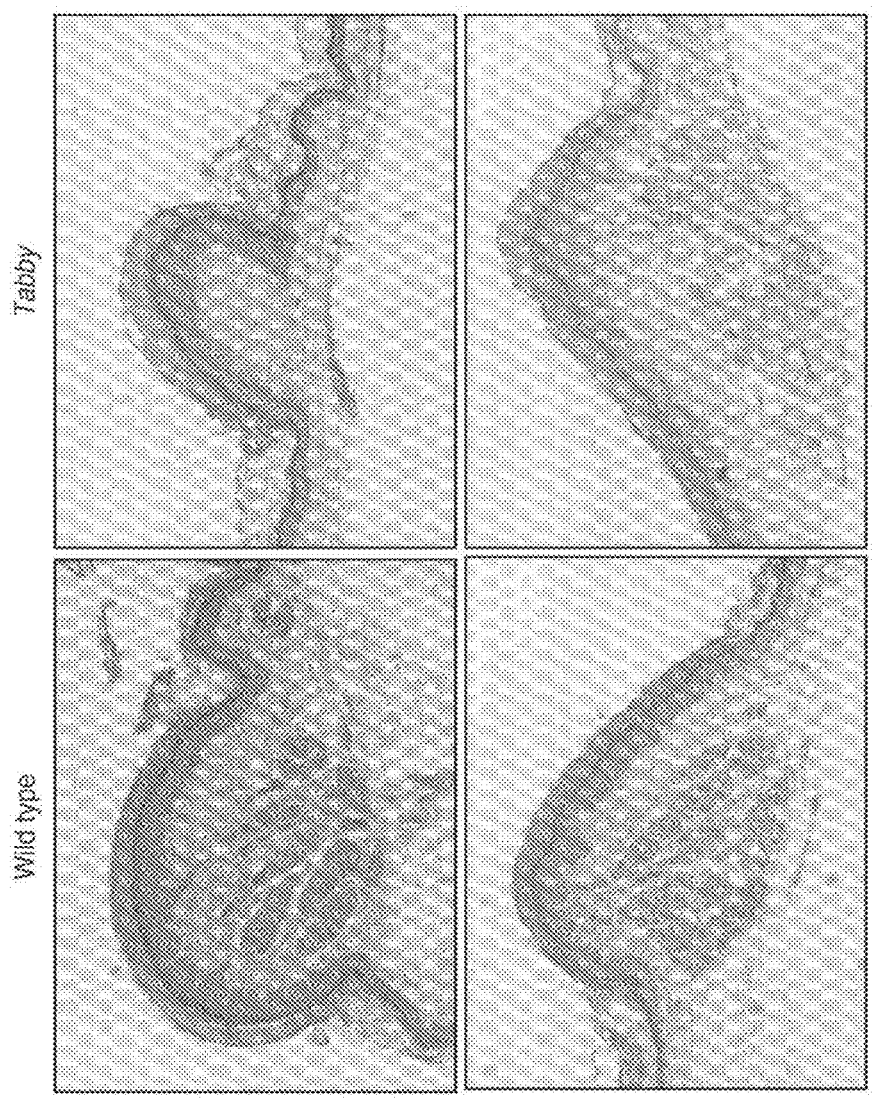
Figure 21:
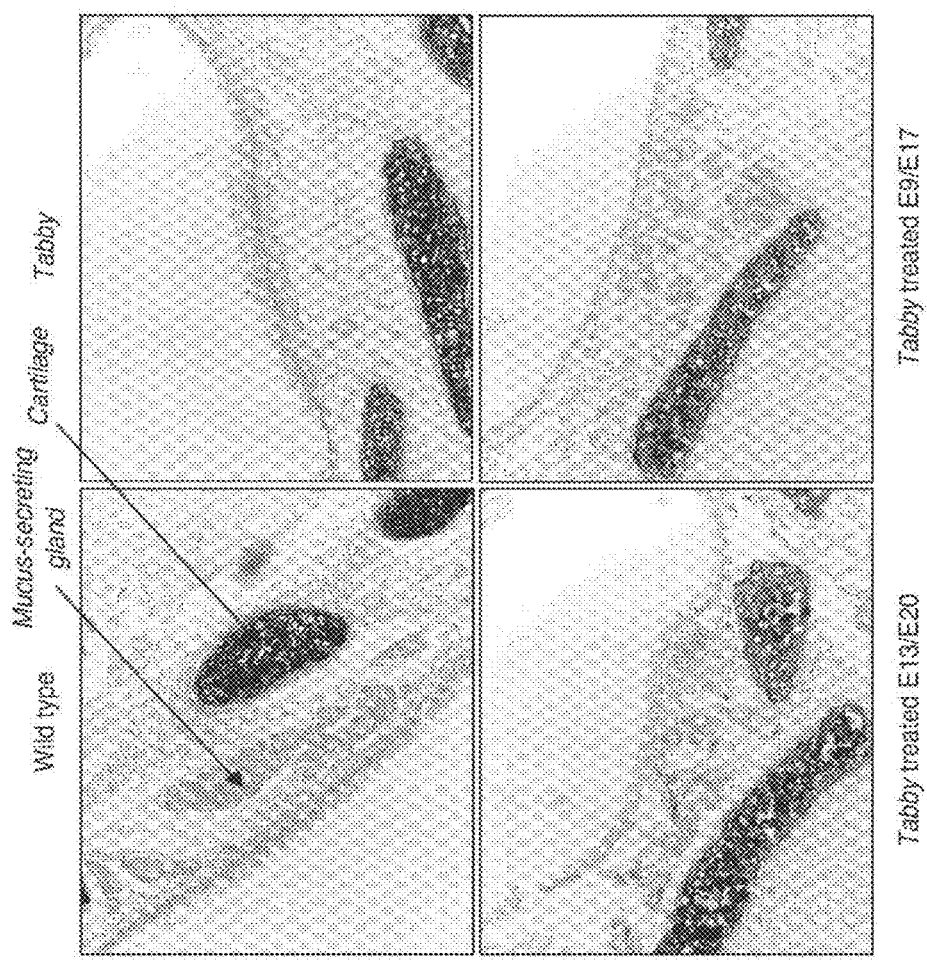

Histological analyses showed that the development of sweat glands on the footpads, mucus-producing cells in the trachea and larynx and hair follicles on the tail of Tabby mice was induced by treatment with anti-EDAR mAb during their foetal life (FIG. 20-22). Remarkably, tissue sections from wild type mice and from treated Tabby mice were undistinguishable, indicating that that the anti-EDAR mAb are capable of largely correcting the skin abnormalities in these mice.

Example 9

Development of Teeth in Tabby Mice Treated During Their Foetal Life with Anti-EDAR mAb (FIG. 23)

The dentition of Tabby mice treated with anti-EDAR mAb during their foetal life was examined at six months of age. The teeth from treated Tabby mice and wild type mice were very similar in terms of number, size and shape (i.e. number of cusps). This was particularly striking for the first molars of the upper and lower jaws, which are largely underdeveloped in Tabby mice. The first molars had similar appearance in treated Tabby mice and in wild type mice.

Example 10

Modified Hair Morphology Following Injection of Anti-EDAR mAb in Newborn Wild Type or Tabby Mice (FIG. 24-28)

In order to study the impact of anti-EDAR mAb on hair growth, newborn wild type mice were injected or not at days 0, 4, 7, 11 and 14 after birth with the anti-EDAR mAb mAbEDAR3 at 5 mg/kg or PBS. Fur of treated mice examined at day 18 after birth had a ruffled and greasy appearance, as compared with fur of control mice, which was smoothly arranged over the body. This feature was apparent for both the dorsal and the ventral sides of the animals (FIG. 24).

Microscopic examination of zig-zag hairs showed that treatment with anti-EDAR mAb resulted in the thinning of both zig-zag and awl hairs as compared with untreated one. Thinning of awl hair was particularly evident on hair of the belly, which are lightly pigmented and presented two instead of three parallel stacks of cells. In addition, the characteristic kinks of zigzag hairs were lost or strongly attenuated. Hair pigmentation was increased, which was particularly apparent in awl hair from the back of the mice (FIG. 25). This latter observation explains the darker appearance of the fur in treated animals (FIG. 24). Treatment did no affect the growth curves of the animals (FIG. 26). Similar effect on fur appearance and hair morphology was observed when newborn mice were treated with mAbEDAR1 (FIG. 27).

It was also questioned whether the appearance of the fur and the morphology of the hairs were stably modified by anti-EDAR mAb treatment, or would eventually revert to the initial prevailing situation. The hair phenotype gradually disappeared as mice were ageing, probably reflecting a situation where the agonist anti-EDAR mAb had been cleared and the modified hair replaced by new hair grown in subsequent hair cycles (FIG. 24, day 175).

Tabby mice have a single hair type that is intermediate between awl and auchene, that we will call "intermediate" type of hair. Newborn Tabby mice treated with mAbEDAR1 at 5 mg/kg at days 0, 4, 7, 11 and 14 also developed fluffy, untidy and darker fur (FIG. 28), characterized by the presence of modified intermediate hair that are thinner and composed of a single stack of cells, reminiscent of the structure of wild type zigzag hair (FIG. 28).

Together, these results indicate that agonist anti-EDAR mAb administered during the first phase of hair growth similarly affect hair morphology and pigmentation in both wild-type and EDA-deficient mice.

Example 11

Modified Hair Morphology Following Injection of Anti-EDAR mAb in Adult Wild-Type and Tabby Mice (FIG. 29-31)

It is a possibility that the hair phenotype observed in newborn mice treated with anti-EDAR antibodies might be the result of an alteration of hair follicle development, but would not take place in established, adult hair follicles. The effects of the anti-EDAR mAb were therefore investigated in adult wild type mice. Three weeks-old mice were depilated on the back, and treated intraperitoneally at 5 mg/kg with mAbEDAR1 at days 0, 4, 7, 11 and 14 post-depilation. This treatment allowed one to make observations only on hairs in the process of growing at the time of antibody application. Remarkably, hair grown back in the depilated area, as assessed at day 21 after depilation, appeared thinner and was considerably darker in treated than in untreated animals (FIG. 29). This correlated with morphological changes, as assessed by microscopy, with deeply coloured awl hair, and thinner zigzag hairs (FIG. 30). Overall, hair morphology in treated adult wild type mice was very similar to that observed in treated newborn wild type mice. The reversibility of the effect was further studied in ageing mice. While fur remained darker in treated mice for about 5 months following mAb treatment (FIG. 29, day 146), hair was replaced by normal-looking hair in subsequent hair cycles (FIG. 29, day 189). These results indicated that the effects of the anti-EDAR mAb on fur appearance and hair morphology are largely reversible.

In order to assess the effects of the anti-EDAR mAb on hair growth and morphology in adult, EDA-deficient mice, 9 weeks-old Tabby mice were depilated on the back, and intraperitoneally injected at days 0, 4, 7, 11 and 14 post-depilation with 5 mg/kg of mAbEDAR1. Hair grown back in the depilated zone of the treated animals by day 17 after depilation was strikingly darker and coarser than in untreated animals (FIG. 31). The difference of hair texture was indeed confirmed by the microscopic analysis of hair morphology (FIG. 31). As observed in treated newborn Tabby mice, the intermediate hair of treated adult Tabby grown during the treatment period have a single stack of cells instead of 2 or 3, resembling the structure of zigzag hair, the most abundant hair type in wild type mice.

Importantly, these results establish that EDAR is expressed and is functional in adult wild type and Tabby mice. This was unanticipated, as the results collected so far indicated that the activity of Fc-EDA1 faded within a few days after birth. These results suggest that the anti-EDAR mAb are therapeutically beneficial in adult XLHED patients.

Furthermore, the effects of the anti-EDAR mAb on hair morphology and colour of newborn and adult, wild type and EDA-deficient mice were not anticipated (see FIGS. 24 to 31). They constitute the first observations that pharmacological EDAR agonists are active in adult wild type and EDA-deficient mice. In the presence of mAbEDARs, hairs become consistently thinner and, at least for awl hairs, darker. It is striking that the intermediate type of hairs in EDA-deficient mice, resembling awl hairs in that they are formed of more than one parallel stack of cells become zigzag-like hairs with a single stack of cells after treatment with EDAR agonists. These morphological changes occur during hair growth, and are reversible when the EDAR agonist have been cleared and that a new hair cycle begins This phenotype implicates that EDAR agonists act on two different cell types: keratinocytes or keratinocyte-derived cells that form the hair and melanocytes that are responsible for hair pigmentation.

Example 12

Sebaceous Gland Response to Administration of an Anti-EDAR Monoclonal Antibody in Mature Tabby Mice In order to determine the effects of administration of an anti-EDAR monoclonal antibody on the size of sebaceous glands, three experiments were conducted. In a first experiment, sebaceous gland size was measured in split ear skin treated with collagenase to remove dermis and stained with oil-red-O. Ear samples were photographed from the dermis side and measurements were taken towards the tip of the ear using ImagePro software, with the apparent area of 20 glands from each of the ventral and dorsal ear skin collected for each animal. The mean size of these 40 glands was used to calculate a value for sebaceous gland size of that individual. A representative photo showing 22 identified sebaceous glands in an ear section is shown in FIG. 37. Table 3 shows area and length (in pixels) of 22 individual sebaceous glands in a single ear sample numbered PG1-PG10 and PG12-PG23.

TABLE 3

Area and length of 22 individual sebaceous glands in a single ear sample

| Sebaceous gland number | Area (pixels) | Length (pixels) |
| --- | --- | --- |
| PG1 | 442 | 89 |
| PG2 | 736 | 166 |
| PG3 | 470 | 104 |
| PG4 | 682 | 138 |
| PG5 | 594 | 138 |
| PG6 | 681 | 147 |
| PG7 | 678 | 143 |
| PG8 | 651 | 149 |
| PG9 | 708 | 148 |
| PG10 | 479 | 130 |
| PG12 | 737 | 156 |
| PG13 | 696 | 157 |
| PG14 | 960 | 174 |
| PG15 | 615 | 149 |
| PG16 | 697 | 144 |
| PG17 | 468 | 120 |
| PG18 | 616 | 134 |
| PG19 | 330 | 86 |
| PG20 | 389 | 85 |
| PG21 | 372 | 75 |
| PG22 | 327 | 71 |
| PG23 | 677 | 140 |

A plot of sebaceous gland sizes in ears of Tabby mice treated with mAb (single treatment after 2 weeks, single treatment for after 2 weeks, continuous treatment after 6 weeks and untreated controls after 2 and 6 weeks) is shown in FIG. 38.

This first experiment indicates that a single administration of mAbEDAR1 to Tabby mice can be detected 6 weeks later using sebaceous gland size in ear skin as a biomarker. The sebaceous gland sizes markedly increase in size after mABEDAR1 administration. This method does not reliably detect the effects of a single administration of mAbEDAR1 at 2 weeks post-treatment. This could be due to insufficient time for sebaceous gland hypertrophy to occur in this period, or possibly due to an age effect on responsiveness to EDAR stimulation (i.e. the mice do not undergo sebaceous hypertrophy in response to mAbEDAR1 until they reach a certain age).

In a second experiment, Tabby mice were matured to three weeks of age (21-26 days of age), then were either not dosed to serve as controls, dosed on a single occasion with mAbEDAR1, or dosed at two week intervals with mAbEDAR1 until sacrifice at 12 weeks from the start of dosage. Ears were collected, treated with collagenase to remove dermis, and stained with oil-red-O to allow visualization and measurement of sebaceous gland size. The results are shown in FIG. 39.

The results of this second experiment provide additional evidence that mAbEDAR1 increases the size of sebaceous glands in the mice, as observed in the first experiment. This glandular increase is not detectable in a sample of this size at two weeks post-administration, but is detectable at six weeks post-administration. A single administration of mAbEDAR1 can be detected in Tabby mice by measuring sebaceous gland size after twelve weeks have elapsed. These results also indicate that continued treatment has a greater effect on sebaceous gland size than a single treatment. The mechanism underlying the intermediate effect of a single mAbEDAR1 administration treatment cannot be inferred from these data. Following single mAbEDAR1 administration, sebaceous glands of the ear are either reduced in size or maintain their size for the next twelve weeks. Cui et al., 2003, reported that upon suppression of expression of an Eda transgene, sebaceous gland size in back skin was somewhat reduced at 1 month and reduced to a greater extent after 3 months (*Hum Mol Genet.* 2003 Nov. 15; 12(22):2931-40). This provides evidence that the sebaceous glands regress only slowly upon removal of an Eda stimulus.

In a third experiment, Tabby and wild type female mice were treated with mAbEDAR1 from approximately 3 weeks of age (between 20-26 days). Untreated Tabby and wild type female mice served as controls. The treatment was either a single dose of mAbEDAR1 at 2 mg/kg or repeated doses at two week intervals until the animals were sacrificed for analysis. Ears were collected from each mouse, skin leaflets were separated and the ears were split into dorsal and ventral halves, treated with collagenase to leave only the epidermis and appendages, and lipid stained with oil-red-0 to reveal the sebaceous glands. The ears were photographed under a microscope and the apparent area of the sebaceous glands associated with 20 hair follicles (just proximal to the ear margin) was determined for each half of the split ear (a total of 40 glands per mouse). A sample photograph and magnified image thereof showing sebaceous glands marked for measurements are shown in FIG. 40 (panels A and B, respectively).

A comparison of sebaceous gland sizes in untreated wild type and Tabby mice is shown in FIG. 41. These data indicate that Tabby sebaceous glands are smaller than wild type and that sebaceous gland size is relatively stable from 5 to 15 weeks of age in both wild type and Tabby mice.

The plot shown in FIG. 42 indicates the effect of a single dose or continuous treatment at two week intervals extending to 24 weeks compared with untreated Tabby mice and untreated wild type mice. The mean ear sebaceous gland area and standard deviation was calculated for groups of mice in each treatment conditions. The sebaceous glands of Tabby mice are smaller than those of wild type mice at all of the time points. It can be seen that continuous treatment more effective than single treatment, with partial rescue of gland size at 6 weeks and full rescue at 12 and 24 weeks. The effect of a single treatment is seen at 6 and 12 weeks, but fades thereafter. There is no significant effect at 2 weeks.

These data sets indicate that mAbEDAR1 treatment can fully correct the ear sebaceous gland size defect in mature Tabby mice. This effect is clearly not linked to an action during development (it is homeostatic). The effect of a single treatment is long-lasting (12 weeks), but reversible. The data also clearly indicate that the corrected phenotype can be maintained if treatment is maintained. It is also seen that the sebaceous glands shrink at 24 weeks for both the treated and untreated Tabby mice and for the untreated wild type mice.

Shown in FIG. 43 is a plot indicating the effect of the mAbEDAR1 treatment regimens in wild type mice. This dataset indicates that in wild type mice, an increase in sebaceous gland size is obtained with the treatment but it is not as pronounced relative to the increase in sebaceous gland size of Tabby mice after treatment. This effect is not significantly observed after 2 weeks and is not observed after 24 weeks.

This example indicates that continuous treatment of wild type and Tabby mice with an anti-EDAR monoclonal antibody increases the size of sebaceous glands and that the effect is more pronounced in Tabby mice. Since Tabby mice have a genetic developmental disorder, it is thus predicted that treatment of other mammals, including humans, with an anti-EDAR1 monoclonal antibody may be effective for increasing the size and/or number of sebaceous glands in an individual affected by a developmental disorder characterized by small or underdeveloped sebaceous glands.

Example 13

Transfer of Antibodies to Newborn Pups Via Milk and Intestinal Absorption

In order to determine if agonist anti-EDAR antibodies can be transferred to newborn pups via mother's milk, Tabby mouse mothers were injected intravenously or intraperitoneally with mAbEDAR1 at 5 mg/kg within 24 h after delivery. Pups were analyzed at one approximately month of age for the presence of tail hairs and sweat glands.

In the intravenous experiment, a female Tabby mouse weighing 18.7 g and designated T142-RTop/1 was injected intravenously with a single dose of mAbEDAR1 (5 mg/kg) after delivery of pups on Feb. 12, 2011. Three littermates were allowed to nurse naturally and were tested for appearance of tail hair, sweat glands and eye. Photographs of tail hair, sweat glands and an eye taken on day 33 are shown in FIG. 44 and a series of photographs of tail hair and of an eye of a single mouse pup taken daily for 20 days is shown in FIG. 45.

In the intraperitoneal experiment, a female Tabby mouse weighing 22.7 g and designated T142-RTop/2 was injected intraperitoneally with a single dose of mAbEDAR1 after delivery of pups on Feb. 12, 2011. Three littermates were allowed to nurse naturally and were tested for appearance of tail hair, sweat glands and eye. Photographs of tail hair, sweat glands and an eye were taken on day 32 and are shown in FIG. 46 and a series of photos of tail hair and of an eye of a single mouse pup taken daily for 20 days is shown in FIG. 47.

The observations made in the intravenous and intraperitoneal experiments using Tabby mice provide evidence that tail hair growth is increased when the pups are nursed by a mother that had received a dose of mAbEDAR1 administered either intravenously or intraperitoneally. This indicates that the agonist antibody is effectively transported via milk from the mother to the pups.

In another mouse experiment, wild type pups of wild type mothers injected with mAbEDAR1 were examined at two time points. Photographs of the pups are shown in FIG. 48. The pup designated W111 mAb1 E10 (born on Mar. 15, 2011) was nursed by a mother which had received an intravenous injection of mAbEDAR1 at a dose of 1 mg/kg. At time points of 23 days and 47 days, this mouse did not exhibit a change in phenotype. The pup designated W114 mAb1 P1 (born on Mar. 20, 2011) was nursed by a mother which had received an intraperitoneal injection of mAbEDAR1 at a dose of 5 mg/kg. At 18 days, this mouse displayed the disheveled hair phenotype. At 42 days, the disheveled hair phenotype was no longer present in this mouse. The disheveled hair phenotype is expected if mAbEDAR1 is passed to the pup via the mother's milk.

The experiments described in this example indicate that mAbEDAR1 is effectively transported via milk from the mother to the pups in both wild type and Tabby mice after the mother is injected with this antibody. It is therefore a reasonable prediction that such transport of milk from mother to young is likely to occur in other mammals, including humans. It is thus predicted that a young nursing mammal (including a human) with a developmental disorder treatable by an anti-EDAR antibody could be treated at a very young age simply by injecting the mother with the anti-EDAR antibody.

What is claimed herein is:

1. A method for increasing the size and/or number of sebaceous glands in a subject in need thereof, the method comprising contacting said subject with an isolated monoclonal anti-EDAR agonist antibody or antigen-binding portion or fragment thereof that binds human and/or mouse EDAR and wherein the isolated monoclonal anti-EDAR antibody or antigen binding portion or fragment thereof comprises:
   a) a heavy chain variable region comprising the complementary determining region (CDR) amino acid sequences: SEQ ID NO: 1, SEQ ID NO: 2, and SEQ ID NO: 3; or SEQ ID NO: 7, SEQ ID NO: 8, and SEQ ID NO: 9; or SEQ ID NO: 13, SEQ ID NO: 14, and SEQ ID NO: 15; or SEQ ID NO: 19, SEQ ID NO: 20, and SEQ ID NO: 21; or SEQ ID NO: 25, SEQ ID NO: 26, and SEQ ID NO: 27; and
   b) a light chain variable region comprising the complementary determining region (CDR) amino acid sequences of SEQ ID NO: 4, SEQ ID NO: 5, and SEQ ID NO: 6; or SEQ ID NO: 10, SEQ ID NO: 11, and SEQ ID NO: 12; or SEQ ID NO: 16, SEQ ID NO: 17, and SEQ ID NO: 18; or SEQ ID NO: 22, SEQ ID NO: 23, and SEQ ID NO: 24; or SEQ ID NO: 28, SEQ ID NO: 29, and SEQ ID NO: 30.

2. The method of claim 1, wherein the subject has an ectodermal disease.

3. The method of claim 2, wherein the ectodermal disease is XLHED, alopecia or tooth agenesis.

4. The method of claim 1, wherein the contacting step comprises parenteral, intravenous, oral, subcutaneous, intradermal, intramuscular, or topical administration.

5. The method of claim 1, wherein the subject is a human or a mouse.

6. The method of claim 1, wherein the isolated monoclonal anti-EDAR antibody or antigen binding portion or fragment thereof comprises: a heavy chain variable region comprising the complementary determining region (CDR) amino acid sequences: SEQ ID NO: 1, SEQ ID NO: 2, and SEQ ID NO: 3; and a light chain variable region comprising the complementary determining region (CDR) amino acid sequences: SEQ ID NO: 4, SEQ ID NO: 5, and SEQ ID NO: 6.

7. The method of claim 1, wherein the isolated monoclonal antibody or fragment or antigen binding portion or fragment thereof is capable of binding human EDAR or a fragment thereof comprising cysteine rich domain I (CRD1).

8. The method of claim 7, wherein the isolated monoclonal antibody or fragment or antigen binding portion or fragment thereof is capable of binding human EDAR or a fragment thereof comprising cysteine rich domain I (CRD1) in the absence of cysteine rich domain II (CRD2).

9. The method of claim 1, wherein the isolated monoclonal antibody or fragment or antigen binding portion or fragment thereof is an agonist of human and/or mouse EDAR.

10. The method of claim 9, wherein the isolated monoclonal antibody or fragment or antigen binding portion or fragment thereof has EC50 for inducing half maximal decrease of cell viability in EDAR-Fas-expressing Jurkat cells equal to or less than 200 ng/mL.

11. The method of claim 10, wherein the isolated monoclonal antibody or fragment or antigen binding portion or fragment thereof has EC50 for inducing half maximal decrease of cell viability in EDAR-Fas-expressing Jurkat cells equal to or less than 100 ng/mL.

12. The method of claim 1, wherein the isolated monoclonal antibody or fragment or antigen binding portion or fragment thereof binds to human and/or mouse EDAR with an affinity constant (KD) of at least $10^{-8}$ M.

13. The method of claim 1, wherein the isolated monoclonal antibody or fragment or antigen binding portion or fragment thereof is a humanized antibody, antibody fragment, or antigen binding portion or fragment thereof.

14. The method of claim 1, wherein the isolated monoclonal antibody or fragment or antigen binding portion or fragment thereof is monovalent.

15. The method of claim 1, wherein the isolated monoclonal antibody or fragment or antigen binding portion or fragment thereof is a single chain antibody, antibody fragment, or antigen binding portion or fragment thereof.

16. The method of claim 1, wherein the isolated monoclonal antibody or fragment or antigen binding portion or fragment thereof is a Fab, F(ab)'$_2$, Fv, single chain Fv (scFv), or Fd fragment.

17. The method of claim 1, wherein the isolated monoclonal antibody or fragment or antigen binding portion or fragment thereof is a chimeric antibody, antibody fragment, or antigen binding portion or fragment thereof.

18. The method of claim 1, wherein the isolated monoclonal antibody or fragment or antigen binding portion or fragment thereof is a fusion protein.

19. The method of claim 13, wherein the isolated monoclonal antibody or fragment or antigen binding portion or fragment thereof has a heavy chain selected from the group consisting of heavy chain of IgG, IgM, IgA, IgE, single chain antibody, and immunoglobulin-derived constructs.

20. The method of claim 19, wherein the IgG is selected from the group consisting of IgG1, IgG2, IgG3, IgG4, mutated IgG 1 that is no longer recognized by FcR, and mutated IgG4 that no longer undergoes heavy chain swapping.

21. The method of claim 1, wherein the isolated monoclonal antibody or fragment or antigen binding portion or fragment thereof is conjugated to a ligand and/or a tag.

22. The method of claim 21, wherein the isolated monoclonal antibody or fragment or antigen binding portion or fragment thereof has a heavy chain conjugated to the ligand and/or tag.

23. The method of claim 21, wherein the ligand and/or tag is polyethylene glycol (PEG) or a label.

24. The method of claim 1, wherein the isolated monoclonal anti-EDAR antibody or antigen binding portion or fragment thereof comprises: a heavy chain variable region comprising the complementary determining region (CDR) amino acid sequences: SEQ ID NO: 13, SEQ ID NO: 14, and SEQ ID NO: 15; and/or a light chain variable region comprising the complementary determining region (CDR) amino acid sequences: SEQ ID NO: 16, SEQ ID NO: 17, and SEQ ID NO: 18.

* * * * *